(12) United States Patent
Van Den Berg Van Saparoea et al.

(10) Patent No.: US 11,059,868 B2
(45) Date of Patent: Jul. 13, 2021

(54) DISPLAY OF HETEROLOGOUS MOLECULES ON BACTERIAL CELLS AND MEMBRANE VESICLES

(71) Applicant: ABERA BIOSCIENCE AB, Stockholm (SE)

(72) Inventors: Hendrik Bart Van Den Berg Van Saparoea, Stockholm (SE); Wouter Simon Petrus Jong, Stockholm (SE); Joen Luirink, Stockholm (SE)

(73) Assignee: ABERA BIOSCIENCE AB

( * ) Notice: Subject to any disclaimer, the term of this patent is extended or adjusted under 35 U.S.C. 154(b) by 0 days.

(21) Appl. No.: 16/753,665

(22) PCT Filed: Oct. 25, 2018

(86) PCT No.: PCT/EP2018/079355
§ 371 (c)(1),
(2) Date: Apr. 3, 2020

(87) PCT Pub. No.: WO2019/081685
PCT Pub. Date: May 2, 2019

(65) Prior Publication Data
US 2020/0377556 A1    Dec. 3, 2020

(30) Foreign Application Priority Data
Oct. 25, 2017    (EP) .................................... 17198241

(51) Int. Cl.
*C07K 14/315*    (2006.01)
*C12N 1/20*    (2006.01)
*C12N 9/52*    (2006.01)

(52) U.S. Cl.
CPC ........ *C07K 14/315* (2013.01); *C07K 14/3156* (2013.01); *C12N 1/20* (2013.01); *C12N 9/52* (2013.01); *C07K 2319/70* (2013.01)

(58) Field of Classification Search
None
See application file for complete search history.

(56) References Cited

U.S. PATENT DOCUMENTS

2016/0222372 A1    8/2016    Walper et al.
2017/0258885 A1    9/2017    Luirink et al.

FOREIGN PATENT DOCUMENTS

| WO | WO2008127094 A2 | 10/2008 |
| WO | WO2011098772 A1 | 8/2011 |
| WO | WO2012041899 A1 | 4/2012 |
| WO | WO2012048199 A1 | 4/2012 |
| WO | WO2016112921 A1 | 7/2016 |
| WO | WO2016193746 A1 | 12/2016 |

OTHER PUBLICATIONS

H Bart Van Den Berg Van Saparoea et al., "Display of Recombinant Proteins on Bacterial Outer Membrane Vesicles by Using Protein Ligation." Applied and Environmental Microbiology 84.8 (2018), 17 pages.

Kuipers, Kirsten et al., "*Salmonella* outer membrane vesicles displaying high densities of pneumococcal antigen at the surface offer protection against colonization", Vaccine 33.17 (2015) pp. 2022-2029.

Jong, Wouter SP et al. "An autotransporter display platform for the development of multivalent recombinant bacterial vector vaccines", Microbial Cell Factories 13.1 (2014), 15 pages.

Rajapaksa, Thejani E., et al. "Intranasal M cell uptake of nanoparticles is independently influenced by targeting ligands and buffer ionic strength." Journal of Biological Chemistry 285.31 (2010): 23739-23746.

Van Ulsen, Peter, et al. "Type V secretion: from biogenesis to biotechnology." Biochimica et Biophysica Acta (BBA)—Molecular Cell Research 1843.8 (2014): 1592-1611.

Daleke-Schermerhorn, Maria H., et al. "Decoration of outer membrane vesicles with multiple antigens by using an autotransporter approach." Appl. Environ. Microbiol. 80.18 (2014): 5854-5865.

Emsley, Paul, et al. "Structure of Bordetella pertussis virulence factor P. 69 pertactin." Nature 381.6577 (1996): 90-92.

Gupta, Prem N., et al. "Lectin anchored stabilized biodegradable nanoparticles for oral immunization: 1. Development and in vitro evaluation." International journal of pharmaceutics 318.1-2 (2006): 163-173.

Burgess, Nancy K., et al. "β-Barrel proteins that reside in the *Escherichia coli* outer membrane in vivo demonstrate varied folding behavior in vitro." Journal of Biological Chemistry 283.39 (2008): 26748-26758.

Rykunov, Dmitry, et al. "Improved scoring function for comparative modeling using the M4T method." Journal of structural and functional genomics 10.1 (2009): 95-99.

Rubas, W., et al. "Incorporation of the reovirus M cell attachment protein into small unilamellar vesicles: incorporation efficiency and binding capability to L929 cells in vitro." Journal of microencapsulation 7.3 (1990): 385-395.

Sauri, Ana, et al. "The Bam (Omp85) complex is involved in secretion of the autotransporter haemoglobin protease." Microbiology 155.12 (2009): 3982-3991.

Hussain, Nasir, and Alexander T. Florence. "Utilizing bacterial mechanisms of epithelial cell entry: invasin-induced oral uptake of latex nanoparticles." Pharmaceutical research 15.1 (1998): 153-156.

Kubala, Marta H., et al. "Structural and thermodynamic analysis of the GFP: GFP-nanobody complex." Protein Science 19.12 (2010): 2389-2401.

(Continued)

*Primary Examiner* — Padmavathi Baskar
(74) *Attorney, Agent, or Firm* — Mendelsohn Dunleavy, P.C.

(57) ABSTRACT

The present invention concerns Gram-negative bacterial cells or Outer Membrane Vesicles (OMVs) which display on their outer surface an autotransporter (AT) fusion protein covalently coupled via an isopeptide bond to a heterologous molecule. These bacterial cells and OMVs are suitable for use in vaccines or targeted drug delivery of antigens or therapeutic agents to specific cells or tissues.

15 Claims, 16 Drawing Sheets

Figure 1A:
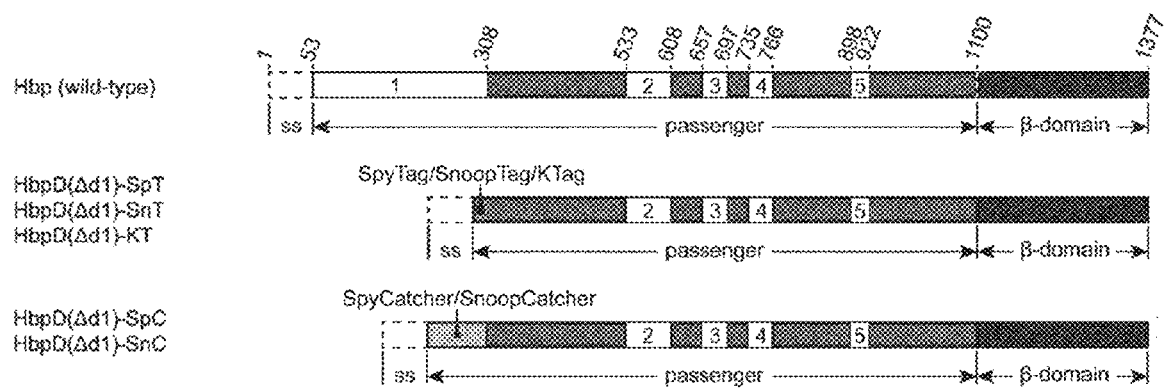
Figure 1B:
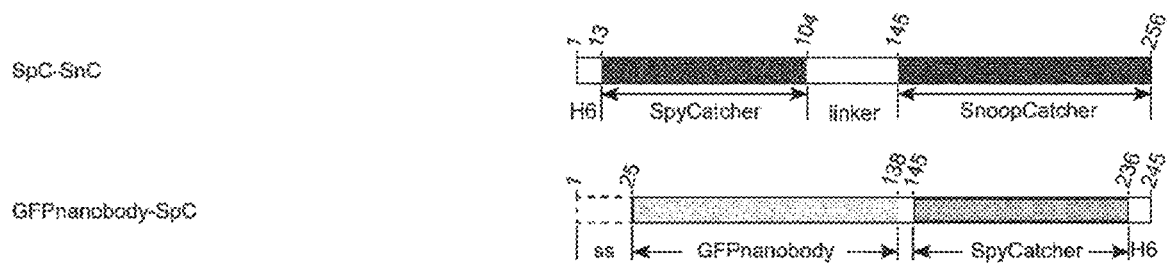
Figure 1C:
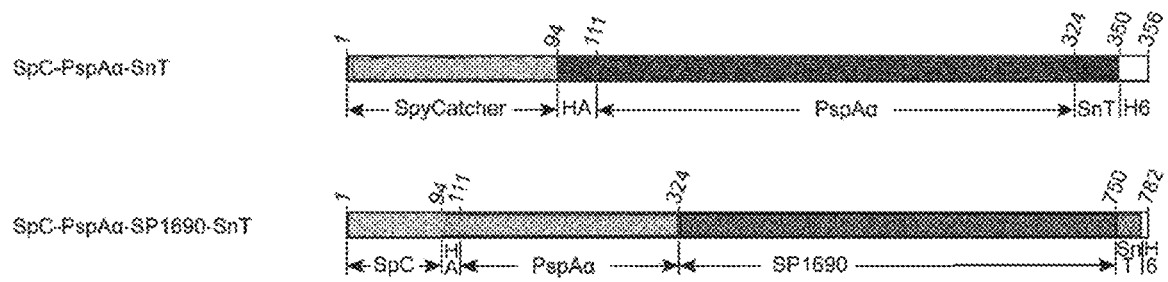
Figure 1D:
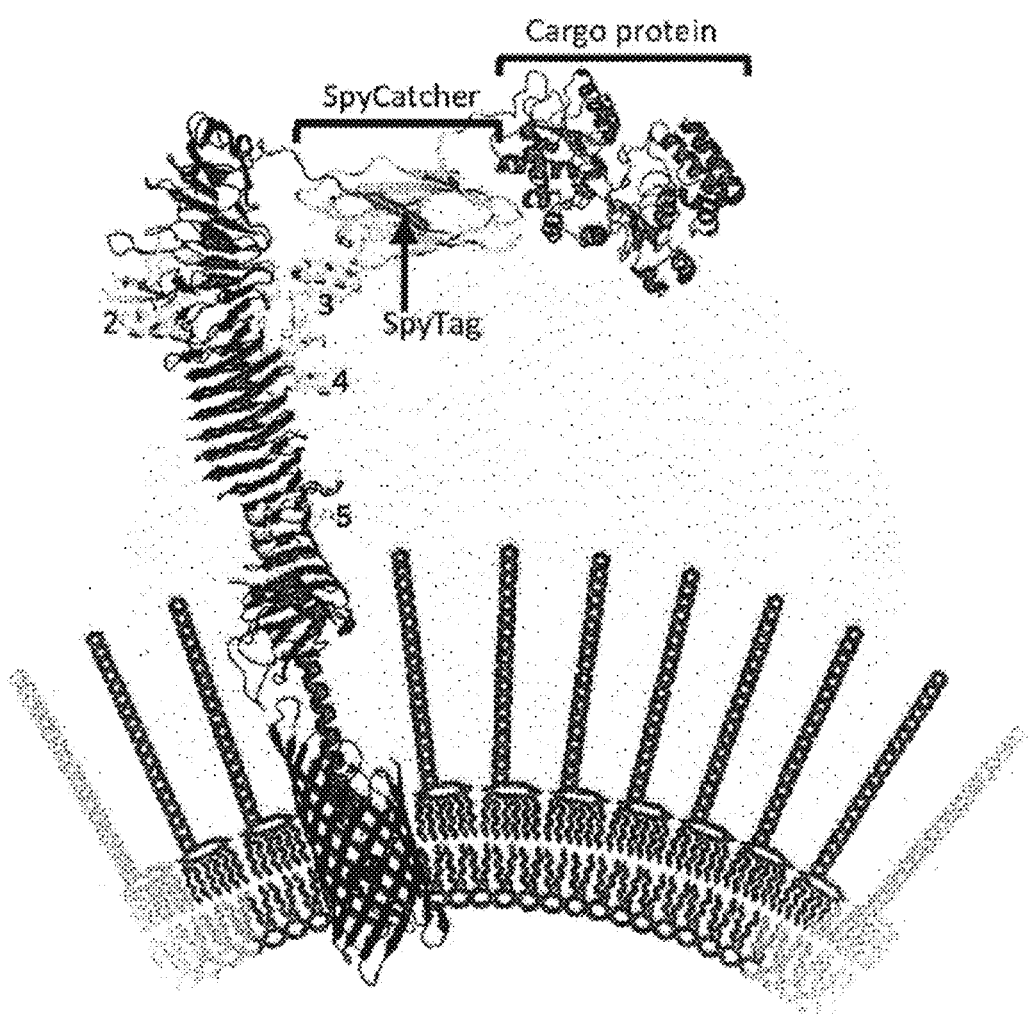

Specification includes a Sequence Listing.

(56) References Cited

OTHER PUBLICATIONS

Nicolay, Toon, et al. "Autotransporter-based cell surface display in Gram-negative bacteria." Critical reviews in microbiology 41.1 (2015): 109-123.
Kitagawa, Ryo, et al. "Biogenesis of *Salmonella enterica* serovar typhimurium membrane vesicles provoked by induction of PagC." Journal of Bacteriology 192.21 (2010): 5645-5656.
Kuipers, Kirsten, et al. "Th17-mediated cross protection against pneumococcal carriage by vaccination with a variable antigen." Infection and immunity 85.10 (2017): e00281-17, 13 pages.
Jong, Wouter SP, et al. "A structurally informed autotransporter platform for efficient heterologous protein secretion and display." Microbial cell factories 11.1 (2012): 85, 11 pages.
Zakeri, Bijan, and Mark Howarth. "Spontaneous intermolecular amide bond formation between side chains for irreversible peptide targeting." Journal of the American Chemical Society 132.13 (2010): 4526-4527.
Bernadac, Alain, et al. "*Escherichia coli* tol-pal mutants form outer membrane vesicles." Journal of bacteriology 180.18 (1998): 4872-4878.
Bäumler, Andreas J. et al. "The Ipf fimbrial operon mediates adhesion of *Salmonella typhimurium* to murine Peyer's patches." Proceedings of the National Academy of Sciences 93.1 (1996): 279-283.
Hussain, Nasir, et al. "Enhanced oral uptake of tomato lectin-conjugated nanoparticles in the rat." Pharmaceutical research 14.5 (1997): 613-618.
Alfsen, Annette, et al. "HIV-1 gp41 envelope residues 650-685 exposed on native virus act as a lectin to bind epithelial cell galactosyl ceramide." Journal of Biological Chemistry 277.28 (2002): 25649-25659.
Junker, Mirco, et al. "Pertactin β-helix folding mechanism suggests common themes for the secretion and folding of autotransporter proteins." Proceedings of the National Academy of Sciences 103.13 (2006): 4918-4923.
Klemm, Per et al. "Bacterial adhesins: function and structure." International Journal of Medical Microbiology 290.1 (2000): 27-35.
Marra, Andrea, and Ralph R. Isberg. "Invasin-dependent and invasin-independent pathways for translocation of Yersinia pseudotuberculosis across the Peyer's patch intestinal epithelium." Infection and immunity 65.8 (1997): 3412-3421.
Barnard, Travis J., et al. "Autotransporter structure reveals intrabarrel cleavage followed by conformational changes." Nature structural & molecular biology 14.12 (2007): 1214-1220.
Chen, David J., et al. "Delivery of foreign antigens by engineered outer membrane vesicle vaccines." Proceedings of the National Academy of Sciences 107.7 (2010): 3099-3104.
Apostolopoulos, V., et al. "Targeting antigens to dendritic cell receptors for vaccine development." Journal of Drug Delivery 2013 (2013): 869718 (22 pages).
Alaniz, Robert C., et al. "Membrane vesicles are immunogenic facsimiles of *Salmonella typhimurium* that potently activate dendritic cells, prime B and T cell responses, and stimulate protective immunity in vivo." The Journal of Immunology 179.11 (2007): 7692-7701.
Drobnak, Igor, et al. "Multiple driving forces required for efficient secretion of autotransporter virulence proteins." Journal of Biological Chemistry 290.16 (2015): 10104-10116.
Veggiani, Gianluca, et al. "Programmable polyproteams built using twin peptide superglues." Proceedings of the National Academy of Sciences 113.5 (2016): 1202-1207.
Johnson, Troy A., et al. "Active-site gating regulates substrate selectivity in a chymotrypsin-like serine protease: the structure of Haemophilus influenzae immunoglobulin A1 protease." Journal of Molecular Biology 389.3 (2009): 559-574.
Roth-Walter, Franziska, et al. "M cell targeting with Aleuria aurantia lectin as a novel approach for oral allergen immunotherapy." Journal of Allergy and Clinical Immunology 114.6 (2004): 1362-1368.

Jong, W. S. P., et al. "Comparing autotransporter β-domain configurations for their capacity to secrete heterologous proteins to the cell surface." PloS one 13.2 (2018): e0191622, 23 pages.
Ertl, Bernhard, et al. "Lectin-mediated bioadhesion: preparation, stability and caco-2 binding of wheat germ agglutinin-functionalized Poly (D, L-lactic-co-glycolic acid)-microspheres." Journal of Drug Targeting 8.3 (2000): 173-184.
Meza-Aguilar, J. Domingo, et al. "X-ray crystal structure of the passenger domain of plasmid encoded toxin (Pet), an autotransporter enterotoxin from enteroaggregative *Escherichia coli* (EAEC)" Biochemical and Biophysical Research Communications 445.2 (2014): 439-444.
Hoiseth, Susan K., and B. A. D. Stocker. "Aromatic-dependent *Salmonella typhimurium* are non-virulent and effective as live vaccines." Nature 291.5812 (1981): 238-239.
Kesty, Nicole C., and Meta J. Kuehn. "Incorporation of heterologous outer membrane and periplasmic proteins into *Escherichia coli* outer membrane vesicles." Journal of Biological Chemistry 279.3 (2004): 2069-2076.
Khan, Shekeb, et al. "Crystal structure of the passenger domain of the *Escherichia coli* autotransporter EspP." Journal of Molecular Biology 413.5 (2011): 985-1000.
Jong, Wouter SP, et al. "Limited tolerance towards folded elements during secretion of the autotransporter Hbp." Molecular Microbiology 63.5 (2007): 1524-1536.
Yen, Yihfen T., et al. "Common themes and variations in serine protease autotransporters." Trends in Microbiology 16.8 (2008): 370-379.
Juncker, Agnieszka S., et al. "Prediction of lipoprotein signal peptides in Gram-negative bacteria." Protein Science 12.8 (2003): 1652-1662.
Goyvaerts, C., et al. "Pros and Cons of Antigen-Presenting Cell Targeted Tumor Vaccines." Journal of immunology Research 2015 (2015): 785634, 19 pages.
Marchler-Bauer, Aron, et al. "CDD/SPARCLE: functional classification of proteins via subfamily domain architectures." Nucleic Acids Research 45.D1 (2017): D200-D203.
Zakeri, Bijan, et al. "Peptide tag forming a rapid covalent bond to a protein, through engineering a bacterial adhesin." Proceedings of the National Academy of Sciences 109.12 (2012): E690-E697.
Otto, Ben R., et al. "Crystal structure of hemoglobin protease, a heme binding autotransporter protein from pathogenic *Escherichia coli*." Journal of Biological Chemistry 280.17 (2005): 17339-17345.
Kolling, Glynis L., and Karl R. Matthews. "Export of virulence genes and Shiga toxin by membrane vesicles of *Escherichia coli* O157: H7." Applied and Environmental Microbiology 65.5 (1999): 1843-1848.
Giannasca, Paul J., et al. "Regional differences in glycoconjugates of intestinal M cells in mice: potential targets for mucosal vaccines." American Journal of Physiology—Gastrointestinal and Liver Physiology 267.6 (1994): G1108-G1121.
Vink, Tom, et al. "A simple, robust and highly efficient transient expression system for producing antibodies." Methods 65.1 (2014): 5-10.
Moreno, María, et al. "*Salmonella* as live trojan horse for vaccine development and cancer gene therapy." Current Gene Therapy 10.1 (2010): 56-76.
Schwechheimer, Carmen, and Meta J. Kuehn. "Outer-membrane vesicles from Gram-negative bacteria: biogenesis and functions." Nature Reviews Microbiology 13.10 (2015): 605-619.
Kijanka, Marta, et al. "Nanobody-based cancer therapy of solid tumors." Nanomedicine 10.1 (2015): 161-174.
Fierer, Jacob O. et al. "SpyLigase peptide-peptide ligation polymerizes affibodies to enhance magnetic cancer cell capture." Proceedings of the National Academy of Sciences 111.13 (2014): E1176-E1181.
Pröschel, Marlene, et al. "Probing the potential of CnaB-type domains for the design of tag/catcher systems." PloS one 12.6 (2017).
International Search Report and Written Opinion for corresponding international application No. PCT/EP2018/079355; dated Jan. 3, 2019 (13 pages).

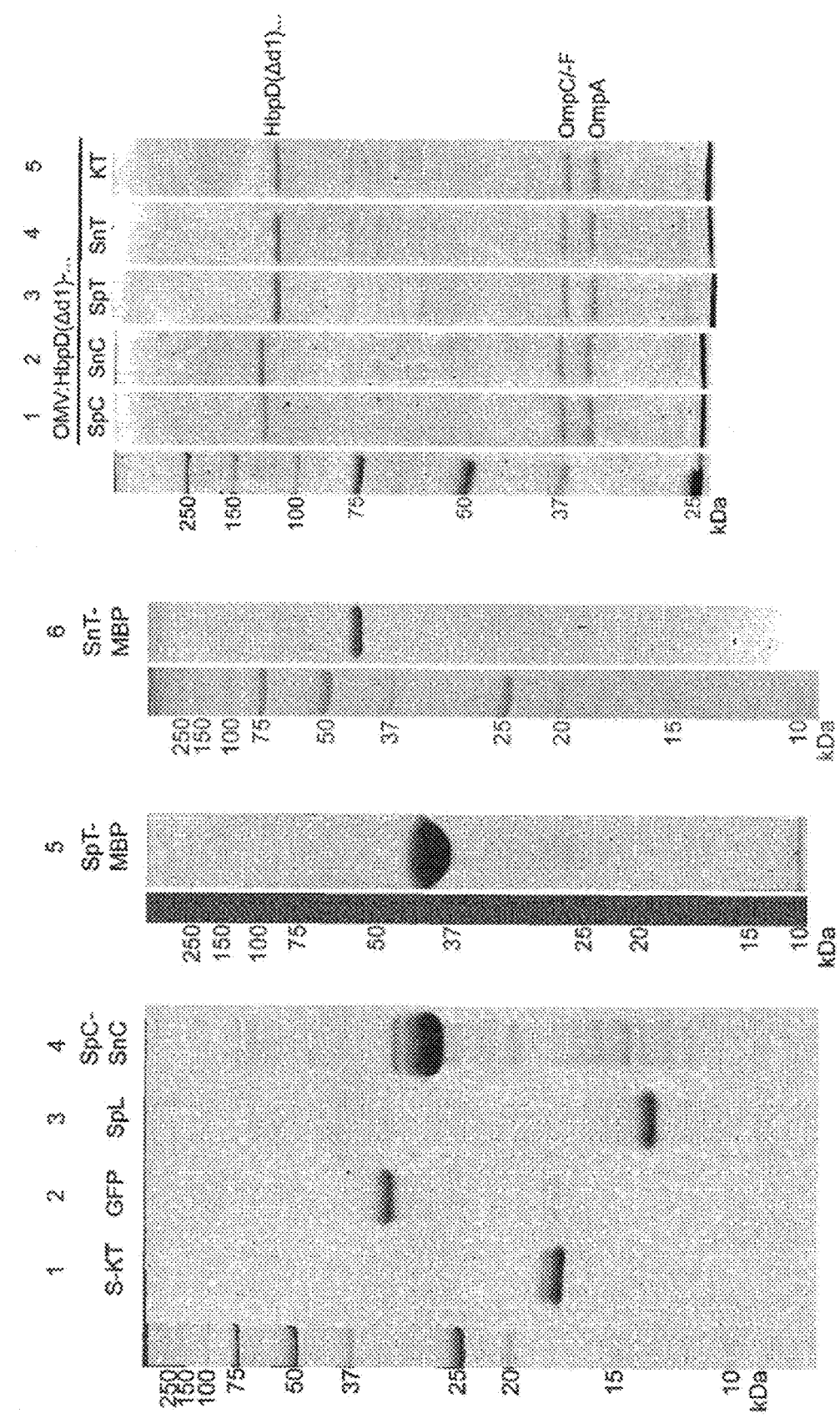

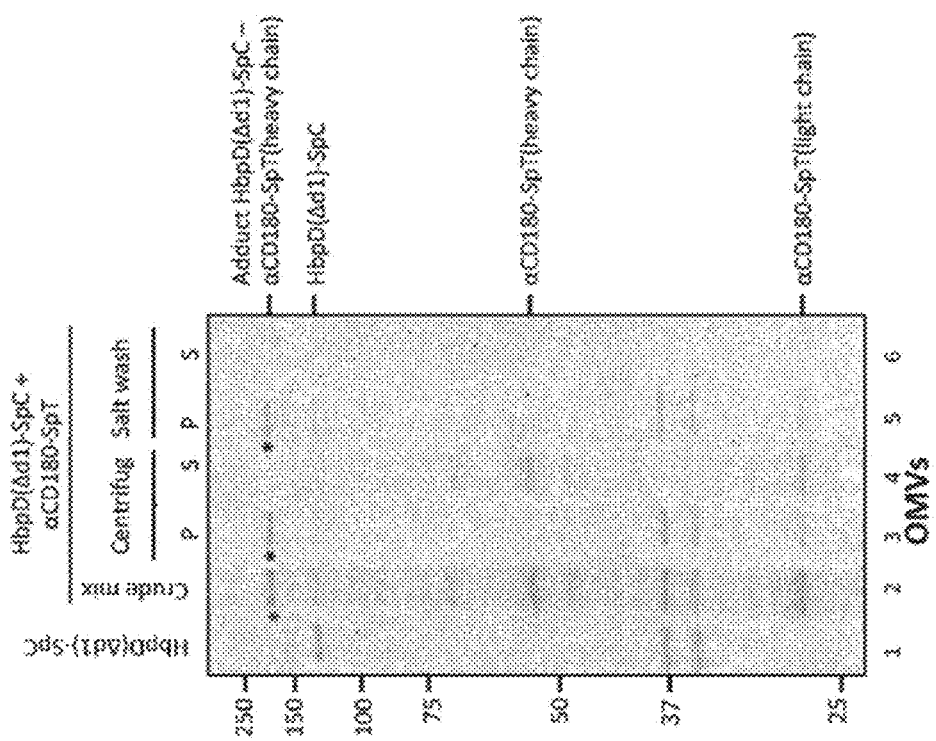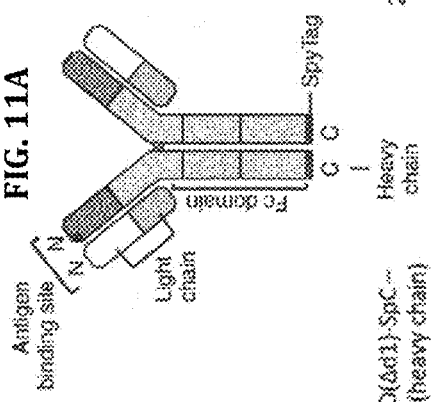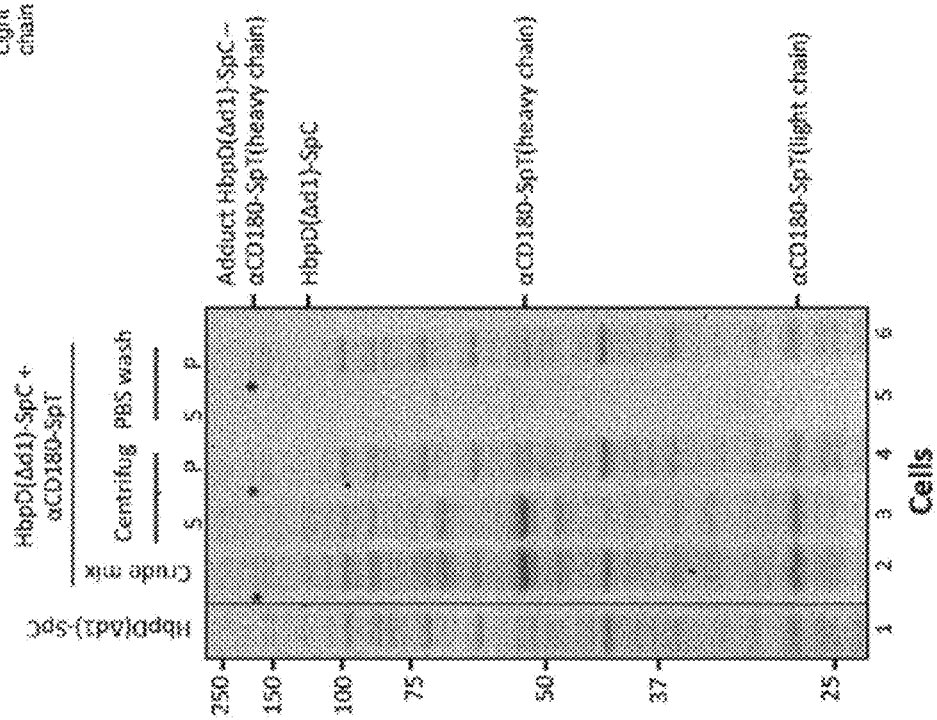
FIG. 11A
FIG. 11B
FIG. 11C

DISPLAY OF HETEROLOGOUS MOLECULES ON BACTERIAL CELLS AND MEMBRANE VESICLES

The present invention concerns novel Gram-negative bacterial cells and outer membrane vesicles (OMVs) derived from these cells, which display heterologous molecules on their surface. These bacterial cells and OMVs are suitable for use in vaccines or targeted drug delivery.

In Gram-negative bacteria, secretion and surface display of heterologous proteins are difficult to achieve due to the presence of a complex, multi-layered cell envelope consisting of an inner membrane, an outer membrane, and a gel like substance between the membranes called the periplasm. Several secretion systems have evolved to overcome this barrier and deliver proteins in the extracellular environment. Of these, the type V secretion system, also known as the Autotransporter (AT) pathway, appears the best suited for piggy-back transport of cargo proteins, because it combines simplicity with a high transport capacity (van Ulsen et al. 2014 Biochim Biophys Acta, 1843(8):1592; Nicolai et al. 2015 Crit Rev Microbial 41(1):109).

Autotransporters (ATs) are large proteins that are secreted by Gram-negative bacteria, such as *E. coli*. The autotransporter system is simple in the sense that the autotransporter, as implied by its name, is suggested to carry all information, for translocation across the periplasm and outer membrane within the protein itself. However, the mechanism whereby the autotransporters are secreted is still not completely understood.

Autotransporters are synthesized as large precursor proteins that contain three domains: (i) an N-terminal signal peptide that targets the protein to the Sec translocon and initiates transfer across the inner membrane, (ii) a passenger domain, which comprises the "cargo" protein that is to be secreted and (iii) a C-terminal β-domain) comprising a beta-barrel structure that integrates into the outer membrane and plays a crucial role in translocation of the passenger domain across the outer membrane into extracellular space.

After translocation, the passenger domain is cleaved from the translocator domain and is released into the extracellular environment. Cleavage can be achieved by the action of an (external) protease or a protease motif situated between the translocator domain and the passenger domain. Alternatively, cleavage takes place through an intramolecular autocatalytic event at a specific site between the translocator domain and the passenger domain. The passenger domain of an autotransporter comprises a beta stem structure and side domains. The beta stem is an elongated structure formed by an extended beta helix. The C-terminus of the passenger domain comprises an autochaperone domain which has been implicated in both passenger folding and translocation across the outer membrane.

The autotransporter is first transported across the inner membrane by the Sec machinery, after which its C-terminal domain inserts into the outer membrane (OM) and forms a β-barrel that, together with a central linker domain, mediates transport of the functional N-terminal passenger domain to the cell surface or medium. Based on this secretion system, the inventors set out to develop a display platform by which attenuated bacterial cells or derived Outer Membrane Vesicles (OMVs) can be decorated with multiple heterologous antigens of choice for optimal stimulation of the immune system or with lectins, adhesins or affinity molecules of choice for optimal targeting to certain tissues or immune cells of interest, and other applications such as drug discovery or drug delivery.

Hbp is an autotransporter protein that belongs to the family of serine protease autotransporters of Enterobacteriaceae (SPATEs). The crystal structure of the passenger domain of Hbp has been determined (Otto et al. 2005 J Biol Chem 280(17): 17339-45). The crystal structure shows that the polypeptide forms a long right-handed beta-helix structure ("beta stem"). Like other classical ATs, Hbp is organized in three domains: (i) the signal peptide at the N-terminus that triggers targeting to and translocation across the inner membrane via the generic protein-conducting Sec-translocon, (ii) the secreted passenger domain that carries the actual effector function of the AT, and (iii) the β-domain at the C-terminus that adopts a β-barrel conformation in the outer membrane (OM) and plays a crucial role in transfer of the passenger domain across the OM (FIGS. 1A and D). This latter step is supported by the generic insertase for outer membrane proteins, the Bam complex, in a concerted, poorly understood mechanism (Sauri A et al. Microbiology 2009, 155 (Pt 12), 3982-91). The passenger domain of the Hbp comprises two larger side domains, domain d1 and domain d2, of which d1 comprises the serine proteinase activity of the protein, and d2 has an unknown function. There are also three smaller domains, domain d3, domain d4 and domain d5. At the cell surface the passenger domain starts to fold, which provides a pulling force to energize translocation across the outer membrane (Drobnak et al. 2015 J Biol Chem 290(16): 10104-16). Finally, upon completion of folding of the passenger-β-domain tandem and release from the Bam complex, the passenger is cleaved from its β-domain through an autocatalytic mechanism that takes place in the barrel interior (Barnard et al. 2007, Nat Struc Mol Biol 14(12): 1214-20). The cleaved and released passenger domain is a long β-helical stem structure from which small loops and larger functional domains protrude (Otto et al. 2005 supra). Similar beta stem domains have also been shown for other autotransporters, such as pertacin (Emsley et al. 1996 Nature 381:90-92), EspP (Khan et al. 2011 J Mol Biol 413(5):985-1000), Pet (Domingo Meza-Aguilar et al. 2014 Biochem Biophys Res Commun 445(2): 439-44)and IgA protease (Johnson et al. 2009 J Mol Biol 389(3): 559-74).

Autotransporters have been used as for surface display purposes. Gram-negative bacterial cells or OMVs displaying heterologous molecules on the outer surface are known in the art. Jong et al Microbial Cell Factories 2012, 11:85 and Jong et al. Microbial Cell Factories 2014, 13:162 describe live bacteria which display an adapted *Escherichia coli* autotransporter, Heamoglobin protease (Hbp), at the surface. The Hbp was engineered into a platform for the secretion and surface display of heterologous polypeptides, by replacement of the passenger side domains with heterologous antigens. By interrupting the cleavage site between passenger and β-domain, the Hbp fusion proteins remain cell associated rather than being released, and facilitate efficient surface exposure of the heterologous proteins at some distance of the cell surface. By using antigens derived from Mycobacterium tuberculosis, Chlamydia trachomatis and influenza A virus, the Hbp platform was demonstrated to be a useful tool for successfully display of heterologous antigens on the cell surface of live bacteria and OMVs (Jong et al. 2012 supra; Jong et al. 2014 supra; Daleke-Schermerhorn et al. 2014 Appl. Environ Microbiol, 80(18):5854-65).

Despite being an efficient and versatile system for bacterial-based display of heterologous proteins, the capacity of Hbp to translocate complex and/or bulky fusion partners across the cell envelop was found to be limited (Jong et al 2014 supra; Daleke-Schermerhorn et al. 2014 supra; Kuipers et al. 2015 Vaccine 33(17): 2022-9; Jong et al. 2007 Mol Microbiol 63(5): 1524-36). Due to inherent limitations in the secretion of Hbp across the outer membrane, translocation of large or structurally complex antigens genetically fused to Hbp generally results in relatively low-level surface exposure. It was found that the number, size and structural complexity of the antigens fused to the Hbp carrier restricts the translocation capacity of the Hbp antigen fusion product. The problem of size can partly be solved by splitting up the antigen and dividing the resulting fragments over the various permissive integration sites in Hbp (Jong et al. 2014 supra; Jong et al. 2012 supra; Kuipers et al. 2015 supra). However, this strategy could result in the loss of conformational epitopes, and is therefore not sufficient for large or structural complex antigens. Since the density of antigens at the OMV surface has shown to be important for protective efficacy, there is a need to increase the display capacity of the Hbp system while maintaining a high expression level.

It was surprisingly found that by covalently linking heterologous molecules to already surface exposed structures, the limitations of the membrane translocation steps could be circumvented. It was found that instead of using genetic fusion, heterologous molecules such as antigens, lectins, nanobodies and antibodies could be linked enzymatically to an autotransporter such as Hbp present at high density at the surface of OMVs using Catcher/Tag coupling technology. Catcher/Tag coupling technology is based on the spontaneous formation of an isopeptide bond between a peptide tag and its peptide binding partner, a so called peptide catcher. The peptide tag and corresponding peptide catcher form a unique Catcher/Tag ligation pair.

Thus, the present invention provides for Gram negative bacterial cells and OMVs derived therefrom, which display on the outer surface an autotransporter fusion protein covalently coupled via isopeptide bonds to a heterologous molecule selected from the group consisting of antigens, lectins, adhesins or affinity molecules, wherein the autotransporter fusion protein comprises at least one moiety of a Catcher/Tag ligation pair, and the heterologous molecule comprises the other moiety of said Catcher/Tag ligation pair.

By genetically fusing the sequence of a moiety of a Catcher/Tag ligation pair to the autotransporter protein, an autotransporter fusion protein could be obtained comprising a Catcher or Tag moiety of a Catcher/Tag ligation pair. By equipping the heterologous molecule with the corresponding moiety of a Catcher/Tag ligation pair, the heterologous molecule could be attached to the autotransporter fusion protein by the formation of an isopeptide bond between the Catcher and Tag moieties of the Catcher/Tag ligation pair. It was surprising to find that heterologous molecules could be covalently linked via an isopeptide bond to the autotransporter fusion carrier expressed on the surface of bacterial cells and OMVs irrespective of the abundant presence of liposaccharides, fimbriae, flagella and other structures present on the surface of the cells and OMVs. Without being bound by theory, it was expected that the presence of other surface structures, in particular liposaccharides would interfere with the formation of the isopeptide bond, thereby hindering the coupling of the heterologous molecule to the displayed autotransporter fusion protein. Thus linking heterologous molecules via Catcher/Tag coupling technology to an autotransporter present at high density at some distance of the surface provides an interesting alternative for displaying heterologous molecules on the surface of bacterial cells and OMVs, especially when complex or large molecules are concerned.

By covalently conjugating heterologous molecules via Catcher/Tag protein ligation to the autotransporter already expressed on the surface, the display capacity of the autotransporter carrier platform could be increased while at the same time a high expression level of the autotransporter on the surface could be maintained. Catcher/Tag protein ligation technology allows for the decoration of bacterial cells and OMVs with heterologous recombinant protein partners without the restrictions observed with genetic fusion of the autotransporter carrier to the heterologous protein and translocation of the autotransporter fusion protein.

Suitable Catcher/Tag ligation pairs for use according to the invention are pairs that have been derived from proteins which are capable of spontaneously forming one or more isopeptide bonds. Isopeptide bonds are amide bonds that are formed between carboxyl/carboxamide and amino groups, whereby at least one of the carboxyl or amino groups is present in the side chain of an amino acid residue that is part of the peptide backbone. The domain of the protein that expresses this spontaneous isopeptide bond can be expressed as separate fragments to give a peptide tag fragment (a "Tag" moiety), and a binding peptide partner for the peptide tag (a "Catcher" moiety). Mixing the two peptide fragments results in the spontaneous formation of an isopeptide bond between the Tag moiety and the Catcher moiety. Of some Catcher/Tag ligation pairs, the Catcher domain could be further split into a small second Tag moiety and a large fragment harboring the Ligase domain to create a tripartite system. In case of a tripartite system, the fragment harboring the Ligase domain mediates the coupling of the Tag- and Catcher moiety, but is not part of the isopeptide bond. Such tripartite systems involving a Catcher/Tag ligation pair and a third peptide fragment harboring the Ligase domain are also encompassed as Catcher/Tag ligation pairs for use according to the invention. Thus, the Catcher/Tag ligation pairs according to the invention include Catcher/Tag ligation pairs of both the bipartite and tripartite systems. The property of spontaneously forming a covalent isopeptide bond enabled the development of Catcher/Tag ligation pairs, wherein the Tag moiety and the Catcher moiety are capable of covalently reconstituting the isopeptide bond, wherein the Tag moiety comprises one of the residues involved in the isopeptide bond (e.g. a lysine), and the Catcher moiety comprises the other residue involved in the isopeptide bond (e.g. an asparagine or aspartate). The binding between a Tag moiety and its corresponding binding partner termed Catcher moiety is unique for each Catcher/Tag pair.

In a preferred embodiment, the Catcher moiety comprises the ligase fragment which mediates isopeptide bond formation. The isopeptide bond formed between the Tag moiety and the Catcher moiety is covalent and, hence, very stable. Catcher/Tag ligation pairs can be derived from any protein that is capable of spontaneously forming isopeptide bonds, such as for instance described in Proschel et al PLoS One. 2017.12(6), Tan et al PLoS One. 2016. 11(10) and WO 2011/098772. Particular suitable Catcher/Tag ligation pairs are the peptide tag and corresponding peptide catcher pairs described in WO 2011/098772, the Spy0128 Catcher/Tag pairs described in Zakeri & Howarth 2010 J Am Chem Soc 132(13), the FbaB Spy Catcher/Tag pair described in Zakeri et al Proc Natl Acad Sci USA. 2012. 109(12), and the Sdy Catcher/Tag pair derived from Fibronectin binding protein (UniProtKb Q53971) described in Tan et al. (2016) supra. Preferably the Catcher/Tag ligation pair is a SpyCatcher/SpyTag pair as described in Zackeri et al. (2012) supra, a SdyCatcher/SdyTag pair described in Tan et al. (2016) supra, or a SnoopCatcher/SnoopTag pair as described in Veggiani et al. Proc Natl Acad Sci USA 2016, 113(5):1202-7, more preferably the SpyCatcher/SpyTag pair (Zackeri et al. (2012) supra) or the SnoopCatcher/SnoopTag pair (Veggiani et al. (2016) supra).

The Spy protein ligation system is based on a domain of fibronectin binding protein FbaB of *Streptococcus pyogenes* in which an intramolecular isopeptide bond is formed between an adjacent lysine and aspartic acid residue through an autocatalytic mechanism (Zackeri et al (2012) supra). By splitting this domain into a 13 amino acid peptide, termed SpyTag, and its remaining 138 amino acid fragment, termed SpyCatcher, a Catcher/Tag pair was created for intermolecular coupling. Fused to different proteins the SpyTag and SpyCatcher reconstitute the domain upon mixing and form a stable intermolecular covalent bond under a wide range of conditions (pH, temperature, buffer). In a similar way a peptide tag and corresponding binding partner was developed based on the *Streptococcus pneumoniae* adhesin RrgA, providing a SnoopTag and SnoopCatcher ligation pair (Veggiani et al. 2016 supra).

The SpyCatcher/SpyTag conjugation system was further adapted into a tripartite system by splitting up the SpyCatcher into the SpyLigase domain and the 10 amino acid peptide KTag (Freirer et al. 2014 Proc Natl Acad Sci USA 111(13): E1176-81). The SpyTag and the KTag each contain one of the cognate amino acid residues (Asp and Lys, respectively) that form the isopeptide bond, while the catalytic activity is included in the SpyLigase domain that can be added separately. Preferred Catcher moieties are the SpyCatcher, KTag and Snoop Catcher moieties. Preferred Tag moieties are the SpyTag and SnoopTag.

Suitable autotransporter proteins that can be used to obtain the bacterial cells and OMVs of the present invention are proteins that belong to the pfam autotransporter family ('Autotransporter' PF03797) and which are known or predicted to form a beta stem motif. The BETAWRAPPRO method for sequence analysis can be used to predict if the passenger domain of an autotransporter will form a beta stem motif (Junker et al. 2006 Proc Natl Acad Sci USA 103(13): 4918-23). It was found that an autotransporter protein can be used for improved display of heterologous molecules on the surface of bacterial cells and OMVs. Care should be taken that the beta stem forming sequence of the passenger domain of the autotransporter is essentially intact. The native passenger domain of an autotransporter protein can be considered as comprising several sections of beta stem forming sequence, linked together by non-beta stem forming sequences. The non-beta stem forming sequences are suitable sites for insertion of one or more heterologous sequences, Thus, a Tag- or Catcher moiety can be placed between two parts of beta stem forming sequence. The Tag- or Catcher moiety can also be fused to the N-terminus of the passenger domain.

Whereas the beta stem forming sequence is essential for optimal expression and display, the side domains of the passenger domain of the autotransporter protein are suitable sites for insertion of a moiety of a Catcher/Tag pair. The Catcher- or Tag moiety can be inserted to replace a part of or the whole side domain, or the moiety can be fused to a side domain. By fusing, i.e. inserting, replacing or partly replacing the Catcher- or Tag moiety to one or more side domains of the passenger domain of the autotransporter, while keeping the beta stem structure intact, an efficient display system for the improved display of heterologous molecules on the bacterial cell and OMV was achieved. Autotransporter proteins that are suitable for producing a fusion product with the at least one Catcher- or Tag moiety are the autotransporter proteins such as described in WO 2012/048199, Jong et al. (2012) supra, Jong et al (2014) supra and Daleke-Schermerhorn et al. (2014 supra, wherein the cleavage site has been disrupted to create display of the passenger domain with the at least one Tag- or Catcher moiety on the surface of the bacterial cell or OMV. The replacement methods described in these references can be used to produce the autotransporter fusion proteins described herein.

Suitable methods for detecting beta stem forming sequence and side domains of passenger domains of autotransporters include biophysical methods such as X-ray crystallography and bioinformatics software such as structure prediction tools. X-ray crystallography is a standard procedure that is highly efficient and automated, and familiar to a person skilled in the art. Examples of high resolution structures of passenger domains and suitable methods for determination of structures of the passenger domain of autotransporters are e.g. found in Otto et al (2005), supra; Emsley et al (1996) Nature 381:90-92; Johnson et al (2009) J Mol Biol 389(3):559-74; Khan et al. 2011 J Mol Biol 413(5):985-1000; and Domingo Meza-Aguilar et al. 2014 Biochem Biophys Res Commun 445(2):439-44). An example of a bioinformatics method that is suitable for determining beta stem structure is the M4T homology modeling method (Rykunov et al 15 2009 J Struct Funct Genomics 10: 95-99). Where a three-dimensional model of the protein is used for the identification of beta stem domains and side domains, it is suitable that the model obtained has a resolution of better than 4 angstrom. Side domains will then be visible as domains that protrude from the beta stem. By observation of the structure of the passenger domains of autotransporters, it can be seen that parts of the sequence are not part of the beta stem but form domains that protrude from the beta stem. Methods such as those described above can be used for determining which domains or amino acids of the native passenger domains are suitable for insertion of heterologous peptide fragment and which should be kept essentially intact. In the fusion protein according to the disclosure, the beta stem forming sequence from the autotransporter passenger domain is essentially intact. Thus, as little as possible of the beta stem forming sequence should be removed. Predicted domain borders are of help to determine where Tag- or Catcher moiety can be inserted.

Preferably the autotransporter protein is a serine protease autotransporter of the *Enterobacteriacea* (SPATE') such as described in Yihfen et al. 2008 Trends in Microbiol 16(8): 370-9. The serine protease autotransporters of Enterobacteriaceae represent a group of large-sized, multi-domain exoproteins found only in pathogenic enteric bacteria. SPATEs form a family of autotransporters linked by commonality in their structural architecture and mechanism of secretion (Yen et al 2008 Trends Microbiol 16(8):370-9). These proteins contain a highly conserved channel-forming C-terminal domain, which facilitates secretion of the passenger domain to the cell surface. The C-terminal domain also mediates autoproteolytic cleavage, which releases the passenger from the bacterial cell. The passenger folds into a characteristic parallel β-helical stalk-like structure (beta stem structure) with an N-terminal globular domain that performs serine proteolytic activity. SPATEs represent a typical example of conventional autotransporters: the beta-domain of each SPATE folds into a single beta stem structure formed by 277 amino acids. Once on the cell surface, the passenger of a SPATE is cleaved from the translocator and released into the extracellular environment. Cleavage occurs in a conserved site located between two consecutive asparagine residues in the linker region joining the passenger and the translocator domains. An aspartate located inside the pore of the translocator domain performs the cleavage task. Following secretion and folding, the mature SPATE passenger becomes functionally active. Although the secreted passenger domain of each SPATE exhibits divergent pathogenic function, the SPATE passenger domains display considerable sequence homology among them, resulting in a similar architecture that is rich in beta-strands, and are predicted to fold into a parallel beta-helical structure. This fold was recently verified by the crystal structure of the SPATE protein Hemoglobin protease Hbp from *E. coli* (Otto et al 2005 supra) and the crystal structures of the SPATEs EspP (Khan et al. 2011 supra) and Pet (Domingo Meza-Aguilar et al. 2014 supra).

In a preferred embodiment the autotransporter that is used to produce an autotransporter fusion protein for display on the surface is a SPATE protein, more preferably a SPATE protein selected from the group of hemoglobin-binding protease (Hbp; SwissProt O88093), extracellular serine protease (EspC) and temperature-sensitive hemagglutinin (Tsh; SwissProt Q47692) from *Escherichia coli*, wherein the cleavage site has been disrupted to prevent secretion of the SPATE. Preferably, the cleavage site is disrupted by substituting the conserved consecutive Asn residues with two other amino acid residues, e.g. a Ser and a Gly residue. The sequence of Tsh is highly homologous to that of Hbp, differing only in amino acid residue from Hbp.

In en even more preferred embodiment the SPATE protein is Hemoglobin protease (Hbp). The Hbp protein which is suitable for use in the present invention is preferably derived from *Escherichia* bacteria, more preferably *E. coli*. Preferably a Hbp protein comprising the amino acid sequence depicted in SEQ ID NO:1 is used to make the Hbp fusion proteins of the invention. Suitable Hbp protein constructs that can be used as carrier have a disrupted cleavage site between the β-domain and the passenger domain, which prevents secretion of the passenger domain into the extracellular space, such as the Hbp proteins that have been described in Jong et al (2012) supra, Jong et al. (2014) supra, WO2012/041899 and US2017/0258885. The Hbp protein preferably comprises the amino acid sequence of SEQ ID NO:2 (HbpD), which corresponds to native Hbp wherein the cleavage site between the β-domain and the passenger domain has been disrupted by substituting the conserved Asn1100 and Asn1101 residues with a Ser and Gly residue, respectively. Also encompassed as Hbp protein that is suitable for use in the present invention are Hbp proteins comprising an amino acid sequence that is homologous to SEQ ID NO:2. Homologous sequences are amino acid sequences that have at least 80%, preferably 85%, more preferably 90%, even more preferably 95%, most preferably 97% sequence identity with SEQ ID NO:2. Sequence homology can be readily determined using publicly available software such as BLAST. The Hbp fusion protein according to the invention comprises the at least one Tag- or Catcher moiety in the N-terminus of the Hbp, preferably at the location of one of the side domains of the passenger domain. The Hbp protein comprises at least five side domains located at aa positions d1: 53-308 (domain d1), 533-608 (domain d2), 657-697 (domain d3), 735-766 (domain d4) and 898-992 (domain d5) of HbpD (SEQ ID NO:2). The Hbp carrier comprising at least one moiety of a Catcher/Tag pair can be obtained by fusion to at least one side domain or by replacing in whole or in part at least one side domain in the passenger domain with a Tag or Catcher moiety. Each of the side domains 1, 2, 3, 4 or 5 of the wild-type Hbp (see FIG. 1A) or other loops projecting from the beta-stem domain may be used for inserting one of the moieties of a Catcher/Tag pair. Preferably a moiety of a Catcher/Tag pair is inserted in or is replacing in whole or in part side domain 1, side domain 2 or side domain 4, more preferably side domain 1. The Hbp fusion protein may comprise at least two, preferably three or more Tag or Catcher moieties. When the Hbp fusion protein comprises two or more Tag- or Catcher moieties, the moieties can be part of the same or orthogonal (i.e. mutually unreactive or non-cognate) Catcher/Tag ligation pairs. In a preferred embodiment, the Tag or Catcher moieties comprised in the Hbp fusion protein comprising two or more Tag or Catcher moieties, correspond to Catcher/Tag pairs that are orthogonal, meaning that they are mutually unreactive, i.e. the Tag- and Catcher moiety of the first pair cannot react with either of the Tag- or Catcher moiety of the second pair. Inserting two or more Catcher- or Tag moieties in the same Hbp carrier will increase flexibility and valency of the Hbp display system. Preferably, the Hbp fusion protein comprises an amino acid sequence selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Also encompassed as Hbp fusion protein according to the invention are Hbp fusion proteins that comprise an amino acid sequence that is homologous to one of the sequences selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Homologous sequences in this context are amino acid sequences that have at least 80% sequence identity with their reference amino acid sequence, more preferably 85%, 90%, 95%, 96%, 97%, 98%, or 99%, provided that the beta-stem domain in the Hbp fusion protein remains essentially intact.

An autotransporter fusion protein comprising at least one Catcher- or Tag moiety of a Catcher/Tag ligation pair can be obtained by genetically fusing the sequence of a moiety of a Catcher/Tag ligation pair to the autotransporter protein using standard molecular biology techniques involving restriction enzymes, DNA ligases, PCR, oligonucleotide synthesis, DNA purification, and other methods well known to a person skilled in the art such as Sambrook, J., E. F. Fritsch, and T. Maniatis. 1989. Molecular Cloning: A Laboratory Manual. Cold Spring Harbor Laboratory Press, Cold Spring Harbor, N.Y.. Using the replacement technology and methods described in Jong et al (2012) supra, Jong et al. (2014) supra, WO2012/041899 and US2017/0258885, an autotransporter fusion protein can be designed comprising at least one moiety of a Catcher/Tag pair. Using these techniques, a nucleic acid comprising the sequence encoding the Hbp carrier according to the invention can be obtained wherein at least one sequence encoding a moiety of a Catcher/Tag pair is inserted into or replacing a side domain of the passenger domain of the autotransporter. By inserting the nucleic acid sequence encoding the autotransporter carrier comprising at least one moiety of a Catcher/Tag pair into an expression vector for bacterial expression, wherein the expression vector carries a promoter that enables expression of said nucleic acid sequence, and by transforming a Gram negative bacteria with said expression vector, an autotransporter fusion protein can be expressed in and subsequently displayed on the surface of Gram negative bacterial cells.

Gram negative bacteria, which are suitable for use according to the invention can be any Gram negative bacterial cell that is capable of expressing and displaying an autotransporter fusion protein comprising at least one moiety of a Catcher/Tag ligation pair on the outer surface. Preferred bacteria are *Escherichia* or *Salmonella* bacteria. More preferably, the Gram-negative bacterial cell is a *Salmonella* spp., e.g. the subspecies *S. enterica* subsp *enterica*, more preferably the serovar *Typhimurium*, even more preferably *S. Typhimurium* strain SL3261. Particularly preferred is *S. Typhimurium* strain SL3261 which is TolRA deficient (ΔtolRA derivative of *S. Typhimurium* strain SL3261). In a preferred embodiment the bacteria are live, attenuated bacteria. In a further embodiment, the bacteria are live, attenuated auxotrophic bacteria, more preferably live, attenuated, auxotrophic *S. Typhymurium* bacteria. The bacteria of the present invention can be obtained by transforming the bacteria with said nucleic acid molecule that encodes an autotransporter fusion protein comprising at least one amino acid sequence of a Catcher- or Tag moiety incorporated therein. The Gram-negative bacterial cells preferably display on their surface an autotransporter fusion protein as described herein, more preferably a SPATE fusion protein, even more preferably a Hbp fusion protein. In a particular preferred embodiment the displayed Hbp fusion protein comprises an amino acid sequence selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Also encompassed Gram-negative bacterial cells according to the invention are Gram-negative bacterial cells which display a Hbp fusion protein that comprises an amino acid sequence that is homologous to one of the sequences selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Homologous sequences in this context are amino acid sequences that have at least 80% sequence identity with their reference amino acid sequence, more preferably 85%, 90%, 95%, 96%, 97%, 98%, or 99%, provided that the beta-stem domain in the Hbp fusion protein remains essentially intact.

Besides live attenuated Gram-negative bacterial cells, the present invention also provides for OMVs displaying on their surface an autotransporter fusion protein as described herein, which are suitable for Catcher/Tag coupling. All Gram-negative bacteria produce OMVs that shed from the outer membrane during growth. OMVs are spherical nanostructures (30-200 nm diameter) composed of phospholipids, LPS and proteins derived from the periplasm and outer membrane (Schwechheimer et al. 2015 Nature reviews Microbiol 13(10): 605-19).

OMVs are an attractive vaccine formulation because, though non-replicating and safe to use, they have intrinsic immunostimulatory properties that are a facsimile of their live parental cells (Alaniz et al. 2007) J Immunol 179(11): 7692-701; Gnopo et al. 2017 Adv Drug Deliv Rev). For this reason, OMVs attract increasing interest in the development of vaccines and therapeutic agents. Compared to live attenuated vaccines OMVs raise less safety concerns because of their non-replicative nature. Yet, the intrinsic constituents of OMVs such as outer membrane polypeptides (OMPs), lipopolysaccharides (LPS) and other pathogen associated molecular patterns (PAMPs) activate innate as well as adaptive immune responses leading to the induction of adaptive immunity. This makes the addition of adjuvant unnecessary, which is an important advantage for vaccine approval. Thus OMVs combine antigen presentation and intrinsic adjuvant activity, which in combination with their non-replicative nature makes them extremely suitable and promising candidates for vaccines and therapeutic agents.

Suitable OMVs which can be used according to the invention are preferably derived from Gram-negative bacterial cells as described herein. Preferably the OMVs are derived from Gram-negative bacterial cells as described herein, which are hypervesiculating. These cells have been modified to shed large amounts of OMVs. More preferably, the OMVs are derived from *Salmonella* spp., e.g. the subspecies *S. enterica* subsp *enterica*, more preferably the serovar *Typhimurium*, even more preferably *S. Typhimurium* strain SL3261. In a preferred embodiment, the OMVs are derived from a hypervesiculating derivative of *S. Typhimurium* strain SL3261, in particular a TolRA deficient derivative wherein the tolRA genes are deleted or inactivated (ΔtolRA derivative). This strain is particularly interesting in that it is capable of shedding high amounts of OMVs displaying on their surface an autotransporter fusion protein comprising at least one moiety of a Catcher/Tag ligation pair. The OMVs preferably display on their surface an autotransporter fusion protein as described herein, more preferably a SPATE fusion protein, even more preferably a Hbp fusion protein. In a particular preferred embodiment the OMVs display on their surface a Hbp fusion protein, which comprises an amino acid sequence selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Also encompassed as OMVs according to the invention are OMVs that display on their surface a Hbp fusion proteins that comprise an amino acid sequence that is homologous to one of the sequences selected from the group of SEQ ID NO: 4, SEQ ID NO: 5, SEQ ID NO:6, SEQ ID NO:7, SEQ ID NO:8, SEQ ID NO: 9, SEQ ID NO:10, SEQ ID NO: 11, SEQ ID NO:12 and SEQ ID NO:13. Homologous sequences in this context are amino acid sequences that have at least 80% sequence identity with their reference amino acid sequence, more preferably 85%, 90%, 95%, 96%, 97%, 98%, or 99%, provided that the beta-stem domain in the Hbp fusion protein remains essentially intact. Methods for OMV production and isolation are known in the art and have been described in e.g. Gnopo et (2017 supra, Chen et al (2010) PNAS 107:3099-3104; Bernadac et al (1998) J Bacteriol 180: 4872-4878; Kesty and Kuehn (2004) J Biol Chem 279: 2069-2076; 10 Kolling and Matthews (1999) App Env Microbiol 65:1843-1848; Kitagawa et al (2010) J Bacteriol 192:5645-5656). The OMVs of the present invention can be prepared from the Gram-negative bacterial cells described herein using any of these methods.

Heterologous molecules that can be coupled via isopeptide bonding technology to Gram-negative bacterial cells or OMVs displaying on their surface an AT fusion protein as described herein can be any molecule that can be produced as a Tag- or Catcher fusion product. Preferably the heterologous molecules are selected from the group consisting of antigens, lectins, adhesins and affinity molecules.

Suitable antigens are any antigen that can be produced as a Tag- or Catcher fusion construct, including proteins that have been modified such as glycoproteins, lipoproteins and the like, oligomeric proteins, and antigenic fragments thereof. Suitable antigens also comprise oligosaccharide that can be produced in fusion with a Tag- or Catcher-moiety.

Preferred antigens that can be coupled via isopeptide bonding technology according to the invention are antigens from infectious microorganisms, including but not limited to Streptococcal antigenic proteins, Mycobacterial antigenic proteins, Chlamydial antigenic proteins, Influenza antigenic proteins, and the like as described in Jong et al (2012) supra, Jong et al. (2014) supra, Daleke-Schermerhorn et al. (2014)

supra, WO2012/041899 and US2017/0258885. Preferably the antigen is a Pneumococcal antigen from *Streptococcal pneumoniae*, more preferably pneumococcal surface protein A (PspA) or SP1690. Even more preferably the antigen is PspAα', which is the N-terminal domain of PspA, or full-length SP1690 lacking the N-terminal Cys residue. In a specific embodiment, the antigen is PspAα comprising the amino acid sequence corresponding to amino acid residues 112-324 of SEQ ID NO:17 (SpC-PspAα-SnT). In another specific embodiment the SP1690 antigen comprises the amino acid sequence corresponding to amino acid residues 112-533 of Seq ID NO:24 (SpC-SP1690-SnT) or amino acid residues 135-556 of SEQ ID NO:25 (SnC-SP1690-SpT).

The present invention also provides for the ligation of multiple antigens or antigenic fragments to a Hbp fusion protein as described herein that is displayed on the surface of Gram-negative bacteria and OMVs. The ligation of multiple antigens can be obtained by using produced fusion constructs consisting of a string of multiple antigens fused to each other, wherein the construct is attached to a Catcher- or Tag moiety of a Catcher/Tag ligation pair. Thus, in a further embodiment, the Gram-negative bacterial cells and OMVs as described herein display on their surface an autotransporter fusion protein covalently linked to a string of multiple antigens.

The string of multiple antigens can be obtained by genetic fusion of the multiple antigens to each other and to a Catcher- or Tag moiety of a Catcher/Tag ligation pair. The string of multiple antigens can be a repetition of the same antigen, or may comprise different antigens or antigenic fragments thereof, provided that the antigens or antigenic fragments thereof are compatible. Compatible antigens or fragments are understood to be antigens or antigenic fragments that do not interfere with the immune response induced by each antigen or fragment. Preferably the string of multiple antigens is a fusion protein comprising PspAα and SP1690, fused to a Catcher moiety at one end and a Tag moiety at the other end, wherein the respective Catcher- and Tag moiety are derived from orthogonal Catcher/Tag pairs to prevent circularization. Preferably the PspAα-SP1690 fusion protein is fused to a Catcher moiety at the N-terminus and a Tag moiety at the C-terminus, more preferably to a SpyCatcher moiety at the N-terminus, and a SnoopTag at the C-terminus. More preferably the string of multiple antigens has the amino acid sequence of SEQ ID NO:18 (SpC-PspAα-SP1690-SnT).

In an alternative embodiment, a string of multiple antigens can be obtained by iterative extension of multiple different antigens by using recombinant antigens, wherein each antigen is flanked at the C- and N-terminal end with a moiety of a Catcher/Tag ligation pair. Care should be taken to use moieties of orthogonal Catcher/Tag pairs for the N- and C-terminal end of each the antigen respectively, to prevent circularization of the C-terminal end to the N-terminal end, thereby creating a circular antigen. Preferably, the antigens are flanked by a Catcher moiety of Catcher/Tag pair 1, and a Tag moiety of Catcher/Tag pair 2, or a Tag-moiety of Catcher/Tag pair 1 and a Catcher moiety of Catcher/Tag pair 2, wherein pair 1 and pair 2 are orthogonal. More preferably each antigen is flanked by a SnoopCatcher- and SpyTag moiety, or a SnoopTag- and SpyCatcher moiety respectively. By iterative extension on the displayed Hbp fusion protein comprising the corresponding Catcher or Tag moiety, a string of compatible antigen modules can be stacked on the Hbp fusion protein. Ligation of multiple antigens via isopeptide bonding technology can be carried out as described in e.g. WO 2016/193746. Using these methods, a SpyCatcher-PspAα-SnoopTag fusion protein could be successfully ligated to a SnoopCatcher-SP1690-SpyTag fusion protein, thereby creating a string of multiple antigens suitable for ligation to cell surface expressed Hbp fusion protein.

Suitable lectins which can be coupled via isopeptide bonding technology to Gram-negative bacterial cells or OMVs displaying on their surface an autotransporter fusion protein as described herein can be HIV-1 envelope gp41 (Alfsen & Bomsel; J Biol Chem. 2002 Jul. 12;277(28): 25649-59), Ulex europaeus 1 (Giannasca et al; Am. J. Physiol., 267 (1994), pp. G1108-G1121), Wheat germ agglutinate (Ertl et al; J. Drug Targeting, 8 (2000), pp. 173-184), Tomato lectin (Hussain et al; Pharm. Res., 14 (1997), pp. 613-618), peanut agglutinin, asparagus pea lectin (Gupta et al; Int. J. Pharm., 318 (2006), pp. 163-173), *Ateuria aurantia* lectin (Roth-Walter et al; J. Allergy Clin. Immunol., 114 (2004), pp. 1362-1368), C-type lectin receptors, DC-SIGN, CD23, CLEC4G, DEC205 (Apostolopoulos et al; J Drug Deliv. 2013;2013:869718).

Suitable adhesins or affinity molecules which can be coupled via isopeptide bonding technology to Gram-negative bacterial cells or OMVs displaying on their surface a Hbp fusion protein as described herein can be any adhesin or affinity molecule that is capable of being attached to a moiety of a Catcher/Tag ligation pair. Suitable adhesin include bacterial adhesins such as FimH, PapG, PrsG, SfaS, FocH, FimD, MrpH, FaeG, FanC, CfaB, MrkD, pilin protein, PilC, CsgA, Afa-IE, DraA, NfaA, AIDA-I (Klemm & Schembri, Int J Med Microbiol. 2000 March;290(1):27-35), and also Claudin-4 (Rajapaksa et al; *J Biol Chem* (2010) 285(31):23739-46), Invasin (Marra & Isburg; Infect. Immun., 65 (1997), pp. 3412-3421), Invasin-C192 (Hussain & Florence; Pharm. Res., 15 (1998), pp. 153-156), Long polar fimbria (Baumler et al; Proc. Natl. Acad. Sci. USA, 93 (1996), pp. 279-283), viral haemagglutinin al protein (Rubas et al; J. Microencapsul., 7 (1990), pp. 385-395), or affinity molecules are antibodies, nanobodies, and the like. Other suitable affinity molecules are immunoglobulin-binding bacterial proteins such as *Streptococcal* Protein A, Protein G or Peptostreptococcus protein L, or immunoglobulin-binding fragments of these proteins. Preferably, the affinity molecule is protein A/G, which is a recombinant fusion protein that combines IgG binding domains of *Streptococcal aureus* Protein A and G with a mass of 50 kDa.

The heterologous molecules of the invention can be coupled to the autotransporter fusion protein displayed on the surface of the Gram-negative bacterial cells or OMVs according to the invention by contacting the bacterial cell or the OMV with a heterologous molecule comprising the other binding moiety of said Catcher/Tag ligation pair to allow the formation of an isopeptide bond between the autotransporter fusion protein and the heterologous molecule. Thus, in a further aspect, the invention provides for a method to prepare Gram-negative bacterial cells or Outer Membrane Vesicles (OMVs) which display on their outer surface an autotransporter (AT) fusion protein covalently coupled via an isopeptide bond to a heterologous molecule, said method comprising;

providing Gram-negative bacterial cells or Outer Membrane Vesicles (OMVs) which display on their outer surface an autotransporter (AT) fusion protein comprising at least one moiety of a Catcher/Tag ligation pair, contacting the bacterial cells or the OMVs with a heterologous molecule comprising the other binding moiety of said Catcher/Tag ligation pair under conditions which allow the formation of an isopeptide bond between the autotransporter fusion protein and the heterologous molecule, and
recovering the bacterial cells or the OMVs.

To allow the formation of an isopeptide bond, the bacterial cells or OMVs can be suspended in isotonic buffers well known in the art, for example phosphate buffered saline (PBS) (pH 7.4), optionally supplemented with a cryopreservative such as glycerol (10-15%). Cell or OMV suspensions can be contacted with the heterologous molecules by mixing the cell or OMV suspensions with preparations of heterologous molecules solubilized in an isotonic buffer such as PBS, possibly supplemented with glycerol (10-15%), and incubated at temperatures ranging from 4° C. to 37° C., preferably 4° C. A molar excess of heterologous molecules over Hbp-fusion protein may be used to achieve optimal decoration of cells or OMVs. Incubation times may be as short as 1 hour but preferably are longer, such as overnight to allow the formation of the isopeptide bond. Following incubation, the cells and OMVs can be recovered by separating the cells and OMVs from the incubation mixture using suitable separation techniques known in the art. The cell and OMV mixtures may be subjected low-speed (e.g. 14,000×g) or high-speed (e.g. 208,000×g) centrifugation, respectively, to separate the Cells and OMVs from the soluble mixture content. To remove non-covalently associated heterologous protein material, Cells and OMVs may be resuspended in fresh PBS, or PBS supplemented with 0.5M NaCl to break non-covalent electrostatic interactions, before being reisolated with low-speed or high-speed centrifugation.

Covalently conjugating the heterologous molecules according to the invention via Catcher/Tag protein ligation to an autotransporter fusion protein already expressed on the surface of Gram-negative bacterial cells or OMVs allows development of a display platform by which attenuated bacterial cells or derived Outer Membrane Vesicles (OMVs) can be decorated with multiple heterologous antigens of choice for optimal stimulation of the immune system or with lectins, adhesins or affinity molecules of choice for optimal targeting to certain tissues or immune cells of interest. Thus, in a further embodiment the invention provides for a pharmaceutical composition comprising the Gram-negative bacterial cells or OMVs that display on their surface an autotransporter fusion protein covalently coupled to a heterologous molecule via isopeptide bond formation, wherein the autotransporter protein comprises at least one moiety of a Catcher/Tag ligation pair, and the heterologous molecule comprises the other moiety of said Catcher/Tag ligation pair.

If the heterologous molecule is an antigen, the Gram-negative bacterial cells and OMVs described herein can be used as candidates for a vaccine. The present invention provides in particular for a vaccine comprising Gram-negative bacterial cells or OMVs that display on their surface a SPATE fusion protein, more particularly a Haemoglobin protease (Hbp) fusion protein, which is covalently coupled to a heterologous antigen via isopeptide bond formation, wherein the SPATE fusion protein, in particular the Hbp fusion protein comprises at least one moiety of a Catcher/Tag ligation pair, and the heterologous molecule comprises the other moiety of said Catcher/Tag ligation pair.

If the heterologous molecule is a lectin, adhesin or affinity molecule, such as an antibody. nanobody or the protein A/G fusion protein and the like, the Gram-negative bacterial cells and OMVs described herein can be used as a drug delivery system for optimal targeting of antigens or therapeutic agents to certain tissues or immune cells of interest. Of particular interest is the use of the bacterial cells and OMVs described herein for targeting of a therapeutic agent. Thus in yet another particular embodiment the present invention provides for a drug delivery system comprising Gram-negative bacterial cells or OMVs that display on their surface a SPATE fusion protein, more particularly a Haemoglobin protease (Hbp) fusion protein coupled to a heterologous adhesin or affinity molecule via isopeptide bond formation, wherein the SPATE fusion protein, in particular the Hbp fusion protein comprises at least one moiety of a Catcher/Tag ligation pair, and the heterologous adhesin or affinity molecule comprises the other moiety of said Catcher/Tag ligation pair.

It will be evident to the skilled person that the various embodiments and aspects of the invention which are described above in different paragraphs may be combined. The invention and certain embodiments are illustrated by the following examples and/or embodiments, without being limited thereto or thereby.

LEGEND OF THE FIGURES

FIG. 1. Schematic representations of the proteins used in this study. (A) Hbp fusions. Wild-type Hbp is synthesized with an N-terminal signal sequence (ss) that is cleaved off after translocation across the inner membrane. The C-terminal β-domain (black) integrates into the outer membrane facilitating translocation of the passenger domain. After translocation, autocatalytic cleavage separates the passenger and the β-domain (after Asn1100). The passenger domain contains five subdomains (white, numbered 1-5) protruding from a β-helical stem structure (dark grey). The derived HbpD(Δd1) display platform lacks subdomain 1 and the autocatalytic cleavage site (Jong et al (2012) supra). Ligation tags and catchers were integrated at the site of subdomain 1. (B) Catcher-fused model proteins. The SpyCatcher-SnoopCatcher fusion protein (SpC-SnC; SEQ ID NO: 14) was constructed by Veggiani et al. containing a 34 amino acid α-helical linker (Veggiani et al. 2016, supra). GFPnanobody-SpyCatcher (GFPnb-SpC; SEQ ID NO: 15) contains an N-terminal PeIB signal sequence (ss) (Kubala et al. 2010 Protein Science: a publication of Protein Society 19(12): 2389-401) for translocation into the periplasm and a hexa-histidine tag (H6) for metal affinity purification. (C) Catcher-fused antigens. Fusion proteins containing pneumococcal antigens PspAα and SP1690, SpyCatcher (SpC) and SnoopTag (SnT) for protein ligation, an HA tag (HA) for detection and a hexa-histidine tag (H6) for metal affinity purification (SEQ ID NO: 17; SEQ ID NO: 24, resp). (D) Cartoon of Hbp-mediated Spy-ligation to the surface of outer membrane vesicles. HbpD(Δd1)-SpT (colouring and numbering as in A) is embedded in the membrane of an outer membrane vesicle. The SpyTag has covalently bound to a chimera of the SpyCatcher and a cargo protein (model structure of SP1690) through the formation of an isopeptide bond between the SpyTag and the SpyCatcher. The protein structures were generated using PyMOL.

FIG. 2. Ligation of OMVs displaying SpyTag using increasing amounts of SpyCatcher-SnoopCatcher (SpC-SnC). (A) SDS-PAGE/Coomassie staining analysis of reaction mixes of OMVs harbouring HbpD(Δd1)-SpT and SpC-SnC incubated for 21 h at 4° C. Reactant proteins, the adduct and the major outer membrane protein OmpA are indicated on the right-hand side of the panel. The sizes of the molecular weight markers are indicated on the left side of the panel. (B) Quantification of ligation efficiency to HbpD(Δd1)-SpT. The intensities of the adduct and HbpD(Δd1)-SpT in the gel shown in panel A were determined by densitometry. The percentage of HbpD(Δd1)-SpT ligated with SpyCatcher-SnoopCatcher is plotted as a function of the molar ratio SpyCatcher-SnoopCatcher:HbpD(Δd1)-SpT.

Figure 3:
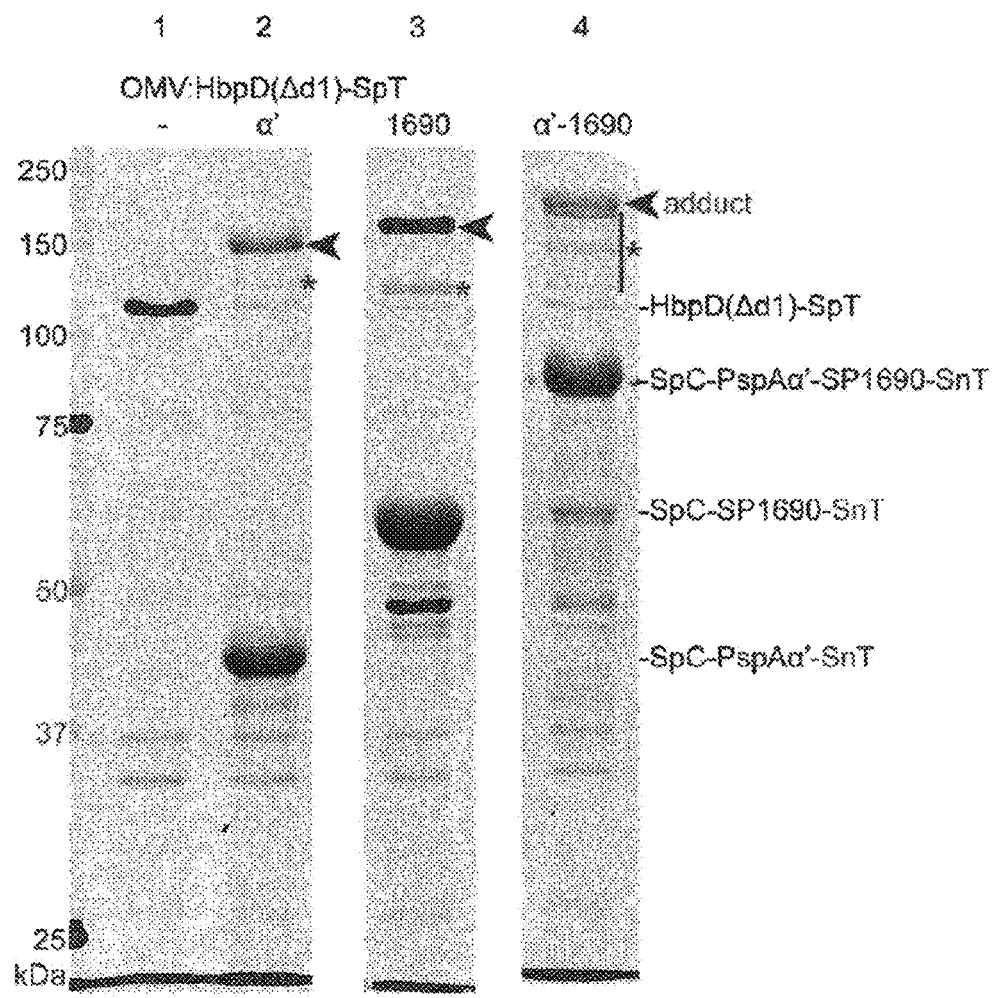

FIG. 3. Ligation to OMVs displaying various Tag and Catcher moieties. Protein ligation of soluble model proteins to OMVs harbouring HbpD(Δd1) fusions containing Spy-Catcher (SpC), SnoopCatcher (SnC), SpyTag (SpT), SnoopTag (SnT) or KTag (KT) was tested (lanes 1-6). The soluble model proteins used are indicated on the left side of the −/+matrix. Ligation of soluble protein partners independent of the OMV context was tested for comparison (lanes 7-9). Reaction mixes were incubated for 24 h at 4° C. and analysed by SDS-PAGE with Coomassie staining. Reactant proteins are indicated with dots in the image and on the right-hand side of the panel (H, HbpD(Δd1) fusion; M, SpT/SnT-MBP; G, SnT-mEGFP-SpT; CC, SpC-SnC; S, SUMO-KT; L, SpyLigase), adducts are indicated with arrowheads. The ligation efficiencies (percentage of HbpD [Δd1] or SpT/SnT-MBP converted) are shown below the lanes. The sizes of the molecular weight markers are indicated on the left side of the panel.

Figure 4:
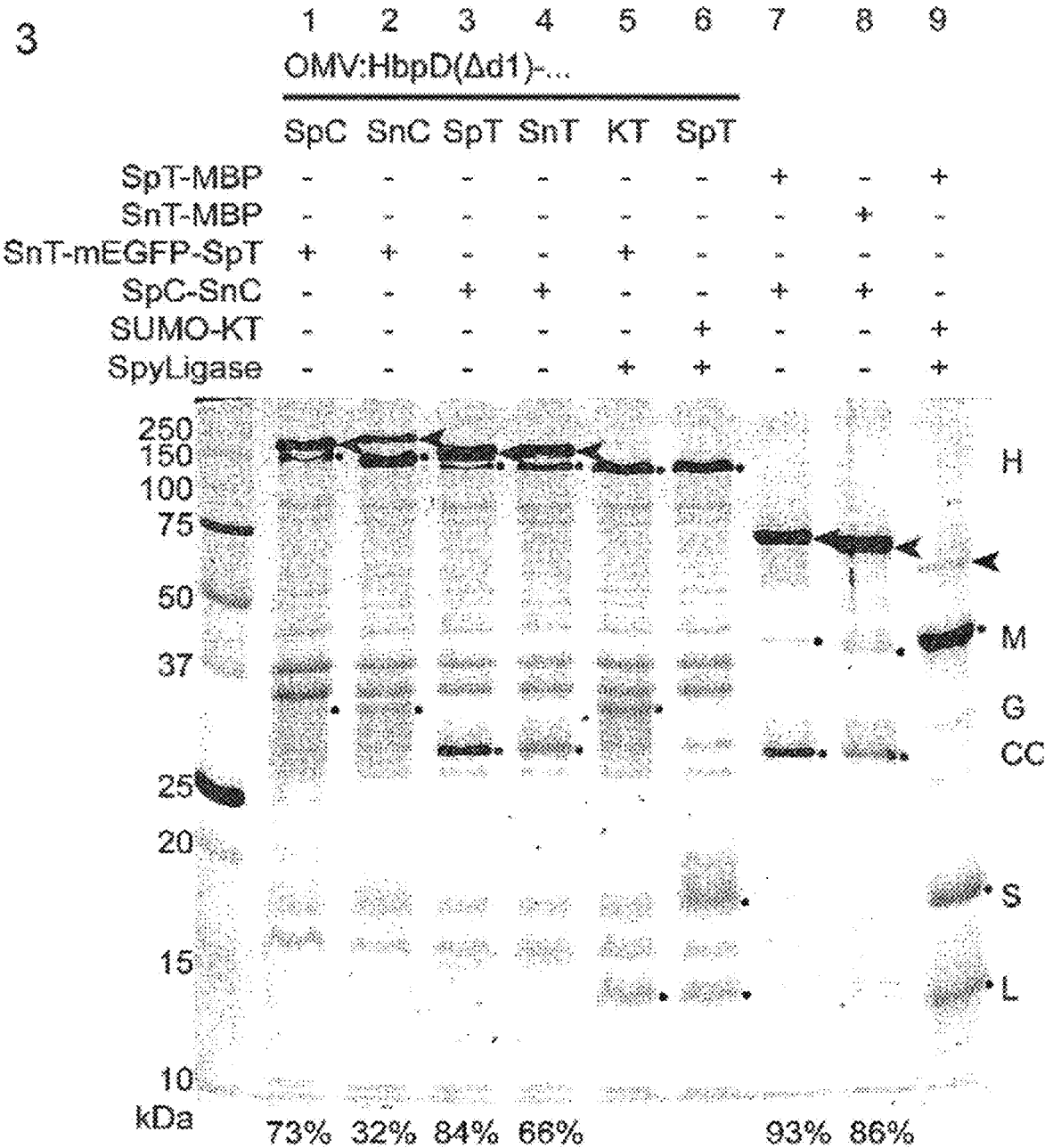

FIG. 4. Spy-ligation of pneumococcal antigens to OMVs. OMVs harbouring HbpD(Δd1)-SpT were mixed with a 5- to 10-fold molar excess of SpC-PspAα'-SnT (α'), SpC-SP1690-SnT (1690) or SpC-PspAα'-SP1690-SNT (α'-1690). The reaction mixes were incubated for 24 h at 4° C. and analysed by SDS-PAGE with Coomassie staining. Reactant proteins are indicated on the right-hand side of the panel. Adducts are indicated with arrowheads. The sizes of the molecular weight markers are indicated on the left side of the figure.

FIG. 5. Adduct extension by alternating Spy-ligation and Snoop-ligation. OMVs harbouring HbpD(Δd1)-SpT were mixed with a 1.5-fold molar excess of SpC-PspAα'-SnT and incubated for 2 h at 4° C. Subsequently a similar amount of SnC-SP1690-SpT was added. After 2 h at 4° C. again the same amount of SpC-PspAα'-SnT was added and after another 2 h at 4° C. same amount of SnC-SP1690-SpT was added. Finally, the mix was incubated for a further 15 h at 4° C. to allow completion of the reaction. The OMVs and suspending buffer were separated by centrifugation. After centrifugation the supernatant (ligation—sol) and the pellet fraction (ligation—OMV) and were analysed by SDS-PAGE with Coomassie staining (A, lanes 4 and 5 respectively). (B) Immunoblotting analysis of OMV pellet fraction after ligation and reference OMVs as described under A. Monoclonal antibodies were used for immunodetection of the HA-tag in SpC-PspAα'-SnT and of the FLAG-tag in SnC-SP1690-SpT. The adducts are indicated with arrowheads (HbpD-P, HbpD (Δd1)-SpT-SpC-PspAα'-SnT; HbpD-P-S, HbpD(Δd1)-SpT-SpC-PspAα'-SnT-SnC-SP1690-SpT; HbpD-P-S-P, HbpD (Δd1)-SpT-SpC-PspAα'-SnT-SnC-SP1690-SpT-SpC-PspAα'-SnT). The sizes of the molecular weight markers are indicated on the left side of the panels.

FIG. 6. Binding of GFP to bacterial cells upon ligation and display of a GFP nanobody. (A) S. Typhimurium cells expressing HbpD(Δd1)-SpT were incubated with GFPnb-SpC or with the unreactive GFPnb-SpC EQ for 60 min at 25° C. The cells were subsequently incubated for 5 min at 4° C. in the presence of GFP and analysed by SDS-PAGE with Coomassie staining (A). HbpD(Δd1)-SpT is indicated on the right hand side of the panel, the adduct is indicated with an arrowhead. The sizes of the molecular weight markers are indicated on the left side of the panel. (B) Fluorescence microscopy analysis of cells produced under A. Phase-contrast images (upper panels) and the corresponding fluorescence images (lower panels) are shown. The lower right panel, showing the fluorescence of the cells incubated with GFPnb-SpC EQ, is split into two parts. In the upper left half the contrast is enhanced to visualize the weak fluorescence signal (autofluorescence of the cells), while the lower right half shows the (absence of) signal at the same settings as the left panel.

FIG. 7. Analysis of OMVs and purified proteins by SDS-PAGE with Coomassie staining. A) S. Typhimurium derived OMVs harboring HbpD(Δd1)-SpyCatcher (SpC), -SnoopCatcher (SnC), -SpyTag (SpT), -SnoopTag (SnT) or Ktag (KT). The HbpD(Δd1) variants and the major outer membrane proteins OmpA, OmpC and OmpF are indicated on the right-hand side of the panel. B) SUMO-KTag (S-KT), SnoopTag-mEGFP-SpyTag (GFP), SpyLigase (SpL), Spy-Catcher-SnoopCatcher (SpC-SnC), SpyTag-MBP (SpT-MBP) and SnoopTag-MBP (SnT-MBP) as purified from E. coli BL21 (DE3) cells. The sizes of the molecular weight markers are indicated on the left side of the panels.

Figure 8:
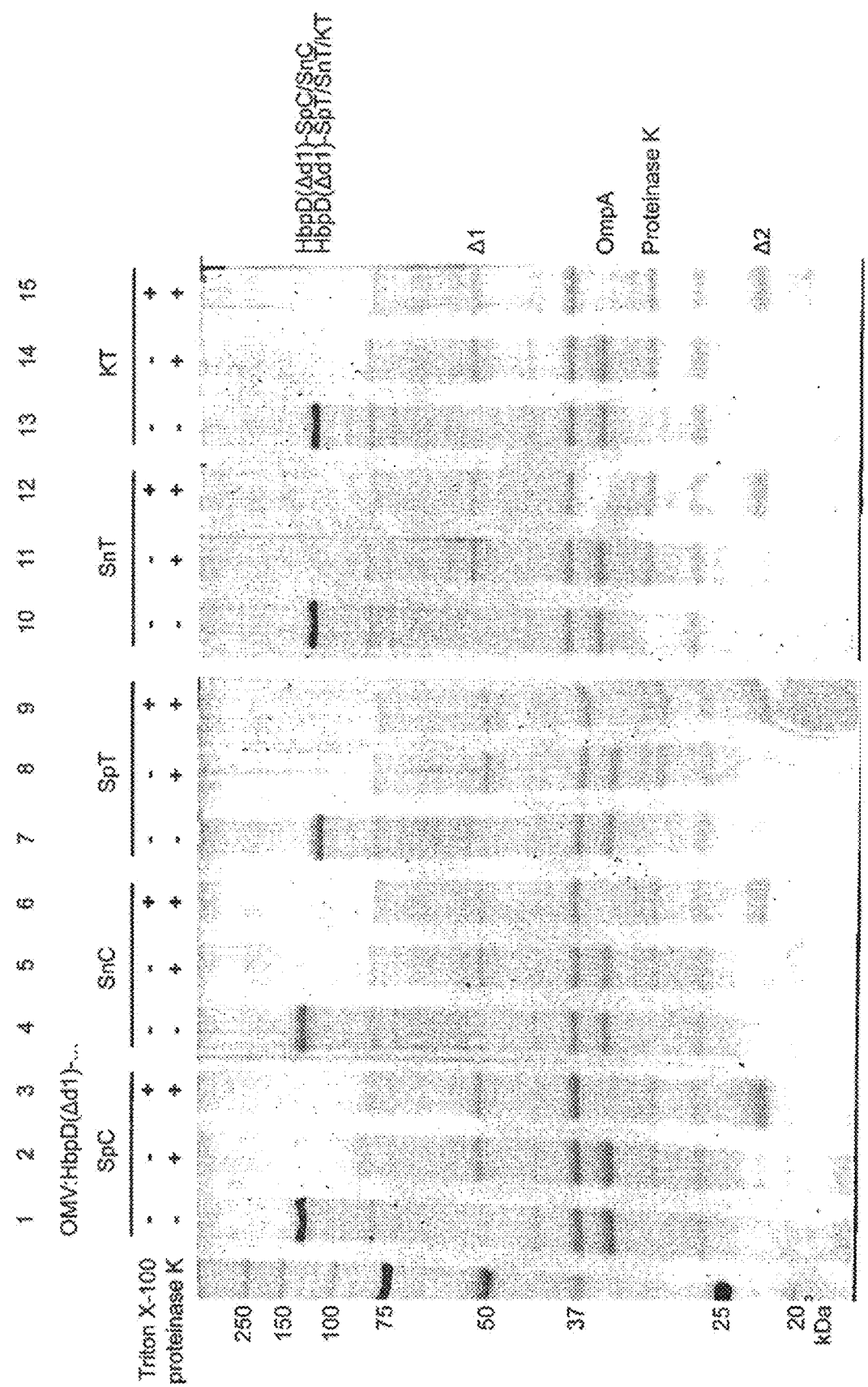

FIG. 8. Surface exposure analysis of HbpD(Δd1) fusion proteins carrying Tag and Catcher moieties. The exposure of the HbpD(Δd1) fusion proteins containing SpyCatcher (SpC), SnoopCatcher (SnC), SpyTag (SpT), SnoopTag (SnT) or KTag (KT) on the exterior surface of the OMVs was analysed by Proteinase K treatment. OMVs were diluted in 50 mM Tris.Cl, pH 7.5, 1 mM CaCl$_2$ to obtain a concentration of approximately 2 pmol of HbpD(Δd1) fusion protein per µL. The suspension was split into three aliquots. To one aliquot Triton X-100 was added to a concentration of 1% to dissolve the OMVs. After incubating all aliquots on ice for 15 min, Proteinase K was added (0.1 mg/mL final concentration) to the dissolved membranes and to one of the other two aliquots. After 30 min of incubation at 37° C., PMSF was added to 0.2 mM. The reaction was stopped by the addition of phenylmethanesulfonylfluoride (PMSF) to 0.2 mM and incubation on ice for 10 min. The samples were analysed by SDS-PAGE with Coomassie staining. Successful exposure of HbpD(Δd1) fusion proteins follows from their degradation upon treatment of OMVs with Proteinase K. A Proteinase K sensitive intracellular loop of OmpA is not accessible under these conditions, unless the OMVs were dissolved with Triton X-100 first, indicating that OMVs remained intact throughout the procedure. Full-length HbpD(Δd1) fusion proteins, OmpA and Proteinase K, as well as degradation products of the HbpD (Δd1) fusion proteins (Δ1) and of OmpA (Δ2) are indicated on the right side of the panel. The sizes of the molecular weight markers are indicated on the left.

Figure 9A:
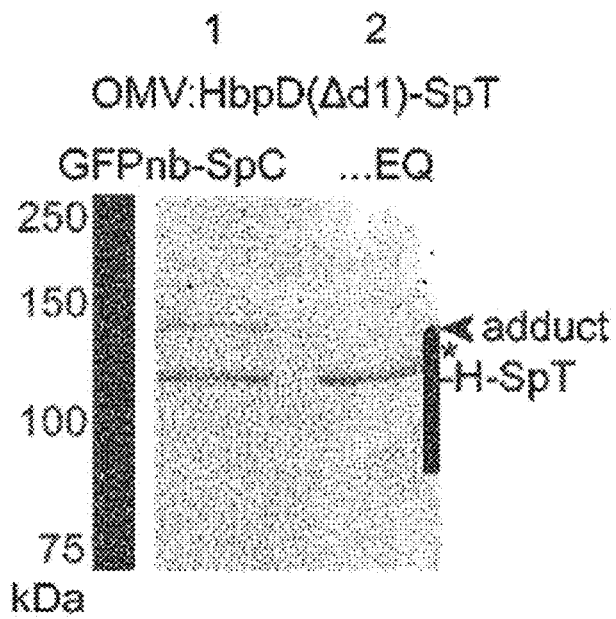
Figure 9B:
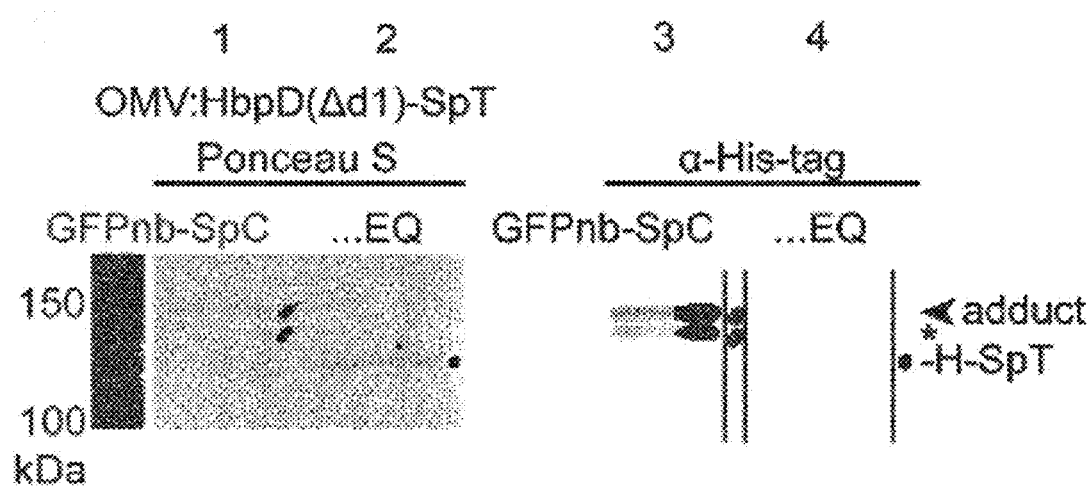

FIG. 9. Presence of the Hiss-tag in the HbpD(Δd1)-SpT-SpC-GFPnb adduct. S. Typhimurium SL3261 ΔtolRA derived OMVs harbouring HbpD(Δd1)-SpT were incubated with GFPnb-SpC or with the unreactive GFPnb-SpC EQ for 60 min at 25° C. and analysed by SDS-PAGE followed by Coomassie staining (A) or by electroblotting onto a nitrocellulose membrane, Ponceau S staining and immunodetection using anti-polyHistidine antibody (B). The C-terminal Hiss-tag of GFPnb-SpC was detected in HbpD(Δd1)-SpT-SpC-GFPnb. HbpD(Δd1)-SpT and the adduct are indicated on the right-hand side of the panels. The sizes of the molecular weight markers are indicated on the left.

Figure 10:
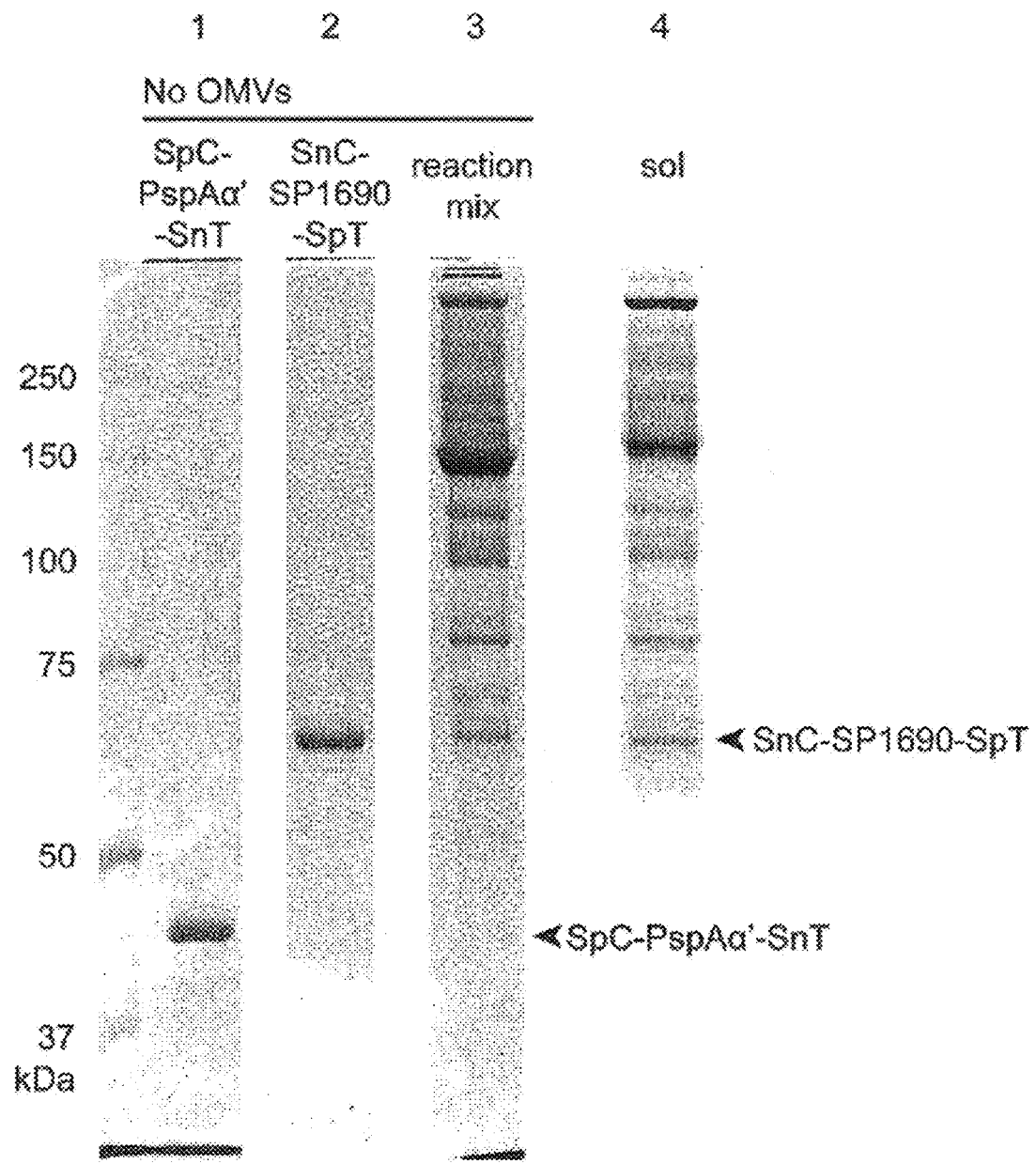

FIG. 10. Adduct extension by alternating Spy-ligation and Snoop-ligation in the absence of OMVs harboring HbpD (Δd1)-SpT. Equimolar amounts of SpC-PspAα'-SnT and SnC-SP1690-SpT were mixed and incubated for 2 hours at 25° C. The reaction mix and the purified proteins separately were analyzed by SDS-PAGE with Coomassie staining. For comparison, to show the similarity, the "sol" sample of FIG.

5A is shown in lane 4. The "sol" sample is the supernatant after centrifugation of the reaction mix containing OMVs harboring HbpD(Δd1)-SpT and SpC-PspAα'-SnT and SnC-SP1690-SpT (for details see FIG. 5A). The sizes of the molecular weight markers are indicated on the left.

FIG. 11. Coupling of rat antibody to the surface of bacterial cells or OMVs harboring HbpD(Δd1)-SpC. (A) cartoon of anti-mouse CD180 antibody comprising heavy chain Fc domains carrying a SpyTag at the extreme C-terminus. (B) SDS-PAGE analysis of cells displaying SL3261ΔtoIRA–HbpD(Δd1)-SpC before addition of aCD180-SpT (lane 1), of the crude SL3261,6,to/RA-HbpD (Δd1)-SpC+αCD180-SpT mix (lane 2) and pellet (p) and supernatant (s) after centrifugation (lanes 3 and 4) and PBS washing (lanes 5 and 6). Molecular weight markers (kDa) are indicated at the left side of the panel. (C) SDS-PAGE analysis of OMVs of SL3261 ΔtoIRA-HbpD(Δd1)-SpC before addition of αCD180-SpT of αCD180-SpT (lane 1). Samples of the crude SL3261ΔtoIRA-HbpD(Δd1)-SpC OMVs+αCD180-SpT mix (lane 2) and pellet (p) and supernatant (s) after centrifugation (lanes 3 and 4) and Salt washing (lanes 5 and 6) were analyzed in parallel by Coomassie stained SDS-PAGE. Molecular weight markers (kDa) are indicated at the left side of the panel.

Figure 12:
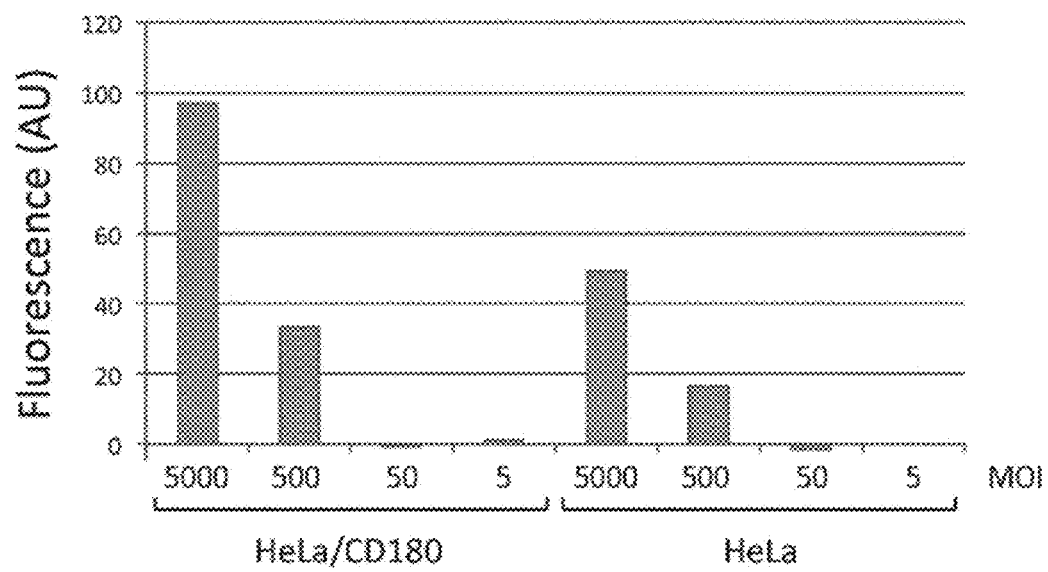

FIG. 12. Median Fluorescence intensity per HeLa cell. Mammalian HeLa cells expressing murine CD180 (Hela/CD180) were incubated with bacterial cells harboring SL3261ΔtoIRA-HbpD(Δd1)-SpC carrying covalently coupled αCD180-SpT. HeLa cells not expressing murine CD180 (HeLa) were used as a control. The HeLa cells, grown on IBIDI microscopy slides, were incubated with various loads of SL3261ΔtoIRA-HbpD(Δd1)-SpC-αCD180-SpT (multiplicity of infection, MOI: 5000, 500, 50 or 5) (2 h, 37° C., 8% $CO_2$).

Figure 13A:
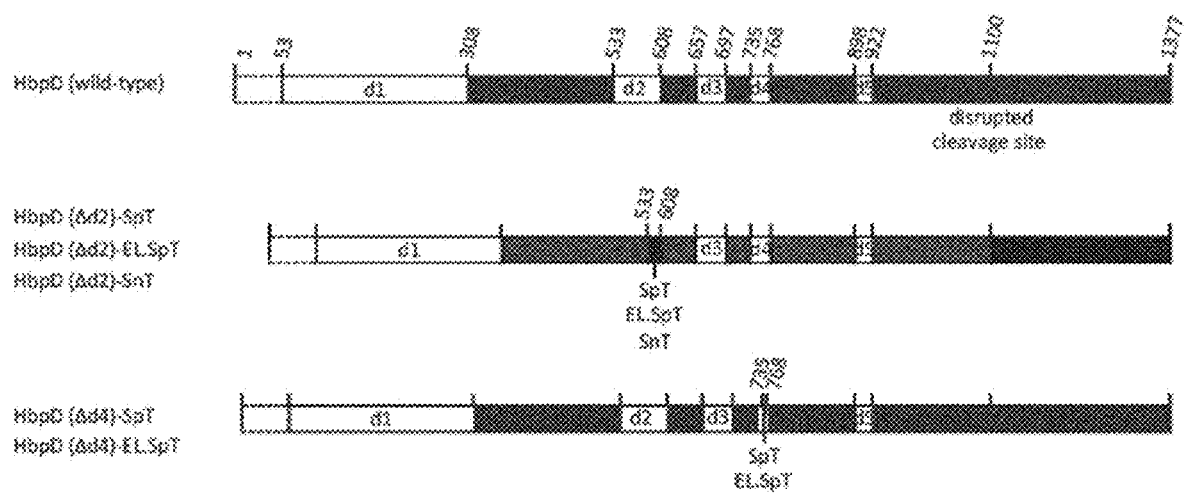

FIG. 13. Coupling of Catcher-equipped model proteins to Tag sequences inserted at position d2 and d4 of HbpD. (A) Schematic representation of wild-type Hbp lacking the autocatalytic cleavage site (HbpD) and Hbp fusion proteins carrying a SpyTag (SpT; flanked by GSGSS and GSGSG linkers), a SpyTag with extended linkers (EL.SpT; flanked by GSGSSGSASG and GEGTGGSGSG linkers), or a SnoopTag (SnT; flanked by GSGSS and GSGSG linkers) at either position d2 (HbpD(Δd2)) or d4 (HbpD(Δd4) of the passenger domain. (B) SDS-PAGE/Coomassie blue analysis of covalent coupling of the model protein comprising a SpyCatcher-SnoopCatcher fusion (SpC-SnC) to OMVs displaying the respective HbpD variants on the surface. The adduct (>) corresponds with a covalent fusion product between the (EL.)SpT-carrying HbpD-variants and the SpyCatcher containing model protein. (C) SDS-PAGE/Coomassie blue analysis of covalent coupling of the model protein comprising a SpyCatcher-SnoopCatcher fusion (SpC-SnC) to OMVs displaying HbpD(Δd2)-SnT. The adduct (*) corresponds with a covalent fusion product between the SnT-carrying HbpD-variant and the SnoopCatcher containing model protein.

FIG. 14. Improved display of a complex protein using isopeptide bonding technology (A) Swissmodel (https://swissmodel.expasy.org/interactive) structure of S. pneumoniae TIGR4 antigen SP1690 (UniProt KB A0A0H2URB7). (B). SDS-PAGE and Coomassie blue staining analysis of S. Typhimurium SL3261ΔtoIRA OMVs displaying HbpD (Δd1), HbpD-SP1690-F1-F2 or HbpD-SP1690-F3-F4. (C) SDS-PAGE and Coomassie blue staining analysis of coupling of SP1690 carrying an N-terminal SpyCatcher (SpC-SP1690-SnT) to S. Typhimurium SL3261ΔtoIRA OMVs displaying HbpD(Δd1) equipped with an N-terminal SpyTag (HbpD(Δd1)-SpT). Molecular weight markers (kDa) are indicated at the left side of the panels. Bands corresponding with endogenous Salmonella outer membrane proteins (OMPs) are indicated. Of note, the folding state of bacterial OMPs is known to be sensitive to subtle changes in SDS concentration and heat encountered during SDS-PAGE analysis (Burgess et al; J Biol Chem. 2008 Sep. 26;283(39): 26748-58). This explains the varying migration behaviors of the indicated OMPs in panels B and C, respectively.

Figure 15:
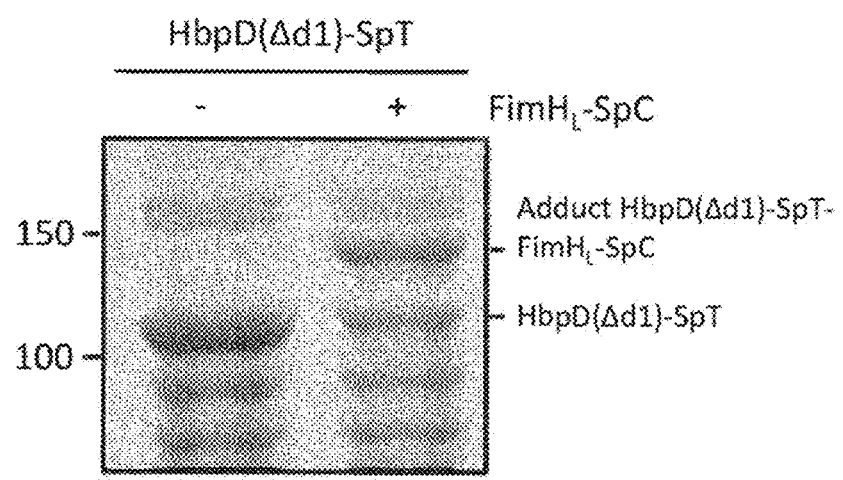

FIG. 15. Coupling of an adhesin to the surface of Gram-negative bacteria. SDS-PAGE and Coomassie blue staining analysis of E. coli TOP10F' cells displaying HbpD(Δd1) with a SpyTag (HbpD(Δd1)-SpT) following incubation in the absence (−) or the presence (+) of $FimH_L$ equipped with a SpyCatcher ($FimH_L$-SpC).

EXAMPLES

General Methods and Material

Strains. E. coli BL21(DE3), S. Typhimurium SL3261 (Hoiseth et al. 1981 Nature 291(5812): 238-9) and the isogenic SL3261 ΔtoIRA (Daleke-Schermerhorn et al 2014, supra) were grown in Lysogeny Broth (LB; 10 g/L tryptone, 5 g/L yeast extract, 10 g/L NaCl).

S. Typhimurium SL3261 ΔtoIRA ΔmsbB (Kuipers et al. 2017 Infect Immun 85(10)) was grown in TYMC (10 g/L tryptone, 5 g/L yeast extract, 2 mM $MgSO_4$, 2 mM $CaCl_2$). The growth medium was supplemented with 0.2% of glucose. Where appropriate antibiotics were added to the following concentrations: ampicillin, 100 μg/mL; kanamycin, 50 μg/mL; chloramphenicol 30 μg/mL. Unless stated otherwise cultures were incubated at 37° C. with shaking.

Construction of expression plasmids: pET28a SpyCatcher-SnoopCatcher, pET28a-SpyTagMBP, pET28a SnoopTag-MBP, pET28a SnoopTag-mEGFP-SpyTag, pET28a SUMO-KTag and pDEST14 SpyLigase were obtained from Addgene. Table 1 gives an overview of the expression plasmids used in the examples. DNA primers which have been used are listed in Table 2.

TABLE 1

Overview of the plasmids used in the examples.

| Name | Protein expressed | $His_6$ tag* | Reference |
|---|---|---|---|
| pET28a SpyCatcher-SnoopCatcher | SpyCatcher-SnoopCatcher fusion linked via a L9 alpha-helix linker | N | Veggiani et al. supra, Addgene #72324 |
| pET28a-SpyTagMBP | SpyTag-MBP | N | Zakeri et al. supra, Addgene #35050 |

TABLE 1-continued

Overview of the plasmids used in the examples.

| Name | Protein expressed | $His_6$ tag* | Reference |
|---|---|---|---|
| pET28a SnoopTag-MBP | SnoopTag-MBP | N | Veggiani et al. supra, Addgene #72323 |
| pET28a SnoopTag-mEGFP-SpyTag | SnoopTag-mEGFP-SpyTag | N | Veggiani et al. supra, Addgene #72325 |
| pET28a SUMO-KTag | SUMO-KTag | N | Fierer et al. supra, Addgene #51723 |
| pDEST14 SpyLigase | SpyLigase | N | Fierer et al. supra, Addgene #51722 |
| pHbpD(Δd1)-SpT | Hbp display platform with the SpyTag at the site of domain 1 (amino-terminus) | — | this work |
| pHbpD(Δd1)-SnT | Hbp display platform with the SnoopTag at the site of domain 1 (amino-terminus) | — | this work |
| pHbpD(Δd1)-SpC | Hbp display platform with the SpyCatcher at the site of domain 1 (amino-terminus) | — | this work |
| pHbpD(Δd1)-SnC | Hbp display platform with the SnoopCatcher at the site of domain 1 (amino-terminus) | — | this work |
| pHbpD(Δd1)-KT | Hbp display platform with the KTag at the site of domain 1 (amino-terminus) | — | this work |
| pET22b GFPnb | PelB signal sequence (PelBss)-GFP-binding nanobody (GFPnb) | C | Kubala et al. supra |
| pET22b GFPnb-SpC | PelBss-GFPnb-SpyCatcher fusion | C | this work |
| pET22b GFPnb-SpC EQ | PelBss-GFPnb fused to SpyCatcher E77Q mutant (E77 is a key residue for isopeptide bond formation) | C | this work |
| pET22b GFPnb-SpT | PelBss-GFPnb-SpyTag fusion | C | this work |
| pET22b GFPnb-SnT | PelBss-GFPnb-SnoopTag fusion | C | this work |
| pET28 SpC-PspAα-SnT | SpyCatcher-HA-PspA$_{32-244}$-SnoopTag | C | this work |
| pET28 SnC-PspAα-SpT | SnoopCatcher-FLAG-PspA$_{32-244}$-SpyTag | C | this work |
| pET28 SpC-SP1690-SnT | SpyCatcher-HA-SP1690-SnoopTag | C | this work |
| pET28 SnC-SP1690-SpT | SnoopCatcher-FLAG-SP1690-SpyTag | C | this work |
| pET20b GFP-His6 | GFP-$His_6$ | C | kind gift from J. W. de Gier |
| pET22b FimH$_L$-SpC | PelBss-FimH$_L$-SpyCatcher | C | This work |
| pcDNA3.3 αCD180$_{Hc}$ | αCD180 heavy chain-SortaseTag-SpyTag | | Gift C. Kuijl |
| pcDNA3.3 αCD180$_{Lc}$ | αCD180 light chain | | Gift C. Kuijl |
| pHbpD(Δd2)-SnT | Hbp display platform with the SnoopTag at the site of domain 2 | | This work |
| pHbpD(Δd2)-SpT | Hbp display platform with the SpyTag at the site of domain 2 | | This work |
| pHbpD(Δd4)-SpT | Hbp display platform with the SpyTag at the site of domain 4 | | This work |
| pHbpD(Δd2)-EL.SpT | Hbp display platform with the SpyTag at the site of domain 2, flanked by extended linkers | | This work |
| pHbpD(Δd4)-EL.SpT | Hbp display platform with the SpyTag at the site of domain 4, flanked by extended linkers | | This work |

*N, $His_6$-tag on the amino-terminus; C, $His_6$-tag on the carboxy-terminus

To construct pHbpD(Δd1)-SpC, a SpyCatcher-encoding fragment was amplified by PCR using pET28a-SpyCatcher-SnoopCatcher as a template and the primers SpyCat fw and SpyCat rv. Using the In-Fusion method (Clontech), the resulting fragment was cloned into SacI/BamHI digested pHbpD(Δd1)-Ag85B, a derivative of pHbpD(Δd1)-ESAT6 carrying mycobacterial ag85B between the SacI/BamHI restriction sites (Jong et al. 2012 supra). This yielded pHbpD(Δd1)-SpC. The same strategy was followed for construction of pEH3-HbpD(Δd1)-SnC but now the primers used were SnoopCat fw and SnoopCat rv.

For construction of pHbpD(Δd1)-SpT, a PCR fragment was generated encoding a fusion product between an N-terminal segment of Hbp and a down-stream SpyTag. Plasmid pEH3-Hbp (Jong et al. 2007 supra) was the template and the primers used were pEH_Xba_InFu fw and Hbp-SpyTag rv. The product was cloned into the XbaI/BamHI sites of pHbpD(Δd1)-Ag85B using In-Fusion methodology to yield pHbpD(Δd1)-SpT. The same strategy was used to create pHbpD(Δd1)-KT but now using the primer pair pEH_Xba_InFu fw and Hbp-KTag rv. To construct pHbpD(Δd1)-SnT, a SnoopTag-encoding fragment was generated by annealing the long oligo's SnoopTag S/B fw and SnoopTag S/B rv. The resulting product was ligated into the SacI/BamH sites of pHbpD(Δd1)-Ag85B, yielding pHbpD(Δd1)-SnT. The same annealed oligo product was ligated into the SacI/BamH sites of pHbpD(Δd2)-ESAT6 (Jong et al., Microb Cell Fact. 2012 Jun 18;11:85) to yield pHbpD(Δd2)-SnT. To construct pHbpD(Δd2)-SpT and pHbpD(Δd4)-SpT, a SpyTagencoding fragment was generated by annealing the long oligo's SpyTag S/B fw and SpyTag S/B rv. The resulting fragment was ligated into the SacI/BamHI sites of pHbpD(Δd2)-ESAT6 and pHbpD(d4in) (Jong et al., Microb Cell Fact. 2014 Nov. 25;13:162), yielding pHbpD (Δd2)-SpT and pHbpD(Δd4)-SpT, respectively. To construct pHbpD(Δd2)-EL.SpT and pHbpD(Δd4)-EL.SpT the same strategy was followed using the long primers EL.SpyTag S/B fw and EL.SpyTag S/B rv.

pET22b GFPnb (kind gift from Hansjorg Gotzke, Center for Biomembrane Research, Department of Biochemistry and Biophysics, Stockholm University, Stockholm, Sweden).

pET22b GFPnb-SpC: the gene encoding a GFP-nanobody (GFPnb) was PCR amplified from pET22b GFPnb using primers ACYC Duet UP1 and GFPnb rv. The SpyCatcher-encoding sequence was PCR amplified from pET28a Spy-Catcher-SnoopCatcher using primers SpyC fw and SpyC rv introducing a carboxy-terminal Hiss-tag. After overlap PCR the GFPnb-SpC sequence was cloned XbaI-HindIII into pET22b (Novagen) yielding pET22b GFPnb-SpC.

pET22b GFPnb-SpC EQ: The E77Q codon mutation was introduced by PCR amplification from pET28a SpyCatcher-SnoopCatcher using either primers SpyC fw and SpyC EQ rv or SpyC EQ fw and SpyC rv followed by overlap PCR using both PCR products. The final product was cloned KpnI-HindIII into pET22b GFPnb-SpC, replacing SpC, yielding pET22b GFPnb-SpC EQ.

pET22b GFPnb-SpT and pET22b GFPnb-SnT: Oligonucleotides SpT-H6 us and SpT-H6 Is or SnT-H6 us and SnT-H6 Is were mixed at 0.25 mM concentration in 100 mM potassium acetate, 30 mM HEPES, pH7.5, heated to 100° C. and allowed to gradually cool down to ambient temperature. The annealed oligonucleotides were cloned into KpnI-HindIII opened pET22b GFPnb-SpC yielding pET22b GFPnb-SpT and pET22b GFPnb-SnT respectively.

pcDNA3.3 αCD180$_{HC}$ and pcDNA3.3 αCD180$_{LC}$: a synthetic DNA fragment was obtained (IDT) encoding the heavy chain of mouse CD180-directed rat IgG2a antibodies carrying a SortaseTag and a SpyTag at the C-terminus (SEQ ID NO: 27). Similarly, a synthetic DNA fragment was obtained (IDT) encoding the light chain of mouse CD180-directed rat IgG2a antibodies. To allow antibody production according to the method by Vink et al. (Methods. 2014 Jan. 1;65(1):5-10), both fragments were ligated under control of a CMV promoter into a derivative of mammalian expression vector pcDNA3.3, yielding pcDNA3.3 αCD180$_{HC}$ and pcDNA3.3 αCD180$_{LC}$, respectively.

pcDNA3.3 αCD180$_{LC}$: a synthetic DNA fragment was obtained (IDT) encoding the light chain of mouse CD180-directed rat IgG2a antibodies. To allow antibody production according to method by Vink et al. (Methods. 2014 Jan. 1;65(1):5-10), the fragment was ligated into mammalian expression vector pcDNA3.3, yielding pcDNA3.3 αCD180$_{HC}$.

pET22b FimH$_L$-SpC: a synthetic DNA fragment was obtained (IDT) encoding a FimH$_L$ (residues 23-181 of SEQ ID NO: 30). The fragment was ligated into pET22b GFPnb-SpC using In-Fusion cloning, yielding pET22b-FimH$_L$-SpC, which encodes a translational fusion between PelBss, FimH$_L$, SpyCatcher and a Hiss tag (SEQ ID NO: 30). pET28 SpC-PspAα'-SnT, pET28 SnC-PspAα'-SpT, pET28 SpC-SP1690-SnT and pET28 SnC-SP1690-SpT: The Spy-Catcher-encoding sequence was PCR amplified from pET28a SpyCatcher-SnoopCatcher using primers NcoI SpyC fw and EcoRI HA SpyC rv introducing an HA tag. The product was cloned NcoI-EcoRI into pET28a yielding pET28 SpC-HA. Next, a SnoopTag-His$_6$-encoding sequence was PCR amplified from pET22b GFPnb-SnT using primers SalI SpT fw and T7 Terminator. The product was cloned SalI-XhoI into pET28 SpC-HA yielding pET28 SpC-HA-SnT-His$_6$. The SnoopCatcher-encoding sequence was PCR amplified from pET28a SpyCatcher-SnoopCatcher using primers NcoI SnC fw and EcoRI FLAG SnC rv introducing a FLAG tag. The product was cloned NcoI-EcoRI into pET28a yielding pET28 SnC-FLAG. Next, a SnoopTag-His$_6$-encoding sequence and a SpyTag-His$_6$-encoding sequence were PCR amplified from pET22b GFPnb-SnT and pET22b GFPnb-SpT respectively using primers SalI SpT fw and T7 Terminator. The products were cloned SalI-XhoI into pET28 SpC-HA and pET28 SnC-FLAG yielding pET28 SpC-HA-SnT-His$_6$ and pET28 SnC-FLAG-SpT-His$_6$ respectively. Last, DNA encoding amino acids 32-244 of PspA or encoding amino acids 24-445 of SP1690 (both *Streptococcus pneumoniae* serotype 4 [TIGR4] sequences), were PCR amplified using primers EcoRI αTIGR4 fw and SalI αTIGR4 rv or EcoRI SP1690 fw and SalI SP1690 rv respectively. The products were cloned EcoRI-SalI into pET28 SpC-HA-SnT-His$_6$ and pET28 SnC-FLAG-SpT-His$_6$ yielding pET28 SpC-alpha-SnT, pET28 SnC-alpha-SpT, pET28 SpC-SP1690-SnT and pET28 SnC-SP1690-SpT.

TABLE 2

DNA primers used in the examples.

| Name | 5'-3' sequence* |
| --- | --- |
| ACYC Duet UP1 | GGATCTCGACGCTCTCCCT |
| GFPnb rv | cggtaccaccactacctTTGCTGCTAACGGTAACC |
| SpyC fw | gcadcadtggtaccggcGATAGTGCTACCCATATTAAATTCTC |
| SpyC rv | GCGGCCGCAAGCTTTTACTAATGATGGTGATGATGATGaccgctgccAATATGAGCGTCACC |
| SpyC EQ fw | GAAAATATACATTTGTCcAAACCGCAGC |
| SpyC EQ rv | GCTGCGGTTTgGACAAATGTATATTTTC |
| SpT-H6 us | cggcgcccacatcgtgatggtggacgcctacaagccgacgaagggtagtggtgaaagtggtCATCATCATCACCATCATTAGTAAA |

TABLE 2-continued

DNA primers used in the examples.

| Name | 5'-3' sequence* |
|---|---|
| SpT-H6 ls | AGCTTTTACTAATGATGGTGATGATGATGaccactttcaccac taccttcgtcggcttgtaggcgtccaccatcacgatgtgggc gccggtac |
| SnT-H6 us | cggcAAACTGGGCGATATTGAATTTATTAAAGTGAACAAAggt agtggtgaaagtggtCATCATCATCACCATCATTAGTAAA |
| SnT-H6 ls | AGCTTTTACTAATGATGGTGATGATGATGaccactttcaccac taccTTTGTTCACTTTAATAAATTCAATATCGCCCAGTTTgcc ggtac |
| NcoI SpyC fw | atatatccatgggCGATAGTGCTACCCATATTAAATTCTC |
| EcoRl HA SpyC rv | atatatgaattcGCCGGACCCCGCATAGTCAGGAACATCGTAT GGGTATCCCGAACCAATATGAGCGTCACCTTTAG |
| SalI SpT fw | atatatgtcgacggcagcggtggtacc |
| T7 Terminator | GCTAGTTATTGCTCAGCGG |
| NcoI SnC fw | atatatccatgggCAAGCCGCTGCGTGG |
| EcoRl FLAG SnC rv | atatatgaattccCCGCCGCTACCGCCTTTATCGTCATCATCC TTATAGTCACCGCCGCTACCGCCTTTCGGCGGTATCGG |
| SalI SpT fw | atatatgtcgacggcagcggtggtacc |
| EcoRl αT1G R4 fw | atatatgaattcGAAGAAAGTCCGCAGGTTG |
| SalI αT1GR4 rv | atatatgtcgacGGTGCCATCATCCGG |
| EcoRl SP1690 fw | atatatgaattcTCAGGAAAAAAAGAAGCTACAACTAGTAC |
| SalI SP1690 rv | atatatgtcgacCTGAACAGCCTCAAATAAATCATTTAATTG |
| SpyCat fw | *ggaagtcttgcggggagctcc*GATAGTGCTACCCATATTAAAT TC |
| SpyCat rv | *taccgctgccggatcc*AATATGAGCGTCACCTTTAGTtg |
| SnoopCat fw | *ggaagtcttgcggggagctcc*AAGCCGCTGCGTGGTGCC |
| SnoopCat rv | *taccgctgccggatcc*TTTCGGCGGTATCGGTTCATTG |
| pEH_Xba_InFu fw | *ttgctaactttctagattacaaaac* |
| Hbp-SpyTag rv | *taccgctgccggatcc*cttcgtcggcttgtaggcgtccaccat cacgatgtgggcggagctccccgcaagacttc |
| Hbp-KTag rv | *taccgctgccggatcc*atcacgttttgagaatttaatatgggt agcggagctccccgcaagacttc |
| SnoopTag S/B fw | CCAAACTGGGCGATATTGAATTTATTAAAGTGAACAAAG |
| SnoopTag S/B rv | GATCCTTTGTTCACTTTAATAAATTCAATATCGCCCAGTTTG GAGCT |
| SpyTag S/B fw | CCGCCCACATCGTGATGGTGGACGCCTACAAGCCGACGAAGG |
| SpyTag S/B rv | GATCCCTTCGTCGGCTTGTAGGCGTCCACCATCACGATGTGGG CGGAGCT |
| EL.SpyTag S/B fw | CCGGCTCGGCTAGCGGTGCCCACATCGTGATGGTGGACGCCTA CAAGCCGACGAAGGGTGAGGGAACCGGCG |
| EL.SpyTag S/B rv | GATCCGCCGGTTCCCTCACCCTTCGTCGGCTTGTAGGCGTCCA CCATCACGATGTGGGCACCGCTAGCCGAGCCGGAGCT |

*Overlapping regions for overlap FOR are underlined;
restriction enzyme recognition sites used for cloning are in bold and overhangs used for In-Fusion cloning are in italics;
mutagenic nucleotides are in lower case.

TABLE 3

List of sequences

| name | SEQ ID No |
|---|---|
| Hbp (wild-type) | 1 |
| HbpD | 2 |
| HbpD(Δd1) | 3 |
| HbpD(Δd1)-SpT | 4 |
| HbpD(Δd1)-SnT | 5 |
| HbpD(Δd1)-KT | 6 |
| HbpD(Δd1)-SpC | 7 |
| HbpD(Δd1)-SnC | 8 |
| HbpD(Δd2)-SpT | 9 |
| HbpD(Δd2)-EL.SpT | 10 |
| HbpD(Δd2)-SnT | 11 |
| HbpD(Δd4)-SpT | 12 |
| HbpD(Δd4)-EL.SpT | 13 |
| SpC-SnC | 14 |
| GFPnanobody-SpC | 15 |
| GFPnanobody-SpC_EQ | 16 |
| SpC-PSpAa-SnT | 17 |
| SpC-PSpAa-SP1690-SnT | 18 |
| SpT-MBP | 19 |
| SnT-MBP | 20 |
| SnT-EGFP-SpT | 21 |
| SUMO-KT | 22 |
| SpyLigase | 23 |
| SpC-SP1690-SnT | 24 |
| SnC-SP1690-SpT | 25 |
| GFP-His$_6$ | 26 |
| Rat-IgG2A_heavy_chain_constant_region_aCD180-SpT | 27 |
| HbpD-SP1690-F1-F2 | 28 |
| HbpD-SP1790-F3-F4 | 29 |
| FimH$_L$-SpC | 30 |
| ACYC Duet UP1 | 31 |
| GFPnb rv | 32 |
| SpyC fw | 33 |
| SpyC rv | 34 |
| SpyC EQ fw | 35 |
| SpyC EQ rv | 36 |
| SpT-H6 us | 37 |
| SpT-H6 ls | 38 |
| SnT-H6 us | 39 |
| SnT-H6 ls | 40 |
| NcoI SpyC fw | 41 |
| EcoRI HA SpyC rv | 42 |
| SalI SpT fw | 43 |
| T7 Terminator | 44 |
| NcoI SnC fw | 45 |
| EcoRI FLAG SnC rv | 46 |
| SalI SpT fw | 47 |
| EcoRI αTIGR4 fw | 48 |
| SalI αTIGR4 rv | 49 |
| EcoRI SP1690 fw | 50 |
| SalI SP1690 rv | 51 |
| SpyCat fw | 52 |
| SpyCat rv | 53 |
| SnoopCat fw | 54 |
| SnoopCat rv | 55 |
| pEH_Xba_InFu fw | 56 |
| Hbp-SpyTag rv | 57 |
| Hbp-KTag rv | 58 |
| SnoopTag S/B fw | 59 |
| SnoopTag S/B rv | 60 |
| SpyTag S/B fw | 61 |
| SpyTag S/B rv | 62 |
| EL.SpyTag S/B fw | 63 |
| EL.SpyTag S/B rv | 64 |

Protein purification cytoplasmic proteins. *E. coli* BL21 (DE3) cells harboring a pET28 or pDEST14 expression plasmid were grown in LB containing 0.2% glucose and kanamycin to an OD$_{600}$ of 0.4-0.5. Protein expression was induced by the addition of isopropyl β-D-thiogalactopyranoside (IPTG) to a final concentration of 0.5 mM and the cells were incubated for a further two hours. Subsequently the cells were washed with PBS (pH 7.4) and stored at −20° C. The cells were resuspended in buffer A (50 mM NaPO$_4$, 300 mM NaCl, pH 7.4) and phenylmethylsulfonyl fluoride (PMSF) was added to a concentration of 125 μM. The cells were disrupted by two passages through a One Shot cell disruptor (Constant Systems Ltd.) at 1.2 kbar. Cell debris and membranes were removed by centrifugation at 10,000 g and 293,000 g respectively at 4° C. His$_6$-tagged proteins were isolated from the cleared lysate using TALON Superflow medium (GE Healthcare Life Sciences) according to the manufacturer's instructions. Eluates were dialyzed overnight at 4° C. against 500 to 1000 volumes of PBS (pH 7.4). After dialysis glycerol was added to 10% and aliquots were stored at −80° C.

*E. coli* BL21 (DE3) cells harboring a pET20b GFP-His$_6$ expression plasmid were grown at 30° C. in LB containing 0.2% glucose and ampicillin to an OD$_{600}$ of 0.2-0.3. Protein expression was induced by the addition of IPTG to a final concentration of 0.4 mM and the cells were incubated for a further four hours. GFP-His$_6$ was purified from the cells as described above.

Protein purification periplasmic proteins. A procedure based on that described by Pardon et al. in Nature Protocols was used.[38] *E. coli* BL21 (DE3) cells harboring a pET22b GFPnb-SpC or pET22b GFPnb-SpC EQ expression plasmid were grown in LB containing 0.2% glucose and ampicillin to an OD$_{600}$ of 0.8-0.9. Both fusion proteins were equipped with a cleavable PelB signal sequence for translocation into the periplasmic space. Isolation of the GFPnb-SpC fusions from the oxidizing periplasmic environment allowed formation of an intramolecular disulphide bond ensuring nanobody functionality. Protein expression was induced by the addition of IPTG to a final concentration of 0.5 mM and the cells were incubated for a further 20 hours at 12° C. with shaking. The cells were harvested by centrifugation and stored at −20° C. The cells were resuspended in PBS (pH 7.4) and incubated for 30 min at 21° C. in a Thermomixer (Eppendorf) at 1400 rpm. Next, the cells were removed by centrifugation (10,000 g) and the His$_6$-tagged proteins were isolated as described above (Protein purification cytoplasmic proteins).

OMV isolation. *S. Typhimurium* SL3261 ΔtolRA cells harboring the HbpD(Δd1) expression plasmid were grown in LB containing glucose and kanamycin to an OD$_{600}$ of 0.2-0.3. Protein expression was induced by the addition of IPTG to a final concentration of 0.1 mM and the cells were incubated for a further two hours. Cells were removed by two successive centrifugation steps at 5000 g. OMVs were isolated from the second supernatant by centrifugation at 235,000 g, resuspended in PBS (pH 7.4) containing 15% glycerol and stored at −80° C. The same strategy was followed for the production of OMVs from *S. Typhimurium* SL3261 ΔtolRA cells harboring plasmids for the expression of HbpD(Δd2)-SpT, HbpD(Δd2)-EL.SpT HbpD(Δd2)-SnT HbpD(Δd4)-SpT and HbpD(Δd4)-EL.SpT, HbpD(Δd1)-SpC, HbpD(Δd1)-SnT, HbpD(Δd1)-SnC and HbpD(Δd1)-KT.

Alternatively, in view of future therapeutic purposes, OMVs were isolated from *S. Typhimurium* SL3261 ΔtolRA ΔmsbB cells harboring the pHbpD(Δd1)-SpT expression plasmid. These cells were grown at 30° C. in TYMC containing glucose and kanamycin. Fresh medium containing 1 mM of IPTG was inoculated to an OD$_{600}$ of 0.02 and incubated at 30° C., shaking, for 17 hours. Cells were removed by two successive centrifugation steps at 5000 g. The supernatant was passed through 0.45 μm pore size filters (Millipore) and centrifuged at 235,000 g for 75 min to sediment the OMVs. The vesicles were resuspended in PBS (pH 7.4) containing 15% glycerol.

Spy-ligation with OMVs containing Hbp(Δd1)-SpT and increasing amounts of SpC-SnC. To OMVs (isolated from *S. Typhimurium* SL3261 ΔtolRA cells) containing approximately 62 pmol of Hbp(Δd1)-SpT purified SpC-SnC was added in the ratios indicated in FIG. 2A. The mixes were supplemented with PBS (pH 7.4) to reach a final volume of 20 μL. After 21 hours of incubation at 4° C. the reaction mixes were analyzed by SDS-PAGE with Coomassie staining.

Protein ligation with Hbp(Δd1)-SpC, -SnC, -SpT, -SnT or -KT in OMVs. To OMVs (isolated from *S. Typhimurium* SL3261 ΔtolRA cells) containing approximately 200 pmol of Hbp(Δd1)-SpC, -SnC, -SpT, -SnT or KT a 2-fold molar excess of purified SnT-mEGFP-SpT, SpC-SnC, or SUMO-KT was added (for the specific combinations see FIG. 3). Where appropriate, 800 pmol of purified SpyLigase was added and the mixes were supplemented with PBS (pH 7.4) to reach a final volume of 50 μL. After 24 hours of incubation at 4° C. the reaction mixes were analyzed by SDS-PAGE with Coomassie staining.

Spy-ligation of antigens to Hbp in OMVs. To 500 μL of OMVs (isolated from *S. Typhimurium* SL3261 ΔtolRA ΔmsbB cells) containing HbpD(Δd1)-SpyTag, obtained from a 1000 $OD_{600}$ equivalent ($OD_{600}$×mL) of cell culture 900 μL of purified SpC-PspAα'-SnT (140 μM), SpC-SP1690-SnT (176 μM) or SpC-PspAα'-SP1690-SnT (72 μM), was added and incubated for 24 h at 4° C. The reaction mixes were analyzed by SDS-PAGE with Coomassie staining and with immunodetection after western blotting. For immunodetection anti-polyHistidine antibody (H1029, Sigma) was used. Using similar strategy Spy- and Snoop ligation was achieved of the model fusion protein Spy-Catcher-SnoopCatcher (Spc-SnC) to *S. Typhimurium* SL3261 ΔtolRA OMVs displaying HbpD(Δd2)- or HbpD(Δd4)-variants, respectively, carrying either a SpyTag (SpT), SpyTag with extended linkers (EL.SpT), or a SnoopTag (SnT). In these cases OMVs obtained from a 1 $OD_{600}$ equivalent ($OD_{600}$×mL) of cell culture were incubated with 15.47 μM of Spc-SnC in a total reaction volume of 50 μl.

Adduct extension by alternating Spy-ligation and Snoop-ligation. To 100 μL of OMVs (isolated from *S. Typhimurium* SL3261 ΔtolRA cells) containing HbpD(Δd1)-SpyTag, obtained from a 100 $OD_{600}$ equivalent ($OD_{600}$×mL) of cell culture 80 μL of purified SpC-PspAα'-SnT (86 μM) was added. After two hours of incubation at 4° C., 120 μL of purified SnC-SP1690-SpT (57 μM) was added. After two hours of incubation at 4° C. another 80 μL of purified SpC-PspAα'-SnT. After a further two hours of incubation at 4° C. another 120 μL of purified SnC-SP1690-SpT was added and the mix was incubated for 15 h at 4° C. The OMVs were isolated by centrifugation at 293,000 g for 45 min at 4° C. The OMVs were resuspended in PBS (pH 7.4) containing 15% glycerol and analyzed by SDS-PAGE with Coomassie staining and with immunodetection after western blotting. For immunodetection monoclonal anti-FLAG M2 antibody (F3165, Sigma), HA-tag monoclonal antibody (2-2.2.14) (ThermoFisher Scientific) and anti-polyHistidine antibody (H1029, Sigma) were used.

Spy-ligation of GFPnb-SpC to Hbp in cells. *S. Typhimurium* SL3261 cells harboring pHbpD(Δd1)-SpyTag were grown in LB containing 0.4% glucose and chloramphenicol to an $OD_{600}$ of 0.3-0.4. Protein expression was induced by the addition of IPTG to a final concentration of 1 mM and the cells were incubated for a further two hours. Subsequently the cells were harvested, resuspended to an $OD_{600}$ of 10 in PBS (pH 7.4) containing 3 μM of GFPnb-SpC or GFPnb-SpC EQ and incubated for 60 min at 25° C. in a Thermomixer (Eppendorf) at 1000 rpm. After incubation with the nanobody-SpyCatcher protein the cells were resuspended to an $OD_{600}$ of 10 in PBS (pH 7.4) containing 3 μM of GFP and incubated at 4° C. for 5 min. Last, the cells were resuspended to an $OD_{600}$ of 10 in PBS (pH 7.4) and analyzed by SDS-PAGE with Coomassie staining and microscopy.

Spy-ligation of GFPnb-SpC to Hbp in OMVs. 1 μL of OMVs containing HbpD(Δd1)-SpyTag, obtained from a 1 $OD_{600}$ equivalent ($OD_{600}$×mL) of cell culture, were diluted in 100 μL of PBS (pH 7.4) containing 3 μM of GFPnb-SpC or GFPnb-SpC EQ. The mixes were incubated for 60 min at 25° C. in a Thermomixer (Eppendorf) at 1000 rpm and analyzed by SDS-PAGE with Coomassie staining and with immunodetection after western blotting. For immunodetection anti-polyHistidine antibody (H1029, Sigma) was used.

Spy-ligation of $FimH_L$ to Hbp on *E. coli* cells. To allow coupling, 1.0 $OD_{660}$ unit of *E. coli* TOP10F' cell material displaying HbpD(Δd1)-SpT was incubated overnight with 50 μg of $FimH_L$-SpC at 4° C. Successful coupling was assessed by SDS-PAGE/Coomassie staining analysis.

Spy-ligation of αCD180 to Hbp on OMVs. To couple SpyTagged anti-mouse CD180 (αCD180-SpT) to bacterial cells, 2 $OD_{660}$ units of Salmonella SL3261ΔtolRA cells expressing HbpD(Δd1)-SpC at the surface were overnight incubated with 200 μl of αCD180-SpT (0.5 mg/ml) at 4° C.). Next day, to separate cell-coupled and non-coupled material, the mixture was centrifuged at low speed (5,000 rpm, 5 min) and the bacterial pellet and supernatant fraction were recovered. Subsequently, the bacterial pellet was resuspended in PBS to wash off loosely associated material. The cell suspension was subjected to low speed centrifugation (5,000 rpm, 5 min) and the bacterial pellet and supernatant were recovered. Coupling of αCD180-SpT to HbpD(Δd1)-SpC was analyzed by Coomassie stained SDS-PAGE.

Quantitation of ligation efficiency. After SDS-PAGE proteins and staining Coomassie Brilliant Blue G250 gels were scanned on a GS-800 Calibrated Densitometer (BioRad). The intensities of protein bands were determined using ImageJ (http://imagej.nih.gove/ij/). After correction for the difference in molecular weight the fractions of Hbp (unmodified and ligated) were calculated.

Microscopy. Cells were photographed using an F-View II CCD camera (Olympus) mounted on a BH2 microscope with a RFCA fluorescence attachment using a DApo100UV PL 1.30 oil 160/0.17 objective and a GFP fluorescence filter cube (BP495/DM505) (Olympus). Image files were processed using ImageJ (http://imagej.nih.gov/ij/).

Example 1

Spy- and Snoop-Ligation to Hbp on the Surface of OMVs

The *E. coli* Hemoglobin protease (Hbp) was used as a carrier. The autocatalytic cleavage site was mutated to create an Hbp carrier that is displayed at the cell surface rather than being released, providing permanent exposure of fused antigens at some distance of the cell surface.

As host for the Hbp antigen display carrier an attenuated *Salmonella Typhimurium* strain was used that provokes strong mucosal and systemic responses of both cellular and humoral nature (Jong et al (2014) supra; Hoiseth et al. (1981) supra; Moreno et al. 2010 Curr Gene Ther 10(1): 56-76). Furthermore, as an alternative non-living platform, we have explored OMVs derived from the same strain. To increase the production of OMVs a ΔtolRA derivative of the attenuated *S. Typhimurium* strain was used.

Figure 2A:
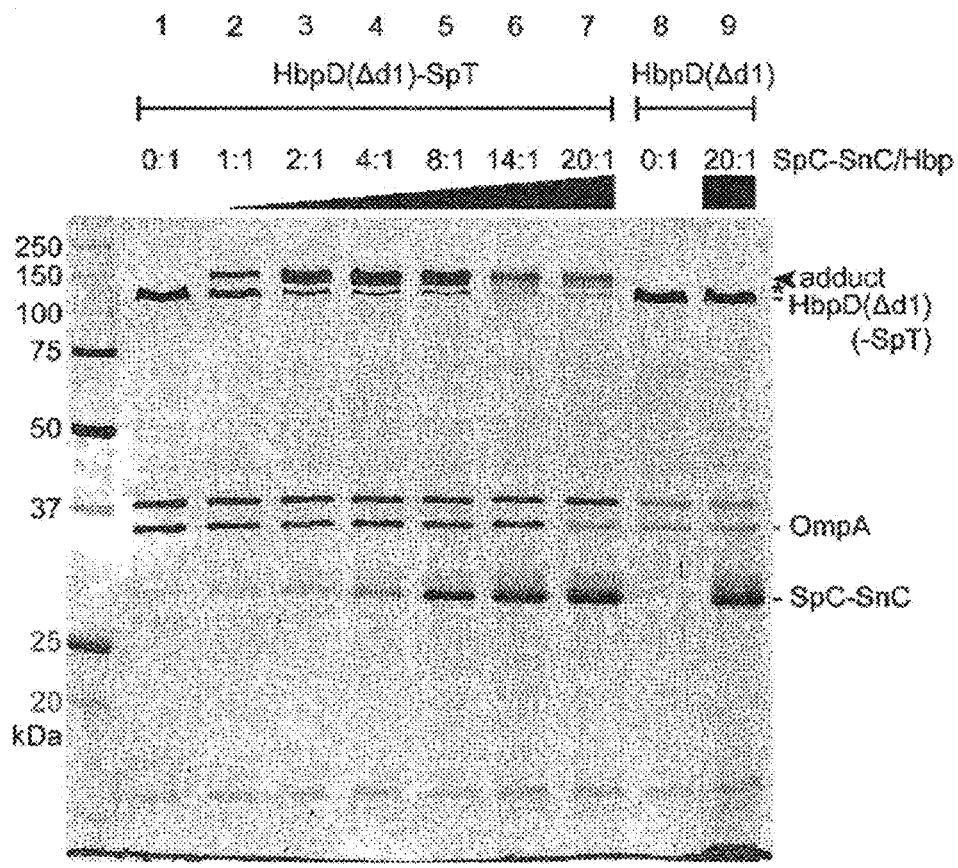

To investigate the suitability of the SpyCatcher/SpyTag system for ligation of proteins to Hbp fixed on the surface of OMVs, we fused the SpyTag (SpT) to the N-terminus of the Hbp display construct HbpD(Δd1) (FIG. 1A). In our experience, this position in Hbp is the most tolerant towards fusion of heterologous sequences. To test display in the context of OMVs, the fusion construct was expressed in the hypervesiculating S. Typhimurium ΔtolRA strain and OMVs were collected by ultracentrifugation. As expected, the small (13 aa long) tag did not impede expression and surface display of Hbp (FIG. 2A, compare lane 1 and 8 and FIG. 8, lanes 7-9 providing a density of the SpyTag at the OMV surface that is similar to the major outer membrane protein OmpA. Importantly, the SpyTag is located at the tip of the β-helical stem structure of Hbp providing considerable distance to the membrane surface and consequent accessibility towards cognate coupling partners.

Figure 2B:
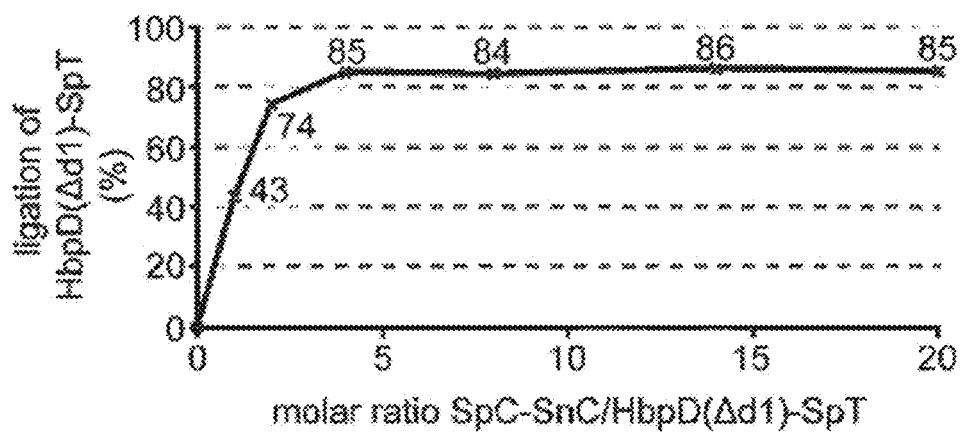

As proof of concept for Spy-mediated ligation, OMVs decorated with HbpD(Δd1)-SpT (SEQ ID NO: 4) were incubated with purified SpyCatcher-SnoopCatcher hybrid protein (SpC-SnC, FIG. 1B) (SEQ ID NO: 14) in incremental molar ratios and subsequently the samples were analyzed by SDS-PAGE and total protein staining. An adduct with an electrophoretic mobility corresponding to that expected of the HbpD(Δd1)-SpT-SpyCatcher-SnoopCatcher ligation product, 145.7 kDa, appeared at the expense of HbpD(Δd1)-SpT (FIG. 2A, lanes 2-7). In a control reaction containing OMVs displaying the carrier HbpD(Δd1) without a SpyTag (SEQ ID NO: 3) this ligation product was not detected (FIG. 2A, lanes 8 and 9). The amount of unligated and ligated Hbp protein was determined by densitometric scanning. Saturation of coupling, at a maximum of ~85% of the Hbp molecules ligated, was reached at an approximate 4-fold molar excess of cargo protein relative to the Hbp carrier (FIG. 2B). This level of ligation efficiency comes close to the levels observed upon co-incubation of purified cognate ligation partners (e.g. FIG. 3, lanes 7 and 8). These results indicate that the SpyTag fused to displayed Hbp is well accessible for coupling at the surface of OMVs.

To investigate if the Spy and Snoop ligation systems are more generally compatible with the Hbp display platform, the SpyCatcher (SpC), KTag (KT), SnoopCatcher (SnC) and SnoopTag (SnT) were also individually introduced at the N-terminus of the Hbp display construct HbpD(Δd1) (SEQ ID NO: 7; SEQ ID NO: 6; SEQ ID NO: 8; and SEQ ID NO: 5, resp) and expressed on OMVs. All fusion proteins were present in the OMV fraction in a density similar to the major OMPs (FIG. 7). For all fusion proteins, protease accessibility experiments confirmed their localization at the cell surface indicating that the Tags and Catchers did not impede translocation of Hbp across the cell envelope (FIG. 8). To further substantiate surface localization and suitability for ligation of cognate partner proteins, ligation tests were carried out. OMVs decorated with the Hbp fusion proteins (FIG. 7A) were incubated with purified recombinant proteins that were used by Howarth and co-workers (FIG. 11B) as tools to demonstrate bipartite and tripartite ligation: SpyCatcher-SnoopCatcher (SEQ ID NO: 14), SpyTag-MBP (SEQ ID NO: 19), SnoopTag-MBP (SEQ ID NO: 20), SnoopTag-mEGFP-SpyTag (SEQ ID NO: 21), SUMO-KTag (SEQ ID NO: 22) and SpyLigase (SEQ ID NO: 23) (Veggiani et al. 2016 supra; Zackeri et al. 2012 supra; Feirer et al. 2014 supra). Summarizing, in the context of OMVs the highest efficiency of display of ligated product was obtained with the HbpD(Δd1)-SpT construct (FIG. 3, lane 3).

Comparing the display efficiencies of (bipartite) ligated adducts, the constructs rank HbpD(Δd1)-SpT> HbpD(Δd1)-SpC>HbpD(Δd1)-SnT>HbpD(Δd1)-SnC (FIG. 3, lanes 1-4). Apparently, the 10.0 kDa SpyCatcher and the 12.6 kDa SnoopCatcher had no major impact on the display of the Hbp carrier and folded into their catalytic structure at the OMV surface enabling binding to Spy or Snoop-tagged partner proteins.

In tripartite ligation the SpyCatcher domain is further split up in the so-called KTag harboring the lysine residue that is part of the isopeptide bond and the larger catalytic "SpyLigase" domain. The isolated SpyLigase is able to couple a KTagged protein and a SpyTagged protein in trans expanding the potential applications of this technology (Fierer et al. 2014 supra). In contrast to the bipartite system, the tripartite system did not yield any appreciable ligation product in the OMV context (FIG. 3, lanes 5 and 6). To verify the activity of the SpyLigase used, purified SUMO-KTag and SpT-MBP were shown to be coupled upon co-incubation, though not very efficiently (FIG. 3, lane 9).

Example 2

Ligation of Antigens to Hbp

Encouraged by the efficient enzymatic coupling of the various cargo proteins in Example 1 to surface-exposed Hbp using Spy/Snoop technology, this approach was tested for the decoration of OMVs with complex antigens. As proof of concept, coupling of the large N-terminal α1α2-domain (213 amino acid, 24.4 kDa, further referred to here as the PspA α'-domain) of the surface exposed pneumococcal PspA antigen (from strain TIGR4) to OMVs pre-decorated with Hbp using Spy technology was explored. Previously, efficient display required splitting up the PspA α'-domain and incorporating the two resulting fragments at different sites in Hbp (HbpD-PspA[α1-α2]) (Kuipers et al. 2015 supra). Yet, the highest achievable concentration of HbpD-PspA[α1-α2] in OMVs was still only one third of that of antigen-free HbpD. For coupling we fused the SpyCatcher to the complete PspA α'-domain. For purposes described in the next section we further included an HA-tag and a SnoopTag at the C-terminus of the fusion construct (FIG. 1C, SpC-PspAα'-SnT; SEQ ID NO: 17). Incubation of S. Typhimurium OMVs decorated with HbpD(Δd1)-SpT (SEQ ID NO: 4) with a 10-fold molar excess of SpC-PspAα'-SnT (SEQ ID NO: 17) resulted in efficient (~85%) ligation as judged by SDS-PAGE analysis (FIG. 4, lane 2). For further proof of principle we followed the same strategy using the conserved pneumococcal antigen SP1690 (WO/2008/127094). SP1690 is a 47.3 kDa component of an ABC-type oligosaccharide transport system belonging to the type 2 periplasmic-binding fold superfamily (Marchler-Bauer et al. 2017 Nucl Acid Res 45(D1): D200-D203). Initial attempts to display intact SP1690 as a fusion to Hbp were unsuccessful necessitating the splitting of SP1690 in four fragments that were inserted in two Hbp carriers (two fragments per carrier). However, even upon splitting, only moderate amounts of SP190 were displayed at the surface (data not shown). For Spy-ligation we created a fusion protein of SpyCatcher and full-length SP1690 (only omitting the N-terminal Cys residue that is most likely acylated in the native protein as predicted from its lipoprotein-like signal peptide) (Juncker et al. 2003 Proten Science: a publication of the Protein Society, 12(8):1652-62). A FLAG-tag and a SnoopTag were included at the C-terminus of the fusion construct (FIG. 1C, SpC-SP1690-SnT; SEQ ID NO: 24). Similar to SpC-PspAα'-SnT, efficient (~85% coupling) was observed upon incubation with OMVs decorated with HbpD (Δd1)-SpT (FIG. 4, lane 3). A further increase in complexity of the fusion partner was achieved by fusing the complete PspAα' domain and full-length SP1690 in one construct. The resultant ~87 kDa bivalent antigen (SEQ ID NO: 18) was coupled through Spy technology to Hbp-decorated OMVs at equally high efficiency (FIG. 4, lane 4).

Together the data indicate that large complex antigens and even chimeras of complex antigens can be displayed at high density the combined Hbp and Spy technologies. By combining the Hbp display technology with protein ligation via isopeptide bond formation, such as the Spy—and Snoop Catcher/Tag technology, antigens and even chimeras of complex antigens can be displayed at high density on the surface of bacterial cells and OMVs.

Example 3

Ligation of Multiple Antigens to Hbp

Figure 5A:
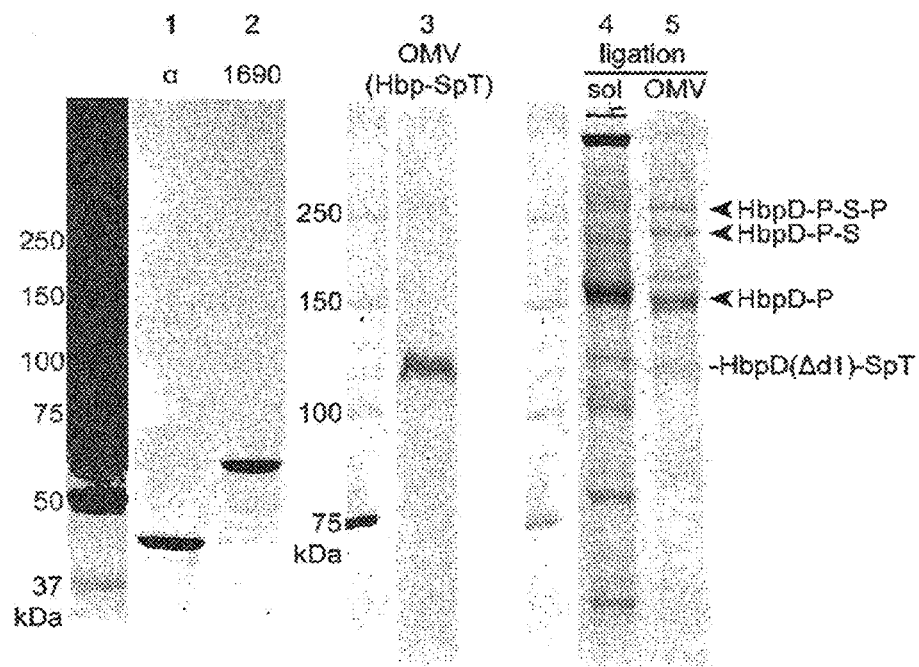

The combined use of the Spy and Snoop ligation systems was investigated to see whether they allow a more attractive iterative approach to couple multiple antigens to the Hbp platform while maintaining high antigen concentrations per OMV. First, HbpD-PspAα' formed by the ligation of SpC-PspAα'-SnT (SEQ ID NO: 17) to HbpD(Δd1)-SpT (SEQ ID NO: 4) was tested to see whether it could be further extended by adding SP1690 fused to SnoopCatcher. To allow subsequent coupling of purified SpC-PspAα'-SnT, the SP1690 fusion protein also contained a SpyTag at its C-terminus (SEQ ID NO: 25). A similar iterative extension approach was shown by Veggiani et al. to efficiently polymerize affibodies into multimeric chains (Veggiani et al. 2016 supra). Importantly, the process was started with an affibody fused to a SpyCatcher immobilized on a solid support. Subsequently the material was incubated with affibody containing both a SpyTag and a SnoopTag at the N- and C-terminus, respectively. After the unreacted affibody was washed away the material was incubated with a SpyCatcher-SnoopCatcher chimera to extend the chain. By iterating this process chains of affibodies were formed. Since immobilizing and washing the OMVs is technically more challenging we explored the principle of the strategy in one reaction mix. This approach therefore has the disadvantage that SpC-PspAα'-SnT and SnC-SP1690-SpT may link to each other, but not to HbpD(Δd1)-SpT. Moreover, polymers of SpC-PspAα'-SnT and SnC-SP1690-SpT might cyclize and form unreactive end products that are not linked to the Hbp platform. To limit undesirable product formation OMVs containing HbpD(Δd1)-SpT were incubated sequentially with SpC-PspAα'-SnT and SnC-SP1690-SpT in two rounds, followed by centrifugation and analysis of the OMVs and the spent medium by SDS-PAGE. In both fractions a complex pattern of adducts was observed, which likely resulted from polymer formation combined with limited proteolysis (FIG. 5A, lanes 4 and 5).

Figure 5B:
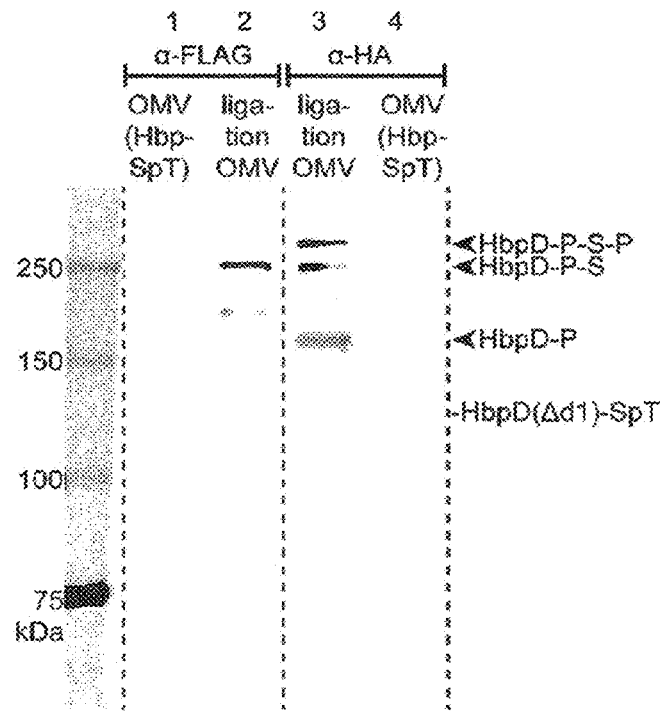

Importantly, in the OMV fraction (FIG. 5A, lane 5) three major adducts that probably correspond to single, double and triple ligation events dominate. Omitting the Spy/Snoop-ligation terms from the nomenclature for clarity, these probably represent HbpD-PspAα' with an expected molecular mass of 157 kDa, HbpD-PspAα'-SP1690 of 222 kDa and HbpD-PspAα'-SP1690-PspAα' of 262 kDa, respectively. The identity of these three adducts was confirmed by immunodetection using anti-HA and anti-FLAG antibodies that recognize the HA- and FLAG epitopes integrated in SpC-PspAα'-SnT and SnC-SP1690-SpT, respectively (FIG. 5B). Quantification of HbpD(Δd1)-SpT and the three major adducts (FIG. 5A, lanes 3 and 5) indicated a total ligation efficiency of ~85% and a ratio of ~5:1:1 (157 kDa/222 kDa/262 kDa) for the adducts. The data thus show that the principle of polymerization worked, and that isopeptide formation can be used for iterative extension of two or more antigens to the Hbp fusion protein.

Example 4

Ligation of Nanobodies to Hbp

Decoration of bacteria or OMVs with lectins, adhesins or affinity molecule handles, such as antibodies or nanobodies, could be used as a tool for OMV targeting to certain tissues and immune cells, thereby increasing the efficacy of antigen delivery. Nanobodies are particularly attractive for this purpose because of their versatility and ease of recombinant production. They are much smaller (15 kDa) than regular antibodies since they consist only of a single variable domain fragment ($V_{HH}$) as found in heavy-chain-only antibodies that occur naturally in camelids and sharks. Previous attempts to incorporate nanobodies in Hbp by gene fusion have met with variable and generally low display efficiencies (data not shown).

Figure 6A:
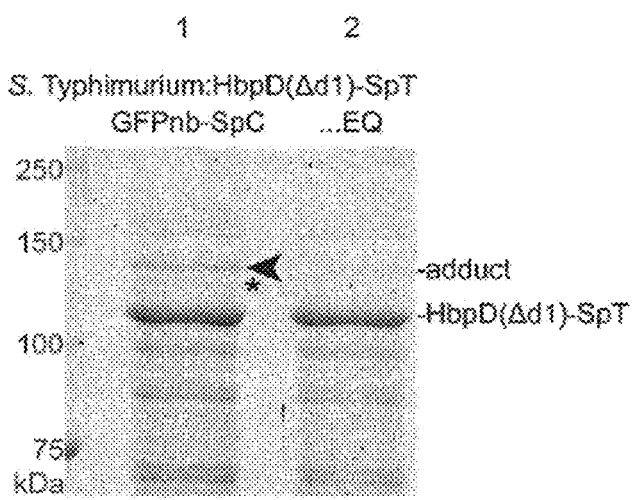
Figure 6B:
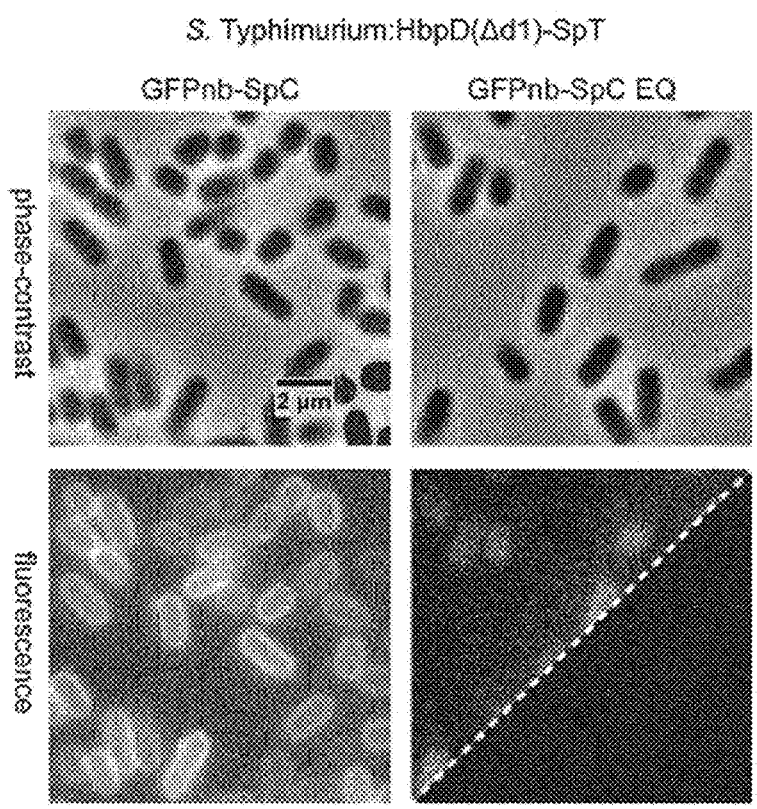

To provide proof of concept for coupling of nanobodies to Hbp on OMVs through Spy technology, we produced a fusion construct in which SpyCatcher and a GFP-specific nanobody (GFPnb; Kubala et al 2010, supra) are connected through a flexible linker to enable independent folding (SEQ ID NO: 15). Sequential incubation of HbpD(Δd1)-SpT decorated bacteria with purified GFPnb-SpC and GFP should lead to covalent coupling of GFPnb-SpC and binding of GFP provided that GFPnb is correctly folded in the context of the fusion construct. Consequently, the bacteria should get a green coat, which can be visualized by whole cell immunofluorescence. S. Typhimurium cells expressing HbpD(Δd1)-SpT (SEQ ID NO: 4) were first incubated with GFPnb-SpC (residues 25-245 of SEQ ID NO: 15) to allow coupling, which was confirmed by SDS-PAGE. As expected, an adduct of ~140 kDa was detected consistent with the combined mass of Hbp-SpT (117.1 kDa) and GFPnb-SpC (24.2 kDa) (FIG. 6A, lane 1). The cells were harvested and briefly incubated in PBS containing purified GFP (SEQ ID NO: 26). Whole cell immunofluorescence revealed a clear circumferential staining as expected for cells decorated with GFP (FIG. 6B).

As a control for non-specific interaction of GFP with the bacterial surface in this procedure, the same sequential labelling was carried out using a catalytically inactive SpyCatcher fused to GFPnb (SEQ ID NO: 16). The catalytic Glu77 in SpyCatcher was substituted by a Gln (SpC EQ) which has been shown to abolish covalent bond formation (Zackeri et al. 2012, supra). Using purified GFPnb-SpC EQ (residues 25-245 of SEQ ID NO: 16), the ~140 kDa adduct was not detected (FIG. 6A, lane 2) and surface labelling with GFP did not occur (FIG. 6B) confirming the specificity of the labelling procedure. Although GFP labelling is better suited for visualization using whole cells, the GFPnb-SpC coupling step was also shown to occur on the surface of OMVs decorated with Hbp-SpT again depending on the catalytic integrity of the SpyCatcher part of the GFPnb-SpC hybrid (FIG. 9).

Previously, a nanobody was inserted into Hbp to achieve display, but with limited success (Jong et al., PLoS One. 2018 Feb 7;13(2):e0191622) indicating that the nanobody is largely translocation-incompetent. In contrast, the observed efficient coupling of Catcher-nanobody chimeras to vesicles, shown in this example, will permit for instance targeted drug delivery in tumor tissue (Kijanka et al. 2015 Nanomedicine (London) 10(1): 161-74). For OMV vaccine development it will be interesting to include surface exposed nanobodies that recognize receptors specific for certain dendritic cell types. In this way, specific T-cell responses can be induced towards the presented antigens (Goyvaerts et al. 2015 J Immunol Res 2015:785634).

Example 5

Coupling of a Rat Antibody to the Surface of Bacterial Cells or Outer Membrane Vesicles This example illustrates successful and high-density coupling of a rat antibody (anti-mouse CD180) to the surface of bacterial cells or derived OMVs using isopeptide bonding technology. Furthermore, the example shows that the coupled antibodies are functional and, as a consequence, allows targeting of bacterial cells decorated with the antibodies to human cells expressing the antibody ligand.

To allow coupling of antibodies using isopeptide bonding technology, SpyTagged rat IgG2a antibodies were isolated directed against mouse CD180. To this end, plasmid constructs encoding anti-mouse CD180 antibodies comprising heavy chain Fc domains carrying a SpyTag at the extreme C-terminus (FIG. 11A) (SEQ ID NO: 27) were transfected to mammalian HEK cells and antibodies were produced and isolated as described (Vink et al., Methods. 2014 Jan. 1;65(1):5-10).

To couple SpyTagged anti-mouse CD180 (αCD180-SpT) to bacterial cells, 2 $OD_{660}$ units of *Salmonella* SL3261ΔdoIRA cells expressing HbpD(Δd1)-SpC (SEQ ID NO: 7) at the surface were overnight incubated with 200 μl of αCD180-SpT (0.5 mg/ml) at 4° C. (crude mix). Next day, to separate cell-coupled and non-coupled material, the mixture was centrifuged (centrifuge.) at low speed (5,000 rpm, 5 min) and the bacterial pellet and supernatant fraction were recovered. Subsequently, the bacterial pellet was resuspended in PBS to wash off loosely associated material (PBS wash). The cell suspension was subjected to low speed centrifugation (5,000 rpm, 5 min) and the bacterial pellet and supernatant were recovered. A sample of SL3261Δto/RA-HbpD(Δd1)-SpC before addition of αCD180-SpT of αCD180-SpT was analyzed by Coomassie stained SDS-PAGE (lane 1). Samples of the crude SL3261ΔdoIRA-HbpD(Δd1)-SpC+αCD180-SpT mix (lane 2) and pellet (p) and supernatant (s) after centrifugation (lanes 3 and 4) and PBS washing (lanes 5 and 6) were analyzed in parallel (FIG. 11, B). Molecular weight markers (kDa) are indicated at the left side of the panel.

The SDS-PAGE analysis shows that αCD180-SpT is covalently coupled to the 125 kDa cell surface expressed HbpD(Δd1)-SpC. This is illustrated by the appearance of a higher molecular weight adduct in the crude mix sample (lane 2), corresponding with a covalent fusion product comprising HbpD(Δd1)-SpC and the αCD180-SpT heavy chain. The appearance of the adduct coincides with the disappearance of non-coupled HbpD(Δd1)-SpC (c.f. lane 2 and 1). The adduct remains detectable in the bacterial pellet following centrifugation and PBS washing, underscoring the covalent association of αCD180-SpT with HbpD(Δd1)-SpC and association with the bacterial cell. Moreover, a band corresponding with the αCD180-SpT light chain remains detectable in the bacterial pellet following centrifugation and PBS washing. The non-covalently associated light chain is dissociated from the coupled HbpD(Δd1)-SpC αCD180-SpT fusion in denaturing conditions analysis, explaining its existence as a separate lower molecular weight protein entity upon SDS-PAGE analysis. Together, the data indicate that complete αCD180-SpT antibodies were successfully coupled to cell surface-exposed HbpD(Δd1) using isopeptide bonding technology.

To couple SpyTagged anti-mouse CD180 (αCD180-SpT) to OMVs, 20 μl of *Salmonella* SL3261ΔtoIRA OMVs expressing HbpD(Δd1)-SpC at the surface, obtained from a 20 $OD_{600}$ equivalent ($OD_{600}$×mL) of cell culture, were overnight incubated with 100 μl of αCD180-SpT (0.5 mg/ml) at 4° C. (crude mix). Next day, to separate cell-coupled and non-coupled material, the mixture was centrifuged (centrifuge.) at high speed (200.000×g, 30 min, 4° C.) and the OMV pellet and supernatant fraction were recovered. Subsequently, the OMV pellet was resuspended in PBS supplemented with 0.5 M NaCl to wash off material associated by electrostatic protein-protein interactions (Salt wash). The OMV suspension was subjected to high speed centrifugation (200.000×g, 30 min, 4° C.) and the bacterial pellet and supernatant were recovered. A sample of SL3261ΔtoIRA-HbpD(Δd1)-SpC OMVs before addition of αCD180-SpT of αCD180-SpT was analyzed by Coomassie stained SDS-PAGE (lane 1). Samples of the crude SL3261ΔtoIRA-HbpD(Δd1)-SpC OMVs +αCD180-SpT mix (lane 2) and pellet (p) and supernatant (s) after centrifugation (lanes 3 and 4) and Salt washing (lanes 5 and 6) were analyzed in parallel (FIG. 11). Molecular weight markers (kDa) are indicated at the left side of the panel.

The SDS-PAGE analysis shows that αCD180-SpT is covalently coupled to the 125 kDa HbpD(Δd1)-SpC expressed at the surface of OMVs. This is illustrated by the appearance of a higher molecular weight adduct in the crude mix sample (lane 2), corresponding with a covalent fusion product comprising HbpD(Δd1)-SpC and the αCD180-SpT heavy chain. The appearance of the adduct coincides with the disappearance of non-coupled HbpD(Δd1)-SpC (c.f. lane 2 and 1). The adduct remains detectable in the OMV pellet following centrifugation and Salt wash, underscoring the covalent association of αCD180-SpT with HbpD(Δd1)-SpC and association with the OMV particle. Moreover, a band corresponding with the αCD180-SpT light chain remains detectable in the OMV pellet following centrifugation and Salt washing. Together, the data indicate that complete αCD180-SpT antibodies were successfully coupled to HbpD(Δd1) at the OMV surface using isopeptide bonding technology.

To demonstrate the functionality of surface-coupled αCD180-SpT for the targeting of bacterial antigen delivery platforms to specific ligands, mammalian HeLa cells expressing murine CD180 were incubated with above-described SL3261ΔtoIRA-HbpD(Δd1)-SpC carrying covalently coupled αCD180-SpT. HeLa cells not expressing murine CD180 were used as a control. The HeLa cells, grown on IBIDI microscopy slides, were incubated with various loads of SL3261ΔtoIRA-HbpD(Δd1)-SpC-αCD180-SpT (multiplicity of infection, MOI: 5000, 500, 50 or 5) (2 h, 37° C., 8% $CO_2$). Upon incubation, the slides were washed with cell culture medium (DMEM+GlutaMAX, 10% FBS, penicillin/streptavidin) and fixed with 4% PFA in PBS (30 minutes, RT) before immersion into fresh PBS. HeLa cells were permeabilized with PBS+0.1% Triton-X100 (10 minutes, RT) before surface localized and internalized SL3261ΔtoIRA-HbpD(Δd1)-SpC-αCD180-SpT were detected by indirect immunofluorescence. In this procedure rabbit polyclonal αHbp (J40) was used as the primary antibody and goat-a-rabbit Alexa 488 as the secondary antibody. Hoechst stain and Phalloidin Alexa 568 were used to stain the DNA and actin content of the HeLa cells, respectively. Post-staining with 0.7% PFA was performed before analysis of the samples at an Olympus IX83 microscope. The median of the green fluorescence intensity per HeLa cell was determined making use of Cell profiler software (FIG. 12).

The data show significantly enhanced fluorescence intensity for HeLa cells expressing murine CD180 compared to HeLa cells not expressing the protein at MOI 5000 and 500. This result demonstrates that more SL3261ΔtoIRA-HbpD (Δd1)-SpC-αCD180-SpT bacteria were localized to the HeLa cells when CD180 was present at the cell surface. In turn, this demonstrates the functionality of αCD180-SpT coupled to SL3261ΔtoIRA-HbpD(Δd1)-SpC using isopeptide bonding technology. Moreover, the data indicate that covalent coupling of affinity molecule handles such as antibodies to bacterial cells and derived OMVs by isopeptide bonding technology is a valid approach to mediate the targeting of these bacterial cells or derived OMVs to specific ligands, cell types or tissues.

Example 6

Coupling of Catcher-Equipped Model Proteins to Tag Sequences Inserted at Position d2 and d4 of HbpD This example illustrates that ligation Tags expressed internally in OMV-surface exposed HbpD are functional for isopeptide bonding of model proteins carrying a cognate Catcher moiety.

Figures 13B, 13C:
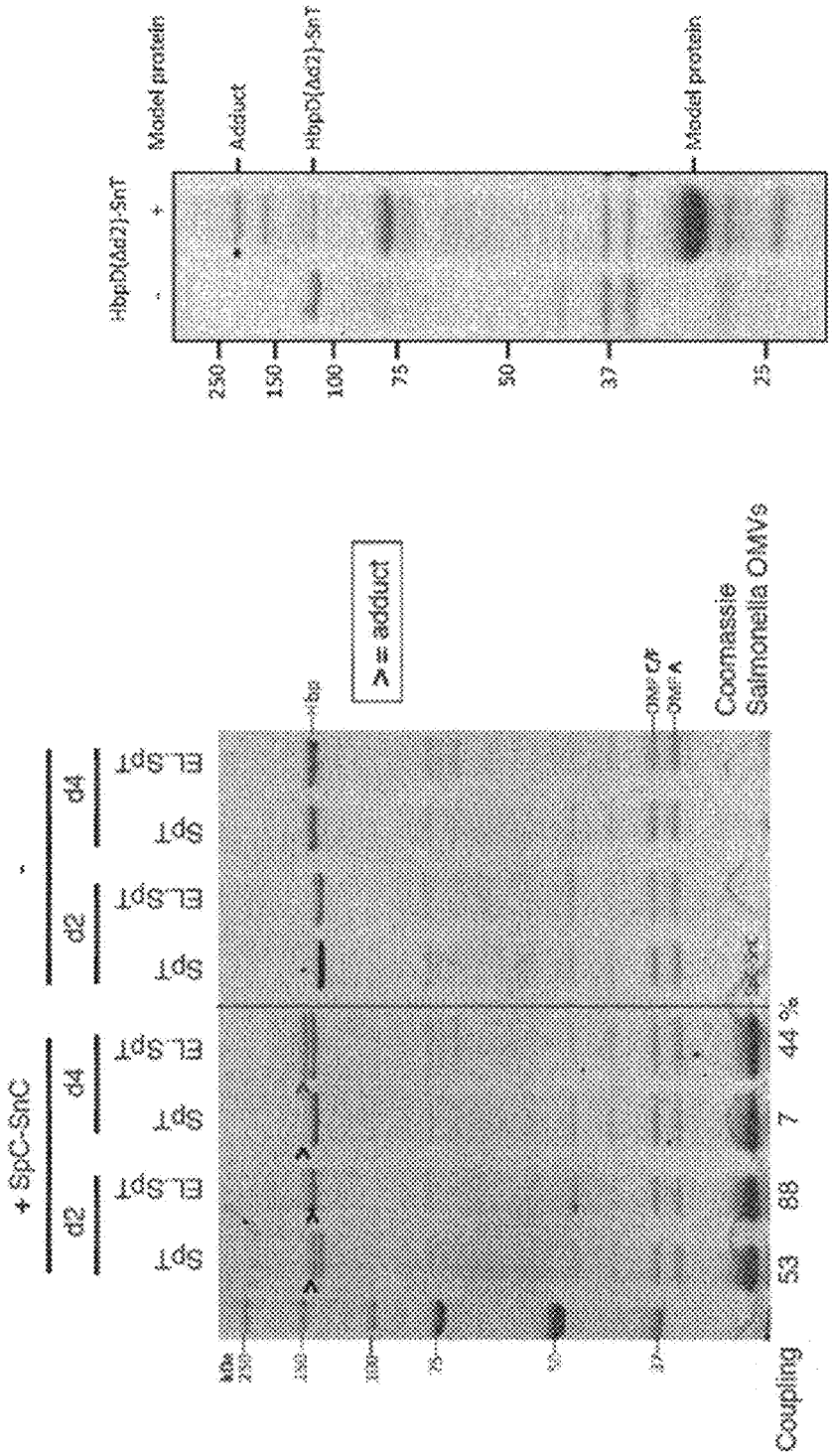

To demonstrate the functionality of internally inserted ligation tags, HbpD variants carrying a SpyTag (SpT; flanked by GSGSS and GSGSG linkers corresponding to residues 534-556 of SEQ ID NO: 9 and residues 760-782 of SEQ ID NO: 12, respectively) or SpyTag with extended linkers (EL.SpT; flanked by GSGSSGSASG and GEGTGGSGSG linkers corresponding to residues 534-566 of SEQ ID NO: 10 and residues 760-792 of SEQ ID NO: 13, respectively) at either position d2 (SEQ ID NO: 9; SEQ ID NO: 10, respectively) or d4 (SEQ ID NO: 12; SEQ ID NO: 13, respectively) of the passenger domain (FIG. 13A) were expressed in Salmonella Typhymurium SL3261ΔtoIRA. The resulting OMVs displaying the respective HbpD variants on the surface were harvested and incubated with a model protein comprising a SpyCatcher-SnoopCatcher fusion (SpC-SnC). Along same lines OMVs displaying HbpD carrying SnoopTag (SnT; flanked by GSGSS and GSGSG linkers corresponding to residues 534-555 of SEQ ID NO: 11) at position d2 of the passenger domain (SEQ ID NO: 11) (FIG. 13A) were prepared and incubated with Snoop-Catcher-containing model protein. Following overnight incubations at 4° C., OMV-model protein mixtures were subjected to SDS-PAGE/Coomassie analysis to assess covalent coupling of the model protein to the respective HbpD variants. Successful isopeptide bonding of the model protein to internal SpT and EL.SpT inserted at either position d2 or d4 of HbpD was observed (FIG. 13B). This is illustrated by the appearance of a higher molecular weight adduct (>) in the OMV samples upon incubation with the model protein. The adduct corresponds with a covalent fusion product between the (EL.)SpT-carrying HbpD-variants and the Spy-Catcher containing model protein. Similarly, successful coupling to SnT inserted at position d2 was observed, as illustrated by the appearance of a higher molecular weight adduct (*) upon incubation of OMVs expressing HbpD (Δd2)-SnT with SnC-model protein (FIG. 13C).

Example 7

Improved Display of a Complex Protein Using Isopeptide Bonding Technology

This example illustrates vastly improved display of complex proteins on the OMV surface when using isopeptide technology compared to conventional translational fusion to the passenger of an autotransporter.

Figure 14C:
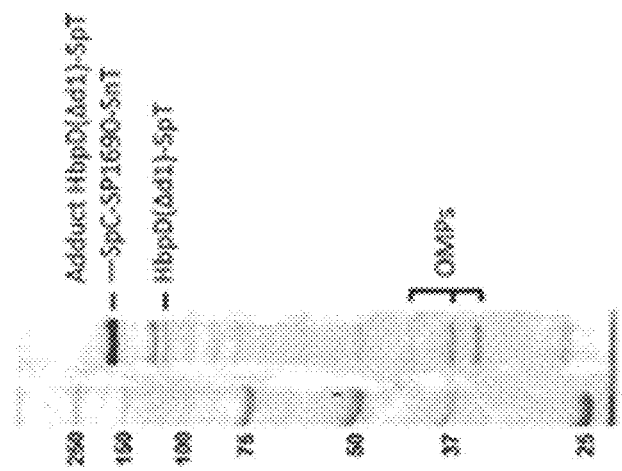
Figure 14B:
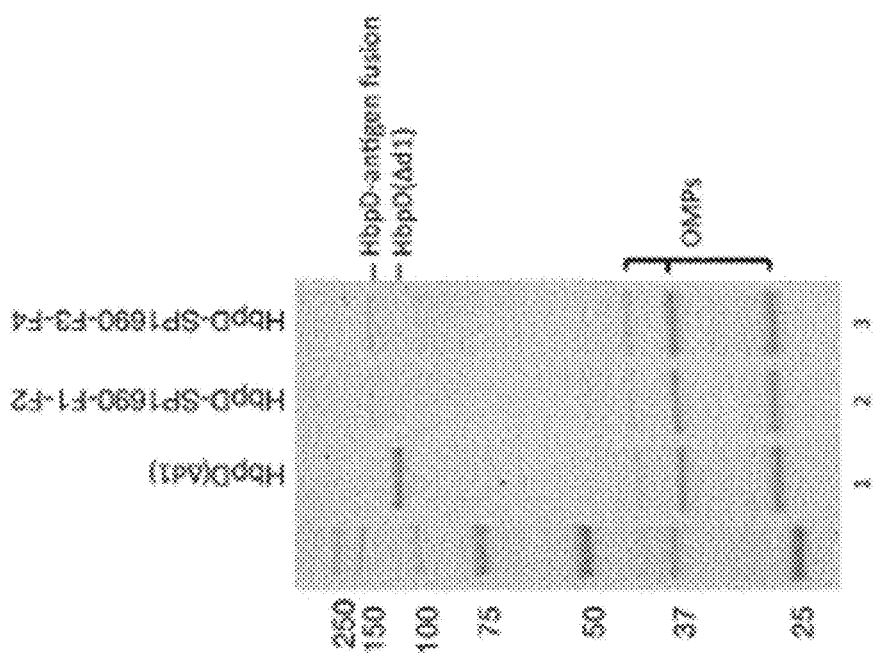
Figure 14A:
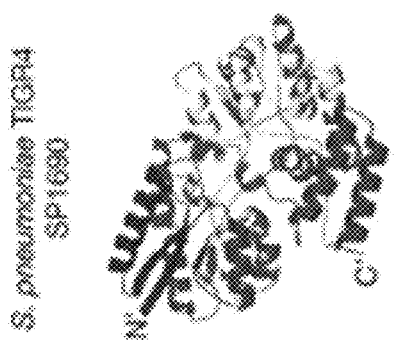

The 47.3-kDa conserved pneumococcal antigen SP1690 is a bulky and complex protein as shown by 3D structural modelling (Swissmodel of S. pneumoniae TIGR4 SP1690; FIG. 14A). Attempts to display intact TIGR4 SP1690 as a translational fusion to the passenger of HbpD were unsuccessful, necessitating the splitting of SP1690 into four fragments F1 (residues 30-130), F2 (residues 161-257), F3 (246-386) and F4 (residues 370-445) that were inserted into the passenger of two separate Hbp carriers (two fragments per carrier). The resulting fusion proteins HbpD-SP1690-F1-F2 (SEQ ID NO: 28) and HbpD-SP1690-F3-F4 (SEQ ID NO: 29) were displayed at the surface of OMVs but only in moderate amounts. This follows from SDS-PAGE/Coomassie analysis of Salmonella Typhimurium SL3161-derived OMVs displaying either HbpD-SP1690-F1-F2 or HbpD-SP1690-F3-F4 showing that both fusions are present in significantly lower amounts than the endogenous outer membrane proteins (OMPs) of the OMVs (FIG. 14B, lanes 2 and 3). In contrast, antigen-less HbpD(Δd1) (SEQ ID NO: 3) expressed in parallel under identical expression conditions (FIG. 14B, lane 1) is detected at a levels vastly exceeding those of the OMPs, indicating that the integration of antigens adversely affects the display capacity of the Hbp platform. In comparison to the translational fusion approach, clearly more favorable results are obtained when isopeptide bonding technology was used to mediate display of SP1690 at the OMV surface. To achieve this, Salmonella Typhimurium SL3161-derived OMVs displaying SpyTagged HbpD variant HbpD(Δd1)-SpT (SEQ ID NO: 4) at the surface were incubated with purified SP1690 carrying a SpyCatcher moiety (SpC-SP1690-SnT; SEQ ID NO: 24). Following a washing step to remove non-bound SpC-SP1690-SnT, the OMVs were analyzed by SDS-PAGE and Coomassie staining (FIG. 14C). An adduct was detected comprising a covalent fusion between HbpD(Δd1)-SpT and SpC-SP1690-SnT. The amounts of the adduct detected far exceeded those of the endogenous OMPs and were similar to those of antigen-less HbpD(Δd1) (FIG. 14B, lane 1).

These data clearly indicate that an isopeptide bonding approach favorably compares to translational fusion to Hbp because it allows for: 1) high-density display of complex proteins at bacterial-derived surfaces, and 2) surface display of complete complex proteins.

Example 8

Coupling of an Adhesin to the Surface of Gram-Negative Bacteria

This example illustrates that isopeptide bonding technology can be used to couple adhesins to the surface of Gram-negative bacteria. Furthermore it demonstrates that molecules that are incompatible with surface display upon integration into the autotransporter passengers can be displayed at the Gram-negative bacterial cell surface using isopeptide-bonding technology.

The fimbrial adhesin FimH is the best characterized adhesin derived from bacteria. FimH is responsible for D-mannose sensitive adhesion, which is mediated by its lectin domain $FimH_L$. The lectin domain contains two cysteine residues that form a disulphide bond in the bacterial periplasmic space. Integration of the domain into the passenger of an autotransporter can therefore not be used as a strategy to translocate the adhesin domain across at the bacterial cell envelope. As an alternative approach, we used isopeptide bond-mediated coupling to display $FimH_L$ at the surface of Escherichia coli cells. To this end, a chimeric protein was constructed and purified comprising $FimH_L$, a C-terminally attached SpyCatcher and a HisTag for purification purposes ($FimH_L$-SpC; residues 23-300 of SEQ ID NO: 30). Furthermore, E. coli TOP10F' cells displaying HbpD(Δd1)-SpT (SEQ ID NO: 4) were prepared. To allow coupling, 1.0 OD660 unit of cell material was incubated overnight with 50 μg of $FimH_L$-SpC at 4° C. Successful coupling was assessed by SDS-PAGE/Coomassie staining analysis of the sample in parallel to a TOP10F'/HbpD(Δd1)-SpT mock sample lacking $FimH_L$-SpC (FIG. 15).

Successful covalent coupling of SpyCatchered $FimH_L$ SpyTagged HbpD at the bacterial cell surface was demonstrated by the occurrence of higher molecular weight adduct upon incubation of TOP10F'/HbpD(Δd1)-SpT with $FimH_L$-SpC, comprising a covalent fusion between the two proteins. As expected, the appearance of the adduct coincides with the disappearance of significant amounts of non-coupled HbpD (Δd1)-SpT material compared to the situation in which no $FimH_L$-SpC was added to the cells. As a further control, no higher molecular weight adduct appeared under these latter conditions. Molecular weight markers (kDa) are indicated at the left side of the panel.

Incorporation of Material of ASCII Text Sequence Listing by Reference

The material in the ASCII text file sequence listing named, "DVME1076US_Corrected_Sequence_Listing_ST25" created on Jun. 30, 2020, which is 216 kb in size, is hereby incorporated by reference in its entirety herein.

The invention claimed is:

1. Gram-negative bacterial cells or Outer Membrane Vesicles (OMVs) derived there from which display on their outer surface an autotransporter (AT) fusion protein covalently coupled via an isopeptide bond to a heterologous molecule, wherein the AT fusion protein comprises at least one moiety of a Catcher/Tag ligation pair, and the heterologous molecule comprises the corresponding binding moiety of said Catcher/Tag ligation pair, wherein the Catcher/Tag ligation pair is derived from Streptococcal pilus proteins, the autotransporter protein is a serine protease autotransporter of Enterobacteriacea (SPATE) and the SPATE protein is selected from the group consisting of hemoglobin-binding protease (Hbp), extracellular serine protease (EspC) and temperature-sensitive hemagglutinin (Tsh) from *Escherichia coli*; and the autotransporter fusion protein comprises a mutation which prevents cleavage.

2. The bacterial cells or OMVs according to claim 1, wherein the Catcher/Tag litigation pair is derived from a Streptococcal protein selected from the group consisting of a major pilin protein Spy0128, a Fibronectin-binding protein FbaB of *Streptococcus pyogenes*, a Fibronectin-binding protein from *Streptococcus dysgalactiae*, and a pilus-subunit RrgA from *Streptococcus pneumoniae*.

3. The bacterial cells or OMVs according to claim 1, wherein the Catcher/Tag pair is selected from the group consisting of SpyTag/SpyCatcher and SnoopTag/Snoop-Catcher.

4. The bacterial cells or OMVs according to claim 1, wherein the SPATE protein is haemoglobin-binding protease (Hbp).

5. The bacterial cells or OMVs according claim 1, wherein the autotransporter fusion protein comprises a mutated autocatalytic cleavage site which prevents cleavage.

6. The bacterial cells or OMVs according to claim 1, wherein the bacterial cell is selected from the group consisting of *Escherichia coli* and *Salmonella* spp.

7. The bacterial cells or OMVs according to claim 1, wherein the bacterial cell is a subspecies of *S. enterica* subsp. *enterica*.

8. The bacterial cells or OMVs according to claim 1, wherein the heterologous molecule is selected from the group consisting of antigens, lectins, adhesins and affinity molecules.

9. The bacterial cells or OMVs according to claim 8, wherein the heterologous molecule is an antigen.

10. The bacterial cells, or OMVs according to claim 8, wherein the antigen is a string of multiple antigens.

11. The bacterial cells or OMVs according to claim 8, wherein the heterologous molecule is a lectin.

12. The bacterial cells or OMVs according to claim 8, wherein the heterologous molecule is an adhesin or affinity molecule.

13. The bacterial cells or OMVs according to claim 1, wherein the bacterial cell is a subspecies of a *S. Typhimurium* cell.

14. A method to prepare the Gram-negative bacterial cells or Outer Membrane Vesicles (OMVs) derived there from of claim 1, said method comprising;
   a) providing Gram-negative bacterial cells or Outer Membrane Vesicles (OMVs) which display on their outer surface the autotransporter (AT) fusion protein of claim 1 comprising at least one moiety of the Catcher/Tag ligation pair of claim 1,
   b) contacting the Gram-negative bacterial cells or the OMVs of step (a) with a heterologous molecule comprising the corresponding binding moiety of said Catcher/Tag ligation pair under conditions which allow the formation of an isopeptide bond between the autotransporter fusion protein and the heterologous molecule, and
   c) recovering the Gram-negative bacterial cells or the OMVs of claim 1.

15. A method comprising a step of using bacterial cells or OMVs according to claim 1 as a display platform for antigen delivery or as a drug-delivery vehicle.

* * * * *

SEQUENCE LISTING

```
<160> NUMBER OF SEQ ID NOS: 64

<210> SEQ ID NO 1
<211> LENGTH: 1377
<212> TYPE: PRT
<213> ORGANISM: Escherichia coli

<400> SEQUENCE: 1

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Leu Ile Pro Val Leu Phe Ser Ala
        35                  40                  45

Gly Ser Leu Ala Gly Thr Val Asn Asn Glu Leu Gly Tyr Gln Leu Phe
    50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

Ala Ala Met Pro Asp Phe Ser Ala Val Asp Ser Glu Ile Gly Val Ala
            100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160

Lys Leu Val Thr Glu Val Ala Pro Thr Ala Val Thr Ala Gln Gly Ala
                165                 170                 175

Val Ala Gly Ala Tyr Leu Asp Lys Glu Arg Tyr Pro Val Phe Tyr Arg
            180                 185                 190

Leu Gly Ser Gly Thr Gln Tyr Ile Lys Asp Ser Asn Gly Gln Leu Thr
        195                 200                 205

Lys Met Gly Gly Ala Tyr Ser Trp Leu Thr Gly Gly Thr Val Gly Ser
    210                 215                 220
```

-continued

Leu Ser Ser Tyr Gln Asn Gly Glu Met Ile Ser Thr Ser Ser Gly Leu
225                 230                 235                 240

Val Phe Asp Tyr Lys Leu Asn Gly Ala Met Pro Ile Tyr Gly Glu Ala
            245                 250                 255

Gly Asp Ser Gly Ser Pro Leu Phe Ala Phe Asp Thr Val Gln Asn Lys
        260                 265                 270

Trp Val Leu Val Gly Val Leu Thr Ala Gly Asn Gly Ala Gly Gly Arg
    275                 280                 285

Gly Asn Asn Trp Ala Val Ile Pro Leu Asp Phe Ile Gly Gln Lys Phe
290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
            325                 330                 335

Gln Gly Thr Thr Thr Tyr Ala Met His Gly Gln Gln Gly Asn Asp Leu
        340                 345                 350

Asn Ala Gly Lys Asn Leu Ile Phe Gln Gly Gln Asn Gly Gln Ile Asn
    355                 360                 365

Leu Lys Asp Ser Val Ser Gln Gly Ala Gly Ser Leu Thr Phe Arg Asp
370                 375                 380

Asn Tyr Thr Val Thr Thr Ser Asn Gly Ser Thr Trp Thr Gly Ala Gly
385                 390                 395                 400

Ile Val Val Asp Asn Gly Val Ser Val Asn Trp Gln Val Asn Gly Val
            405                 410                 415

Lys Gly Asp Asn Leu His Lys Ile Gly Glu Gly Thr Leu Thr Val Gln
        420                 425                 430

Gly Thr Gly Ile Asn Glu Gly Gly Leu Lys Val Gly Asp Gly Lys Val
    435                 440                 445

Val Leu Asn Gln Gln Ala Asp Asn Lys Gly Gln Val Gln Ala Phe Ser
450                 455                 460

Ser Val Asn Ile Ala Ser Gly Arg Pro Thr Val Val Leu Thr Asp Glu
465                 470                 475                 480

Arg Gln Val Asn Pro Asp Thr Val Ser Trp Gly Tyr Arg Gly Gly Thr
            485                 490                 495

Leu Asp Val Asn Gly Asn Ser Leu Thr Phe His Gln Leu Lys Ala Ala
        500                 505                 510

Asp Tyr Gly Ala Val Leu Ala Asn Asn Val Asp Lys Arg Ala Thr Ile
    515                 520                 525

Thr Leu Asp Tyr Ala Leu Arg Ala Asp Lys Val Ala Leu Asn Gly Trp
530                 535                 540

Ser Glu Ser Gly Lys Gly Thr Ala Gly Asn Leu Tyr Lys Tyr Asn Asn
545                 550                 555                 560

Pro Tyr Thr Asn Thr Thr Asp Tyr Phe Ile Leu Lys Gln Ser Thr Tyr
            565                 570                 575

Gly Tyr Phe Pro Thr Asp Gln Ser Ser Asn Ala Thr Trp Glu Phe Val
        580                 585                 590

Gly His Ser Gln Gly Asp Ala Gln Lys Leu Val Ala Asp Arg Phe Asn
    595                 600                 605

Thr Ala Gly Tyr Leu Phe His Gly Gln Leu Lys Gly Asn Leu Asn Val
610                 615                 620

Asp Asn Arg Leu Pro Glu Gly Val Thr Gly Ala Leu Val Met Asp Gly
625                 630                 635                 640

Ala Ala Asp Ile Ser Gly Thr Phe Thr Gln Glu Asn Gly Arg Leu Thr

-continued

```
                645                 650                 655
Leu Gln Gly His Pro Val Ile His Ala Tyr Asn Thr Gln Ser Val Ala
                    660                 665                 670
Asp Lys Leu Ala Ala Ser Gly Asp His Ser Val Leu Thr Gln Pro Thr
                    675                 680                 685
Ser Phe Ser Gln Glu Asp Trp Glu Asn Arg Ser Phe Thr Phe Asp Arg
                    690                 695                 700
Leu Ser Leu Lys Asn Thr Asp Phe Gly Leu Gly Arg Asn Ala Thr Leu
705                 710                 715                 720
Asn Thr Thr Ile Gln Ala Asp Asn Ser Ser Val Thr Leu Gly Asp Ser
                    725                 730                 735
Arg Val Phe Ile Asp Lys Asn Asp Gly Gln Gly Thr Ala Phe Thr Leu
                    740                 745                 750
Glu Glu Gly Thr Ser Val Ala Thr Lys Asp Ala Asp Lys Ser Val Phe
                    755                 760                 765
Asn Gly Thr Val Asn Leu Asp Asn Gln Ser Val Leu Asn Ile Asn Asp
                    770                 775                 780
Ile Phe Asn Gly Gly Ile Gln Ala Asn Asn Ser Thr Val Asn Ile Ser
785                 790                 795                 800
Ser Asp Ser Ala Val Leu Gly Asn Ser Thr Leu Ser Thr Ala Leu
                    805                 810                 815
Asn Leu Asn Lys Gly Ala Asn Ala Leu Ala Ser Gln Ser Phe Val Ser
                    820                 825                 830
Asp Gly Pro Val Asn Ile Ser Asp Ala Thr Leu Ser Leu Asn Ser Arg
                    835                 840                 845
Pro Asp Glu Val Ser His Thr Leu Leu Pro Val Tyr Asp Tyr Ala Gly
                    850                 855                 860
Ser Trp Asn Leu Lys Gly Asp Asp Ala Arg Leu Asn Val Gly Pro Tyr
865                 870                 875                 880
Ser Met Leu Ser Gly Asn Ile Asn Val Gln Asp Lys Gly Thr Val Thr
                    885                 890                 895
Leu Gly Gly Glu Gly Glu Leu Ser Pro Asp Leu Thr Leu Gln Asn Gln
                    900                 905                 910
Met Leu Tyr Ser Leu Phe Asn Gly Tyr Arg Asn Ile Trp Ser Gly Ser
                    915                 920                 925
Leu Asn Ala Pro Asp Ala Thr Val Ser Met Thr Asp Thr Gln Trp Ser
                    930                 935                 940
Met Asn Gly Asn Ser Thr Ala Gly Asn Met Lys Leu Asn Arg Thr Ile
945                 950                 955                 960
Val Gly Phe Asn Gly Gly Thr Ser Pro Phe Thr Thr Leu Thr Thr Asp
                    965                 970                 975
Asn Leu Asp Ala Val Gln Ser Ala Phe Val Met Arg Thr Asp Leu Asn
                    980                 985                 990
Lys Ala Asp Lys Leu Val Ile Asn Lys Ser Ala Thr Gly His Asp Asn
                    995                1000                1005
Ser Ile Trp Val Asn Phe Leu Lys Lys Pro Ser Asn Lys Asp Thr
                   1010                1015                1020
Leu Asp Ile Pro Leu Val Ser Ala Pro Glu Ala Thr Ala Asp Asn
                   1025                1030                1035
Leu Phe Arg Ala Ser Thr Arg Val Val Gly Phe Ser Asp Val Thr
                   1040                1045                1050
Pro Ile Leu Ser Val Arg Lys Glu Asp Gly Lys Lys Glu Trp Val
                   1055                1060                1065
```

-continued

Leu Asp Gly Tyr Gln Val Ala Arg Asn Asp Gly Gln Gly Lys Ala
    1070                1075                1080

Ala Ala Thr Phe Met His Ile Ser Tyr Asn Asn Phe Ile Thr Glu
    1085                1090                1095

Val Asn Asn Leu Asn Lys Arg Met Gly Asp Leu Arg Asp Ile Asn
    1100                1105                1110

Gly Glu Ala Gly Thr Trp Val Arg Leu Leu Asn Gly Ser Gly Ser
    1115                1120                1125

Ala Asp Gly Gly Phe Thr Asp His Tyr Thr Leu Leu Gln Met Gly
    1130                1135                1140

Ala Asp Arg Lys His Glu Leu Gly Ser Met Asp Leu Phe Thr Gly
    1145                1150                1155

Val Met Ala Thr Tyr Thr Asp Thr Asp Ala Ser Ala Asp Leu Tyr
    1160                1165                1170

Ser Gly Lys Thr Lys Ser Trp Gly Gly Phe Tyr Ala Ser Gly
    1175                1180                1185

Leu Phe Arg Ser Gly Ala Tyr Phe Asp Val Ile Ala Lys Tyr Ile
    1190                1195                1200

His Asn Glu Asn Lys Tyr Asp Leu Asn Phe Ala Gly Ala Gly Lys
    1205                1210                1215

Gln Asn Phe Arg Ser His Ser Leu Tyr Ala Gly Ala Glu Val Gly
    1220                1225                1230

Tyr Arg Tyr His Leu Thr Asp Thr Thr Phe Val Glu Pro Gln Ala
    1235                1240                1245

Glu Leu Val Trp Gly Arg Leu Gln Gly Gln Thr Phe Asn Trp Asn
    1250                1255                1260

Asp Ser Gly Met Asp Val Ser Met Arg Arg Asn Ser Val Asn Pro
    1265                1270                1275

Leu Val Gly Arg Thr Gly Val Val Ser Gly Lys Thr Phe Ser Gly
    1280                1285                1290

Lys Asp Trp Ser Leu Thr Ala Arg Ala Gly Leu His Tyr Glu Phe
    1295                1300                1305

Asp Leu Thr Asp Ser Ala Asp Val His Leu Lys Asp Ala Ala Gly
    1310                1315                1320

Glu His Gln Ile Asn Gly Arg Lys Asp Ser Arg Met Leu Tyr Gly
    1325                1330                1335

Val Gly Leu Asn Ala Arg Phe Gly Asp Asn Thr Arg Leu Gly Leu
    1340                1345                1350

Glu Val Glu Arg Ser Ala Phe Gly Lys Tyr Asn Thr Asp Asp Ala
    1355                1360                1365

Ile Asn Ala Asn Ile Arg Tyr Ser Phe
    1370                1375

<210> SEQ ID NO 2
<211> LENGTH: 1377
<212> TYPE: PRT
<213> ORGANISM: Unknown
<220> FEATURE:
<223> OTHER INFORMATION: Escherichia coli

<400> SEQUENCE: 2

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

```
Arg Leu Cys Phe Pro Val Leu Leu Ile Pro Val Leu Phe Ser Ala
        35                  40                  45

Gly Ser Leu Ala Gly Thr Val Asn Asn Glu Leu Gly Tyr Gln Leu Phe
    50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

Ala Ala Met Pro Asp Phe Ser Ala Val Asp Ser Glu Ile Gly Val Ala
            100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160

Lys Leu Val Thr Glu Val Ala Pro Thr Ala Val Thr Ala Gln Gly Ala
                165                 170                 175

Val Ala Gly Ala Tyr Leu Asp Lys Glu Arg Tyr Pro Val Phe Tyr Arg
            180                 185                 190

Leu Gly Ser Gly Thr Gln Tyr Ile Lys Asp Ser Asn Gly Gln Leu Thr
        195                 200                 205

Lys Met Gly Gly Ala Tyr Ser Trp Leu Thr Gly Gly Thr Val Gly Ser
    210                 215                 220

Leu Ser Ser Tyr Gln Asn Gly Glu Met Ile Ser Thr Ser Ser Gly Leu
225                 230                 235                 240

Val Phe Asp Tyr Lys Leu Asn Gly Ala Met Pro Ile Tyr Gly Glu Ala
                245                 250                 255

Gly Asp Ser Gly Ser Pro Leu Phe Ala Phe Asp Thr Val Gln Asn Lys
            260                 265                 270

Trp Val Leu Val Gly Val Leu Thr Ala Gly Asn Gly Ala Gly Gly Arg
        275                 280                 285

Gly Asn Asn Trp Ala Val Ile Pro Leu Asp Phe Ile Gly Gln Lys Phe
    290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
                325                 330                 335

Gln Gly Thr Thr Thr Tyr Ala Met His Gly Gln Gly Asn Asp Leu
            340                 345                 350

Asn Ala Gly Lys Asn Leu Ile Phe Gln Gly Gln Asn Gly Gln Ile Asn
        355                 360                 365

Leu Lys Asp Ser Val Ser Gln Gly Ala Gly Ser Leu Thr Phe Arg Asp
    370                 375                 380

Asn Tyr Thr Val Thr Thr Ser Asn Gly Ser Thr Trp Thr Gly Ala Gly
385                 390                 395                 400

Ile Val Val Asp Asn Gly Val Ser Val Asn Trp Gln Val Asn Gly Val
                405                 410                 415

Lys Gly Asp Asn Leu His Lys Ile Gly Glu Gly Thr Leu Thr Val Gln
            420                 425                 430

Gly Thr Gly Ile Asn Glu Gly Gly Leu Lys Val Gly Asp Gly Lys Val
        435                 440                 445
```

```
Val Leu Asn Gln Gln Ala Asp Asn Lys Gly Gln Val Gln Ala Phe Ser
    450                 455                 460

Ser Val Asn Ile Ala Ser Gly Arg Pro Thr Val Val Leu Thr Asp Glu
465                 470                 475                 480

Arg Gln Val Asn Pro Asp Thr Val Ser Trp Gly Tyr Arg Gly Gly Thr
                485                 490                 495

Leu Asp Val Asn Gly Asn Ser Leu Thr Phe His Gln Leu Lys Ala Ala
                500                 505                 510

Asp Tyr Gly Ala Val Leu Ala Asn Val Asp Lys Arg Ala Thr Ile
                515                 520                 525

Thr Leu Asp Tyr Ala Leu Arg Ala Asp Lys Val Ala Leu Asn Gly Trp
530                 535                 540

Ser Glu Ser Gly Lys Gly Thr Ala Gly Asn Leu Tyr Lys Tyr Asn Asn
545                 550                 555                 560

Pro Tyr Thr Asn Thr Thr Asp Tyr Phe Ile Leu Lys Gln Ser Thr Tyr
                565                 570                 575

Gly Tyr Phe Pro Thr Asp Gln Ser Ser Asn Ala Thr Trp Glu Phe Val
                580                 585                 590

Gly His Ser Gln Gly Asp Ala Gln Lys Leu Val Ala Asp Arg Phe Asn
                595                 600                 605

Thr Ala Gly Tyr Leu Phe His Gly Gln Leu Lys Gly Asn Leu Asn Val
                610                 615                 620

Asp Asn Arg Leu Pro Glu Gly Val Thr Gly Ala Leu Val Met Asp Gly
625                 630                 635                 640

Ala Ala Asp Ile Ser Gly Thr Phe Thr Gln Glu Asn Gly Arg Leu Thr
                645                 650                 655

Leu Gln Gly His Pro Val Ile His Ala Tyr Asn Thr Gln Ser Val Ala
                660                 665                 670

Asp Lys Leu Ala Ala Ser Gly Asp His Ser Val Leu Thr Gln Pro Thr
                675                 680                 685

Ser Phe Ser Gln Glu Asp Trp Glu Asn Arg Ser Phe Thr Phe Asp Arg
690                 695                 700

Leu Ser Leu Lys Asn Thr Asp Phe Gly Leu Gly Arg Asn Ala Thr Leu
705                 710                 715                 720

Asn Thr Thr Ile Gln Ala Asp Asn Ser Ser Val Thr Leu Gly Asp Ser
                725                 730                 735

Arg Val Phe Ile Asp Lys Asn Asp Gly Gln Gly Thr Ala Phe Thr Leu
                740                 745                 750

Glu Glu Gly Thr Ser Val Ala Thr Lys Asp Ala Asp Lys Ser Val Phe
                755                 760                 765

Asn Gly Thr Val Asn Leu Asp Asn Gln Ser Val Leu Asn Ile Asn Asp
770                 775                 780

Ile Phe Asn Gly Gly Ile Gln Ala Asn Asn Ser Thr Val Asn Ile Ser
785                 790                 795                 800

Ser Asp Ser Ala Val Leu Gly Asn Ser Thr Leu Thr Ser Thr Ala Leu
                805                 810                 815

Asn Leu Asn Lys Gly Ala Asn Ala Leu Ala Ser Gln Ser Phe Val Ser
                820                 825                 830

Asp Gly Pro Val Asn Ile Ser Asp Ala Thr Leu Ser Leu Asn Ser Arg
                835                 840                 845

Pro Asp Glu Val Ser His Thr Leu Leu Pro Val Tyr Asp Tyr Ala Gly
                850                 855                 860

Ser Trp Asn Leu Lys Gly Asp Asp Ala Arg Leu Asn Val Gly Pro Tyr
```

-continued

```
            865                 870                 875                 880
        Ser Met Leu Ser Gly Asn Ile Asn Val Gln Asp Lys Gly Thr Val Thr
                        885                 890                 895
        Leu Gly Gly Glu Gly Glu Leu Ser Pro Asp Leu Thr Leu Gln Asn Gln
                        900                 905                 910
        Met Leu Tyr Ser Leu Phe Asn Gly Tyr Arg Asn Ile Trp Ser Gly Ser
                        915                 920                 925
        Leu Asn Ala Pro Asp Ala Thr Val Ser Met Asp Thr Gln Trp Ser
                        930                 935                 940
        Met Asn Gly Asn Ser Thr Ala Gly Asn Met Lys Leu Asn Arg Thr Ile
        945                 950                 955                 960
        Val Gly Phe Asn Gly Gly Thr Ser Pro Phe Thr Thr Leu Thr Thr Asp
                        965                 970                 975
        Asn Leu Asp Ala Val Gln Ser Ala Phe Val Met Arg Thr Asp Leu Asn
                        980                 985                 990
        Lys Ala Asp Lys Leu Val Ile Asn Lys Ser Ala Thr Gly His Asp Asn
                        995                 1000                1005
        Ser Ile Trp Val Asn Phe Leu Lys Lys Pro Ser Asn Lys Asp Thr
        1010                1015                1020
        Leu Asp Ile Pro Leu Val Ser Ala Pro Glu Ala Thr Ala Asp Asn
        1025                1030                1035
        Leu Phe Arg Ala Ser Thr Arg Val Val Gly Phe Ser Asp Val Thr
        1040                1045                1050
        Pro Ile Leu Ser Val Arg Lys Glu Asp Gly Lys Lys Glu Trp Val
        1055                1060                1065
        Leu Asp Gly Tyr Gln Val Ala Arg Asn Asp Gly Gln Gly Lys Ala
        1070                1075                1080
        Ala Ala Thr Phe Met His Ile Ser Tyr Asn Asn Phe Ile Thr Glu
        1085                1090                1095
        Val Gly Ser Leu Asn Lys Arg Met Gly Asp Leu Arg Asp Ile Asn
        1100                1105                1110
        Gly Glu Ala Gly Thr Trp Val Arg Leu Leu Asn Gly Ser Gly Ser
        1115                1120                1125
        Ala Asp Gly Gly Phe Thr Asp His Tyr Thr Leu Leu Gln Met Gly
        1130                1135                1140
        Ala Asp Arg Lys His Glu Leu Gly Ser Met Asp Leu Phe Thr Gly
        1145                1150                1155
        Val Met Ala Thr Tyr Thr Asp Thr Asp Ala Ser Ala Asp Leu Tyr
        1160                1165                1170
        Ser Gly Lys Thr Lys Ser Trp Gly Gly Gly Phe Tyr Ala Ser Gly
        1175                1180                1185
        Leu Phe Arg Ser Gly Ala Tyr Phe Asp Val Ile Ala Lys Tyr Ile
        1190                1195                1200
        His Asn Glu Asn Lys Tyr Asp Leu Asn Phe Ala Gly Ala Gly Lys
        1205                1210                1215
        Gln Asn Phe Arg Ser His Ser Leu Tyr Ala Gly Ala Glu Val Gly
        1220                1225                1230
        Tyr Arg Tyr His Leu Thr Asp Thr Thr Phe Val Glu Pro Gln Ala
        1235                1240                1245
        Glu Leu Val Trp Gly Arg Leu Gln Gly Gln Thr Phe Asn Trp Asn
        1250                1255                1260
        Asp Ser Gly Met Asp Val Ser Met Arg Arg Asn Ser Val Asn Pro
        1265                1270                1275
```

-continued

```
Leu Val Gly Arg Thr Gly Val Val Ser Gly Lys Thr Phe Ser Gly
    1280                1285                1290

Lys Asp Trp Ser Leu Thr Ala Arg Ala Gly Leu His Tyr Glu Phe
    1295                1300                1305

Asp Leu Thr Asp Ser Ala Asp Val His Leu Lys Asp Ala Ala Gly
    1310                1315                1320

Glu His Gln Ile Asn Gly Arg Lys Asp Ser Arg Met Leu Tyr Gly
    1325                1330                1335

Val Gly Leu Asn Ala Arg Phe Gly Asp Asn Thr Arg Leu Gly Leu
    1340                1345                1350

Glu Val Glu Arg Ser Ala Phe Gly Lys Tyr Asn Thr Asp Asp Ala
    1355                1360                1365

Ile Asn Ala Asn Ile Arg Tyr Ser Phe
    1370                1375

<210> SEQ ID NO 3
<211> LENGTH: 1131
<212> TYPE: PRT
<213> ORGANISM: Unknown
<220> FEATURE:
<223> OTHER INFORMATION: Escherichia coli

<400> SEQUENCE: 3

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
                20                  25                  30

Arg Leu Cys Phe Pro Val Leu Leu Leu Ile Pro Val Leu Phe Ser Ala
                35                  40                  45

Gly Ser Leu Ala Gly Ser Ser Cys Gly Ser Gly Ser Gly Asn Asp Ala
    50                  55                  60

Pro Val Thr Phe Arg Thr Ser Glu Gly Ala Leu Glu Trp Ser Phe
65                  70                  75                  80

Asn Ser Ser Thr Gly Ala Gly Ala Leu Thr Gln Gly Thr Thr Tyr
                85                  90                  95

Ala Met His Gly Gln Gln Gly Asn Asp Leu Asn Ala Gly Lys Asn Leu
                100                 105                 110

Ile Phe Gln Gly Gln Asn Gly Gln Ile Asn Leu Lys Asp Ser Val Ser
                115                 120                 125

Gln Gly Ala Gly Ser Leu Thr Phe Arg Asp Asn Tyr Thr Val Thr Thr
    130                 135                 140

Ser Asn Gly Ser Thr Trp Thr Gly Ala Gly Ile Val Val Asp Asn Gly
145                 150                 155                 160

Val Ser Val Asn Trp Gln Val Asn Gly Val Lys Gly Asp Asn Leu His
                165                 170                 175

Lys Ile Gly Glu Gly Thr Leu Thr Val Gln Gly Thr Gly Ile Asn Glu
                180                 185                 190

Gly Gly Leu Lys Val Gly Asp Gly Lys Val Val Leu Asn Gln Gln Ala
                195                 200                 205

Asp Asn Lys Gly Gln Val Gln Ala Phe Ser Ser Val Asn Ile Ala Ser
    210                 215                 220

Gly Arg Pro Thr Val Val Leu Thr Asp Glu Arg Gln Val Asn Pro Asp
225                 230                 235                 240

Thr Val Ser Trp Gly Tyr Arg Gly Gly Thr Leu Asp Val Asn Gly Asn
                245                 250                 255
```

-continued

```
Ser Leu Thr Phe His Gln Leu Lys Ala Ala Asp Tyr Gly Ala Val Leu
            260                 265                 270

Ala Asn Asn Val Asp Lys Arg Ala Thr Ile Thr Leu Asp Tyr Ala Leu
        275                 280                 285

Arg Ala Asp Lys Val Ala Leu Asn Gly Trp Ser Glu Ser Gly Lys Gly
290                 295                 300

Thr Ala Gly Asn Leu Tyr Lys Tyr Asn Asn Pro Tyr Thr Asn Thr Thr
305                 310                 315                 320

Asp Tyr Phe Ile Leu Lys Gln Ser Thr Tyr Gly Tyr Phe Pro Thr Asp
                325                 330                 335

Gln Ser Ser Asn Ala Thr Trp Glu Phe Val Gly His Ser Gln Gly Asp
            340                 345                 350

Ala Gln Lys Leu Val Ala Asp Arg Phe Asn Thr Ala Gly Tyr Leu Phe
        355                 360                 365

His Gly Gln Leu Lys Gly Asn Leu Asn Val Asp Asn Arg Leu Pro Glu
    370                 375                 380

Gly Val Thr Gly Ala Leu Val Met Asp Gly Ala Ala Asp Ile Ser Gly
385                 390                 395                 400

Thr Phe Thr Gln Glu Asn Gly Arg Leu Thr Leu Gln Gly His Pro Val
                405                 410                 415

Ile His Ala Tyr Asn Thr Gln Ser Val Ala Asp Lys Leu Ala Ala Ser
            420                 425                 430

Gly Asp His Ser Val Leu Thr Gln Pro Thr Ser Phe Ser Gln Glu Asp
        435                 440                 445

Trp Glu Asn Arg Ser Phe Thr Phe Asp Arg Leu Ser Leu Lys Asn Thr
    450                 455                 460

Asp Phe Gly Leu Gly Arg Asn Ala Thr Leu Asn Thr Thr Ile Gln Ala
465                 470                 475                 480

Asp Asn Ser Ser Val Thr Leu Gly Asp Ser Arg Val Phe Ile Asp Lys
                485                 490                 495

Asn Asp Gly Gln Gly Thr Ala Phe Thr Leu Glu Glu Gly Thr Ser Val
            500                 505                 510

Ala Thr Lys Asp Ala Asp Lys Ser Val Phe Asn Gly Thr Val Asn Leu
        515                 520                 525

Asp Asn Gln Ser Val Leu Asn Ile Asn Asp Ile Phe Asn Gly Gly Ile
    530                 535                 540

Gln Ala Asn Asn Ser Thr Val Asn Ile Ser Ser Asp Ser Ala Val Leu
545                 550                 555                 560

Gly Asn Ser Thr Leu Thr Ser Thr Ala Leu Asn Leu Asn Lys Gly Ala
                565                 570                 575

Asn Ala Leu Ala Ser Gln Ser Phe Val Ser Asp Gly Pro Val Asn Ile
            580                 585                 590

Ser Asp Ala Thr Leu Ser Leu Asn Ser Arg Pro Asp Glu Val Ser His
        595                 600                 605

Thr Leu Leu Pro Val Tyr Asp Tyr Ala Gly Ser Trp Asn Leu Lys Gly
    610                 615                 620

Asp Asp Ala Arg Leu Asn Val Gly Pro Tyr Ser Met Leu Ser Gly Asn
625                 630                 635                 640

Ile Asn Val Gln Asp Lys Gly Thr Val Thr Leu Gly Gly Glu Gly Glu
                645                 650                 655

Leu Ser Pro Asp Leu Thr Leu Gln Asn Gln Met Leu Tyr Ser Leu Phe
            660                 665                 670
```

-continued

Asn Gly Tyr Arg Asn Ile Trp Ser Gly Ser Leu Asn Ala Pro Asp Ala
                675                 680                 685

Thr Val Ser Met Thr Asp Thr Gln Trp Ser Met Asn Gly Asn Ser Thr
690                 695                 700

Ala Gly Asn Met Lys Leu Asn Arg Thr Ile Val Gly Phe Asn Gly Gly
705                 710                 715                 720

Thr Ser Pro Phe Thr Thr Leu Thr Thr Asp Asn Leu Asp Ala Val Gln
                725                 730                 735

Ser Ala Phe Val Met Arg Thr Asp Leu Asn Lys Ala Asp Lys Leu Val
                740                 745                 750

Ile Asn Lys Ser Ala Thr Gly His Asp Asn Ser Ile Trp Val Asn Phe
                755                 760                 765

Leu Lys Lys Pro Ser Asn Lys Asp Thr Leu Asp Ile Pro Leu Val Ser
770                 775                 780

Ala Pro Glu Ala Thr Ala Asp Asn Leu Phe Arg Ala Ser Thr Arg Val
785                 790                 795                 800

Val Gly Phe Ser Asp Val Thr Pro Ile Leu Ser Val Arg Lys Glu Asp
                805                 810                 815

Gly Lys Lys Glu Trp Val Leu Asp Gly Tyr Gln Val Ala Arg Asn Asp
                820                 825                 830

Gly Gln Gly Lys Ala Ala Ala Thr Phe Met His Ile Ser Tyr Asn Asn
                835                 840                 845

Phe Ile Thr Glu Val Gly Ser Leu Asn Lys Arg Met Gly Asp Leu Arg
                850                 855                 860

Asp Ile Asn Gly Glu Ala Gly Thr Trp Val Arg Leu Leu Asn Gly Ser
865                 870                 875                 880

Gly Ser Ala Asp Gly Gly Phe Thr Asp His Tyr Thr Leu Leu Gln Met
                885                 890                 895

Gly Ala Asp Arg Lys His Glu Leu Gly Ser Met Asp Leu Phe Thr Gly
                900                 905                 910

Val Met Ala Thr Tyr Thr Asp Thr Asp Ala Ser Ala Asp Leu Tyr Ser
                915                 920                 925

Gly Lys Thr Lys Ser Trp Gly Gly Phe Tyr Ala Ser Gly Leu Phe
930                 935                 940

Arg Ser Gly Ala Tyr Phe Asp Val Ile Ala Lys Tyr Ile His Asn Glu
945                 950                 955                 960

Asn Lys Tyr Asp Leu Asn Phe Ala Gly Ala Gly Lys Gln Asn Phe Arg
                965                 970                 975

Ser His Ser Leu Tyr Ala Gly Ala Glu Val Gly Tyr Arg Tyr His Leu
                980                 985                 990

Thr Asp Thr Thr Phe Val Glu Pro Gln Ala Glu Leu Val Trp Gly Arg
                995                 1000                1005

Leu Gln Gly Gln Thr Phe Asn Trp Asn Asp Ser Gly Met Asp Val
        1010                1015                1020

Ser Met Arg Arg Asn Ser Val Asn Pro Leu Val Gly Arg Thr Gly
        1025                1030                1035

Val Val Ser Gly Lys Thr Phe Ser Gly Lys Asp Trp Ser Leu Thr
        1040                1045                1050

Ala Arg Ala Gly Leu His Tyr Glu Phe Asp Leu Thr Asp Ser Ala
        1055                1060                1065

Asp Val His Leu Lys Asp Ala Ala Gly Glu His Gln Ile Asn Gly
        1070                1075                1080

Arg Lys Asp Ser Arg Met Leu Tyr Gly Val Gly Leu Asn Ala Arg

```
        1085                1090                1095

Phe Gly  Asp Asn Thr Arg Leu  Gly Leu Glu Val Glu  Arg Ser Ala
        1100                1105                1110

Phe Gly  Lys Tyr Asn Thr Asp  Asp Ala Ile Asn Ala  Asn Ile Arg
        1115                1120                1125

Tyr Ser  Phe
        1130

<210> SEQ ID NO 4
<211> LENGTH: 1143
<212> TYPE: PRT
<213> ORGANISM: Unknown
<220> FEATURE:
<223> OTHER INFORMATION: Escherichia coli - Streptococcus pyogenes

<400> SEQUENCE: 4

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
                20                  25                  30

Arg Leu Cys Phe Pro Val Leu Leu Leu Ile Pro Val Leu Phe Ser Ala
            35                  40                  45

Gly Ser Leu Ala Gly Ser Ser Ala His Ile Val Met Val Asp Ala Tyr
        50                  55                  60

Lys Pro Thr Lys Gly Ser Gly Ser Gly Asn Asp Ala Pro Val Thr Phe
65                  70                  75                  80

Arg Thr Ser Glu Gly Gly Ala Leu Glu Trp Ser Phe Asn Ser Ser Thr
                85                  90                  95

Gly Ala Gly Ala Leu Thr Gln Gly Thr Thr Thr Tyr Ala Met His Gly
            100                 105                 110

Gln Gln Gly Asn Asp Leu Asn Ala Gly Lys Asn Leu Ile Phe Gln Gly
        115                 120                 125

Gln Asn Gly Gln Ile Asn Leu Lys Asp Ser Val Ser Gln Gly Ala Gly
    130                 135                 140

Ser Leu Thr Phe Arg Asp Asn Tyr Thr Val Thr Thr Ser Asn Gly Ser
145                 150                 155                 160

Thr Trp Thr Gly Ala Gly Ile Val Val Asp Asn Gly Val Ser Val Asn
                165                 170                 175

Trp Gln Val Asn Gly Val Lys Gly Asp Asn Leu His Lys Ile Gly Glu
            180                 185                 190

Gly Thr Leu Thr Val Gln Gly Thr Gly Ile Asn Glu Gly Gly Leu Lys
        195                 200                 205

Val Gly Asp Gly Lys Val Val Leu Asn Gln Gln Ala Asp Asn Lys Gly
    210                 215                 220

Gln Val Gln Ala Phe Ser Ser Val Asn Ile Ala Ser Gly Arg Pro Thr
225                 230                 235                 240

Val Val Leu Thr Asp Glu Arg Gln Val Asn Pro Asp Thr Val Ser Trp
                245                 250                 255

Gly Tyr Arg Gly Gly Thr Leu Asp Val Asn Gly Asn Ser Leu Thr Phe
            260                 265                 270

His Gln Leu Lys Ala Ala Asp Tyr Gly Ala Val Leu Ala Asn Asn Val
        275                 280                 285

Asp Lys Arg Ala Thr Ile Thr Leu Asp Tyr Ala Leu Arg Ala Asp Lys
    290                 295                 300

Val Ala Leu Asn Gly Trp Ser Glu Ser Gly Lys Gly Thr Ala Gly Asn
```

```
            305                 310                 315                 320
Leu Tyr Lys Tyr Asn Asn Pro Tyr Thr Asn Thr Thr Asp Tyr Phe Ile
                325                 330                 335

Leu Lys Gln Ser Thr Tyr Gly Tyr Phe Pro Thr Asp Gln Ser Ser Asn
                340                 345                 350

Ala Thr Trp Glu Phe Val Gly His Ser Gln Gly Asp Ala Gln Lys Leu
                355                 360                 365

Val Ala Asp Arg Phe Asn Thr Ala Gly Tyr Leu Phe His Gly Gln Leu
                370                 375                 380

Lys Gly Asn Leu Asn Val Asp Asn Arg Leu Pro Glu Gly Val Thr Gly
385                 390                 395                 400

Ala Leu Val Met Asp Gly Ala Ala Asp Ile Ser Gly Thr Phe Thr Gln
                405                 410                 415

Glu Asn Gly Arg Leu Thr Leu Gln Gly His Pro Val Ile His Ala Tyr
                420                 425                 430

Asn Thr Gln Ser Val Ala Asp Lys Leu Ala Ala Ser Gly Asp His Ser
                435                 440                 445

Val Leu Thr Gln Pro Thr Ser Phe Ser Gln Glu Asp Trp Glu Asn Arg
450                 455                 460

Ser Phe Thr Phe Asp Arg Leu Ser Leu Lys Asn Thr Asp Phe Gly Leu
465                 470                 475                 480

Gly Arg Asn Ala Thr Leu Asn Thr Thr Ile Gln Ala Asp Asn Ser Ser
                485                 490                 495

Val Thr Leu Gly Asp Ser Arg Val Phe Ile Asp Lys Asn Asp Gly Gln
                500                 505                 510

Gly Thr Ala Phe Thr Leu Glu Glu Gly Thr Ser Val Ala Thr Lys Asp
                515                 520                 525

Ala Asp Lys Ser Val Phe Asn Gly Thr Val Asn Leu Asp Asn Gln Ser
                530                 535                 540

Val Leu Asn Ile Asn Asp Ile Phe Asn Gly Gly Ile Gln Ala Asn Asn
545                 550                 555                 560

Ser Thr Val Asn Ile Ser Ser Asp Ser Ala Val Leu Gly Asn Ser Thr
                565                 570                 575

Leu Thr Ser Thr Ala Leu Asn Leu Asn Lys Gly Ala Asn Ala Leu Ala
                580                 585                 590

Ser Gln Ser Phe Val Ser Asp Gly Pro Val Asn Ile Ser Asp Ala Thr
                595                 600                 605

Leu Ser Leu Asn Ser Arg Pro Asp Glu Val Ser His Thr Leu Leu Pro
                610                 615                 620

Val Tyr Asp Tyr Ala Gly Ser Trp Asn Leu Lys Gly Asp Asp Ala Arg
625                 630                 635                 640

Leu Asn Val Gly Pro Tyr Ser Met Leu Ser Gly Asn Ile Asn Val Gln
                645                 650                 655

Asp Lys Gly Thr Val Thr Leu Gly Gly Glu Gly Glu Leu Ser Pro Asp
                660                 665                 670

Leu Thr Leu Gln Asn Gln Met Leu Tyr Ser Leu Phe Asn Gly Tyr Arg
                675                 680                 685

Asn Ile Trp Ser Gly Ser Leu Asn Ala Pro Asp Ala Thr Val Ser Met
                690                 695                 700

Thr Asp Thr Gln Trp Ser Met Asn Gly Asn Ser Thr Ala Gly Asn Met
705                 710                 715                 720

Lys Leu Asn Arg Thr Ile Val Gly Phe Asn Gly Gly Thr Ser Pro Phe
                725                 730                 735
```

```
Thr Thr Leu Thr Thr Asp Asn Leu Asp Ala Val Gln Ser Ala Phe Val
            740                 745                 750

Met Arg Thr Asp Leu Asn Lys Ala Asp Lys Leu Val Ile Asn Lys Ser
            755                 760                 765

Ala Thr Gly His Asp Asn Ser Ile Trp Val Asn Phe Leu Lys Lys Pro
        770                 775                 780

Ser Asn Lys Asp Thr Leu Asp Ile Pro Leu Val Ser Ala Pro Glu Ala
785                 790                 795                 800

Thr Ala Asp Asn Leu Phe Arg Ala Ser Thr Arg Val Val Gly Phe Ser
                805                 810                 815

Asp Val Thr Pro Ile Leu Ser Val Arg Lys Glu Asp Gly Lys Lys Glu
            820                 825                 830

Trp Val Leu Asp Gly Tyr Gln Val Ala Arg Asn Asp Gly Gln Gly Lys
            835                 840                 845

Ala Ala Ala Thr Phe Met His Ile Ser Tyr Asn Asn Phe Ile Thr Glu
        850                 855                 860

Val Gly Ser Leu Asn Lys Arg Met Gly Asp Leu Arg Asp Ile Asn Gly
865                 870                 875                 880

Glu Ala Gly Thr Trp Val Arg Leu Leu Asn Gly Ser Gly Ser Ala Asp
                885                 890                 895

Gly Gly Phe Thr Asp His Tyr Thr Leu Leu Gln Met Gly Ala Asp Arg
            900                 905                 910

Lys His Glu Leu Gly Ser Met Asp Leu Phe Thr Gly Val Met Ala Thr
            915                 920                 925

Tyr Thr Asp Thr Asp Ala Ser Ala Asp Leu Tyr Ser Gly Lys Thr Lys
        930                 935                 940

Ser Trp Gly Gly Gly Phe Tyr Ala Ser Gly Leu Phe Arg Ser Gly Ala
945                 950                 955                 960

Tyr Phe Asp Val Ile Ala Lys Tyr Ile His Asn Glu Asn Lys Tyr Asp
                965                 970                 975

Leu Asn Phe Ala Gly Ala Gly Lys Gln Asn Phe Arg Ser His Ser Leu
            980                 985                 990

Tyr Ala Gly Ala Glu Val Gly Tyr Arg Tyr His Leu Thr Asp Thr Thr
            995                 1000                1005

Phe Val Glu Pro Gln Ala Glu Leu Val Trp Gly Arg Leu Gln Gly
        1010                1015                1020

Gln Thr Phe Asn Trp Asn Asp Ser Gly Met Asp Val Ser Met Arg
        1025                1030                1035

Arg Asn Ser Val Asn Pro Leu Val Gly Arg Thr Gly Val Val Ser
        1040                1045                1050

Gly Lys Thr Phe Ser Gly Lys Asp Trp Ser Leu Thr Ala Arg Ala
        1055                1060                1065

Gly Leu His Tyr Glu Phe Asp Leu Thr Asp Ser Ala Asp Val His
        1070                1075                1080

Leu Lys Asp Ala Ala Gly Glu His Gln Ile Asn Gly Arg Lys Asp
        1085                1090                1095

Ser Arg Met Leu Tyr Gly Val Gly Leu Asn Ala Arg Phe Gly Asp
        1100                1105                1110

Asn Thr Arg Leu Gly Leu Glu Val Glu Arg Ser Ala Phe Gly Lys
        1115                1120                1125

Tyr Asn Thr Asp Asp Ala Ile Asn Ala Asn Ile Arg Tyr Ser Phe
        1130                1135                1140
```

```
<210> SEQ ID NO 5
<211> LENGTH: 1142
<212> TYPE: PRT
<213> ORGANISM: Unknown
<220> FEATURE:
<223> OTHER INFORMATION: Escherichia coli - Streptococcus pneumoniae

<400> SEQUENCE: 5

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Ile Pro Val Leu Phe Ser Ala
        35                  40                  45

Gly Ser Leu Ala Gly Ser Ser Lys Leu Gly Asp Ile Glu Phe Ile Lys
    50                  55                  60

Val Asn Lys Gly Ser Gly Ser Gly Asn Asp Ala Pro Val Thr Phe Arg
65                  70                  75                  80

Thr Ser Glu Gly Gly Ala Leu Glu Trp Ser Phe Asn Ser Ser Thr Gly
                85                  90                  95

Ala Gly Ala Leu Thr Gln Gly Thr Thr Thr Tyr Ala Met His Gly Gln
            100                 105                 110

Gln Gly Asn Asp Leu Asn Ala Gly Lys Asn Leu Ile Phe Gln Gly Gln
        115                 120                 125

Asn Gly Gln Ile Asn Leu Lys Asp Ser Val Ser Gln Gly Ala Gly Ser
    130                 135                 140

Leu Thr Phe Arg Asp Asn Tyr Thr Val Thr Thr Ser Asn Gly Ser Thr
145                 150                 155                 160

Trp Thr Gly Ala Gly Ile Val Val Asp Asn Gly Val Ser Val Asn Trp
                165                 170                 175

Gln Val Asn Gly Val Lys Gly Asp Asn Leu His Lys Ile Gly Glu Gly
            180                 185                 190

Thr Leu Thr Val Gln Gly Thr Gly Ile Asn Glu Gly Gly Leu Lys Val
        195                 200                 205

Gly Asp Gly Lys Val Val Leu Asn Gln Gln Ala Asp Asn Lys Gly Gln
    210                 215                 220

Val Gln Ala Phe Ser Ser Val Asn Ile Ala Ser Gly Arg Pro Thr Val
225                 230                 235                 240

Val Leu Thr Asp Glu Arg Gln Val Asn Pro Asp Thr Val Ser Trp Gly
                245                 250                 255

Tyr Arg Gly Gly Thr Leu Asp Val Asn Gly Asn Ser Leu Thr Phe His
            260                 265                 270

Gln Leu Lys Ala Ala Asp Tyr Gly Ala Val Leu Ala Asn Asn Val Asp
        275                 280                 285

Lys Arg Ala Thr Ile Thr Leu Asp Tyr Ala Leu Arg Ala Asp Lys Val
    290                 295                 300

Ala Leu Asn Gly Trp Ser Glu Ser Gly Lys Gly Thr Ala Gly Asn Leu
305                 310                 315                 320

Tyr Lys Tyr Asn Asn Pro Tyr Thr Asn Thr Thr Asp Tyr Phe Ile Leu
                325                 330                 335

Lys Gln Ser Thr Tyr Gly Tyr Phe Pro Thr Asp Gln Ser Ser Asn Ala
            340                 345                 350

Thr Trp Glu Phe Val Gly His Ser Gln Gly Asp Ala Gln Lys Leu Val
        355                 360                 365
```

```
Ala Asp Arg Phe Asn Thr Ala Gly Tyr Leu Phe His Gly Gln Leu Lys
    370                 375                 380

Gly Asn Leu Asn Val Asp Asn Arg Leu Pro Glu Gly Val Thr Gly Ala
385                 390                 395                 400

Leu Val Met Asp Gly Ala Asp Ile Ser Gly Thr Phe Thr Gln Glu
            405                 410                 415

Asn Gly Arg Leu Thr Leu Gln Gly His Pro Val Ile His Ala Tyr Asn
            420                 425                 430

Thr Gln Ser Val Ala Asp Lys Leu Ala Ala Ser Gly Asp His Ser Val
        435                 440                 445

Leu Thr Gln Pro Thr Ser Phe Ser Gln Glu Asp Trp Glu Asn Arg Ser
450                 455                 460

Phe Thr Phe Asp Arg Leu Ser Leu Lys Asn Thr Asp Phe Gly Leu Gly
465                 470                 475                 480

Arg Asn Ala Thr Leu Asn Thr Thr Ile Gln Ala Asp Asn Ser Ser Val
                485                 490                 495

Thr Leu Gly Asp Ser Arg Val Phe Ile Asp Lys Asn Asp Gly Gln Gly
            500                 505                 510

Thr Ala Phe Thr Leu Glu Glu Gly Thr Ser Val Ala Thr Lys Asp Ala
        515                 520                 525

Asp Lys Ser Val Phe Asn Gly Thr Val Asn Leu Asp Asn Gln Ser Val
530                 535                 540

Leu Asn Ile Asn Asp Ile Phe Asn Gly Gly Ile Gln Ala Asn Asn Ser
545                 550                 555                 560

Thr Val Asn Ile Ser Ser Asp Ser Ala Val Leu Gly Asn Ser Thr Leu
                565                 570                 575

Thr Ser Thr Ala Leu Asn Leu Asn Lys Gly Ala Asn Ala Leu Ala Ser
            580                 585                 590

Gln Ser Phe Val Ser Asp Gly Pro Val Asn Ile Ser Asp Ala Thr Leu
        595                 600                 605

Ser Leu Asn Ser Arg Pro Asp Glu Val Ser His Thr Leu Leu Pro Val
        610                 615                 620

Tyr Asp Tyr Ala Gly Ser Trp Asn Leu Lys Gly Asp Asp Ala Arg Leu
625                 630                 635                 640

Asn Val Gly Pro Tyr Ser Met Leu Ser Gly Asn Ile Asn Val Gln Asp
                645                 650                 655

Lys Gly Thr Val Thr Leu Gly Gly Glu Gly Leu Ser Pro Asp Leu
            660                 665                 670

Thr Leu Gln Asn Gln Met Leu Tyr Ser Leu Phe Asn Gly Tyr Arg Asn
        675                 680                 685

Ile Trp Ser Gly Ser Leu Asn Ala Pro Asp Ala Thr Val Ser Met Thr
690                 695                 700

Asp Thr Gln Trp Ser Met Asn Gly Asn Ser Thr Ala Gly Asn Met Lys
705                 710                 715                 720

Leu Asn Arg Thr Ile Val Gly Phe Asn Gly Gly Thr Ser Pro Phe Thr
                725                 730                 735

Thr Leu Thr Thr Asp Asn Leu Asp Ala Val Gln Ser Ala Phe Val Met
            740                 745                 750

Arg Thr Asp Leu Asn Lys Ala Asp Lys Leu Val Ile Asn Lys Ser Ala
        755                 760                 765

Thr Gly His Asp Asn Ser Ile Trp Val Asn Phe Leu Lys Lys Pro Ser
770                 775                 780

Asn Lys Asp Thr Leu Asp Ile Pro Leu Val Ser Ala Pro Glu Ala Thr
```

```
                785                 790                 795                 800
Ala Asp Asn Leu Phe Arg Ala Ser Thr Arg Val Val Gly Phe Ser Asp
                    805                 810                 815

Val Thr Pro Ile Leu Ser Val Arg Lys Glu Asp Gly Lys Lys Glu Trp
                820                 825                 830

Val Leu Asp Gly Tyr Gln Val Ala Arg Asn Asp Gly Gln Gly Lys Ala
                835                 840                 845

Ala Ala Thr Phe Met His Ile Ser Tyr Asn Asn Phe Ile Thr Glu Val
                850                 855                 860

Gly Ser Leu Asn Lys Arg Met Gly Asp Leu Arg Asp Ile Asn Gly Glu
865                 870                 875                 880

Ala Gly Thr Trp Val Arg Leu Leu Asn Gly Ser Gly Ser Ala Asp Gly
                    885                 890                 895

Gly Phe Thr Asp His Tyr Thr Leu Leu Gln Met Gly Ala Asp Arg Lys
                900                 905                 910

His Glu Leu Gly Ser Met Asp Leu Phe Thr Gly Val Met Ala Thr Tyr
                915                 920                 925

Thr Asp Thr Asp Ala Ser Ala Asp Leu Tyr Ser Gly Lys Thr Lys Ser
                930                 935                 940

Trp Gly Gly Gly Phe Tyr Ala Ser Gly Leu Phe Arg Ser Gly Ala Tyr
945                 950                 955                 960

Phe Asp Val Ile Ala Lys Tyr Ile His Asn Glu Asn Lys Tyr Asp Leu
                    965                 970                 975

Asn Phe Ala Gly Ala Gly Lys Gln Asn Phe Arg Ser His Ser Leu Tyr
                980                 985                 990

Ala Gly Ala Glu Val Gly Tyr Arg Tyr His Leu Thr Asp Thr Thr Phe
                995                1000                1005

Val Glu Pro Gln Ala Glu Leu Val Trp Gly Arg Leu Gln Gly Gln
             1010                1015                1020

Thr Phe Asn Trp Asn Asp Ser Gly Met Asp Val Ser Met Arg Arg
             1025                1030                1035

Asn Ser Val Asn Pro Leu Val Gly Arg Thr Gly Val Val Ser Gly
             1040                1045                1050

Lys Thr Phe Ser Gly Lys Asp Trp Ser Leu Thr Ala Arg Ala Gly
             1055                1060                1065

Leu His Tyr Glu Phe Asp Leu Thr Asp Ser Ala Asp Val His Leu
             1070                1075                1080

Lys Asp Ala Ala Gly Glu His Gln Ile Asn Gly Arg Lys Asp Ser
             1085                1090                1095

Arg Met Leu Tyr Gly Val Gly Leu Asn Ala Arg Phe Gly Asp Asn
             1100                1105                1110

Thr Arg Leu Gly Leu Glu Val Glu Arg Ser Ala Phe Gly Lys Tyr
             1115                1120                1125

Asn Thr Asp Asp Ala Ile Asn Ala Asn Ile Arg Tyr Ser Phe
             1130                1135                1140

<210> SEQ ID NO 6
<211> LENGTH: 1140
<212> TYPE: PRT
<213> ORGANISM: Unknown
<220> FEATURE:
<223> OTHER INFORMATION: Escherichia coli - Streptococcus pyogenes

<400> SEQUENCE: 6

Met Asn Arg Ile Tyr Ser Leu Arg Tyr Ser Ala Val Ala Arg Gly Phe
```

-continued

```
1               5                   10                  15
Ile Ala Val Ser Glu Phe Ala Arg Lys Cys Val His Lys Ser Val Arg
            20                  25                  30
Arg Leu Cys Phe Pro Val Leu Leu Ile Pro Val Leu Phe Ser Ala
            35                  40                  45
Gly Ser Leu Ala Gly Ser Ser Ala Thr His Ile Lys Phe Ser Lys Arg
            50                  55                  60
Asp Gly Ser Gly Ser Gly Asn Asp Ala Pro Val Thr Phe Arg Thr Ser
65                  70                  75                  80
Glu Gly Gly Ala Leu Glu Trp Ser Phe Asn Ser Ser Thr Gly Ala Gly
                85                  90                  95
Ala Leu Thr Gln Gly Thr Thr Thr Tyr Ala Met His Gly Gln Gln Gly
            100                 105                 110
Asn Asp Leu Asn Ala Gly Lys Asn Leu Ile Phe Gln Gly Gln Asn Gly
            115                 120                 125
Gln Ile Asn Leu Lys Asp Ser Val Ser Gln Gly Ala Gly Ser Leu Thr
        130                 135                 140
Phe Arg Asp Asn Tyr Thr Val Thr Thr Ser Asn Gly Ser Thr Trp Thr
145                 150                 155                 160
Gly Ala Gly Ile Val Val Asp Asn Gly Val Ser Val Asn Trp Gln Val
                165                 170                 175
Asn Gly Val Lys Gly Asp Asn Leu His Lys Ile Gly Glu Gly Thr Leu
            180                 185                 190
Thr Val Gln Gly Thr Gly Ile Asn Glu Gly Gly Leu Lys Val Gly Asp
                195                 200                 205
Gly Lys Val Val Leu Asn Gln Gln Ala Asp Asn Lys Gly Gln Val Gln
        210                 215                 220
Ala Phe Ser Ser Val Asn Ile Ala Ser Gly Arg Pro Thr Val Val Leu
225                 230                 235                 240
Thr Asp Glu Arg Gln Val Asn Pro Asp Thr Val Ser Trp Gly Tyr Arg
                245                 250                 255
Gly Gly Thr Leu Asp Val Asn Gly Asn Ser Leu Thr Phe His Gln Leu
            260                 265                 270
Lys Ala Ala Asp Tyr Gly Ala Val Leu Ala Asn Asn Val Asp Lys Arg
        275                 280                 285
Ala Thr Ile Thr Leu Asp Tyr Ala Leu Arg Ala Asp Lys Val Ala Leu
        290                 295                 300
Asn Gly Trp Ser Glu Ser Gly Lys Gly Thr Ala Gly Asn Leu Tyr Lys
305                 310                 315                 320
Tyr Asn Asn Pro Tyr Thr Asn Thr Thr Asp Tyr Phe Ile Leu Lys Gln
                325                 330                 335
Ser Thr Tyr Gly Tyr Phe Pro Thr Asp Gln Ser Ser Asn Ala Thr Trp
            340                 345                 350
Glu Phe Val Gly His Ser Gln Gly Asp Ala Gln Lys Leu Val Ala Asp
            355                 360                 365
Arg Phe Asn Thr Ala Gly Tyr Leu Phe His Gly Gln Leu Lys Gly Asn
        370                 375                 380
Leu Asn Val Asp Asn Arg Leu Pro Glu Gly Val Thr Gly Ala Leu Val
385                 390                 395                 400
Met Asp Gly Ala Ala Asp Ile Ser Gly Thr Phe Thr Gln Glu Asn Gly
                405                 410                 415
Arg Leu Thr Leu Gln Gly His Pro Val Ile His Ala Tyr Asn Thr Gln
            420                 425                 430
```

-continued

Ser Val Ala Asp Lys Leu Ala Ala Ser Gly Asp His Ser Val Leu Thr
        435             440             445
Gln Pro Thr Ser Phe Ser Gln Glu Asp Trp Glu Asn Arg Ser Phe Thr
    450             455             460
Phe Asp Arg Leu Ser Leu Lys Asn Thr Asp Phe Gly Leu Gly Arg Asn
465             470             475             480
Ala Thr Leu Asn Thr Thr Ile Gln Ala Asp Asn Ser Ser Val Thr Leu
            485             490             495
Gly Asp Ser Arg Val Phe Ile Asp Lys Asn Asp Gly Gln Gly Thr Ala
        500             505             510
Phe Thr Leu Glu Glu Gly Thr Ser Val Ala Thr Lys Asp Ala Asp Lys
    515             520             525
Ser Val Phe Asn Gly Thr Val Asn Leu Asp Asn Gln Ser Val Leu Asn
    530             535             540
Ile Asn Asp Ile Phe Asn Gly Gly Ile Gln Ala Asn Asn Ser Thr Val
545             550             555             560
Asn Ile Ser Ser Asp Ser Ala Val Leu Gly Asn Ser Thr Leu Thr Ser
            565             570             575
Thr Ala Leu Asn Leu Asn Lys Gly Ala Asn Ala Leu Ala Ser Gln Ser
        580             585             590
Phe Val Ser Asp Gly Pro Val Asn Ile Ser Asp Ala Thr Leu Ser Leu
    595             600             605
Asn Ser Arg Pro Asp Glu Val Ser His Thr Leu Leu Pro Val Tyr Asp
    610             615             620
Tyr Ala Gly Ser Trp Asn Leu Lys Gly Asp Asp Ala Arg Leu Asn Val
625             630             635             640
Gly Pro Tyr Ser Met Leu Ser Gly Asn Ile Asn Val Gln Asp Lys Gly
            645             650             655
Thr Val Thr Leu Gly Gly Glu Gly Glu Leu Ser Pro Asp Leu Thr Leu
        660             665             670
Gln Asn Gln Met Leu Tyr Ser Leu Phe Asn Gly Tyr Arg Asn Ile Trp
    675             680             685
Ser Gly Ser Leu Asn Ala Pro Asp Ala Thr Val Ser Met Thr Asp Thr
    690             695             700
Gln Trp Ser Met Asn Gly Asn Ser Thr Ala Gly Asn Met Lys Leu Asn
705             710             715             720
Arg Thr Ile Val Gly Phe Asn Gly Gly Thr Ser Pro Phe Thr Thr Leu
            725             730             735
Thr Thr Asp Asn Leu Asp Ala Val Gln Ser Ala Phe Val Met Arg Thr
        740             745             750
Asp Leu Asn Lys Ala Asp Lys Leu Val Ile Asn Lys Ser Ala Thr Gly
    755             760             765
His Asp Asn Ser Ile Trp Val Asn Phe Leu Lys Lys Pro Ser Asn Lys
    770             775             780
Asp Thr Leu Asp Ile Pro Leu Val Ser Ala Pro Glu Ala Thr Ala Asp
785             790             795             800
Asn Leu Phe Arg Ala Ser Thr Arg Val Val Gly Phe Ser Asp Val Thr
            805             810             815
Pro Ile Leu Ser Val Arg Lys Glu Asp Gly Lys Lys Glu Trp Val Leu
        820             825             830
Asp Gly Tyr Gln Val Ala Arg Asn Asp Gly Gln Gly Lys Ala Ala Ala
    835             840             845

```
Thr Phe Met His Ile Ser Tyr Asn Asn Phe Ile Thr Glu Val Gly Ser
            850                 855                 860

Leu Asn Lys Arg Met Gly Asp Leu Arg Asp Ile Asn Gly Glu Ala Gly
865                 870                 875                 880

Thr Trp Val Arg Leu Leu Asn Gly Ser Gly Ala Asp Gly Gly Phe
            885                 890                 895

Thr Asp His Tyr Thr Leu Leu Gln Met Gly Ala Asp Arg Lys His Glu
            900                 905                 910

Leu Gly Ser Met Asp Leu Phe Thr Gly Val Met Ala Thr Tyr Thr Asp
            915                 920                 925

Thr Asp Ala Ser Ala Asp Leu Tyr Ser Gly Lys Thr Lys Ser Trp Gly
930                 935                 940

Gly Gly Phe Tyr Ala Ser Gly Leu Phe Arg Ser Gly Ala Tyr Phe Asp
945                 950                 955                 960

Val Ile Ala Lys Tyr Ile His Asn Glu Asn Lys Tyr Asp Leu Asn Phe
            965                 970                 975

Ala Gly Ala Gly Lys Gln Asn Phe Arg Ser His Ser Leu Tyr Ala Gly
            980                 985                 990

Ala Glu Val Gly Tyr Arg Tyr His Leu Thr Asp Thr Thr Phe Val Glu
            995                 1000                1005

Pro Gln Ala Glu Leu Val Trp Gly Arg Leu Gln Gly Gln Thr Phe
            1010                1015                1020

Asn Trp Asn Asp Ser Gly Met Asp Val Ser Met Arg Arg Asn Ser
            1025                1030                1035

Val Asn Pro Leu Val Gly Arg Thr Gly Val Val Ser Gly Lys Thr
            1040                1045                1050

Phe Ser Gly Lys Asp Trp Ser Leu Thr Ala Arg Ala Gly Leu His
            1055                1060                1065

Tyr Glu Phe Asp Leu Thr Asp Ser Ala Asp Val His Leu Lys Asp
            1070                1075                1080

Ala Ala Gly Glu His Gln Ile Asn Gly Arg Lys Asp Ser Arg Met
            1085                1090                1095

Leu Tyr Gly Val Gly Leu Asn Ala Arg Phe Gly Asp Asn Thr Arg
            1100                1105                1110

Leu Gly Leu Glu Val Glu Arg Ser Ala Phe Gly Lys Tyr Asn Thr
            1115                1120                1125

Asp Asp Ala Ile Asn Ala Asn Ile Arg Tyr Ser Phe
            1130                1135                1140

<210> SEQ ID NO 7
<211> LENGTH: 1222
<212> TYPE: PRT
<213> ORGANISM: Unknown
<220> FEATURE:
<223> OTHER INFORMATION: Streptococcus pyogenes - Streptococcus pyogenes

<400> SEQUENCE: 7

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Ile Pro Val Leu Phe Ser Ala
        35                  40                  45

Gly Ser Leu Ala Gly Ser Ser Asp Ser Ala Thr His Ile Lys Phe Ser
50                  55                  60
```

-continued

```
Lys Arg Asp Glu Asp Gly Lys Glu Leu Ala Gly Ala Thr Met Glu Leu
 65                  70                  75                  80

Arg Asp Ser Ser Gly Lys Thr Ile Ser Thr Trp Ile Ser Asp Gly Gln
                 85                  90                  95

Val Lys Asp Phe Tyr Leu Tyr Pro Gly Lys Tyr Thr Phe Val Glu Thr
            100                 105                 110

Ala Ala Pro Asp Gly Tyr Glu Val Ala Thr Ala Ile Thr Phe Thr Val
        115                 120                 125

Asn Glu Gln Gly Gln Val Thr Val Asn Gly Lys Ala Thr Lys Gly Asp
130                 135                 140

Ala His Ile Gly Ser Gly Ser Asn Asp Ala Pro Val Thr Phe Arg
145                 150                 155                 160

Thr Ser Glu Gly Gly Ala Leu Glu Trp Ser Phe Asn Ser Ser Thr Gly
                165                 170                 175

Ala Gly Ala Leu Thr Gln Gly Thr Thr Thr Tyr Ala Met His Gly Gln
            180                 185                 190

Gln Gly Asn Asp Leu Asn Ala Gly Lys Asn Leu Ile Phe Gln Gly Gln
        195                 200                 205

Asn Gly Gln Ile Asn Leu Lys Asp Ser Val Ser Gln Gly Ala Gly Ser
210                 215                 220

Leu Thr Phe Arg Asp Asn Tyr Thr Val Thr Thr Ser Asn Gly Ser Thr
225                 230                 235                 240

Trp Thr Gly Ala Gly Ile Val Val Asp Asn Gly Val Ser Val Asn Trp
                245                 250                 255

Gln Val Asn Gly Val Lys Gly Asp Asn Leu His Lys Ile Gly Glu Gly
            260                 265                 270

Thr Leu Thr Val Gln Gly Thr Gly Ile Asn Glu Gly Gly Leu Lys Val
        275                 280                 285

Gly Asp Gly Lys Val Val Leu Asn Gln Gln Ala Asp Asn Lys Gly Gln
290                 295                 300

Val Gln Ala Phe Ser Ser Val Asn Ile Ala Ser Gly Arg Pro Thr Val
305                 310                 315                 320

Val Leu Thr Asp Glu Arg Gln Val Asn Pro Asp Thr Val Ser Trp Gly
                325                 330                 335

Tyr Arg Gly Gly Thr Leu Asp Val Asn Gly Asn Ser Leu Thr Phe His
            340                 345                 350

Gln Leu Lys Ala Ala Asp Tyr Gly Ala Val Leu Ala Asn Asn Val Asp
        355                 360                 365

Lys Arg Ala Thr Ile Thr Leu Asp Tyr Ala Leu Arg Ala Asp Lys Val
370                 375                 380

Ala Leu Asn Gly Trp Ser Glu Ser Gly Lys Gly Thr Ala Gly Asn Leu
385                 390                 395                 400

Tyr Lys Tyr Asn Asn Pro Tyr Thr Asn Thr Thr Asp Tyr Phe Ile Leu
                405                 410                 415

Lys Gln Ser Thr Tyr Gly Tyr Phe Pro Thr Asp Gln Ser Ser Asn Ala
            420                 425                 430

Thr Trp Glu Phe Val Gly His Ser Gln Gly Asp Ala Gln Lys Leu Val
        435                 440                 445

Ala Asp Arg Phe Asn Thr Ala Gly Tyr Leu Phe His Gly Gln Leu Lys
450                 455                 460

Gly Asn Leu Asn Val Asp Asn Arg Leu Pro Glu Gly Val Thr Gly Ala
465                 470                 475                 480

Leu Val Met Asp Gly Ala Ala Asp Ile Ser Gly Thr Phe Thr Gln Glu
```

```
                485                 490                 495
Asn Gly Arg Leu Thr Leu Gln Gly His Pro Val Ile His Ala Tyr Asn
            500                 505                 510

Thr Gln Ser Val Ala Asp Lys Leu Ala Ala Ser Gly Asp His Ser Val
            515                 520                 525

Leu Thr Gln Pro Thr Ser Phe Ser Gln Glu Asp Trp Glu Asn Arg Ser
530                 535                 540

Phe Thr Phe Asp Arg Leu Ser Leu Lys Asn Thr Asp Phe Gly Leu Gly
545                 550                 555                 560

Arg Asn Ala Thr Leu Asn Thr Thr Ile Gln Ala Asp Asn Ser Ser Val
                565                 570                 575

Thr Leu Gly Asp Ser Arg Val Phe Ile Asp Lys Asn Asp Gly Gln Gly
            580                 585                 590

Thr Ala Phe Thr Leu Glu Glu Gly Thr Ser Val Ala Thr Lys Asp Ala
            595                 600                 605

Asp Lys Ser Val Phe Asn Gly Thr Val Asn Leu Asp Asn Gln Ser Val
            610                 615                 620

Leu Asn Ile Asn Asp Ile Phe Asn Gly Gly Ile Gln Ala Asn Asn Ser
625                 630                 635                 640

Thr Val Asn Ile Ser Ser Asp Ser Ala Val Leu Gly Asn Ser Thr Leu
                645                 650                 655

Thr Ser Thr Ala Leu Asn Leu Asn Lys Gly Ala Asn Ala Leu Ala Ser
            660                 665                 670

Gln Ser Phe Val Ser Asp Gly Pro Val Asn Ile Ser Asp Ala Thr Leu
            675                 680                 685

Ser Leu Asn Ser Arg Pro Asp Glu Val Ser His Thr Leu Leu Pro Val
            690                 695                 700

Tyr Asp Tyr Ala Gly Ser Trp Asn Leu Lys Gly Asp Asp Ala Arg Leu
705                 710                 715                 720

Asn Val Gly Pro Tyr Ser Met Leu Ser Gly Asn Ile Asn Val Gln Asp
                725                 730                 735

Lys Gly Thr Val Thr Leu Gly Gly Glu Gly Glu Leu Ser Pro Asp Leu
            740                 745                 750

Thr Leu Gln Asn Gln Met Leu Tyr Ser Leu Phe Asn Gly Tyr Arg Asn
            755                 760                 765

Ile Trp Ser Gly Ser Leu Asn Ala Pro Asp Ala Thr Val Ser Met Thr
770                 775                 780

Asp Thr Gln Trp Ser Met Asn Gly Asn Ser Thr Ala Gly Asn Met Lys
                785                 790                 795                 800

Leu Asn Arg Thr Ile Val Gly Phe Asn Gly Thr Ser Pro Phe Thr
            805                 810                 815

Thr Leu Thr Thr Asp Asn Leu Asp Ala Val Gln Ser Ala Phe Val Met
            820                 825                 830

Arg Thr Asp Leu Asn Lys Ala Asp Lys Leu Val Ile Asn Lys Ser Ala
            835                 840                 845

Thr Gly His Asp Asn Ser Ile Trp Val Asn Phe Leu Lys Lys Pro Ser
            850                 855                 860

Asn Lys Asp Thr Leu Asp Ile Pro Leu Val Ser Ala Pro Glu Ala Thr
865                 870                 875                 880

Ala Asp Asn Leu Phe Arg Ala Ser Thr Arg Val Val Gly Phe Ser Asp
                885                 890                 895

Val Thr Pro Ile Leu Ser Val Arg Lys Glu Asp Gly Lys Lys Glu Trp
            900                 905                 910
```

Val Leu Asp Gly Tyr Gln Val Ala Arg Asn Asp Gly Gln Gly Lys Ala
            915                 920                 925

Ala Ala Thr Phe Met His Ile Ser Tyr Asn Asn Phe Ile Thr Glu Val
        930                 935                 940

Gly Ser Leu Asn Lys Arg Met Gly Asp Leu Arg Asp Ile Asn Gly Glu
945                 950                 955                 960

Ala Gly Thr Trp Val Arg Leu Leu Asn Gly Ser Gly Ser Ala Asp Gly
            965                 970                 975

Gly Phe Thr Asp His Tyr Thr Leu Leu Gln Met Gly Ala Asp Arg Lys
        980                 985                 990

His Glu Leu Gly Ser Met Asp Leu Phe Thr Gly Val Met Ala Thr Tyr
            995                 1000                1005

Thr Asp Thr Asp Ala Ser Ala Asp Leu Tyr Ser Gly Lys Thr Lys
    1010                1015                1020

Ser Trp Gly Gly Gly Phe Tyr Ala Ser Gly Leu Phe Arg Ser Gly
    1025                1030                1035

Ala Tyr Phe Asp Val Ile Ala Lys Tyr Ile His Asn Glu Asn Lys
    1040                1045                1050

Tyr Asp Leu Asn Phe Ala Gly Ala Gly Lys Gln Asn Phe Arg Ser
    1055                1060                1065

His Ser Leu Tyr Ala Gly Ala Glu Val Gly Tyr Arg Tyr His Leu
    1070                1075                1080

Thr Asp Thr Thr Phe Val Glu Pro Gln Ala Glu Leu Val Trp Gly
    1085                1090                1095

Arg Leu Gln Gly Gln Thr Phe Asn Trp Asn Asp Ser Gly Met Asp
    1100                1105                1110

Val Ser Met Arg Arg Asn Ser Val Asn Pro Leu Val Gly Arg Thr
    1115                1120                1125

Gly Val Val Ser Gly Lys Thr Phe Ser Gly Lys Asp Trp Ser Leu
    1130                1135                1140

Thr Ala Arg Ala Gly Leu His Tyr Glu Phe Asp Leu Thr Asp Ser
    1145                1150                1155

Ala Asp Val His Leu Lys Asp Ala Ala Gly Glu His Gln Ile Asn
    1160                1165                1170

Gly Arg Lys Asp Ser Arg Met Leu Tyr Gly Val Gly Leu Asn Ala
    1175                1180                1185

Arg Phe Gly Asp Asn Thr Arg Leu Gly Leu Glu Val Glu Arg Ser
    1190                1195                1200

Ala Phe Gly Lys Tyr Asn Thr Asp Asp Ala Ile Asn Ala Asn Ile
    1205                1210                1215

Arg Tyr Ser Phe
    1220

<210> SEQ ID NO 8
<211> LENGTH: 1242
<212> TYPE: PRT
<213> ORGANISM: Unknown
<220> FEATURE:
<223> OTHER INFORMATION: Camelus dromedarius - Streptococcus pneumoniae

<400> SEQUENCE: 8

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

```
Arg Leu Cys Phe Pro Val Leu Leu Ile Pro Val Leu Phe Ser Ala
         35                  40                  45

Gly Ser Leu Ala Gly Ser Ser Lys Pro Leu Arg Gly Ala Val Phe Ser
     50                  55                  60

Leu Gln Lys Gln His Pro Asp Tyr Pro Asp Ile Tyr Gly Ala Ile Asp
65                  70                  75                  80

Gln Asn Gly Thr Tyr Gln Asn Val Arg Thr Gly Glu Asp Gly Lys Leu
                 85                  90                  95

Thr Phe Lys Asn Leu Ser Asp Gly Lys Tyr Arg Leu Phe Glu Asn Ser
             100                 105                 110

Glu Pro Ala Gly Tyr Lys Pro Val Gln Asn Lys Pro Ile Val Ala Phe
             115                 120                 125

Gln Ile Val Asn Gly Glu Val Arg Asp Val Thr Ser Ile Val Pro Gln
             130                 135                 140

Asp Ile Pro Ala Thr Tyr Glu Phe Thr Asn Gly Lys His Tyr Ile Thr
145                 150                 155                 160

Asn Glu Pro Ile Pro Pro Lys Gly Ser Gly Ser Gly Asn Asp Ala Pro
                 165                 170                 175

Val Thr Phe Arg Thr Ser Glu Gly Gly Ala Leu Glu Trp Ser Phe Asn
             180                 185                 190

Ser Ser Thr Gly Ala Gly Ala Leu Thr Gln Gly Thr Thr Thr Tyr Ala
             195                 200                 205

Met His Gly Gln Gln Gly Asn Asp Leu Asn Ala Gly Lys Asn Leu Ile
             210                 215                 220

Phe Gln Gly Gln Asn Gly Gln Ile Asn Leu Lys Asp Ser Val Ser Gln
225                 230                 235                 240

Gly Ala Gly Ser Leu Thr Phe Arg Asp Asn Tyr Thr Val Thr Thr Ser
                 245                 250                 255

Asn Gly Ser Thr Trp Thr Gly Ala Gly Ile Val Val Asp Asn Gly Val
             260                 265                 270

Ser Val Asn Trp Gln Val Asn Gly Val Lys Gly Asp Asn Leu His Lys
             275                 280                 285

Ile Gly Glu Gly Thr Leu Thr Val Gln Gly Thr Gly Ile Asn Glu Gly
             290                 295                 300

Gly Leu Lys Val Gly Asp Gly Lys Val Val Leu Asn Gln Gln Ala Asp
305                 310                 315                 320

Asn Lys Gly Gln Val Gln Ala Phe Ser Ser Val Asn Ile Ala Ser Gly
                 325                 330                 335

Arg Pro Thr Val Val Leu Thr Asp Glu Arg Gln Val Asn Pro Asp Thr
             340                 345                 350

Val Ser Trp Gly Tyr Arg Gly Gly Thr Leu Asp Val Asn Gly Asn Ser
             355                 360                 365

Leu Thr Phe His Gln Leu Lys Ala Ala Asp Tyr Gly Ala Val Leu Ala
             370                 375                 380

Asn Asn Val Asp Lys Arg Ala Thr Ile Thr Leu Asp Tyr Ala Leu Arg
385                 390                 395                 400

Ala Asp Lys Val Ala Leu Asn Gly Trp Ser Glu Ser Gly Lys Gly Thr
                 405                 410                 415

Ala Gly Asn Leu Tyr Lys Tyr Asn Asn Pro Tyr Thr Asn Thr Thr Asp
             420                 425                 430

Tyr Phe Ile Leu Lys Gln Ser Thr Tyr Gly Tyr Phe Pro Thr Asp Gln
             435                 440                 445
```

-continued

Ser Ser Asn Ala Thr Trp Glu Phe Val Gly His Ser Gln Gly Asp Ala
450                 455                 460

Gln Lys Leu Val Ala Asp Arg Phe Asn Thr Ala Gly Tyr Leu Phe His
465                 470                 475                 480

Gly Gln Leu Lys Gly Asn Leu Asn Val Asp Asn Arg Leu Pro Glu Gly
                485                 490                 495

Val Thr Gly Ala Leu Val Met Asp Gly Ala Ala Asp Ile Ser Gly Thr
            500                 505                 510

Phe Thr Gln Glu Asn Gly Arg Leu Thr Leu Gln Gly His Pro Val Ile
        515                 520                 525

His Ala Tyr Asn Thr Gln Ser Val Ala Asp Lys Leu Ala Ala Ser Gly
530                 535                 540

Asp His Ser Val Leu Thr Gln Pro Thr Ser Phe Ser Gln Glu Asp Trp
545                 550                 555                 560

Glu Asn Arg Ser Phe Thr Phe Asp Arg Leu Ser Leu Lys Asn Thr Asp
                565                 570                 575

Phe Gly Leu Gly Arg Asn Ala Thr Leu Asn Thr Thr Ile Gln Ala Asp
            580                 585                 590

Asn Ser Ser Val Thr Leu Gly Asp Ser Arg Val Phe Ile Asp Lys Asn
        595                 600                 605

Asp Gly Gln Gly Thr Ala Phe Thr Leu Glu Glu Gly Thr Ser Val Ala
610                 615                 620

Thr Lys Asp Ala Asp Lys Ser Val Phe Asn Gly Thr Val Asn Leu Asp
625                 630                 635                 640

Asn Gln Ser Val Leu Asn Ile Asn Asp Ile Phe Asn Gly Gly Ile Gln
                645                 650                 655

Ala Asn Asn Ser Thr Val Asn Ile Ser Ser Asp Ser Ala Val Leu Gly
            660                 665                 670

Asn Ser Thr Leu Thr Ser Thr Ala Leu Asn Leu Asn Lys Gly Ala Asn
        675                 680                 685

Ala Leu Ala Ser Gln Ser Phe Val Ser Asp Gly Pro Val Asn Ile Ser
690                 695                 700

Asp Ala Thr Leu Ser Leu Asn Ser Arg Pro Asp Glu Val Ser His Thr
705                 710                 715                 720

Leu Leu Pro Val Tyr Asp Tyr Ala Gly Ser Trp Asn Leu Lys Gly Asp
                725                 730                 735

Asp Ala Arg Leu Asn Val Gly Pro Tyr Ser Met Leu Ser Gly Asn Ile
            740                 745                 750

Asn Val Gln Asp Lys Gly Thr Val Thr Leu Gly Gly Glu Gly Glu Leu
        755                 760                 765

Ser Pro Asp Leu Thr Leu Gln Asn Gln Met Leu Tyr Ser Leu Phe Asn
770                 775                 780

Gly Tyr Arg Asn Ile Trp Ser Gly Ser Leu Asn Ala Pro Asp Ala Thr
785                 790                 795                 800

Val Ser Met Thr Asp Thr Gln Trp Ser Met Gly Asn Ser Thr Ala
                805                 810                 815

Gly Asn Met Lys Leu Asn Arg Thr Ile Val Gly Phe Asn Gly Gly Thr
            820                 825                 830

Ser Pro Phe Thr Thr Leu Thr Thr Asp Asn Leu Asp Ala Val Gln Ser
        835                 840                 845

Ala Phe Val Met Arg Thr Asp Leu Asn Lys Ala Asp Lys Leu Val Ile
850                 855                 860

Asn Lys Ser Ala Thr Gly His Asp Asn Ser Ile Trp Val Asn Phe Leu

```
                865                 870                 875                 880
Lys Lys Pro Ser Asn Lys Asp Thr Leu Asp Ile Pro Leu Val Ser Ala
                    885                 890                 895

Pro Glu Ala Thr Ala Asp Asn Leu Phe Arg Ala Ser Thr Arg Val Val
                900                 905                 910

Gly Phe Ser Asp Val Thr Pro Ile Leu Ser Val Arg Lys Glu Asp Gly
                915                 920                 925

Lys Lys Glu Trp Val Leu Asp Gly Tyr Gln Val Ala Arg Asn Asp Gly
            930                 935                 940

Gln Gly Lys Ala Ala Ala Thr Phe Met His Ile Ser Tyr Asn Asn Phe
945                 950                 955                 960

Ile Thr Glu Val Gly Ser Leu Asn Lys Arg Met Gly Asp Leu Arg Asp
                    965                 970                 975

Ile Asn Gly Glu Ala Gly Thr Trp Val Arg Leu Leu Asn Gly Ser Gly
                980                 985                 990

Ser Ala Asp Gly Gly Phe Thr Asp His Tyr Thr Leu Leu Gln Met Gly
                995                 1000                1005

Ala Asp Arg Lys His Glu Leu Gly Ser Met Asp Leu Phe Thr Gly
    1010                1015                1020

Val Met Ala Thr Tyr Thr Asp Thr Asp Ala Ser Ala Asp Leu Tyr
    1025                1030                1035

Ser Gly Lys Thr Lys Ser Trp Gly Gly Gly Phe Tyr Ala Ser Gly
    1040                1045                1050

Leu Phe Arg Ser Gly Ala Tyr Phe Asp Val Ile Ala Lys Tyr Ile
    1055                1060                1065

His Asn Glu Asn Lys Tyr Asp Leu Asn Phe Ala Gly Ala Gly Lys
    1070                1075                1080

Gln Asn Phe Arg Ser His Ser Leu Tyr Ala Gly Ala Glu Val Gly
    1085                1090                1095

Tyr Arg Tyr His Leu Thr Asp Thr Thr Phe Val Glu Pro Gln Ala
    1100                1105                1110

Glu Leu Val Trp Gly Arg Leu Gln Gly Gln Thr Phe Asn Trp Asn
    1115                1120                1125

Asp Ser Gly Met Asp Val Ser Met Arg Arg Asn Ser Val Asn Pro
    1130                1135                1140

Leu Val Gly Arg Thr Gly Val Val Ser Gly Lys Thr Phe Ser Gly
    1145                1150                1155

Lys Asp Trp Ser Leu Thr Ala Arg Ala Gly Leu His Tyr Glu Phe
    1160                1165                1170

Asp Leu Thr Asp Ser Ala Asp Val His Leu Lys Asp Ala Ala Gly
    1175                1180                1185

Glu His Gln Ile Asn Gly Arg Lys Asp Ser Arg Met Leu Tyr Gly
    1190                1195                1200

Val Gly Leu Asn Ala Arg Phe Gly Asp Asn Thr Arg Leu Gly Leu
    1205                1210                1215

Glu Val Glu Arg Ser Ala Phe Gly Lys Tyr Asn Thr Asp Asp Ala
    1220                1225                1230

Ile Asn Ala Asn Ile Arg Tyr Ser Phe
    1235                1240

<210> SEQ ID NO 9
<211> LENGTH: 1326
<212> TYPE: PRT
<213> ORGANISM: Unknown
```

```
<220> FEATURE:
<223> OTHER INFORMATION: Escherichia coli - Streptococcus pyogenes

<400> SEQUENCE: 9

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Ile Pro Val Leu Phe Ser Ala
        35                  40                  45

Gly Ser Leu Ala Gly Thr Val Asn Asn Glu Leu Gly Tyr Gln Leu Phe
    50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

Ala Ala Met Pro Asp Phe Ser Val Asp Ser Glu Ile Gly Val Ala
                100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160

Lys Leu Val Thr Glu Val Ala Pro Thr Ala Val Thr Ala Gln Gly Ala
                165                 170                 175

Val Ala Gly Ala Tyr Leu Asp Lys Glu Arg Tyr Pro Val Phe Tyr Arg
            180                 185                 190

Leu Gly Ser Gly Thr Gln Tyr Ile Lys Asp Ser Asn Gly Gln Leu Thr
        195                 200                 205

Lys Met Gly Gly Ala Tyr Ser Trp Leu Thr Gly Gly Thr Val Gly Ser
    210                 215                 220

Leu Ser Ser Tyr Gln Asn Gly Glu Met Ile Ser Thr Ser Ser Gly Leu
225                 230                 235                 240

Val Phe Asp Tyr Lys Leu Asn Gly Ala Met Pro Ile Tyr Gly Glu Ala
                245                 250                 255

Gly Asp Ser Gly Ser Pro Leu Phe Ala Phe Asp Thr Val Gln Asn Lys
            260                 265                 270

Trp Val Leu Val Gly Val Leu Thr Ala Gly Asn Gly Ala Gly Gly Arg
        275                 280                 285

Gly Asn Asn Trp Ala Val Ile Pro Leu Asp Phe Ile Gly Gln Lys Phe
    290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
                325                 330                 335

Gln Gly Thr Thr Thr Tyr Ala Met His Gly Gln Gln Gly Asn Asp Leu
            340                 345                 350

Asn Ala Gly Lys Asn Leu Ile Phe Gln Gly Gln Asn Gly Gln Ile Asn
        355                 360                 365

Leu Lys Asp Ser Val Ser Gln Gly Ala Gly Ser Leu Thr Phe Arg Asp
    370                 375                 380

Asn Tyr Thr Val Thr Thr Ser Asn Gly Ser Thr Trp Thr Gly Ala Gly
385                 390                 395                 400
```

Ile Val Val Asp Asn Gly Val Ser Val Asn Trp Gln Val Asn Gly Val
                    405                 410                 415

Lys Gly Asp Asn Leu His Lys Ile Gly Glu Gly Thr Leu Thr Val Gln
            420                 425                 430

Gly Thr Gly Ile Asn Glu Gly Gly Leu Lys Val Gly Asp Gly Lys Val
        435                 440                 445

Val Leu Asn Gln Gln Ala Asp Asn Lys Gly Gln Val Gln Ala Phe Ser
    450                 455                 460

Ser Val Asn Ile Ala Ser Gly Arg Pro Thr Val Leu Thr Asp Glu
465                 470                 475                 480

Arg Gln Val Asn Pro Asp Thr Val Ser Trp Gly Tyr Arg Gly Gly Thr
                485                 490                 495

Leu Asp Val Asn Gly Asn Ser Leu Thr Phe His Gln Leu Lys Ala Ala
            500                 505                 510

Asp Tyr Gly Ala Val Leu Ala Asn Asn Val Asp Lys Arg Ala Thr Ile
        515                 520                 525

Thr Leu Asp Tyr Ala Gly Ser Gly Ser Ser Ala His Ile Val Met Val
    530                 535                 540

Asp Ala Tyr Lys Pro Thr Lys Gly Ser Gly Ser Gly Asn Thr Ala Gly
545                 550                 555                 560

Tyr Leu Phe His Gly Gln Leu Lys Gly Asn Leu Asn Val Asp Asn Arg
                565                 570                 575

Leu Pro Glu Gly Val Thr Gly Ala Leu Val Met Asp Gly Ala Ala Asp
            580                 585                 590

Ile Ser Gly Thr Phe Thr Gln Glu Asn Gly Arg Leu Thr Leu Gln Gly
        595                 600                 605

His Pro Val Ile His Ala Tyr Asn Thr Gln Ser Val Ala Asp Lys Leu
    610                 615                 620

Ala Ala Ser Gly Asp His Ser Val Leu Thr Gln Pro Thr Ser Phe Ser
625                 630                 635                 640

Gln Glu Asp Trp Glu Asn Arg Ser Phe Thr Phe Asp Arg Leu Ser Leu
                645                 650                 655

Lys Asn Thr Asp Phe Gly Leu Gly Arg Asn Ala Thr Leu Asn Thr Thr
            660                 665                 670

Ile Gln Ala Asp Asn Ser Ser Val Thr Leu Gly Asp Ser Arg Val Phe
        675                 680                 685

Ile Asp Lys Asn Asp Gly Gln Gly Thr Ala Phe Thr Leu Glu Glu Gly
    690                 695                 700

Thr Ser Val Ala Thr Lys Asp Ala Asp Lys Ser Val Phe Asn Gly Thr
705                 710                 715                 720

Val Asn Leu Asp Asn Gln Ser Val Leu Asn Ile Asn Asp Ile Phe Asn
                725                 730                 735

Gly Gly Ile Gln Ala Asn Asn Ser Thr Val Asn Ile Ser Ser Asp Ser
            740                 745                 750

Ala Val Leu Gly Asn Ser Thr Leu Thr Ser Thr Ala Leu Asn Leu Asn
        755                 760                 765

Lys Gly Ala Asn Ala Leu Ala Ser Gln Ser Phe Val Ser Asp Gly Pro
    770                 775                 780

Val Asn Ile Ser Asp Ala Thr Leu Ser Leu Asn Ser Arg Pro Asp Glu
785                 790                 795                 800

Val Ser His Thr Leu Leu Pro Val Tyr Asp Tyr Ala Gly Ser Trp Asn
                805                 810                 815

```
Leu Lys Gly Asp Asp Ala Arg Leu Asn Val Gly Pro Tyr Ser Met Leu
            820                 825                 830

Ser Gly Asn Ile Asn Val Gln Asp Lys Gly Thr Val Thr Leu Gly Gly
        835                 840                 845

Glu Gly Glu Leu Ser Pro Asp Leu Thr Leu Gln Asn Gln Met Leu Tyr
    850                 855                 860

Ser Leu Phe Asn Gly Tyr Arg Asn Ile Trp Ser Gly Ser Leu Asn Ala
865                 870                 875                 880

Pro Asp Ala Thr Val Ser Met Thr Asp Thr Gln Trp Ser Met Asn Gly
                885                 890                 895

Asn Ser Thr Ala Gly Asn Met Lys Leu Asn Arg Thr Ile Val Gly Phe
            900                 905                 910

Asn Gly Gly Thr Ser Pro Phe Thr Thr Leu Thr Thr Asp Asn Leu Asp
        915                 920                 925

Ala Val Gln Ser Ala Phe Val Met Arg Thr Asp Leu Asn Lys Ala Asp
    930                 935                 940

Lys Leu Val Ile Asn Lys Ser Ala Thr Gly His Asp Asn Ser Ile Trp
945                 950                 955                 960

Val Asn Phe Leu Lys Lys Pro Ser Asn Lys Asp Thr Leu Asp Ile Pro
                965                 970                 975

Leu Val Ser Ala Pro Glu Ala Thr Ala Asp Asn Leu Phe Arg Ala Ser
            980                 985                 990

Thr Arg Val Val Gly Phe Ser Asp  Val Thr Pro Ile Leu  Ser Val Arg
            995             1000                 1005

Lys Glu  Asp Gly Lys Lys Glu  Trp Val Leu Asp Gly  Tyr Gln Val
    1010                 1015                 1020

Ala Arg  Asn Asp Gly Gln Gly  Lys Ala Ala Ala Thr  Phe Met His
    1025                 1030                 1035

Ile Ser  Tyr Asn Asn Phe Ile  Thr Glu Val Gly Ser  Leu Asn Lys
    1040                 1045                 1050

Arg Met  Gly Asp Leu Arg Asp  Ile Asn Gly Glu Ala  Gly Thr Trp
    1055                 1060                 1065

Val Arg  Leu Leu Asn Gly Ser  Gly Ser Ala Asp Gly  Gly Phe Thr
    1070                 1075                 1080

Asp His  Tyr Thr Leu Leu Gln  Met Gly Ala Asp Arg  Lys His Glu
    1085                 1090                 1095

Leu Gly  Ser Met Asp Leu Phe  Thr Gly Val Met Ala  Thr Tyr Thr
    1100                 1105                 1110

Asp Thr  Asp Ala Ser Ala Asp  Leu Tyr Ser Gly Lys  Thr Lys Ser
    1115                 1120                 1125

Trp Gly  Gly Gly Phe Tyr Ala  Ser Gly Leu Phe Arg  Ser Gly Ala
    1130                 1135                 1140

Tyr Phe  Asp Val Ile Ala Lys  Tyr Ile His Asn Glu  Asn Lys Tyr
    1145                 1150                 1155

Asp Leu  Asn Phe Ala Gly Ala  Gly Lys Gln Asn Phe  Arg Ser His
    1160                 1165                 1170

Ser Leu  Tyr Ala Gly Ala Glu  Val Gly Tyr Arg Tyr  His Leu Thr
    1175                 1180                 1185

Asp Thr  Thr Phe Val Glu Pro  Gln Ala Glu Leu Val  Trp Gly Arg
    1190                 1195                 1200

Leu Gln  Gly Gln Thr Phe Asn  Trp Asn Asp Ser Gly  Met Asp Val
    1205                 1210                 1215

Ser Met  Arg Arg Asn Ser Val  Asn Pro Leu Val Gly  Arg Thr Gly
```

```
                1220                1225                1230
Val Val Ser Gly Lys Thr Phe Ser Gly Lys Asp Trp Ser Leu Thr
        1235                1240                1245
Ala Arg Ala Gly Leu His Tyr Glu Phe Asp Leu Thr Asp Ser Ala
    1250                1255                1260
Asp Val His Leu Lys Asp Ala Ala Gly Glu His Gln Ile Asn Gly
    1265                1270                1275
Arg Lys Asp Ser Arg Met Leu Tyr Gly Val Gly Leu Asn Ala Arg
    1280                1285                1290
Phe Gly Asp Asn Thr Arg Leu Gly Leu Glu Val Glu Arg Ser Ala
    1295                1300                1305
Phe Gly Lys Tyr Asn Thr Asp Asp Ala Ile Asn Ala Asn Ile Arg
    1310                1315                1320

Tyr Ser Phe
    1325

<210> SEQ ID NO 10
<211> LENGTH: 1336
<212> TYPE: PRT
<213> ORGANISM: Unknown
<220> FEATURE:
<223> OTHER INFORMATION: Escherichia coli - Streptococcus pyogenes

<400> SEQUENCE: 10

Met Asn Arg Ile Tyr Ser Leu Arg Tyr Ser Ala Val Ala Arg Gly Phe
1               5                   10                  15
Ile Ala Val Ser Glu Phe Ala Arg Lys Cys Val His Lys Ser Val Arg
                20                  25                  30
Arg Leu Cys Phe Pro Val Leu Leu Leu Ile Pro Val Leu Phe Ser Ala
            35                  40                  45
Gly Ser Leu Ala Gly Thr Val Asn Asn Glu Leu Gly Tyr Gln Leu Phe
        50                  55                  60
Arg Asp Phe Ala Glu Asn Lys Gly Met Phe Arg Pro Gly Ala Thr Asn
65                  70                  75                  80
Ile Ala Ile Tyr Asn Lys Gln Gly Glu Phe Val Gly Thr Leu Asp Lys
                85                  90                  95
Ala Ala Met Pro Asp Phe Ser Ala Val Asp Ser Glu Ile Gly Val Ala
            100                 105                 110
Thr Leu Ile Asn Pro Gln Tyr Ile Ala Ser Val Lys His Asn Gly Gly
        115                 120                 125
Tyr Thr Asn Val Ser Phe Gly Asp Gly Glu Asn Arg Tyr Asn Ile Val
    130                 135                 140
Asp Arg Asn Asn Ala Pro Ser Leu Asp Phe His Ala Pro Arg Leu Asp
145                 150                 155                 160
Lys Leu Val Thr Glu Val Ala Pro Thr Ala Val Thr Ala Gln Gly Ala
                165                 170                 175
Val Ala Gly Ala Tyr Leu Asp Lys Glu Arg Tyr Pro Val Phe Tyr Arg
            180                 185                 190
Leu Gly Ser Gly Thr Gln Tyr Ile Lys Asp Ser Asn Gly Gln Leu Thr
        195                 200                 205
Lys Met Gly Gly Ala Tyr Ser Trp Leu Thr Gly Gly Thr Val Gly Ser
    210                 215                 220
Leu Ser Ser Tyr Gln Asn Gly Glu Met Ile Ser Thr Ser Ser Gly Leu
225                 230                 235                 240
Val Phe Asp Tyr Lys Leu Asn Gly Ala Met Pro Ile Tyr Gly Glu Ala
```

```
                  245                 250                 255
Gly Asp Ser Gly Ser Pro Leu Phe Ala Phe Asp Thr Val Gln Asn Lys
            260                 265                 270

Trp Val Leu Val Gly Val Leu Thr Ala Gly Asn Gly Ala Gly Gly Arg
        275                 280                 285

Gly Asn Asn Trp Ala Val Ile Pro Leu Asp Phe Ile Gly Gln Lys Phe
    290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
                325                 330                 335

Gln Gly Thr Thr Thr Tyr Ala Met His Gly Gln Gln Gly Asn Asp Leu
            340                 345                 350

Asn Ala Gly Lys Asn Leu Ile Phe Gln Gly Gln Asn Gly Gln Ile Asn
        355                 360                 365

Leu Lys Asp Ser Val Ser Gln Gly Ala Gly Ser Leu Thr Phe Arg Asp
    370                 375                 380

Asn Tyr Thr Val Thr Thr Ser Asn Gly Ser Thr Trp Thr Gly Ala Gly
385                 390                 395                 400

Ile Val Val Asp Asn Gly Val Ser Val Asn Trp Gln Val Asn Gly Val
                405                 410                 415

Lys Gly Asp Asn Leu His Lys Ile Gly Glu Gly Thr Leu Thr Val Gln
            420                 425                 430

Gly Thr Gly Ile Asn Glu Gly Gly Leu Lys Val Gly Asp Gly Lys Val
        435                 440                 445

Val Leu Asn Gln Gln Ala Asp Asn Lys Gly Gln Val Gln Ala Phe Ser
    450                 455                 460

Ser Val Asn Ile Ala Ser Gly Arg Pro Thr Val Leu Thr Asp Glu
465                 470                 475                 480

Arg Gln Val Asn Pro Asp Thr Val Ser Trp Gly Tyr Arg Gly Gly Thr
                485                 490                 495

Leu Asp Val Asn Gly Asn Ser Leu Thr Phe His Gln Leu Lys Ala Ala
            500                 505                 510

Asp Tyr Gly Ala Val Leu Ala Asn Asn Val Asp Lys Arg Ala Thr Ile
        515                 520                 525

Thr Leu Asp Tyr Ala Gly Ser Gly Ser Ser Gly Ser Ala Ser Gly Ala
    530                 535                 540

His Ile Val Met Val Asp Ala Tyr Lys Pro Thr Lys Gly Glu Gly Thr
545                 550                 555                 560

Gly Gly Ser Gly Ser Gly Asn Thr Ala Gly Tyr Leu Phe His Gly Gln
                565                 570                 575

Leu Lys Gly Asn Leu Asn Val Asp Asn Arg Leu Pro Glu Gly Val Thr
            580                 585                 590

Gly Ala Leu Val Met Asp Gly Ala Ala Asp Ile Ser Gly Thr Phe Thr
        595                 600                 605

Gln Glu Asn Gly Arg Leu Thr Leu Gln Gly His Pro Val Ile His Ala
    610                 615                 620

Tyr Asn Thr Gln Ser Val Ala Asp Lys Leu Ala Ser Gly Asp His
625                 630                 635                 640

Ser Val Leu Thr Gln Pro Thr Ser Phe Ser Gln Glu Asp Trp Glu Asn
                645                 650                 655

Arg Ser Phe Thr Phe Asp Arg Leu Ser Leu Lys Asn Thr Asp Phe Gly
            660                 665                 670
```

```
Leu Gly Arg Asn Ala Thr Leu Asn Thr Thr Ile Gln Ala Asp Asn Ser
        675                 680                 685

Ser Val Thr Leu Gly Asp Ser Arg Val Phe Ile Asp Lys Asn Asp Gly
        690                 695                 700

Gln Gly Thr Ala Phe Thr Leu Glu Glu Gly Thr Ser Val Ala Thr Lys
705                 710                 715                 720

Asp Ala Asp Lys Ser Val Phe Asn Gly Thr Val Asn Leu Asp Asn Gln
                725                 730                 735

Ser Val Leu Asn Ile Asn Asp Ile Phe Asn Gly Gly Ile Gln Ala Asn
                740                 745                 750

Asn Ser Thr Val Asn Ile Ser Ser Asp Ser Ala Val Leu Gly Asn Ser
            755                 760                 765

Thr Leu Thr Ser Thr Ala Leu Asn Leu Asn Lys Gly Ala Asn Ala Leu
        770                 775                 780

Ala Ser Gln Ser Phe Val Ser Asp Gly Pro Val Asn Ile Ser Asp Ala
785                 790                 795                 800

Thr Leu Ser Leu Asn Ser Arg Pro Asp Glu Val Ser His Thr Leu Leu
                805                 810                 815

Pro Val Tyr Asp Tyr Ala Gly Ser Trp Asn Leu Lys Gly Asp Asp Ala
                820                 825                 830

Arg Leu Asn Val Gly Pro Tyr Ser Met Leu Ser Gly Asn Ile Asn Val
            835                 840                 845

Gln Asp Lys Gly Thr Val Thr Leu Gly Gly Glu Gly Glu Leu Ser Pro
        850                 855                 860

Asp Leu Thr Leu Gln Asn Gln Met Leu Tyr Ser Leu Phe Asn Gly Tyr
865                 870                 875                 880

Arg Asn Ile Trp Ser Gly Ser Leu Asn Ala Pro Asp Ala Thr Val Ser
                885                 890                 895

Met Thr Asp Thr Gln Trp Ser Met Asn Gly Asn Ser Thr Ala Gly Asn
                900                 905                 910

Met Lys Leu Asn Arg Thr Ile Val Gly Phe Asn Gly Gly Thr Ser Pro
        915                 920                 925

Phe Thr Thr Leu Thr Thr Asp Asn Leu Asp Ala Val Gln Ser Ala Phe
        930                 935                 940

Val Met Arg Thr Asp Leu Asn Lys Ala Asp Lys Leu Val Ile Asn Lys
945                 950                 955                 960

Ser Ala Thr Gly His Asp Asn Ser Ile Trp Val Asn Phe Leu Lys Lys
                965                 970                 975

Pro Ser Asn Lys Asp Thr Leu Asp Ile Pro Leu Val Ser Ala Pro Glu
                980                 985                 990

Ala Thr Ala Asp Asn Leu Phe Arg Ala Ser Thr Arg Val  Val Gly Phe
            995                 1000                 1005

Ser Asp Val Thr Pro Ile Leu  Ser Val Arg Lys Glu  Asp Gly Lys
        1010                 1015                 1020

Lys Glu Trp Val Leu Asp Gly  Tyr Gln Val Ala Arg  Asn Asp Gly
        1025                 1030                 1035

Gln Gly Lys Ala Ala Ala Thr  Phe Met His Ile Ser  Tyr Asn Asn
        1040                 1045                 1050

Phe Ile Thr Glu Val Gly Ser  Leu Asn Lys Arg Met  Gly Asp Leu
        1055                 1060                 1065

Arg Asp Ile Asn Gly Glu Ala  Gly Thr Trp Val Arg  Leu Leu Asn
        1070                 1075                 1080
```

Gly Ser Gly Ser Ala Asp Gly Gly Phe Thr Asp His Tyr Thr Leu
    1085            1090            1095

Leu Gln Met Gly Ala Asp Arg Lys His Glu Leu Gly Ser Met Asp
    1100            1105            1110

Leu Phe Thr Gly Val Met Ala Thr Tyr Thr Asp Thr Asp Ala Ser
    1115            1120            1125

Ala Asp Leu Tyr Ser Gly Lys Thr Lys Ser Trp Gly Gly Gly Phe
    1130            1135            1140

Tyr Ala Ser Gly Leu Phe Arg Ser Gly Ala Tyr Phe Asp Val Ile
    1145            1150            1155

Ala Lys Tyr Ile His Asn Glu Asn Lys Tyr Asp Leu Asn Phe Ala
    1160            1165            1170

Gly Ala Gly Lys Gln Asn Phe Arg Ser His Ser Leu Tyr Ala Gly
    1175            1180            1185

Ala Glu Val Gly Tyr Arg Tyr His Leu Thr Asp Thr Thr Phe Val
    1190            1195            1200

Glu Pro Gln Ala Glu Leu Val Trp Gly Arg Leu Gln Gly Gln Thr
    1205            1210            1215

Phe Asn Trp Asn Asp Ser Gly Met Asp Val Ser Met Arg Arg Asn
    1220            1225            1230

Ser Val Asn Pro Leu Val Gly Arg Thr Gly Val Ser Gly Lys
    1235            1240            1245

Thr Phe Ser Gly Lys Asp Trp Ser Leu Thr Ala Arg Ala Gly Leu
    1250            1255            1260

His Tyr Glu Phe Asp Leu Thr Asp Ser Ala Asp Val His Leu Lys
    1265            1270            1275

Asp Ala Ala Gly Glu His Gln Ile Asn Gly Arg Lys Asp Ser Arg
    1280            1285            1290

Met Leu Tyr Gly Val Gly Leu Asn Ala Arg Phe Gly Asp Asn Thr
    1295            1300            1305

Arg Leu Gly Leu Glu Val Glu Arg Ser Ala Phe Gly Lys Tyr Asn
    1310            1315            1320

Thr Asp Asp Ala Ile Asn Ala Asn Ile Arg Tyr Ser Phe
    1325            1330            1335

<210> SEQ ID NO 11
<211> LENGTH: 1325
<212> TYPE: PRT
<213> ORGANISM: Unknown
<220> FEATURE:
<223> OTHER INFORMATION: Escherichia coli - Streptococcus pneumoniae

<400> SEQUENCE: 11

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
                20                  25                  30

Arg Leu Cys Phe Pro Val Leu Leu Leu Ile Pro Val Leu Phe Ser Ala
            35                  40                  45

Gly Ser Leu Ala Gly Thr Val Asn Asn Glu Leu Gly Tyr Gln Leu Phe
        50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

-continued

Ala Ala Met Pro Asp Phe Ser Ala Val Asp Ser Glu Ile Gly Val Ala
            100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160

Lys Leu Val Thr Glu Val Ala Pro Thr Ala Val Thr Ala Gln Gly Ala
                165                 170                 175

Val Ala Gly Ala Tyr Leu Asp Lys Glu Arg Tyr Pro Val Phe Tyr Arg
            180                 185                 190

Leu Gly Ser Gly Thr Gln Tyr Ile Lys Asp Ser Asn Gly Gln Leu Thr
        195                 200                 205

Lys Met Gly Gly Ala Tyr Ser Trp Leu Thr Gly Gly Thr Val Gly Ser
    210                 215                 220

Leu Ser Ser Tyr Gln Asn Gly Glu Met Ile Ser Thr Ser Ser Gly Leu
225                 230                 235                 240

Val Phe Asp Tyr Lys Leu Asn Gly Ala Met Pro Ile Tyr Gly Glu Ala
                245                 250                 255

Gly Asp Ser Gly Ser Pro Leu Phe Ala Phe Asp Thr Val Gln Asn Lys
            260                 265                 270

Trp Val Leu Val Gly Val Leu Thr Ala Gly Asn Gly Ala Gly Gly Arg
        275                 280                 285

Gly Asn Asn Trp Ala Val Ile Pro Leu Asp Phe Ile Gly Gln Lys Phe
    290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
                325                 330                 335

Gln Gly Thr Thr Thr Tyr Ala Met His Gly Gln Gln Gly Asn Asp Leu
            340                 345                 350

Asn Ala Gly Lys Asn Leu Ile Phe Gln Gly Gln Asn Gly Gln Ile Asn
        355                 360                 365

Leu Lys Asp Ser Val Ser Gln Gly Ala Gly Ser Leu Thr Phe Arg Asp
    370                 375                 380

Asn Tyr Thr Val Thr Thr Ser Asn Gly Ser Thr Trp Thr Gly Ala Gly
385                 390                 395                 400

Ile Val Val Asp Asn Gly Val Ser Val Asn Trp Gln Val Asn Gly Val
                405                 410                 415

Lys Gly Asp Asn Leu His Lys Ile Gly Glu Gly Thr Leu Thr Val Gln
            420                 425                 430

Gly Thr Gly Ile Asn Glu Gly Gly Leu Lys Val Gly Asp Gly Lys Val
        435                 440                 445

Val Leu Asn Gln Gln Ala Asp Asn Lys Gly Gln Val Gln Ala Phe Ser
    450                 455                 460

Ser Val Asn Ile Ala Ser Gly Arg Pro Thr Val Val Leu Thr Asp Glu
465                 470                 475                 480

Arg Gln Val Asn Pro Asp Thr Val Ser Trp Gly Tyr Arg Gly Gly Thr
                485                 490                 495

Leu Asp Val Asn Gly Asn Ser Leu Thr Phe His Gln Leu Lys Ala Ala
            500                 505                 510

Asp Tyr Gly Ala Val Leu Ala Asn Asn Val Asp Lys Arg Ala Thr Ile

-continued

```
            515                 520                 525
Thr Leu Asp Tyr Ala Gly Ser Gly Ser Ser Lys Leu Gly Asp Ile Glu
    530                 535                 540
Phe Ile Lys Val Asn Lys Gly Ser Gly Ser Gly Asn Thr Ala Gly Tyr
545                 550                 555                 560
Leu Phe His Gly Gln Leu Lys Gly Asn Leu Asn Val Asp Asn Arg Leu
                565                 570                 575
Pro Glu Gly Val Thr Gly Ala Leu Val Met Asp Gly Ala Ala Asp Ile
                580                 585                 590
Ser Gly Thr Phe Thr Gln Glu Asn Gly Arg Leu Thr Leu Gln Gly His
                595                 600                 605
Pro Val Ile His Ala Tyr Asn Thr Gln Ser Val Ala Asp Lys Leu Ala
            610                 615                 620
Ala Ser Gly Asp His Ser Val Leu Thr Gln Pro Thr Ser Phe Ser Gln
625                 630                 635                 640
Glu Asp Trp Glu Asn Arg Ser Phe Thr Phe Asp Arg Leu Ser Leu Lys
                645                 650                 655
Asn Thr Asp Phe Gly Leu Gly Arg Asn Ala Thr Leu Asn Thr Thr Ile
                660                 665                 670
Gln Ala Asp Asn Ser Ser Val Thr Leu Gly Asp Ser Arg Val Phe Ile
            675                 680                 685
Asp Lys Asn Asp Gly Gln Gly Thr Ala Phe Thr Leu Glu Glu Gly Thr
690                 695                 700
Ser Val Ala Thr Lys Asp Ala Asp Lys Ser Val Phe Asn Gly Thr Val
705                 710                 715                 720
Asn Leu Asp Asn Gln Ser Val Leu Asn Ile Asn Asp Ile Phe Asn Gly
                725                 730                 735
Gly Ile Gln Ala Asn Asn Ser Thr Val Asn Ile Ser Ser Asp Ser Ala
            740                 745                 750
Val Leu Gly Asn Ser Thr Leu Thr Ser Thr Ala Leu Asn Leu Asn Lys
                755                 760                 765
Gly Ala Asn Ala Leu Ala Ser Gln Ser Phe Val Ser Asp Gly Pro Val
            770                 775                 780
Asn Ile Ser Asp Ala Thr Leu Ser Leu Asn Ser Arg Pro Asp Glu Val
785                 790                 795                 800
Ser His Thr Leu Leu Pro Val Tyr Asp Tyr Ala Gly Ser Trp Asn Leu
                805                 810                 815
Lys Gly Asp Asp Ala Arg Leu Asn Val Gly Pro Tyr Ser Met Leu Ser
                820                 825                 830
Gly Asn Ile Asn Val Gln Asp Lys Gly Thr Val Thr Leu Gly Gly Glu
            835                 840                 845
Gly Glu Leu Ser Pro Asp Leu Thr Leu Gln Asn Gln Met Leu Tyr Ser
            850                 855                 860
Leu Phe Asn Gly Tyr Arg Asn Ile Trp Ser Gly Ser Leu Asn Ala Pro
865                 870                 875                 880
Asp Ala Thr Val Ser Met Thr Asp Thr Gln Trp Ser Met Asn Gly Asn
                885                 890                 895
Ser Thr Ala Gly Asn Met Lys Leu Asn Arg Thr Ile Val Gly Phe Asn
                900                 905                 910
Gly Gly Thr Ser Pro Phe Thr Thr Leu Thr Thr Asp Asn Leu Asp Ala
                915                 920                 925
Val Gln Ser Ala Phe Val Met Arg Thr Asp Leu Asn Lys Ala Asp Lys
            930                 935                 940
```

```
Leu Val Ile Asn Lys Ser Ala Thr Gly His Asp Asn Ser Ile Trp Val
945                 950                 955                 960

Asn Phe Leu Lys Lys Pro Ser Asn Lys Asp Thr Leu Asp Ile Pro Leu
                965                 970                 975

Val Ser Ala Pro Glu Ala Thr Ala Asp Asn Leu Phe Arg Ala Ser Thr
            980                 985                 990

Arg Val Val Gly Phe Ser Asp Val Thr Pro Ile Leu Ser Val Arg Lys
        995                 1000                1005

Glu Asp Gly Lys Lys Glu Trp Val Leu Asp Gly Tyr Gln Val Ala
    1010                1015                1020

Arg Asn Asp Gly Gln Gly Lys Ala Ala Ala Thr Phe Met His Ile
    1025                1030                1035

Ser Tyr Asn Asn Phe Ile Thr Glu Val Gly Ser Leu Asn Lys Arg
    1040                1045                1050

Met Gly Asp Leu Arg Asp Ile Asn Gly Glu Ala Gly Thr Trp Val
    1055                1060                1065

Arg Leu Leu Asn Gly Ser Gly Ser Ala Asp Gly Gly Phe Thr Asp
    1070                1075                1080

His Tyr Thr Leu Leu Gln Met Gly Ala Asp Arg Lys His Glu Leu
    1085                1090                1095

Gly Ser Met Asp Leu Phe Thr Gly Val Met Ala Thr Tyr Thr Asp
    1100                1105                1110

Thr Asp Ala Ser Ala Asp Leu Tyr Ser Gly Lys Thr Lys Ser Trp
    1115                1120                1125

Gly Gly Gly Phe Tyr Ala Ser Gly Leu Phe Arg Ser Gly Ala Tyr
    1130                1135                1140

Phe Asp Val Ile Ala Lys Tyr Ile His Asn Glu Asn Lys Tyr Asp
    1145                1150                1155

Leu Asn Phe Ala Gly Ala Gly Lys Gln Asn Phe Arg Ser His Ser
    1160                1165                1170

Leu Tyr Ala Gly Ala Glu Val Gly Tyr Arg Tyr His Leu Thr Asp
    1175                1180                1185

Thr Thr Phe Val Glu Pro Gln Ala Glu Leu Val Trp Gly Arg Leu
    1190                1195                1200

Gln Gly Gln Thr Phe Asn Trp Asn Asp Ser Gly Met Asp Val Ser
    1205                1210                1215

Met Arg Arg Asn Ser Val Asn Pro Leu Val Gly Arg Thr Gly Val
    1220                1225                1230

Val Ser Gly Lys Thr Phe Ser Gly Lys Asp Trp Ser Leu Thr Ala
    1235                1240                1245

Arg Ala Gly Leu His Tyr Glu Phe Asp Leu Thr Asp Ser Ala Asp
    1250                1255                1260

Val His Leu Lys Asp Ala Ala Gly Glu His Gln Ile Asn Gly Arg
    1265                1270                1275

Lys Asp Ser Arg Met Leu Tyr Gly Val Gly Leu Asn Ala Arg Phe
    1280                1285                1290

Gly Asp Asn Thr Arg Leu Gly Leu Glu Val Glu Arg Ser Ala Phe
    1295                1300                1305

Gly Lys Tyr Asn Thr Asp Asp Ala Ile Asn Ala Asn Ile Arg Tyr
    1310                1315                1320

Ser Phe
    1325
```

<210> SEQ ID NO 12
<211> LENGTH: 1395
<212> TYPE: PRT
<213> ORGANISM: Unknown
<220> FEATURE:
<223> OTHER INFORMATION: Escherichia coli - Streptococcus pyogenes

<400> SEQUENCE: 12

```
Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Leu Ile Pro Val Leu Phe Ser Ala
        35                  40                  45

Gly Ser Leu Ala Gly Thr Val Asn Asn Glu Leu Gly Tyr Gln Leu Phe
    50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

Ala Ala Met Pro Asp Phe Ser Ala Val Asp Ser Glu Ile Gly Val Ala
            100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160

Lys Leu Val Thr Glu Val Ala Pro Thr Ala Val Thr Ala Gln Gly Ala
                165                 170                 175

Val Ala Gly Ala Tyr Leu Asp Lys Glu Arg Tyr Pro Val Phe Tyr Arg
            180                 185                 190

Leu Gly Ser Gly Thr Gln Tyr Ile Lys Asp Ser Asn Gly Gln Leu Thr
        195                 200                 205

Lys Met Gly Gly Ala Tyr Ser Trp Leu Thr Gly Thr Val Gly Ser
    210                 215                 220

Leu Ser Ser Tyr Gln Asn Gly Glu Met Ile Ser Thr Ser Gly Leu
225                 230                 235                 240

Val Phe Asp Tyr Lys Leu Asn Gly Ala Met Pro Ile Tyr Gly Glu Ala
                245                 250                 255

Gly Asp Ser Gly Ser Pro Leu Phe Ala Phe Asp Thr Val Gln Asn Lys
            260                 265                 270

Trp Val Leu Val Gly Val Leu Thr Ala Gly Asn Gly Ala Gly Gly Arg
        275                 280                 285

Gly Asn Asn Trp Ala Val Ile Pro Leu Asp Phe Ile Gly Gln Lys Phe
    290                 295                 300

Asn Glu Asp Asn Asp Ala Pro Val Thr Phe Arg Thr Ser Glu Gly Gly
305                 310                 315                 320

Ala Leu Glu Trp Ser Phe Asn Ser Ser Thr Gly Ala Gly Ala Leu Thr
                325                 330                 335

Gln Gly Thr Thr Thr Tyr Ala Met His Gly Gln Gln Gly Asn Asp Leu
            340                 345                 350

Asn Ala Gly Lys Asn Leu Ile Phe Gln Gly Gln Asn Gly Gln Ile Asn
        355                 360                 365
```

```
Leu Lys Asp Ser Val Ser Gln Gly Ala Gly Ser Leu Thr Phe Arg Asp
370                 375                 380

Asn Tyr Thr Val Thr Thr Ser Asn Gly Ser Thr Trp Thr Gly Ala Gly
385                 390                 395                 400

Ile Val Val Asp Asn Gly Val Ser Val Asn Trp Gln Val Asn Gly Val
                405                 410                 415

Lys Gly Asp Asn Leu His Lys Ile Gly Glu Gly Thr Leu Thr Val Gln
            420                 425                 430

Gly Thr Gly Ile Asn Glu Gly Gly Leu Lys Val Gly Asp Gly Lys Val
            435                 440                 445

Val Leu Asn Gln Gln Ala Asp Asn Lys Gly Gln Val Gln Ala Phe Ser
450                 455                 460

Ser Val Asn Ile Ala Ser Gly Arg Pro Thr Val Val Leu Thr Asp Glu
465                 470                 475                 480

Arg Gln Val Asn Pro Asp Thr Val Ser Trp Gly Tyr Arg Gly Gly Thr
                485                 490                 495

Leu Asp Val Asn Gly Asn Ser Leu Thr Phe His Gln Leu Lys Ala Ala
            500                 505                 510

Asp Tyr Gly Ala Val Leu Ala Asn Asn Val Asp Lys Arg Ala Thr Ile
            515                 520                 525

Thr Leu Asp Tyr Ala Leu Arg Ala Asp Lys Val Ala Leu Asn Gly Trp
530                 535                 540

Ser Glu Ser Gly Lys Gly Thr Ala Gly Asn Leu Tyr Lys Tyr Asn Asn
545                 550                 555                 560

Pro Tyr Thr Asn Thr Thr Asp Tyr Phe Ile Leu Lys Gln Ser Thr Tyr
                565                 570                 575

Gly Tyr Phe Pro Thr Asp Gln Ser Ser Asn Ala Thr Trp Glu Phe Val
            580                 585                 590

Gly His Ser Gln Gly Asp Ala Gln Lys Leu Val Ala Asp Arg Phe Asn
            595                 600                 605

Thr Ala Gly Tyr Leu Phe His Gly Gln Leu Lys Gly Asn Leu Asn Val
610                 615                 620

Asp Asn Arg Leu Pro Glu Gly Val Thr Gly Ala Leu Val Met Asp Gly
625                 630                 635                 640

Ala Ala Asp Ile Ser Gly Thr Phe Thr Gln Glu Asn Gly Arg Leu Thr
                645                 650                 655

Leu Gln Gly His Pro Val Ile His Ala Tyr Asn Thr Gln Ser Val Ala
            660                 665                 670

Asp Lys Leu Ala Ala Ser Gly Asp His Ser Val Leu Thr Gln Pro Thr
            675                 680                 685

Ser Phe Ser Gln Glu Asp Trp Glu Asn Arg Ser Phe Thr Phe Asp Arg
690                 695                 700

Leu Ser Leu Lys Asn Thr Asp Phe Gly Leu Gly Arg Asn Ala Thr Leu
705                 710                 715                 720

Asn Thr Thr Ile Gln Ala Asp Asn Ser Ser Val Thr Leu Gly Asp Ser
                725                 730                 735

Arg Val Phe Ile Asp Lys Asn Asp Gly Gln Gly Thr Ala Phe Thr Leu
            740                 745                 750

Glu Glu Gly Thr Ser Val Ala Gly Ser Gly Ser Ser Ala His Ile Val
            755                 760                 765

Met Val Asp Ala Tyr Lys Pro Thr Lys Gly Ser Gly Ser Gly Lys Ser
770                 775                 780

Val Phe Asn Gly Thr Val Asn Leu Asp Asn Gln Ser Val Leu Asn Ile
```

```
                         785                 790                 795                 800
        Asn Asp Ile Phe Asn Gly Gly Ile Gln Ala Asn Asn Ser Thr Val Asn
                             805                 810                 815

Ile Ser Ser Asp Ser Ala Val Leu Gly Asn Ser Thr Leu Thr Ser Thr
                             820                 825                 830

Ala Leu Asn Leu Asn Lys Gly Ala Asn Ala Leu Ala Ser Gln Ser Phe
                             835                 840                 845

Val Ser Asp Gly Pro Val Asn Ile Ser Asp Ala Thr Leu Ser Leu Asn
                 850                 855                 860

Ser Arg Pro Asp Glu Val Ser His Thr Leu Leu Pro Val Tyr Asp Tyr
        865                 870                 875                 880

Ala Gly Ser Trp Asn Leu Lys Gly Asp Asp Ala Arg Leu Asn Val Gly
                             885                 890                 895

Pro Tyr Ser Met Leu Ser Gly Asn Ile Asn Val Gln Asp Lys Gly Thr
                         900                 905                 910

Val Thr Leu Gly Gly Glu Gly Glu Leu Ser Pro Asp Leu Thr Leu Gln
                     915                 920                 925

Asn Gln Met Leu Tyr Ser Leu Phe Asn Gly Tyr Arg Asn Ile Trp Ser
                 930                 935                 940

Gly Ser Leu Asn Ala Pro Asp Ala Thr Val Ser Met Thr Asp Thr Gln
        945                 950                 955                 960

Trp Ser Met Asn Gly Asn Ser Thr Ala Gly Asn Met Lys Leu Asn Arg
                             965                 970                 975

Thr Ile Val Gly Phe Asn Gly Gly Thr Ser Pro Phe Thr Thr Leu Thr
                         980                 985                 990

Thr Asp Asn Leu Asp Ala Val Gln Ser Ala Phe Val Met Arg Thr Asp
                     995                 1000                1005

Leu Asn Lys Ala Asp Lys Leu Val Ile Asn Lys Ser Ala Thr Gly
                1010                1015                1020

His Asp Asn Ser Ile Trp Val Asn Phe Leu Lys Lys Pro Ser Asn
                1025                1030                1035

Lys Asp Thr Leu Asp Ile Pro Leu Val Ser Ala Pro Glu Ala Thr
                1040                1045                1050

Ala Asp Asn Leu Phe Arg Ala Ser Thr Arg Val Val Gly Phe Ser
                1055                1060                1065

Asp Val Thr Pro Ile Leu Ser Val Arg Lys Glu Asp Gly Lys Lys
                1070                1075                1080

Glu Trp Val Leu Asp Gly Tyr Gln Val Ala Arg Asn Asp Gly Gln
                1085                1090                1095

Gly Lys Ala Ala Ala Thr Phe Met His Ile Ser Tyr Asn Asn Phe
                1100                1105                1110

Ile Thr Glu Val Gly Ser Leu Asn Lys Arg Met Gly Asp Leu Arg
                1115                1120                1125

Asp Ile Asn Gly Glu Ala Gly Thr Trp Val Arg Leu Leu Asn Gly
                1130                1135                1140

Ser Gly Ser Ala Asp Gly Gly Phe Thr Asp His Tyr Thr Leu Leu
                1145                1150                1155

Gln Met Gly Ala Asp Arg Lys His Glu Leu Gly Ser Met Asp Leu
                1160                1165                1170

Phe Thr Gly Val Met Ala Thr Tyr Thr Asp Thr Asp Ala Ser Ala
                1175                1180                1185

Asp Leu Tyr Ser Gly Lys Thr Lys Ser Trp Gly Gly Gly Phe Tyr
                1190                1195                1200
```

```
Ala Ser Gly Leu Phe Arg Ser Gly Ala Tyr Phe Asp Val Ile Ala
    1205                1210                1215

Lys Tyr Ile His Asn Glu Asn Lys Tyr Asp Leu Asn Phe Ala Gly
    1220                1225                1230

Ala Gly Lys Gln Asn Phe Arg Ser His Ser Leu Tyr Ala Gly Ala
    1235                1240                1245

Glu Val Gly Tyr Arg Tyr His Leu Thr Asp Thr Thr Phe Val Glu
    1250                1255                1260

Pro Gln Ala Glu Leu Val Trp Gly Arg Leu Gln Gly Gln Thr Phe
    1265                1270                1275

Asn Trp Asn Asp Ser Gly Met Asp Val Ser Met Arg Arg Asn Ser
    1280                1285                1290

Val Asn Pro Leu Val Gly Arg Thr Gly Val Val Ser Gly Lys Thr
    1295                1300                1305

Phe Ser Gly Lys Asp Trp Ser Leu Thr Ala Arg Ala Gly Leu His
    1310                1315                1320

Tyr Glu Phe Asp Leu Thr Asp Ser Ala Asp Val His Leu Lys Asp
    1325                1330                1335

Ala Ala Gly Glu His Gln Ile Asn Gly Arg Lys Asp Ser Arg Met
    1340                1345                1350

Leu Tyr Gly Val Gly Leu Asn Ala Arg Phe Gly Asp Asn Thr Arg
    1355                1360                1365

Leu Gly Leu Glu Val Glu Arg Ser Ala Phe Gly Lys Tyr Asn Thr
    1370                1375                1380

Asp Asp Ala Ile Asn Ala Asn Ile Arg Tyr Ser Phe
    1385                1390                1395

<210> SEQ ID NO 13
<211> LENGTH: 1405
<212> TYPE: PRT
<213> ORGANISM: Unknown
<220> FEATURE:
<223> OTHER INFORMATION: Escherichia coli - Streptococcus pyogenes

<400> SEQUENCE: 13

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
                20                  25                  30

Arg Leu Cys Phe Pro Val Leu Leu Leu Ile Pro Val Leu Phe Ser Ala
            35                  40                  45

Gly Ser Leu Ala Gly Thr Val Asn Asn Glu Leu Gly Tyr Gln Leu Phe
        50                  55                  60

Arg Asp Phe Ala Glu Asn Lys Gly Met Phe Arg Pro Gly Ala Thr Asn
65                  70                  75                  80

Ile Ala Ile Tyr Asn Lys Gln Gly Glu Phe Val Gly Thr Leu Asp Lys
                85                  90                  95

Ala Ala Met Pro Asp Phe Ser Ala Val Asp Ser Glu Ile Gly Val Ala
            100                 105                 110

Thr Leu Ile Asn Pro Gln Tyr Ile Ala Ser Val Lys His Asn Gly Gly
        115                 120                 125

Tyr Thr Asn Val Ser Phe Gly Asp Gly Glu Asn Arg Tyr Asn Ile Val
    130                 135                 140

Asp Arg Asn Asn Ala Pro Ser Leu Asp Phe His Ala Pro Arg Leu Asp
145                 150                 155                 160
```

```
Lys Leu Val Thr Glu Val Ala Pro Thr Ala Val Thr Ala Gln Gly Ala
                165                 170                 175
Val Ala Gly Ala Tyr Leu Asp Lys Glu Arg Tyr Pro Val Phe Tyr Arg
            180                 185                 190
Leu Gly Ser Gly Thr Gln Tyr Ile Lys Asp Ser Asn Gly Gln Leu Thr
        195                 200                 205
Lys Met Gly Gly Ala Tyr Ser Trp Leu Thr Gly Gly Thr Val Gly Ser
210                 215                 220
Leu Ser Ser Tyr Gln Asn Gly Glu Met Ile Ser Thr Ser Ser Gly Leu
225                 230                 235                 240
Val Phe Asp Tyr Lys Leu Asn Gly Ala Met Pro Ile Tyr Gly Glu Ala
                245                 250                 255
Gly Asp Ser Gly Ser Pro Leu Phe Ala Phe Asp Thr Val Gln Asn Lys
            260                 265                 270
Trp Val Leu Val Gly Val Leu Thr Ala Gly Asn Gly Ala Gly Gly Arg
        275                 280                 285
Gly Asn Asn Trp Ala Val Ile Pro Leu Asp Phe Ile Gly Gln Lys Phe
290                 295                 300
Asn Glu Asp Asn Asp Ala Pro Val Thr Phe Arg Thr Ser Glu Gly Gly
305                 310                 315                 320
Ala Leu Glu Trp Ser Phe Asn Ser Ser Thr Gly Ala Gly Ala Leu Thr
                325                 330                 335
Gln Gly Thr Thr Thr Tyr Ala Met His Gly Gln Gln Gly Asn Asp Leu
            340                 345                 350
Asn Ala Gly Lys Asn Leu Ile Phe Gln Gly Gln Asn Gly Gln Ile Asn
        355                 360                 365
Leu Lys Asp Ser Val Ser Gln Gly Ala Gly Ser Leu Thr Phe Arg Asp
370                 375                 380
Asn Tyr Thr Val Thr Thr Ser Asn Gly Ser Thr Trp Thr Gly Ala Gly
385                 390                 395                 400
Ile Val Val Asp Asn Gly Val Ser Val Asn Trp Gln Val Asn Gly Val
                405                 410                 415
Lys Gly Asp Asn Leu His Lys Ile Gly Glu Gly Thr Leu Thr Val Gln
            420                 425                 430
Gly Thr Gly Ile Asn Glu Gly Gly Leu Lys Val Gly Asp Gly Lys Val
        435                 440                 445
Val Leu Asn Gln Gln Ala Asp Asn Lys Gly Gln Val Gln Ala Phe Ser
450                 455                 460
Ser Val Asn Ile Ala Ser Gly Arg Pro Thr Val Leu Thr Asp Glu
465                 470                 475                 480
Arg Gln Val Asn Pro Asp Thr Val Ser Trp Gly Tyr Arg Gly Gly Thr
                485                 490                 495
Leu Asp Val Asn Gly Asn Ser Leu Thr Phe His Gln Leu Lys Ala Ala
            500                 505                 510
Asp Tyr Gly Ala Val Leu Ala Asn Asn Val Asp Lys Arg Ala Thr Ile
        515                 520                 525
Thr Leu Asp Tyr Ala Leu Arg Ala Asp Lys Val Ala Leu Asn Gly Trp
530                 535                 540
Ser Glu Ser Gly Lys Gly Thr Ala Gly Asn Leu Tyr Lys Tyr Asn Asn
545                 550                 555                 560
Pro Tyr Thr Asn Thr Thr Asp Tyr Phe Ile Leu Lys Gln Ser Thr Tyr
                565                 570                 575
```

Gly Tyr Phe Pro Thr Asp Gln Ser Ser Asn Ala Thr Trp Glu Phe Val
            580                 585                 590

Gly His Ser Gln Gly Asp Ala Gln Lys Leu Val Ala Asp Arg Phe Asn
        595                 600                 605

Thr Ala Gly Tyr Leu Phe His Gly Gln Leu Lys Gly Asn Leu Asn Val
    610                 615                 620

Asp Asn Arg Leu Pro Glu Gly Val Thr Gly Ala Leu Val Met Asp Gly
625                 630                 635                 640

Ala Ala Asp Ile Ser Gly Thr Phe Thr Gln Glu Asn Gly Arg Leu Thr
                645                 650                 655

Leu Gln Gly His Pro Val Ile His Ala Tyr Asn Thr Gln Ser Val Ala
            660                 665                 670

Asp Lys Leu Ala Ala Ser Gly Asp His Ser Val Leu Thr Gln Pro Thr
        675                 680                 685

Ser Phe Ser Gln Glu Asp Trp Glu Asn Arg Ser Phe Thr Phe Asp Arg
    690                 695                 700

Leu Ser Leu Lys Asn Thr Asp Phe Gly Leu Gly Arg Asn Ala Thr Leu
705                 710                 715                 720

Asn Thr Thr Ile Gln Ala Asp Asn Ser Ser Val Thr Leu Gly Asp Ser
                725                 730                 735

Arg Val Phe Ile Asp Lys Asn Asp Gly Gln Gly Thr Ala Phe Thr Leu
            740                 745                 750

Glu Glu Gly Thr Ser Val Ala Gly Ser Gly Ser Ser Gly Ser Ala Ser
        755                 760                 765

Gly Ala His Ile Val Met Val Asp Ala Tyr Lys Pro Thr Lys Gly Glu
    770                 775                 780

Gly Thr Gly Gly Ser Gly Ser Gly Lys Ser Val Phe Asn Gly Thr Val
785                 790                 795                 800

Asn Leu Asp Asn Gln Ser Val Leu Asn Ile Asn Asp Ile Phe Asn Gly
                805                 810                 815

Gly Ile Gln Ala Asn Asn Ser Thr Val Asn Ile Ser Ser Asp Ser Ala
            820                 825                 830

Val Leu Gly Asn Ser Thr Leu Thr Ser Thr Ala Leu Asn Leu Asn Lys
        835                 840                 845

Gly Ala Asn Ala Leu Ala Ser Gln Ser Phe Val Ser Asp Gly Pro Val
    850                 855                 860

Asn Ile Ser Asp Ala Thr Leu Ser Leu Asn Ser Arg Pro Asp Glu Val
865                 870                 875                 880

Ser His Thr Leu Leu Pro Val Tyr Asp Tyr Ala Gly Ser Leu Asn Leu
                885                 890                 895

Lys Gly Asp Asp Ala Arg Leu Asn Val Gly Pro Tyr Ser Met Leu Ser
            900                 905                 910

Gly Asn Ile Asn Val Gln Asp Lys Gly Thr Val Thr Leu Gly Gly Glu
        915                 920                 925

Gly Glu Leu Ser Pro Asp Leu Thr Leu Gln Asn Gln Met Leu Tyr Ser
    930                 935                 940

Leu Phe Asn Gly Tyr Arg Asn Ile Trp Ser Gly Ser Leu Asn Ala Pro
945                 950                 955                 960

Asp Ala Thr Val Ser Met Thr Asp Thr Gln Trp Ser Met Asn Gly Asn
                965                 970                 975

Ser Thr Ala Gly Asn Met Lys Leu Asn Arg Thr Ile Val Gly Phe Asn
            980                 985                 990

Gly Gly Thr Ser Pro Phe Thr Thr  Leu Thr Thr Asp Asn  Leu Asp Ala

-continued

```
            995                 1000                1005
Val Gln Ser Ala Phe Val Met Arg Thr Asp Leu Asn Lys Ala Asp
            1010                1015                1020

Lys Leu Val Ile Asn Lys Ser Ala Thr Gly His Asp Asn Ser Ile
            1025                1030                1035

Trp Val Asn Phe Leu Lys Lys Pro Ser Asn Lys Asp Thr Leu Asp
            1040                1045                1050

Ile Pro Leu Val Ser Ala Pro Glu Ala Thr Ala Asp Asn Leu Phe
            1055                1060                1065

Arg Ala Ser Thr Arg Val Val Gly Phe Ser Asp Val Thr Pro Ile
            1070                1075                1080

Leu Ser Val Arg Lys Glu Asp Gly Lys Lys Glu Trp Val Leu Asp
            1085                1090                1095

Gly Tyr Gln Val Ala Arg Asn Asp Gly Gln Gly Lys Ala Ala Ala
            1100                1105                1110

Thr Phe Met His Ile Ser Tyr Asn Asn Phe Ile Thr Glu Val Gly
            1115                1120                1125

Ser Leu Asn Lys Arg Met Gly Asp Leu Arg Asp Ile Asn Gly Glu
            1130                1135                1140

Ala Gly Thr Trp Val Arg Leu Leu Asn Gly Ser Gly Ser Ala Asp
            1145                1150                1155

Gly Gly Phe Thr Asp His Tyr Thr Leu Leu Gln Met Gly Ala Asp
            1160                1165                1170

Arg Lys His Glu Leu Gly Ser Met Asp Leu Phe Thr Gly Val Met
            1175                1180                1185

Ala Thr Tyr Thr Asp Thr Asp Ala Ser Ala Asp Leu Tyr Ser Gly
            1190                1195                1200

Lys Thr Lys Ser Trp Gly Gly Gly Phe Tyr Ala Ser Gly Leu Phe
            1205                1210                1215

Arg Ser Gly Ala Tyr Phe Asp Val Ile Ala Lys Tyr Ile His Asn
            1220                1225                1230

Glu Asn Lys Tyr Asp Leu Asn Phe Ala Gly Ala Gly Lys Gln Asn
            1235                1240                1245

Phe Arg Ser His Ser Leu Tyr Ala Gly Ala Glu Val Gly Tyr Arg
            1250                1255                1260

Tyr His Leu Thr Asp Thr Thr Phe Val Glu Pro Gln Ala Glu Leu
            1265                1270                1275

Val Trp Gly Arg Leu Gln Gly Gln Thr Phe Asn Trp Asn Asp Ser
            1280                1285                1290

Gly Met Asp Val Ser Met Arg Arg Asn Ser Val Asn Pro Leu Val
            1295                1300                1305

Gly Arg Thr Gly Val Val Ser Gly Lys Thr Phe Ser Gly Lys Asp
            1310                1315                1320

Trp Ser Leu Thr Ala Arg Ala Gly Leu His Tyr Glu Phe Asp Leu
            1325                1330                1335

Thr Asp Ser Ala Asp Val His Leu Lys Asp Ala Ala Gly Glu His
            1340                1345                1350

Gln Ile Asn Gly Arg Lys Asp Ser Arg Met Leu Tyr Gly Val Gly
            1355                1360                1365

Leu Asn Ala Arg Phe Gly Asp Asn Thr Arg Leu Gly Leu Glu Val
            1370                1375                1380

Glu Arg Ser Ala Phe Gly Lys Tyr Asn Thr Asp Asp Ala Ile Asn
            1385                1390                1395
```

Ala Asn Ile Arg Tyr Ser Phe
         1400            1405

<210> SEQ ID NO 14
<211> LENGTH: 256
<212> TYPE: PRT
<213> ORGANISM: Unknown
<220> FEATURE:
<223> OTHER INFORMATION: Streptococcus pyogenes - Streptococcus
      pneumoniae

<400> SEQUENCE: 14

Met Ser Tyr Tyr His His His His His His Asp Tyr Asp Ser Ala Thr
1               5                   10                  15

His Ile Lys Phe Ser Lys Arg Asp Glu Asp Gly Lys Glu Leu Ala Gly
            20                  25                  30

Ala Thr Met Glu Leu Arg Asp Ser Ser Gly Lys Thr Ile Ser Thr Trp
        35                  40                  45

Ile Ser Asp Gly Gln Val Lys Asp Phe Tyr Leu Tyr Pro Gly Lys Tyr
    50                  55                  60

Thr Phe Val Glu Thr Ala Ala Pro Asp Gly Tyr Glu Val Ala Thr Ala
65                  70                  75                  80

Ile Thr Phe Thr Val Asn Glu Gln Gly Gln Val Thr Val Asn Gly Lys
                85                  90                  95

Ala Thr Lys Gly Asp Ala His Ile Gly Ser Pro Ala Asn Leu Lys Ala
            100                 105                 110

Leu Glu Ala Gln Lys Gln Lys Glu Gln Arg Gln Ala Ala Glu Glu Leu
        115                 120                 125

Ala Asn Ala Lys Lys Leu Lys Glu Gln Leu Glu Lys Gly Ser His Met
130                 135                 140

Lys Pro Leu Arg Gly Ala Val Phe Ser Leu Gln Lys Gln His Pro Asp
145                 150                 155                 160

Tyr Pro Asp Ile Tyr Gly Ala Ile Asp Gln Asn Gly Thr Tyr Gln Asn
                165                 170                 175

Val Arg Thr Gly Glu Asp Gly Lys Leu Thr Phe Lys Asn Leu Ser Asp
            180                 185                 190

Gly Lys Tyr Arg Leu Phe Glu Asn Ser Glu Pro Ala Gly Tyr Lys Pro
        195                 200                 205

Val Gln Asn Lys Pro Ile Val Ala Phe Gln Ile Val Asn Gly Glu Val
210                 215                 220

Arg Asp Val Thr Ser Ile Val Pro Gln Asp Ile Pro Ala Thr Tyr Glu
225                 230                 235                 240

Phe Thr Asn Gly Lys His Tyr Ile Thr Asn Glu Pro Ile Pro Pro Lys
                245                 250                 255

<210> SEQ ID NO 15
<211> LENGTH: 245
<212> TYPE: PRT
<213> ORGANISM: Unknown
<220> FEATURE:
<223> OTHER INFORMATION: Camelus dromedarius - Streptococcus pyogenes

<400> SEQUENCE: 15

Met Lys Tyr Leu Leu Pro Thr Ala Ala Ala Gly Leu Leu Leu Leu Ala
1               5                   10                  15

Ala Gln Pro Ala Met Ala Met Val Gln Leu Val Glu Ser Gly Gly Ala
            20                  25                  30

Leu Val Gln Pro Gly Gly Ser Leu Arg Leu Ser Cys Ala Ala Ser Gly
            35                  40                  45

Phe Pro Val Asn Arg Tyr Ser Met Arg Trp Tyr Arg Gln Ala Pro Gly
    50                  55                  60

Lys Glu Arg Glu Trp Val Ala Gly Met Ser Ser Ala Gly Asp Arg Ser
65                  70                  75                  80

Ser Tyr Glu Asp Ser Val Lys Gly Arg Phe Thr Ile Ser Arg Asp Asp
                85                  90                  95

Ala Arg Asn Thr Val Tyr Leu Gln Met Asn Ser Leu Lys Pro Glu Asp
            100                 105                 110

Thr Ala Val Tyr Tyr Cys Asn Val Asn Val Gly Phe Glu Tyr Trp Gly
            115                 120                 125

Gln Gly Thr Gln Val Thr Val Ser Ser Lys Gly Ser Gly Gly Thr Gly
        130                 135                 140

Asp Ser Ala Thr His Ile Lys Phe Ser Lys Arg Asp Glu Asp Gly Lys
145                 150                 155                 160

Glu Leu Ala Gly Ala Thr Met Glu Leu Arg Asp Ser Ser Gly Lys Thr
                165                 170                 175

Ile Ser Thr Trp Ile Ser Asp Gly Gln Val Lys Asp Phe Tyr Leu Tyr
            180                 185                 190

Pro Gly Lys Tyr Thr Phe Val Glu Thr Ala Ala Pro Asp Gly Tyr Glu
        195                 200                 205

Val Ala Thr Ala Ile Thr Phe Thr Val Asn Glu Gln Gly Gln Val Thr
    210                 215                 220

Val Asn Gly Lys Ala Thr Lys Gly Asp Ala His Ile Gly Ser Gly His
225                 230                 235                 240

His His His His His
            245

<210> SEQ ID NO 16
<211> LENGTH: 245
<212> TYPE: PRT
<213> ORGANISM: Unknown
<220> FEATURE:
<223> OTHER INFORMATION: Camelus dromedarius - Streptococcus pyogenes

<400> SEQUENCE: 16

Met Lys Tyr Leu Leu Pro Thr Ala Ala Ala Gly Leu Leu Leu Leu Ala
1               5                   10                  15

Ala Gln Pro Ala Met Ala Met Val Gln Leu Val Glu Ser Gly Gly Ala
            20                  25                  30

Leu Val Gln Pro Gly Gly Ser Leu Arg Leu Ser Cys Ala Ala Ser Gly
            35                  40                  45

Phe Pro Val Asn Arg Tyr Ser Met Arg Trp Tyr Arg Gln Ala Pro Gly
    50                  55                  60

Lys Glu Arg Glu Trp Val Ala Gly Met Ser Ser Ala Gly Asp Arg Ser
65                  70                  75                  80

Ser Tyr Glu Asp Ser Val Lys Gly Arg Phe Thr Ile Ser Arg Asp Asp
                85                  90                  95

Ala Arg Asn Thr Val Tyr Leu Gln Met Asn Ser Leu Lys Pro Glu Asp
            100                 105                 110

Thr Ala Val Tyr Tyr Cys Asn Val Asn Val Gly Phe Glu Tyr Trp Gly
            115                 120                 125

Gln Gly Thr Gln Val Thr Val Ser Ser Lys Gly Ser Gly Gly Thr Gly
        130                 135                 140

```
Asp Ser Ala Thr His Ile Lys Phe Ser Lys Arg Asp Glu Asp Gly Lys
145                 150                 155                 160

Glu Leu Ala Gly Ala Thr Met Glu Leu Arg Asp Ser Ser Gly Lys Thr
            165                 170                 175

Ile Ser Thr Trp Ile Ser Asp Gly Gln Val Lys Asp Phe Tyr Leu Tyr
            180                 185                 190

Pro Gly Lys Tyr Thr Phe Val Gln Thr Ala Ala Pro Asp Gly Tyr Glu
        195                 200                 205

Val Ala Thr Ala Ile Thr Phe Thr Val Asn Glu Gln Gly Gln Val Thr
        210                 215                 220

Val Asn Gly Lys Ala Thr Lys Gly Asp Ala His Ile Gly Ser Gly His
225                 230                 235                 240

His His His His His
            245

<210> SEQ ID NO 17
<211> LENGTH: 356
<212> TYPE: PRT
<213> ORGANISM: Unknown
<220> FEATURE:
<223> OTHER INFORMATION: Streptococcus pyogenes - Streptococcus
      pneumoniae

<400> SEQUENCE: 17

Met Gly Asp Ser Ala Thr His Ile Lys Phe Ser Lys Arg Asp Glu Asp
1               5                   10                  15

Gly Lys Glu Leu Ala Gly Ala Thr Met Glu Leu Arg Asp Ser Ser Gly
            20                  25                  30

Lys Thr Ile Ser Thr Trp Ile Ser Asp Gly Gln Val Lys Asp Phe Tyr
        35                  40                  45

Leu Tyr Pro Gly Lys Tyr Thr Phe Val Glu Thr Ala Ala Pro Asp Gly
    50                  55                  60

Tyr Glu Val Ala Thr Ala Ile Thr Phe Thr Val Asn Glu Gln Gly Gln
65                  70                  75                  80

Val Thr Val Asn Gly Lys Ala Thr Lys Gly Asp Ala His Ile Gly Ser
                85                  90                  95

Gly Tyr Pro Tyr Asp Val Pro Asp Tyr Ala Gly Ser Gly Glu Phe Glu
            100                 105                 110

Glu Ser Pro Gln Val Val Glu Lys Ser Ser Leu Glu Lys Lys Tyr Glu
        115                 120                 125

Glu Ala Lys Ala Lys Ala Asp Thr Ala Lys Lys Asp Tyr Glu Thr Ala
    130                 135                 140

Lys Lys Lys Ala Glu Asp Ala Gln Lys Lys Tyr Glu Asp Asp Gln Lys
145                 150                 155                 160

Arg Thr Glu Glu Lys Ala Arg Lys Glu Ala Glu Ala Ser Gln Lys Leu
                165                 170                 175

Asn Asp Val Ala Leu Val Val Gln Asn Ala Tyr Lys Glu Tyr Arg Glu
            180                 185                 190

Val Gln Asn Gln Arg Ser Lys Tyr Lys Ser Asp Ala Glu Tyr Gln Lys
        195                 200                 205

Lys Leu Thr Glu Val Asp Ser Lys Ile Glu Lys Ala Arg Lys Glu Gln
    210                 215                 220

Gln Asp Leu Gln Asn Lys Phe Asn Glu Val Arg Ala Val Val Val Pro
225                 230                 235                 240

Glu Pro Asn Ala Leu Ala Glu Thr Lys Lys Lys Ala Glu Glu Ala Lys
                245                 250                 255
```

Ala Glu Glu Lys Val Ala Lys Arg Lys Tyr Asp Tyr Ala Thr Leu Lys
            260                 265                 270

Val Ala Leu Ala Lys Lys Glu Val Ala Lys Glu Leu Glu Ile Glu
        275                 280                 285

Lys Leu Gln Tyr Glu Ile Ser Thr Leu Glu Gln Glu Val Ala Thr Ala
    290                 295                 300

Gln His Gln Val Asp Asn Leu Lys Lys Leu Leu Ala Gly Ala Asp Pro
305                 310                 315                 320

Asp Asp Gly Thr Val Asp Gly Ser Gly Gly Thr Gly Lys Leu Gly Asp
                325                 330                 335

Ile Glu Phe Ile Lys Val Asn Lys Gly Ser Gly Glu Ser Gly His His
            340                 345                 350

His His His His
        355

<210> SEQ ID NO 18
<211> LENGTH: 782
<212> TYPE: PRT
<213> ORGANISM: Unknown
<220> FEATURE:
<223> OTHER INFORMATION: Streptococcus pyogenes - Streptococcus
      pneumoniae

<400> SEQUENCE: 18

Met Gly Asp Ser Ala Thr His Ile Lys Phe Ser Lys Arg Asp Glu Asp
1               5                   10                  15

Gly Lys Glu Leu Ala Gly Ala Thr Met Glu Leu Arg Asp Ser Ser Gly
            20                  25                  30

Lys Thr Ile Ser Thr Trp Ile Ser Asp Gly Gln Val Lys Asp Phe Tyr
        35                  40                  45

Leu Tyr Pro Gly Lys Tyr Thr Phe Val Glu Thr Ala Ala Pro Asp Gly
    50                  55                  60

Tyr Glu Val Ala Thr Ala Ile Thr Phe Thr Val Asn Glu Gln Gly Gln
65                  70                  75                  80

Val Thr Val Asn Gly Lys Ala Thr Lys Gly Asp Ala His Ile Gly Ser
                85                  90                  95

Gly Tyr Pro Tyr Asp Val Pro Asp Tyr Ala Gly Ser Gly Glu Phe Glu
            100                 105                 110

Glu Ser Pro Gln Val Val Glu Lys Ser Ser Leu Glu Lys Lys Tyr Glu
        115                 120                 125

Glu Ala Lys Ala Lys Ala Asp Thr Ala Lys Lys Asp Tyr Glu Thr Ala
    130                 135                 140

Lys Lys Lys Ala Glu Asp Ala Gln Lys Lys Tyr Glu Asp Asp Gln Lys
145                 150                 155                 160

Arg Thr Glu Glu Lys Ala Arg Lys Glu Ala Glu Ala Ser Gln Lys Leu
                165                 170                 175

Asn Asp Val Ala Leu Val Val Gln Asn Ala Tyr Lys Glu Tyr Arg Glu
            180                 185                 190

Val Gln Asn Gln Arg Ser Lys Tyr Lys Ser Asp Ala Glu Tyr Gln Lys
        195                 200                 205

Lys Leu Thr Glu Val Asp Ser Lys Ile Glu Lys Ala Arg Lys Glu Gln
    210                 215                 220

Gln Asp Leu Gln Asn Lys Phe Asn Glu Val Arg Ala Val Val Val Pro
225                 230                 235                 240

Glu Pro Asn Ala Leu Ala Glu Thr Lys Lys Lys Ala Glu Glu Ala Lys

```
            245                 250                 255
Ala Glu Glu Lys Val Ala Lys Arg Lys Tyr Asp Tyr Ala Thr Leu Lys
            260                 265                 270

Val Ala Leu Ala Lys Lys Glu Val Glu Ala Lys Glu Leu Glu Ile Glu
            275                 280                 285

Lys Leu Gln Tyr Glu Ile Ser Thr Leu Glu Gln Glu Val Ala Thr Ala
290                 295                 300

Gln His Gln Val Asp Asn Leu Lys Lys Leu Leu Ala Gly Ala Asp Pro
305                 310                 315                 320

Asp Asp Gly Thr Val Glu Ala Ser Ser Gly Lys Lys Glu Ala Thr Thr
            325                 330                 335

Ser Thr Glu Pro Pro Thr Glu Leu Ser Gly Glu Ile Thr Met Trp His
            340                 345                 350

Ser Phe Thr Gln Gly Pro Arg Leu Glu Ser Ile Gln Lys Ser Ala Asp
            355                 360                 365

Ala Phe Met Gln Lys His Pro Lys Thr Lys Ile Lys Ile Glu Thr Phe
            370                 375                 380

Ser Trp Asn Asp Phe Tyr Thr Lys Trp Thr Thr Gly Leu Ala Asn Gly
385                 390                 395                 400

Asn Val Pro Asp Ile Ser Thr Ala Leu Pro Asn Gln Val Met Glu Met
            405                 410                 415

Val Asn Ser Asp Ala Leu Val Pro Leu Asn Asp Ser Ile Lys Arg Ile
            420                 425                 430

Gly Gln Asp Lys Phe Asn Glu Thr Ala Leu Asn Glu Ala Lys Ile Gly
            435                 440                 445

Asp Asp Tyr Tyr Ser Val Pro Leu Tyr Ser His Ala Gln Val Met Trp
            450                 455                 460

Val Arg Thr Asp Leu Leu Lys Glu His Asn Ile Glu Val Pro Lys Thr
465                 470                 475                 480

Trp Asp Gln Leu Tyr Glu Ala Ser Lys Lys Leu Lys Glu Ala Gly Val
            485                 490                 495

Tyr Gly Leu Ser Val Pro Phe Gly Thr Asn Asp Leu Met Ala Thr Arg
            500                 505                 510

Phe Leu Asn Phe Tyr Val Arg Ser Gly Gly Gly Ser Leu Leu Thr Lys
            515                 520                 525

Asp Leu Lys Ala Asp Leu Thr Ser Gln Leu Ala Gln Asp Gly Ile Lys
            530                 535                 540

Tyr Trp Val Lys Leu Tyr Lys Glu Ile Ser Pro Gln Asp Ser Leu Asn
545                 550                 555                 560

Phe Asn Val Leu Gln Gln Ala Thr Leu Phe Tyr Gln Gly Lys Thr Ala
            565                 570                 575

Phe Asp Phe Asn Ser Gly Phe His Ile Gly Gly Ile Asn Ala Asn Ser
            580                 585                 590

Pro Gln Leu Ile Asp Ser Ile Asp Ala Tyr Pro Ile Pro Lys Ile Lys
            595                 600                 605

Glu Ser Asp Lys Asp Gln Gly Ile Glu Thr Ser Asn Ile Pro Met Val
            610                 615                 620

Val Trp Lys Asn Ser Lys His Pro Glu Val Ala Lys Ala Phe Leu Glu
625                 630                 635                 640

Ala Leu Tyr Asn Glu Glu Asp Tyr Val Lys Phe Leu Asp Ser Thr Pro
            645                 650                 655

Val Gly Met Leu Pro Thr Ile Lys Gly Ile Ser Asp Ser Ala Ala Tyr
            660                 665                 670
```

```
Lys Glu Asn Glu Thr Arg Lys Lys Phe Lys His Ala Glu Glu Val Ile
            675                 680                 685

Thr Glu Ala Val Lys Lys Gly Thr Ala Ile Gly Tyr Glu Asn Gly Pro
        690                 695                 700

Ser Val Gln Ala Gly Met Leu Thr Asn Gln His Ile Ile Glu Gln Met
705                 710                 715                 720

Phe Gln Asp Ile Ile Thr Asn Gly Thr Asp Pro Met Lys Ala Ala Lys
                725                 730                 735

Glu Ala Glu Lys Gln Leu Asn Asp Leu Phe Glu Ala Val Gln Val Asp
            740                 745                 750

Gly Ser Gly Thr Gly Lys Leu Gly Asp Ile Glu Phe Ile Lys Val
        755                 760                 765

Asn Lys Gly Ser Gly Glu Ser Gly His His His His His His
770                 775                 780
```

<210> SEQ ID NO 19
<211> LENGTH: 411
<212> TYPE: PRT
<213> ORGANISM: Unknown
<220> FEATURE:
<223> OTHER INFORMATION: Streptococcus pyogenes - Escherichia coli

<400> SEQUENCE: 19

```
Met Gly Ser Ser His His His His His His Ser Ser Gly Leu Val Pro
1               5                   10                  15

Arg Gly Ser His Met Gly Ala His Ile Val Met Val Asp Ala Tyr Lys
            20                  25                  30

Pro Thr Lys Gly Ser Gly Glu Ser Gly Lys Ile Glu Glu Gly Lys Leu
        35                  40                  45

Val Ile Trp Ile Asn Gly Asp Lys Gly Tyr Asn Gly Leu Ala Glu Val
    50                  55                  60

Gly Lys Lys Phe Glu Lys Asp Thr Gly Ile Lys Val Thr Val Glu His
65                  70                  75                  80

Pro Asp Lys Leu Glu Glu Lys Phe Pro Gln Val Ala Ala Thr Gly Asp
                85                  90                  95

Gly Pro Asp Ile Ile Phe Trp Ala His Asp Arg Phe Gly Gly Tyr Ala
            100                 105                 110

Gln Ser Gly Leu Leu Ala Glu Ile Thr Pro Asp Lys Ala Phe Gln Asp
        115                 120                 125

Lys Leu Tyr Pro Phe Thr Trp Asp Ala Val Arg Tyr Asn Gly Lys Leu
    130                 135                 140

Ile Ala Tyr Pro Ile Ala Val Glu Ala Leu Ser Leu Ile Tyr Asn Lys
145                 150                 155                 160

Asp Leu Leu Pro Asn Pro Pro Lys Thr Trp Glu Glu Ile Pro Ala Leu
                165                 170                 175

Asp Lys Glu Leu Lys Ala Lys Gly Lys Ser Ala Leu Met Phe Asn Leu
            180                 185                 190

Gln Glu Pro Tyr Phe Thr Trp Pro Leu Ile Ala Ala Asp Gly Gly Tyr
        195                 200                 205

Ala Phe Lys Tyr Glu Asn Gly Lys Tyr Asp Ile Lys Asp Val Gly Val
    210                 215                 220

Asp Asn Ala Gly Ala Lys Ala Gly Leu Thr Phe Leu Val Asp Leu Ile
225                 230                 235                 240

Lys Asn Lys His Met Asn Ala Asp Thr Asp Tyr Ser Ile Ala Glu Ala
                245                 250                 255
```

```
Ala Phe Asn Lys Gly Glu Thr Ala Met Thr Ile Asn Gly Pro Trp Ala
            260                 265                 270

Trp Ser Asn Ile Asp Thr Ser Lys Val Asn Tyr Gly Val Thr Val Leu
            275                 280                 285

Pro Thr Phe Lys Gly Gln Pro Ser Lys Pro Phe Val Gly Val Leu Ser
290                 295                 300

Ala Gly Ile Asn Ala Ala Ser Pro Asn Lys Glu Leu Ala Lys Glu Phe
305                 310                 315                 320

Leu Glu Asn Tyr Leu Leu Thr Asp Glu Gly Leu Glu Ala Val Asn Lys
            325                 330                 335

Asp Lys Pro Leu Gly Ala Val Ala Leu Lys Ser Tyr Glu Glu Glu Leu
            340                 345                 350

Ala Lys Asp Pro Arg Ile Ala Ala Thr Met Glu Asn Ala Gln Lys Gly
            355                 360                 365

Glu Ile Met Pro Asn Ile Pro Gln Met Ser Ala Phe Trp Tyr Ala Val
370                 375                 380

Arg Thr Ala Val Ile Asn Ala Ala Ser Gly Arg Gln Thr Val Asp Glu
385                 390                 395                 400

Ala Leu Lys Asp Ala Gln Thr Asn Ser Ser Ser
            405                 410

<210> SEQ ID NO 20
<211> LENGTH: 410
<212> TYPE: PRT
<213> ORGANISM: Unknown
<220> FEATURE:
<223> OTHER INFORMATION: Streptococcus pneumoniae - Escherichia coli

<400> SEQUENCE: 20

Met Gly Ser Ser His His His His His His Ser Ser Gly Leu Val Pro
1               5                   10                  15

Arg Gly Ser His Met Gly Lys Leu Gly Asp Ile Glu Phe Ile Lys Val
            20                  25                  30

Asn Lys Gly Ser Gly Glu Ser Gly Lys Ile Glu Glu Gly Lys Leu Val
            35                  40                  45

Ile Trp Ile Asn Gly Asp Lys Gly Tyr Asn Gly Leu Ala Glu Val Gly
50                  55                  60

Lys Lys Phe Glu Lys Asp Thr Gly Ile Lys Val Thr Val Glu His Pro
65                  70                  75                  80

Asp Lys Leu Glu Glu Lys Phe Pro Gln Val Ala Ala Thr Gly Asp Gly
            85                  90                  95

Pro Asp Ile Ile Phe Trp Ala His Asp Arg Phe Gly Gly Tyr Ala Gln
            100                 105                 110

Ser Gly Leu Leu Ala Glu Ile Thr Pro Asp Lys Ala Phe Gln Asp Lys
            115                 120                 125

Leu Tyr Pro Phe Thr Trp Asp Ala Val Arg Tyr Asn Gly Lys Leu Ile
            130                 135                 140

Ala Tyr Pro Ile Ala Val Glu Ala Leu Ser Leu Ile Tyr Asn Lys Asp
145                 150                 155                 160

Leu Leu Pro Asn Pro Pro Lys Thr Trp Glu Glu Ile Pro Ala Leu Asp
            165                 170                 175

Lys Glu Leu Lys Ala Lys Gly Lys Ser Ala Leu Met Phe Asn Leu Gln
            180                 185                 190

Glu Pro Tyr Phe Thr Trp Pro Leu Ile Ala Ala Asp Gly Gly Tyr Ala
            195                 200                 205
```

```
Phe Lys Tyr Glu Asn Gly Lys Tyr Asp Ile Lys Asp Val Gly Val Asp
    210                 215                 220

Asn Ala Gly Ala Lys Ala Gly Leu Thr Phe Leu Val Asp Leu Ile Lys
225                 230                 235                 240

Asn Lys His Met Asn Ala Asp Thr Asp Tyr Ser Ile Ala Glu Ala Ala
                245                 250                 255

Phe Asn Lys Gly Glu Thr Ala Met Thr Ile Asn Gly Pro Trp Ala Trp
                260                 265                 270

Ser Asn Ile Asp Thr Ser Lys Val Asn Tyr Gly Val Thr Val Leu Pro
                275                 280                 285

Thr Phe Lys Gly Gln Pro Ser Lys Pro Phe Val Gly Val Leu Ser Ala
            290                 295                 300

Gly Ile Asn Ala Ala Ser Pro Asn Lys Glu Leu Ala Lys Glu Phe Leu
305                 310                 315                 320

Glu Asn Tyr Leu Leu Thr Asp Glu Gly Leu Glu Ala Val Asn Lys Asp
                325                 330                 335

Lys Pro Leu Gly Ala Val Ala Leu Lys Ser Tyr Glu Glu Leu Ala
                340                 345                 350

Lys Asp Pro Arg Ile Ala Ala Thr Met Glu Asn Ala Gln Lys Gly Glu
            355                 360                 365

Ile Met Pro Asn Ile Pro Gln Met Ser Ala Phe Trp Tyr Ala Val Arg
370                 375                 380

Thr Ala Val Ile Asn Ala Ala Ser Gly Arg Gln Thr Val Asp Glu Ala
385                 390                 395                 400

Leu Lys Asp Ala Gln Thr Asn Ser Ser Ser
                405                 410

<210> SEQ ID NO 21
<211> LENGTH: 305
<212> TYPE: PRT
<213> ORGANISM: Unknown
<220> FEATURE:
<223> OTHER INFORMATION: Streptococcus pneumoniae  - Aequorea victoria -
      Streptococcus pneumoniae

<400> SEQUENCE: 21

Met Gly Ser Ser His His His His His His Ser Ser Gly Leu Val Pro
1               5                   10                  15

Arg Gly Ser His Met Gly Lys Leu Gly Asp Ile Glu Phe Ile Lys Val
                20                  25                  30

Asn Lys Gly Ser Gly Glu Ser Gly Ser Gly Val Ser Lys Gly Glu Glu
            35                  40                  45

Leu Phe Thr Gly Val Val Pro Ile Leu Val Glu Leu Asp Gly Asp Val
50                  55                  60

Asn Gly His Lys Phe Ser Val Ser Gly Glu Gly Glu Gly Asp Ala Thr
65                  70                  75                  80

Tyr Gly Lys Leu Thr Leu Lys Phe Ile Cys Thr Thr Gly Lys Leu Pro
                85                  90                  95

Val Pro Trp Pro Thr Leu Val Thr Thr Leu Thr Tyr Gly Val Gln Cys
            100                 105                 110

Phe Ser Arg Tyr Pro Asp His Met Lys Gln His Asp Phe Phe Lys Ser
            115                 120                 125

Ala Met Pro Glu Gly Tyr Val Gln Glu Arg Thr Ile Phe Phe Lys Asp
130                 135                 140

Asp Gly Asn Tyr Lys Thr Arg Ala Glu Val Lys Phe Glu Gly Asp Thr
```

```
                145                 150                 155                 160
Leu Val Asn Arg Ile Glu Leu Lys Gly Ile Asp Phe Lys Glu Asp Gly
                    165                 170                 175

Asn Ile Leu Gly His Lys Leu Glu Tyr Asn Tyr Asn Ser His Asn Val
                180                 185                 190

Tyr Ile Met Ala Asp Lys Gln Lys Asn Gly Ile Lys Val Asn Phe Lys
            195                 200                 205

Ile Arg His Asn Ile Glu Asp Gly Ser Val Gln Leu Ala Asp His Tyr
        210                 215                 220

Gln Gln Asn Thr Pro Ile Gly Asp Gly Pro Val Leu Leu Pro Asp Asn
225                 230                 235                 240

His Tyr Leu Ser Thr Gln Ser Lys Leu Ser Lys Asp Pro Asn Glu Lys
                245                 250                 255

Arg Asp His Met Val Leu Leu Glu Phe Val Thr Ala Ala Gly Ile Thr
                    260                 265                 270

Leu Gly Met Asp Glu Leu Tyr Lys Gly Ser Gly Glu Gly Ser Gly Ser
                275                 280                 285

Gly Ser Gly Ser Ala His Ile Val Met Val Asp Ala Tyr Lys Pro Thr
            290                 295                 300

Lys
305

<210> SEQ ID NO 22
<211> LENGTH: 121
<212> TYPE: PRT
<213> ORGANISM: Unknown
<220> FEATURE:
<223> OTHER INFORMATION: Saccharomyces cerevisiae - Streptococcus
      pyogenes

<400> SEQUENCE: 22

Met Gly Ser Ser His His His His His His Gly Ser Asp Ser Glu Val
1               5                   10                  15

Asn Gln Glu Ala Lys Pro Glu Val Lys Pro Glu Val Lys Pro Glu Thr
            20                  25                  30

His Ile Asn Leu Lys Val Ser Asp Gly Ser Ser Glu Ile Phe Phe Lys
        35                  40                  45

Ile Lys Lys Thr Thr Pro Leu Arg Arg Leu Met Glu Ala Phe Ala Lys
    50                  55                  60

Arg Gln Gly Lys Glu Met Asp Ser Leu Arg Phe Leu Tyr Asp Gly Ile
65                  70                  75                  80

Arg Ile Gln Ala Asp Gln Thr Pro Glu Asp Leu Asp Met Glu Asp Asn
                85                  90                  95

Asp Ile Ile Glu Ala His Arg Glu Gln Ile Gly Gly Gly Ala Thr His
            100                 105                 110

Ile Lys Phe Ser Lys Arg Asp Gly Tyr
        115                 120

<210> SEQ ID NO 23
<211> LENGTH: 108
<212> TYPE: PRT
<213> ORGANISM: Unknown
<220> FEATURE:
<223> OTHER INFORMATION: Streptococcus pyogenes

<400> SEQUENCE: 23

Met Ser Tyr Tyr His His His His His His Asp Tyr Asp Gly Gln Ser
1               5                   10                  15
```

```
Gly Asp Gly Lys Glu Leu Ala Gly Ala Thr Met Glu Leu Arg Asp Ser
            20                  25                  30

Ser Gly Lys Thr Ile Ser Thr Trp Ile Ser Asp Gly Gln Val Lys Asp
        35                  40                  45

Phe Tyr Leu Tyr Pro Gly Lys Tyr Thr Phe Val Glu Thr Ala Ala Pro
    50                  55                  60

Asp Gly Tyr Glu Val Ala Thr Ala Ile Thr Phe Thr Val Asn Glu Gln
65                  70                  75                  80

Gly Gln Val Thr Val Asn Gly Lys Ala Thr Lys Gly Ser Gly Gly
                85                  90                  95

Ser Gly Gly Ser Gly Glu Asp Ser Ala Thr His Ile
            100                 105
```

<210> SEQ ID NO 24
<211> LENGTH: 565
<212> TYPE: PRT
<213> ORGANISM: Unknown
<220> FEATURE:
<223> OTHER INFORMATION: Streptococcus pyogenes - Streptococcus
      pneumoniae

<400> SEQUENCE: 24

```
Met Gly Asp Ser Ala Thr His Ile Lys Phe Ser Lys Arg Asp Glu Asp
1               5                   10                  15

Gly Lys Glu Leu Ala Gly Ala Thr Met Glu Leu Arg Asp Ser Ser Gly
            20                  25                  30

Lys Thr Ile Ser Thr Trp Ile Ser Asp Gly Gln Val Lys Asp Phe Tyr
        35                  40                  45

Leu Tyr Pro Gly Lys Tyr Thr Phe Val Glu Thr Ala Ala Pro Asp Gly
    50                  55                  60

Tyr Glu Val Ala Thr Ala Ile Thr Phe Thr Val Asn Glu Gln Gly Gln
65                  70                  75                  80

Val Thr Val Asn Gly Lys Ala Thr Lys Gly Asp Ala His Ile Gly Ser
                85                  90                  95

Gly Tyr Pro Tyr Asp Val Pro Asp Tyr Ala Gly Ser Gly Glu Phe Ser
            100                 105                 110

Gly Lys Lys Glu Ala Thr Thr Ser Thr Glu Pro Pro Thr Glu Leu Ser
        115                 120                 125

Gly Glu Ile Thr Met Trp His Ser Phe Thr Gln Gly Pro Arg Leu Glu
    130                 135                 140

Ser Ile Gln Lys Ser Ala Asp Ala Phe Met Lys His Pro Lys Thr
145                 150                 155                 160

Lys Ile Lys Ile Glu Thr Phe Ser Trp Asn Asp Phe Tyr Thr Lys Trp
                165                 170                 175

Thr Thr Gly Leu Ala Asn Gly Asn Val Pro Asp Ile Ser Thr Ala Leu
            180                 185                 190

Pro Asn Gln Val Met Glu Met Val Asn Ser Asp Ala Leu Val Pro Leu
        195                 200                 205

Asn Asp Ser Ile Lys Arg Ile Gly Gln Asp Lys Phe Asn Glu Thr Ala
    210                 215                 220

Leu Asn Glu Ala Lys Ile Gly Asp Asp Tyr Tyr Ser Val Pro Leu Tyr
225                 230                 235                 240

Ser His Ala Gln Val Met Trp Val Arg Thr Asp Leu Leu Lys Glu His
                245                 250                 255

Asn Ile Glu Val Pro Lys Thr Trp Asp Gln Leu Tyr Glu Ala Ser Lys
```

```
            260                 265                 270
Lys Leu Lys Glu Ala Gly Val Tyr Gly Leu Ser Val Pro Phe Gly Thr
            275                 280                 285

Asn Asp Leu Met Ala Thr Arg Phe Leu Asn Phe Tyr Val Arg Ser Gly
        290                 295                 300

Gly Gly Ser Leu Leu Thr Lys Asp Leu Lys Ala Asp Leu Thr Ser Gln
305                 310                 315                 320

Leu Ala Gln Asp Gly Ile Lys Tyr Trp Val Lys Leu Tyr Lys Glu Ile
                325                 330                 335

Ser Pro Gln Asp Ser Leu Asn Phe Asn Val Leu Gln Ala Thr Leu
            340                 345                 350

Phe Tyr Gln Gly Lys Thr Ala Phe Asp Phe Asn Ser Gly Phe His Ile
        355                 360                 365

Gly Gly Ile Asn Ala Asn Ser Pro Gln Leu Ile Asp Ser Ile Asp Ala
370                 375                 380

Tyr Pro Ile Pro Lys Ile Lys Glu Ser Asp Lys Asp Gln Gly Ile Glu
385                 390                 395                 400

Thr Ser Asn Ile Pro Met Val Val Trp Lys Asn Ser Lys His Pro Glu
                405                 410                 415

Val Ala Lys Ala Phe Leu Glu Ala Leu Tyr Asn Glu Glu Asp Tyr Val
            420                 425                 430

Lys Phe Leu Asp Ser Thr Pro Val Gly Met Leu Pro Thr Ile Lys Gly
        435                 440                 445

Ile Ser Asp Ser Ala Ala Tyr Lys Glu Asn Glu Thr Arg Lys Lys Phe
450                 455                 460

Lys His Ala Glu Glu Val Ile Thr Glu Ala Val Lys Lys Gly Thr Ala
465                 470                 475                 480

Ile Gly Tyr Glu Asn Gly Pro Ser Val Gln Ala Gly Met Leu Thr Asn
                485                 490                 495

Gln His Ile Ile Glu Gln Met Phe Gln Asp Ile Ile Thr Asn Gly Thr
            500                 505                 510

Asp Pro Met Lys Ala Ala Lys Glu Ala Glu Lys Gln Leu Asn Asp Leu
        515                 520                 525

Phe Glu Ala Val Gln Val Asp Gly Ser Gly Thr Gly Lys Leu Gly
530                 535                 540

Asp Ile Glu Phe Ile Lys Val Asn Lys Gly Ser Gly Glu Ser Gly His
545                 550                 555                 560

His His His His His
                565

<210> SEQ ID NO 25
<211> LENGTH: 589
<212> TYPE: PRT
<213> ORGANISM: Unknown
<220> FEATURE:
<223> OTHER INFORMATION: Streptococcus pneumoniae - Streptococcus
      pyogenes

<400> SEQUENCE: 25

Met Gly Lys Pro Leu Arg Gly Ala Val Phe Ser Leu Gln Lys Gln His
1               5                   10                  15

Pro Asp Tyr Pro Asp Ile Tyr Gly Ala Ile Asp Gln Asn Gly Thr Tyr
            20                  25                  30

Gln Asn Val Arg Thr Gly Glu Asp Gly Lys Leu Thr Phe Lys Asn Leu
        35                  40                  45
```

```
Ser Asp Gly Lys Tyr Arg Leu Phe Glu Asn Ser Glu Pro Ala Gly Tyr
    50                  55                  60
Lys Pro Val Gln Asn Lys Pro Ile Val Ala Phe Gln Ile Val Asn Gly
 65                  70                  75                  80
Glu Val Arg Asp Val Thr Ser Ile Val Pro Gln Asp Ile Pro Ala Thr
                 85                  90                  95
Tyr Glu Phe Thr Asn Gly Lys His Tyr Ile Thr Asn Glu Pro Ile Pro
            100                 105                 110
Pro Lys Gly Gly Ser Gly Gly Asp Tyr Lys Asp Asp Asp Lys Gly
            115                 120                 125
Gly Ser Gly Gly Glu Phe Ser Gly Lys Lys Glu Ala Thr Thr Ser Thr
    130                 135                 140
Glu Pro Pro Thr Glu Leu Ser Gly Glu Ile Thr Met Trp His Ser Phe
145                 150                 155                 160
Thr Gln Gly Pro Arg Leu Glu Ser Ile Gln Lys Ser Ala Asp Ala Phe
                165                 170                 175
Met Gln Lys His Pro Lys Thr Lys Ile Lys Ile Glu Thr Phe Ser Trp
            180                 185                 190
Asn Asp Phe Tyr Thr Lys Trp Thr Thr Gly Leu Ala Asn Gly Asn Val
            195                 200                 205
Pro Asp Ile Ser Thr Ala Leu Pro Asn Gln Val Met Glu Met Val Asn
210                 215                 220
Ser Asp Ala Leu Val Pro Leu Asn Asp Ser Ile Lys Arg Ile Gly Gln
225                 230                 235                 240
Asp Lys Phe Asn Glu Thr Ala Leu Asn Glu Ala Lys Ile Gly Asp Asp
                245                 250                 255
Tyr Tyr Ser Val Pro Leu Tyr Ser His Ala Gln Val Met Trp Val Arg
            260                 265                 270
Thr Asp Leu Leu Lys Glu His Asn Ile Glu Val Pro Lys Thr Trp Asp
            275                 280                 285
Gln Leu Tyr Glu Ala Ser Lys Lys Leu Lys Ala Gly Val Tyr Gly
            290                 295                 300
Leu Ser Val Pro Phe Gly Thr Asn Asp Leu Met Ala Thr Arg Phe Leu
305                 310                 315                 320
Asn Phe Tyr Val Arg Ser Gly Gly Ser Leu Leu Thr Lys Asp Leu
                325                 330                 335
Lys Ala Asp Leu Thr Ser Gln Leu Ala Gln Asp Gly Ile Lys Tyr Trp
            340                 345                 350
Val Lys Leu Tyr Lys Glu Ile Ser Pro Gln Asp Ser Leu Asn Phe Asn
            355                 360                 365
Val Leu Gln Gln Ala Thr Leu Phe Tyr Gln Gly Lys Thr Ala Phe Asp
370                 375                 380
Phe Asn Ser Gly Phe His Ile Gly Gly Ile Asn Ala Asn Ser Pro Gln
385                 390                 395                 400
Leu Ile Asp Ser Ile Asp Ala Tyr Pro Ile Pro Lys Ile Lys Glu Ser
                405                 410                 415
Asp Lys Asp Gln Gly Ile Glu Thr Ser Asn Ile Pro Met Val Val Trp
            420                 425                 430
Lys Asn Ser Lys His Pro Glu Val Ala Lys Ala Phe Leu Glu Ala Leu
            435                 440                 445
Tyr Asn Glu Glu Asp Tyr Val Lys Phe Leu Asp Ser Thr Pro Val Gly
450                 455                 460
Met Leu Pro Thr Ile Lys Gly Ile Ser Asp Ser Ala Ala Tyr Lys Glu
```

465                 470                 475                 480
Asn Glu Thr Arg Lys Lys Phe Lys His Ala Glu Glu Val Ile Thr Glu
                    485                 490                 495

Ala Val Lys Lys Gly Thr Ala Ile Gly Tyr Glu Asn Gly Pro Ser Val
                500                 505                 510

Gln Ala Gly Met Leu Thr Asn Gln His Ile Ile Glu Gln Met Phe Gln
            515                 520                 525

Asp Ile Ile Thr Asn Gly Thr Asp Pro Met Lys Ala Ala Lys Glu Ala
        530                 535                 540

Glu Lys Gln Leu Asn Asp Leu Phe Glu Ala Val Gln Val Asp Gly Ser
545                 550                 555                 560

Gly Gly Thr Gly Ala His Ile Val Met Val Asp Ala Tyr Lys Pro Thr
                565                 570                 575

Lys Gly Ser Gly Glu Ser Gly His His His His His His
            580                 585

<210> SEQ ID NO 26
<211> LENGTH: 251
<212> TYPE: PRT
<213> ORGANISM: Unknown
<220> FEATURE:
<223> OTHER INFORMATION: Aequorea victoria

<400> SEQUENCE: 26

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Lys Leu
225                 230                 235                 240

Ala Ala Ala Leu Glu His His His His His His

<210> SEQ ID NO 27
<211> LENGTH: 355
<212> TYPE: PRT
<213> ORGANISM: Unknown
<220> FEATURE:
<223> OTHER INFORMATION: Rattus norvegicus - Streptococcus pyogenes

<400> SEQUENCE: 27

```
Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile Val Pro Arg Glu Cys Asn Pro Cys Gly Cys Thr Gly Ser Glu Val
            100                 105                 110

Ser Ser Val Phe Ile Phe Pro Pro Lys Thr Lys Asp Val Leu Thr Ile
        115                 120                 125

Thr Leu Thr Pro Lys Val Thr Cys Val Val Val Asp Ile Ser Gln Asn
    130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
            180                 185                 190

Thr Phe Ala Cys Ala Val Asn Ser Gly Ala Phe Pro Ala Pro Ile Glu
        195                 200                 205

Lys Ser Ile Ser Lys Pro Glu Gly Thr Pro Arg Gly Pro Gln Val Tyr
    210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
            260                 265                 270

Met Asp Thr Asp Gly Ser Tyr Phe Leu Tyr Ser Lys Leu Asn Val Lys
        275                 280                 285

Lys Glu Thr Trp Gln Gln Gly Asn Thr Phe Thr Cys Ser Val Leu His
    290                 295                 300

Glu Gly Leu His Asn His His Thr Glu Lys Ser Leu Ser His Ser Pro
305                 310                 315                 320

Gly Lys Leu Pro Glu Thr Gly Gly Ser Gly Gly Ser Gly Gly Ser
                325                 330                 335

Gly Gly Ser Gly Gly Ser Ala His Ile Val Met Val Asp Ala Tyr Lys
            340                 345                 350

Pro Thr Lys
```

<210> SEQ ID NO 28
<211> LENGTH: 1304
<212> TYPE: PRT
<213> ORGANISM: Unknown
<220> FEATURE:
<223> OTHER INFORMATION: Escherichia coli

<400> SEQUENCE: 28

```
Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
            20                  25                  30

Arg Leu Cys Phe Pro Val Leu Leu Ile Pro Val Leu Phe Ser Ala
        35                  40                  45

Gly Ser Leu Ala Gly Ser Ser Thr Thr Ser Thr Glu Pro Pro Thr Glu
    50                  55                  60

Leu Ser Gly Glu Ile Thr Met Trp His Ser Phe Thr Gln Gly Pro Arg
65                  70                  75                  80

Leu Glu Ser Ile Gln Lys Ser Ala Asp Ala Phe Met Gln Lys His Pro
                85                  90                  95

Lys Thr Lys Ile Lys Ile Glu Thr Phe Ser Trp Asn Asp Phe Tyr Thr
            100                 105                 110

Lys Trp Thr Thr Gly Leu Ala Asn Gly Asn Val Pro Asp Ile Ser Thr
        115                 120                 125

Ala Leu Pro Asn Gln Val Met Glu Met Val Asn Ser Asp Ala Leu Val
    130                 135                 140

Pro Leu Asn Asp Ser Ile Lys Arg Ile Gly Gln Asp Lys Phe Asn Glu
145                 150                 155                 160

Thr Ala Leu Asn Glu Ala Lys Ile Gly Asp Asp Tyr Tyr Ser Val Pro
                165                 170                 175

Leu Tyr Ser His Ala Gln Val Met Trp Val Arg Thr Asp Leu Leu Lys
            180                 185                 190

Glu His Asn Ile Gly Ser Gly Ser Gly Asn Asp Ala Pro Val Thr Phe
        195                 200                 205

Arg Thr Ser Glu Gly Gly Ala Leu Glu Trp Ser Phe Asn Ser Ser Thr
    210                 215                 220

Gly Ala Gly Ala Leu Thr Gln Gly Thr Thr Thr Tyr Ala Met His Gly
225                 230                 235                 240

Gln Gln Gly Asn Asp Leu Asn Ala Gly Lys Asn Leu Ile Phe Gln Gly
                245                 250                 255

Gln Asn Gly Gln Ile Asn Leu Lys Asp Ser Val Ser Gln Gly Ala Gly
            260                 265                 270

Ser Leu Thr Phe Arg Asp Asn Tyr Thr Val Thr Thr Ser Asn Gly Ser
        275                 280                 285

Thr Trp Thr Gly Ala Gly Ile Val Val Asp Asn Gly Val Ser Val Asn
    290                 295                 300

Trp Gln Val Asn Gly Val Lys Gly Asp Asn Leu His Lys Ile Gly Glu
305                 310                 315                 320

Gly Thr Leu Thr Val Gln Gly Thr Gly Ile Asn Glu Gly Gly Leu Lys
                325                 330                 335

Val Gly Asp Gly Lys Val Val Leu Asn Gln Gln Ala Asp Asn Lys Gly
            340                 345                 350

Gln Val Gln Ala Phe Ser Ser Val Asn Ile Ala Ser Gly Arg Pro Thr
```

```
            355                 360                 365
Val Val Leu Thr Asp Glu Arg Gln Val Asn Pro Asp Thr Val Ser Trp
370                 375                 380

Gly Tyr Arg Gly Gly Thr Leu Asp Val Asn Gly Asn Ser Leu Thr Phe
385                 390                 395                 400

His Gln Leu Lys Ala Ala Asp Tyr Gly Ala Val Leu Ala Asn Asn Val
                405                 410                 415

Asp Lys Arg Ala Thr Ile Thr Leu Asp Tyr Ala Gly Ser Gly Ser Ser
                420                 425                 430

Arg Thr Asp Leu Leu Lys Glu His Asn Ile Glu Val Pro Lys Thr Trp
                435                 440                 445

Asp Gln Leu Tyr Glu Ala Ser Lys Lys Leu Lys Glu Ala Gly Val Tyr
                450                 455                 460

Gly Leu Ser Val Pro Phe Gly Thr Asn Asp Leu Met Ala Thr Arg Phe
465                 470                 475                 480

Leu Asn Phe Tyr Val Arg Ser Gly Gly Ser Leu Leu Thr Lys Asp
                485                 490                 495

Leu Lys Ala Asp Leu Thr Ser Gln Leu Ala Gln Asp Gly Ile Lys Tyr
                500                 505                 510

Trp Val Lys Leu Tyr Lys Glu Ile Ser Pro Gln Asp Ser Leu Asn Phe
                515                 520                 525

Asn Gly Ser Gly Ser Gly Asn Thr Ala Gly Tyr Leu Phe His Gly Gln
530                 535                 540

Leu Lys Gly Asn Leu Asn Val Asp Asn Arg Leu Pro Glu Gly Val Thr
545                 550                 555                 560

Gly Ala Leu Val Met Asp Gly Ala Ala Asp Ile Ser Gly Thr Phe Thr
                565                 570                 575

Gln Glu Asn Gly Arg Leu Thr Leu Gln Gly His Pro Val Ile His Ala
                580                 585                 590

Tyr Asn Thr Gln Ser Val Ala Asp Lys Leu Ala Ala Ser Gly Asp His
                595                 600                 605

Ser Val Leu Thr Gln Pro Thr Ser Phe Ser Gln Glu Asp Trp Glu Asn
                610                 615                 620

Arg Ser Phe Thr Phe Asp Arg Leu Ser Leu Lys Asn Thr Asp Phe Gly
625                 630                 635                 640

Leu Gly Arg Asn Ala Thr Leu Asn Thr Thr Ile Gln Ala Asp Asn Ser
                645                 650                 655

Ser Val Thr Leu Gly Asp Ser Arg Val Phe Ile Asp Lys Asn Asp Gly
                660                 665                 670

Gln Gly Thr Ala Phe Thr Leu Glu Glu Gly Thr Ser Val Ala Thr Lys
                675                 680                 685

Asp Ala Asp Lys Ser Val Phe Asn Gly Thr Val Asn Leu Asp Asn Gln
                690                 695                 700

Ser Val Leu Asn Ile Asn Asp Ile Phe Asn Gly Gly Ile Gln Ala Asn
705                 710                 715                 720

Asn Ser Thr Val Asn Ile Ser Ser Asp Ser Ala Val Leu Gly Asn Ser
                725                 730                 735

Thr Leu Thr Ser Thr Ala Leu Asn Leu Asn Lys Gly Ala Asn Ala Leu
                740                 745                 750

Ala Ser Gln Ser Phe Val Ser Asp Gly Pro Val Asn Ile Ser Asp Ala
                755                 760                 765

Thr Leu Ser Leu Asn Ser Arg Pro Asp Glu Val Ser His Thr Leu Leu
                770                 775                 780
```

Pro Val Tyr Asp Tyr Ala Gly Ser Trp Asn Leu Lys Gly Asp Ala
785                 790                 795                 800

Arg Leu Asn Val Gly Pro Tyr Ser Met Leu Ser Gly Asn Ile Asn Val
            805                 810                 815

Gln Asp Lys Gly Thr Val Thr Leu Gly Gly Glu Gly Glu Leu Ser Pro
        820                 825                 830

Asp Leu Thr Leu Gln Asn Gln Met Leu Tyr Ser Leu Phe Asn Gly Tyr
            835                 840                 845

Arg Asn Ile Trp Ser Gly Ser Leu Asn Ala Pro Asp Ala Thr Val Ser
        850                 855                 860

Met Thr Asp Thr Gln Trp Ser Met Asn Gly Asn Ser Thr Ala Gly Asn
865                 870                 875                 880

Met Lys Leu Asn Arg Thr Ile Val Gly Phe Asn Gly Gly Thr Ser Pro
                885                 890                 895

Phe Thr Thr Leu Thr Thr Asp Asn Leu Asp Ala Val Gln Ser Ala Phe
            900                 905                 910

Val Met Arg Thr Asp Leu Asn Lys Ala Asp Lys Leu Val Ile Asn Lys
            915                 920                 925

Ser Ala Thr Gly His Asp Asn Ser Ile Trp Val Asn Phe Leu Lys Lys
        930                 935                 940

Pro Ser Asn Lys Asp Thr Leu Asp Ile Pro Leu Val Ser Ala Pro Glu
945                 950                 955                 960

Ala Thr Ala Asp Asn Leu Phe Arg Ala Ser Thr Arg Val Val Gly Phe
                965                 970                 975

Ser Asp Val Thr Pro Ile Leu Ser Val Arg Lys Glu Asp Gly Lys Lys
            980                 985                 990

Glu Trp Val Leu Asp Gly Tyr Gln Val Ala Arg Asn Asp Gly Gln Gly
        995                 1000                1005

Lys Ala Ala Ala Thr Phe Met His Ile Ser Tyr Asn Asn Phe Ile
    1010                1015                1020

Thr Glu Val Gly Ser Leu Asn Lys Arg Met Gly Asp Leu Arg Asp
    1025                1030                1035

Ile Asn Gly Glu Ala Gly Thr Trp Val Arg Leu Leu Asn Gly Ser
    1040                1045                1050

Gly Ser Ala Asp Gly Gly Phe Thr Asp His Tyr Thr Leu Leu Gln
    1055                1060                1065

Met Gly Ala Asp Arg Lys His Glu Leu Gly Ser Met Asp Leu Phe
    1070                1075                1080

Thr Gly Val Met Ala Thr Tyr Thr Asp Thr Asp Ala Ser Ala Asp
    1085                1090                1095

Leu Tyr Ser Gly Lys Thr Lys Ser Trp Gly Gly Gly Phe Tyr Ala
    1100                1105                1110

Ser Gly Leu Phe Arg Ser Gly Ala Tyr Phe Asp Val Ile Ala Lys
    1115                1120                1125

Tyr Ile His Asn Glu Asn Lys Tyr Asp Leu Asn Phe Ala Gly Ala
    1130                1135                1140

Gly Lys Gln Asn Phe Arg Ser His Ser Leu Tyr Ala Gly Ala Glu
    1145                1150                1155

Val Gly Tyr Arg Tyr His Leu Thr Asp Thr Thr Phe Val Glu Pro
    1160                1165                1170

Gln Ala Glu Leu Val Trp Gly Arg Leu Gln Gly Gln Thr Phe Asn
    1175                1180                1185

```
Trp Asn Asp Ser Gly Met Asp Val Ser Met Arg Arg Asn Ser Val
    1190                1195                1200

Asn Pro Leu Val Gly Arg Thr Gly Val Val Ser Gly Lys Thr Phe
    1205                1210                1215

Ser Gly Lys Asp Trp Ser Leu Thr Ala Arg Ala Gly Leu His Tyr
    1220                1225                1230

Glu Phe Asp Leu Thr Asp Ser Ala Asp Val His Leu Lys Asp Ala
    1235                1240                1245

Ala Gly Glu His Gln Ile Asn Gly Arg Lys Asp Ser Arg Met Leu
    1250                1255                1260

Tyr Gly Val Gly Leu Asn Ala Arg Phe Gly Asp Asn Thr Arg Leu
    1265                1270                1275

Gly Leu Glu Val Glu Arg Ser Ala Phe Gly Lys Tyr Asn Thr Asp
    1280                1285                1290

Asp Ala Ile Asn Ala Asn Ile Arg Tyr Ser Phe
    1295                1300

<210> SEQ ID NO 29
<211> LENGTH: 1281
<212> TYPE: PRT
<213> ORGANISM: Unknown
<220> FEATURE:
<223> OTHER INFORMATION: Escherichia coli

<400> SEQUENCE: 29

Met Asn Arg Ile Tyr Ser Leu Arg Tyr Ser Ala Val Ala Arg Gly Phe
1               5                   10                  15

Ile Ala Val Ser Glu Phe Ala Arg Lys Cys Val His Lys Ser Val Arg
                20                  25                  30

Arg Leu Cys Phe Pro Val Leu Leu Leu Ile Pro Val Leu Phe Ser Ala
            35                  40                  45

Gly Ser Leu Ala Gly Ser Ser Ile Ser Pro Gln Asp Ser Leu Asn Phe
        50                  55                  60

Asn Val Leu Gln Gln Ala Thr Leu Phe Tyr Gln Gly Lys Thr Ala Phe
65                  70                  75                  80

Asp Phe Asn Ser Gly Phe His Ile Gly Gly Ile Asn Ala Asn Ser Pro
                85                  90                  95

Gln Leu Ile Asp Ser Ile Asp Ala Tyr Pro Ile Pro Lys Ile Lys Glu
            100                 105                 110

Ser Asp Lys Asp Gln Gly Ile Glu Thr Ser Asn Ile Pro Met Val Val
        115                 120                 125

Trp Lys Asn Ser Lys His Pro Glu Val Ala Lys Ala Phe Leu Glu Ala
    130                 135                 140

Leu Tyr Asn Glu Glu Asp Tyr Val Lys Phe Leu Asp Ser Thr Pro Val
145                 150                 155                 160

Gly Met Leu Pro Thr Ile Lys Gly Ile Ser Asp Ser Ala Ala Tyr Lys
                165                 170                 175

Glu Asn Glu Thr Arg Lys Lys Phe Lys His Ala Glu Glu Val Ile Thr
            180                 185                 190

Glu Ala Gly Ser Gly Ser Gly Asn Asp Ala Pro Val Thr Phe Arg Thr
        195                 200                 205

Ser Glu Gly Gly Ala Leu Glu Trp Ser Phe Asn Ser Ser Thr Gly Ala
    210                 215                 220

Gly Ala Leu Thr Gln Gly Thr Thr Tyr Ala Met His Gly Gln Gln
225                 230                 235                 240
```

```
Gly Asn Asp Leu Asn Ala Gly Lys Asn Leu Ile Phe Gln Gly Gln Asn
            245                 250                 255

Gly Gln Ile Asn Leu Lys Asp Ser Val Ser Gln Gly Ala Gly Ser Leu
        260                 265                 270

Thr Phe Arg Asp Asn Tyr Thr Val Thr Thr Ser Asn Gly Ser Thr Trp
    275                 280                 285

Thr Gly Ala Gly Ile Val Val Asp Asn Gly Val Ser Val Asn Trp Gln
290                 295                 300

Val Asn Gly Val Lys Gly Asp Asn Leu His Lys Ile Gly Glu Gly Thr
305                 310                 315                 320

Leu Thr Val Gln Gly Thr Gly Ile Asn Glu Gly Gly Leu Lys Val Gly
                325                 330                 335

Asp Gly Lys Val Val Leu Asn Gln Gln Ala Asp Asn Lys Gly Gln Val
            340                 345                 350

Gln Ala Phe Ser Ser Val Asn Ile Ala Ser Gly Arg Pro Thr Val Val
        355                 360                 365

Leu Thr Asp Glu Arg Gln Val Asn Pro Asp Thr Val Ser Trp Gly Tyr
    370                 375                 380

Arg Gly Gly Thr Leu Asp Val Asn Gly Asn Ser Leu Thr Phe His Gln
385                 390                 395                 400

Leu Lys Ala Ala Asp Tyr Gly Ala Val Leu Ala Asn Asn Val Asp Lys
                405                 410                 415

Arg Ala Thr Ile Thr Leu Asp Tyr Ala Gly Ser Gly Ser Ser Asn Glu
            420                 425                 430

Thr Arg Lys Lys Phe Lys His Ala Glu Glu Val Ile Thr Glu Ala Val
        435                 440                 445

Lys Lys Gly Thr Ala Ile Gly Tyr Glu Asn Gly Pro Ser Val Gln Ala
    450                 455                 460

Gly Met Leu Thr Asn Gln His Ile Ile Glu Gln Met Phe Gln Asp Ile
465                 470                 475                 480

Ile Thr Asn Gly Thr Asp Pro Met Lys Ala Ala Lys Glu Ala Glu Lys
                485                 490                 495

Gln Leu Asn Asp Leu Phe Glu Ala Val Gln Gly Ser Gly Ser Gly Asn
            500                 505                 510

Thr Ala Gly Tyr Leu Phe His Gly Gln Leu Lys Gly Asn Leu Asn Val
        515                 520                 525

Asp Asn Arg Leu Pro Glu Gly Val Thr Gly Ala Leu Val Met Asp Gly
    530                 535                 540

Ala Ala Asp Ile Ser Gly Thr Phe Thr Gln Glu Asn Gly Arg Leu Thr
545                 550                 555                 560

Leu Gln Gly His Pro Val Ile His Ala Tyr Asn Thr Gln Ser Val Ala
                565                 570                 575

Asp Lys Leu Ala Ala Ser Gly Asp His Ser Val Leu Thr Gln Pro Thr
            580                 585                 590

Ser Phe Ser Gln Glu Asp Trp Glu Asn Arg Ser Phe Thr Phe Asp Arg
        595                 600                 605

Leu Ser Leu Lys Asn Thr Asp Phe Gly Leu Gly Arg Asn Ala Thr Leu
    610                 615                 620

Asn Thr Thr Ile Gln Ala Asp Asn Ser Ser Val Thr Leu Gly Asp Ser
625                 630                 635                 640

Arg Val Phe Ile Asp Lys Asn Asp Gly Gln Gly Thr Ala Phe Thr Leu
                645                 650                 655

Glu Glu Gly Thr Ser Val Ala Thr Lys Asp Ala Asp Lys Ser Val Phe
```

```
              660                 665                 670
Asn Gly Thr Val Asn Leu Asp Asn Gln Ser Val Leu Asn Ile Asn Asp
                675                 680                 685
Ile Phe Asn Gly Gly Ile Gln Ala Asn Asn Ser Thr Val Asn Ile Ser
                690                 695                 700
Ser Asp Ser Ala Val Leu Gly Asn Ser Thr Leu Thr Ser Thr Ala Leu
705                 710                 715                 720
Asn Leu Asn Lys Gly Ala Asn Ala Leu Ala Ser Gln Ser Phe Val Ser
                    725                 730                 735
Asp Gly Pro Val Asn Ile Ser Asp Ala Thr Leu Ser Leu Asn Ser Arg
                740                 745                 750
Pro Asp Glu Val Ser His Thr Leu Leu Pro Val Tyr Asp Tyr Ala Gly
                755                 760                 765
Ser Trp Asn Leu Lys Gly Asp Asp Ala Arg Leu Asn Val Gly Pro Tyr
                770                 775                 780
Ser Met Leu Ser Gly Asn Ile Asn Val Gln Asp Lys Gly Thr Val Thr
785                 790                 795                 800
Leu Gly Gly Glu Gly Glu Leu Ser Pro Asp Leu Thr Leu Gln Asn Gln
                    805                 810                 815
Met Leu Tyr Ser Leu Phe Asn Gly Tyr Arg Asn Ile Trp Ser Gly Ser
                820                 825                 830
Leu Asn Ala Pro Asp Ala Thr Val Ser Met Thr Asp Thr Gln Trp Ser
                835                 840                 845
Met Asn Gly Asn Ser Thr Ala Gly Asn Met Lys Leu Asn Arg Thr Ile
                850                 855                 860
Val Gly Phe Asn Gly Gly Thr Ser Pro Phe Thr Thr Leu Thr Thr Asp
865                 870                 875                 880
Asn Leu Asp Ala Val Gln Ser Ala Phe Val Met Arg Thr Asp Leu Asn
                    885                 890                 895
Lys Ala Asp Lys Leu Val Ile Asn Lys Ser Ala Thr Gly His Asp Asn
                900                 905                 910
Ser Ile Trp Val Asn Phe Leu Lys Lys Pro Ser Asn Lys Asp Thr Leu
                915                 920                 925
Asp Ile Pro Leu Val Ser Ala Pro Glu Ala Thr Ala Asp Asn Leu Phe
                930                 935                 940
Arg Ala Ser Thr Arg Val Val Gly Phe Ser Asp Val Thr Pro Ile Leu
945                 950                 955                 960
Ser Val Arg Lys Glu Asp Gly Lys Lys Glu Trp Val Leu Asp Gly Tyr
                    965                 970                 975
Gln Val Ala Arg Asn Asp Gly Gln Gly Lys Ala Ala Ala Thr Phe Met
                980                 985                 990
His Ile Ser Tyr Asn Asn Phe Ile Thr Glu Val Gly Ser Leu Asn Lys
                995                 1000                1005
Arg Met Gly Asp Leu Arg Asp Ile Asn Gly Glu Ala Gly Thr Trp
     1010                1015                1020
Val Arg Leu Leu Asn Gly Ser Gly Ser Ala Asp Gly Gly Phe Thr
     1025                1030                1035
Asp His Tyr Thr Leu Leu Gln Met Gly Ala Asp Arg Lys His Glu
     1040                1045                1050
Leu Gly Ser Met Asp Leu Phe Thr Gly Val Met Ala Thr Tyr Thr
     1055                1060                1065
Asp Thr Asp Ala Ser Ala Asp Leu Tyr Ser Gly Lys Thr Lys Ser
     1070                1075                1080
```

```
Trp Gly Gly Gly Phe Tyr Ala Ser Gly Leu Phe Arg Ser Gly Ala
    1085                1090                1095

Tyr Phe Asp Val Ile Ala Lys Tyr Ile His Asn Glu Asn Lys Tyr
    1100                1105                1110

Asp Leu Asn Phe Ala Gly Ala Gly Lys Gln Asn Phe Arg Ser His
    1115                1120                1125

Ser Leu Tyr Ala Gly Ala Glu Val Gly Tyr Arg Tyr His Leu Thr
    1130                1135                1140

Asp Thr Thr Phe Val Glu Pro Gln Ala Glu Leu Val Trp Gly Arg
    1145                1150                1155

Leu Gln Gly Gln Thr Phe Asn Trp Asn Asp Ser Gly Met Asp Val
    1160                1165                1170

Ser Met Arg Arg Asn Ser Val Asn Pro Leu Val Gly Arg Thr Gly
    1175                1180                1185

Val Val Ser Gly Lys Thr Phe Ser Gly Lys Asp Trp Ser Leu Thr
    1190                1195                1200

Ala Arg Ala Gly Leu His Tyr Glu Phe Asp Leu Thr Asp Ser Ala
    1205                1210                1215

Asp Val His Leu Lys Asp Ala Ala Gly Glu His Gln Ile Asn Gly
    1220                1225                1230

Arg Lys Asp Ser Arg Met Leu Tyr Gly Val Gly Leu Asn Ala Arg
    1235                1240                1245

Phe Gly Asp Asn Thr Arg Leu Gly Leu Glu Val Glu Arg Ser Ala
    1250                1255                1260

Phe Gly Lys Tyr Asn Thr Asp Asp Ala Ile Asn Ala Asn Ile Arg
    1265                1270                1275

Tyr Ser Phe
    1280

<210> SEQ ID NO 30
<211> LENGTH: 300
<212> TYPE: PRT
<213> ORGANISM: Unknown
<220> FEATURE:
<223> OTHER INFORMATION: Escherichia coli - Streptococcus pyogenes

<400> SEQUENCE: 30

Met Lys Tyr Leu Leu Pro Thr Ala Ala Ala Gly Leu Leu Leu Leu Ala
1               5                   10                  15

Ala Gln Pro Ala Met Ala Phe Ala Cys Lys Thr Ala Asn Gly Thr Ala
                20                  25                  30

Ile Pro Ile Gly Gly Gly Ser Ala Asn Val Tyr Val Asn Leu Ala Pro
            35                  40                  45

Ala Val Asn Val Gly Gln Asn Leu Val Val Asp Leu Ser Thr Gln Ile
        50                  55                  60

Phe Cys His Asn Asp Tyr Pro Glu Thr Ile Thr Asp Tyr Val Thr Leu
65                  70                  75                  80

Gln Arg Gly Ala Ala Tyr Gly Gly Val Leu Ser Ser Phe Ser Gly Thr
                85                  90                  95

Val Lys Tyr Asn Gly Ser Ser Tyr Pro Phe Pro Thr Thr Ser Glu Thr
                100                 105                 110

Pro Arg Val Val Tyr Asn Ser Arg Thr Asp Lys Pro Trp Pro Val Ala
            115                 120                 125

Leu Tyr Leu Thr Pro Val Ser Ser Ala Gly Gly Val Ala Ile Lys Ala
        130                 135                 140
```

-continued

```
Gly Ser Leu Ile Ala Val Leu Ile Leu Arg Gln Thr Asn Asn Tyr Asn
145                 150                 155                 160

Ser Asp Asp Phe Gln Phe Val Trp Asn Ile Tyr Ala Asn Asn Asp Val
                165                 170                 175

Val Val Pro Thr Gly Ser Gly Gly Tyr Pro Tyr Asp Val Pro Asp Tyr
            180                 185                 190

Ala Gly Ser Gly Gly Thr Gly Asp Ser Ala Thr His Ile Lys Phe Ser
        195                 200                 205

Lys Arg Asp Glu Asp Gly Lys Glu Leu Ala Gly Ala Thr Met Glu Leu
    210                 215                 220

Arg Asp Ser Ser Gly Lys Thr Ile Ser Thr Trp Ile Ser Asp Gly Gln
225                 230                 235                 240

Val Lys Asp Phe Tyr Leu Tyr Pro Gly Lys Tyr Thr Phe Val Glu Thr
                245                 250                 255

Ala Ala Pro Asp Gly Tyr Glu Val Ala Thr Ala Ile Thr Phe Thr Val
            260                 265                 270

Asn Glu Gln Gly Gln Val Thr Val Asn Gly Lys Ala Thr Lys Gly Asp
        275                 280                 285

Ala His Ile Gly Ser Gly His His His His His His
    290                 295                 300
```

<210> SEQ ID NO 31
<211> LENGTH: 19
<212> TYPE: DNA
<213> ORGANISM: Artificial sequence
<220> FEATURE:
<223> OTHER INFORMATION: DNA primer

<400> SEQUENCE: 31
ggatctcgac gctctccct                                              19

<210> SEQ ID NO 32
<211> LENGTH: 35
<212> TYPE: DNA
<213> ORGANISM: Artificial sequence
<220> FEATURE:
<223> OTHER INFORMATION: DNA primer

<400> SEQUENCE: 32
cggtaccacc gctgcctttg ctgctaacgg taacc                            35

<210> SEQ ID NO 33
<211> LENGTH: 43
<212> TYPE: DNA
<213> ORGANISM: Artificial sequence
<220> FEATURE:
<223> OTHER INFORMATION: DNA primer

<400> SEQUENCE: 33
gcagcggtgg taccggcgat agtgctaccc atattaaatt ctc                   43

<210> SEQ ID NO 34
<211> LENGTH: 62
<212> TYPE: DNA
<213> ORGANISM: Artificial sequence
<220> FEATURE:
<223> OTHER INFORMATION: DNA primer

<400> SEQUENCE: 34
gcggccgcaa gctttttacta atgatggtga tgatgatgac cgctgccaat atgagcgtca    60
cc 62

<210> SEQ ID NO 35
<211> LENGTH: 28
<212> TYPE: DNA
<213> ORGANISM: Artificial sequence
<220> FEATURE:
<223> OTHER INFORMATION: DNA primer

<400> SEQUENCE: 35
gaaaatatac atttgtccaa accgcagc 28

<210> SEQ ID NO 36
<211> LENGTH: 28
<212> TYPE: DNA
<213> ORGANISM: Artificial sequence
<220> FEATURE:
<223> OTHER INFORMATION: DNA primer

<400> SEQUENCE: 36
gctgcggttt ggacaaatgt atattttc 28

<210> SEQ ID NO 37
<211> LENGTH: 86
<212> TYPE: DNA
<213> ORGANISM: Artificial sequence
<220> FEATURE:
<223> OTHER INFORMATION: DNA primer

<400> SEQUENCE: 37
cggcgcccac atcgtgatgg tggacgccta caagccgacg aagggtagtg gtgaaagtgg 60
tcatcatcat caccatcatt agtaaa 86

<210> SEQ ID NO 38
<211> LENGTH: 94
<212> TYPE: DNA
<213> ORGANISM: Artificial sequence
<220> FEATURE:
<223> OTHER INFORMATION: DNA primer

<400> SEQUENCE: 38 agctttact aatgatggtg atgatgatga ccactttcac cactaccctt cgtcggcttg 60
taggcgtcca ccatcacgat gtgggcgccg gtac 94

<210> SEQ ID NO 39
<211> LENGTH: 83
<212> TYPE: DNA
<213> ORGANISM: Artificial sequence
<220> FEATURE:
<223> OTHER INFORMATION: DNA primer

<400> SEQUENCE: 39
cggcaaactg ggcgatattg aatttattaa agtgaacaaa ggtagtggtg aaagtggtca 60
tcatcatcac catcattagt aaa 83

<210> SEQ ID NO 40
<211> LENGTH: 91
<212> TYPE: DNA
<213> ORGANISM: Artificial sequence
<220> FEATURE:
<223> OTHER INFORMATION: DNA primer

<400> SEQUENCE: 40 agctttact aatgatggtg atgatgatga ccactttcac cactaccttt gttcactta 60

```
ataaattcaa tatcgcccag tttgccggta c                                    91
```

<210> SEQ ID NO 41
<211> LENGTH: 40
<212> TYPE: DNA
<213> ORGANISM: Artificial sequence
<220> FEATURE:
<223> OTHER INFORMATION: DNA primer

<400> SEQUENCE: 41

```
atatatccat gggcgatagt gctacccata ttaaattctc                           40
```

<210> SEQ ID NO 42
<211> LENGTH: 77
<212> TYPE: DNA
<213> ORGANISM: Artificial sequence
<220> FEATURE:
<223> OTHER INFORMATION: DNA primer

<400> SEQUENCE: 42

```
atatatgaat tcgccggacc ccgcatagtc aggaacatcg tatgggtatc ccgaaccaat     60
atgagcgtca cctttag                                                    77
```

<210> SEQ ID NO 43
<211> LENGTH: 27
<212> TYPE: DNA
<213> ORGANISM: Artificial sequence
<220> FEATURE:
<223> OTHER INFORMATION: DNA primer

<400> SEQUENCE: 43

```
atatatgtcg acggcagcgg tggtacc                                         27
```

<210> SEQ ID NO 44
<211> LENGTH: 19
<212> TYPE: DNA
<213> ORGANISM: Artificial sequence
<220> FEATURE:
<223> OTHER INFORMATION: DNA primer

<400> SEQUENCE: 44

```
gctagttatt gctcagcgg                                                  19
```

<210> SEQ ID NO 45
<211> LENGTH: 28
<212> TYPE: DNA
<213> ORGANISM: Artificial sequence
<220> FEATURE:
<223> OTHER INFORMATION: DNA primer

<400> SEQUENCE: 45

```
atatatccat gggcaagccg ctgcgtgg                                        28
```

<210> SEQ ID NO 46
<211> LENGTH: 81
<212> TYPE: DNA
<213> ORGANISM: Artificial sequence
<220> FEATURE:
<223> OTHER INFORMATION: DNA primer

<400> SEQUENCE: 46

```
atatatgaat tccccgccgc taccgccttt atcgtcatca tccttatagt caccgccgct     60
accgcctttc ggcggtatcg g                                               81
```

<210> SEQ ID NO 47
<211> LENGTH: 27
<212> TYPE: DNA
<213> ORGANISM: Artificial sequence
<220> FEATURE:
<223> OTHER INFORMATION: DNA primer

<400> SEQUENCE: 47
atatatgtcg acggcagcgg tggtacc                                    27

<210> SEQ ID NO 48
<211> LENGTH: 31
<212> TYPE: DNA
<213> ORGANISM: Artificial sequence
<220> FEATURE:
<223> OTHER INFORMATION: DNA primer

<400> SEQUENCE: 48
atatatgaat tcgaagaaag tccgcaggtt g                               31

<210> SEQ ID NO 49
<211> LENGTH: 27
<212> TYPE: DNA
<213> ORGANISM: Artificial sequence
<220> FEATURE:
<223> OTHER INFORMATION: DNA primer

<400> SEQUENCE: 49
atatatgtcg acggtgccat catccgg                                    27

<210> SEQ ID NO 50
<211> LENGTH: 41
<212> TYPE: DNA
<213> ORGANISM: Artificial sequence
<220> FEATURE:
<223> OTHER INFORMATION: DNA primer

<400> SEQUENCE: 50
atatatgaat tctcaggaaa aaagaagct acaactagta c                     41

<210> SEQ ID NO 51
<211> LENGTH: 42
<212> TYPE: DNA
<213> ORGANISM: Artificial sequence
<220> FEATURE:
<223> OTHER INFORMATION: DNA primer

<400> SEQUENCE: 51
atatatgtcg acctgaacag cctcaaataa atcatttaat tg                   42

<210> SEQ ID NO 52
<211> LENGTH: 45
<212> TYPE: DNA
<213> ORGANISM: Artificial sequence
<220> FEATURE:
<223> OTHER INFORMATION: DNA primer

<400> SEQUENCE: 52
ggaagtcttg cggggagctc cgatagtgct acccatatta aattc                45

<210> SEQ ID NO 53
<211> LENGTH: 39
<212> TYPE: DNA
<213> ORGANISM: Artificial sequence
<220> FEATURE:
<223> OTHER INFORMATION: DNA primer

```
<400> SEQUENCE: 53
taccgctgcc ggatccaata tgagcgtcac ctttagttg                    39

<210> SEQ ID NO 54
<211> LENGTH: 39
<212> TYPE: DNA
<213> ORGANISM: Artificial sequence
<220> FEATURE:
<223> OTHER INFORMATION: DNA primer

<400> SEQUENCE: 54
ggaagtcttg cggggagctc caagccgctg cgtggtgcc                    39

<210> SEQ ID NO 55
<211> LENGTH: 38
<212> TYPE: DNA
<213> ORGANISM: Artificial sequence
<220> FEATURE:
<223> OTHER INFORMATION: DNA primer

<400> SEQUENCE: 55
taccgctgcc ggatcctttc ggcggtatcg gttcattg                     38

<210> SEQ ID NO 56
<211> LENGTH: 25
<212> TYPE: DNA
<213> ORGANISM: Artificial sequence
<220> FEATURE:
<223> OTHER INFORMATION: DNA primer

<400> SEQUENCE: 56
ttgctaactt tctagattac aaaac                                   25

<210> SEQ ID NO 57
<211> LENGTH: 75
<212> TYPE: DNA
<213> ORGANISM: Artificial sequence
<220> FEATURE:
<223> OTHER INFORMATION: DNA primer

<400> SEQUENCE: 57
taccgctgcc ggatcccttc gtcggcttgt aggcgtccac catcacgatg tgggcggagc    60
tccccgcaag acttc                                              75

<210> SEQ ID NO 58
<211> LENGTH: 66
<212> TYPE: DNA
<213> ORGANISM: Artificial sequence
<220> FEATURE:
<223> OTHER INFORMATION: DNA primer

<400> SEQUENCE: 58
taccgctgcc ggatccatca cgttttgaga atttaatatg ggtagcggag ctccccgcaa    60
gacttc                                                        66

<210> SEQ ID NO 59
<211> LENGTH: 39
<212> TYPE: DNA
<213> ORGANISM: Artificial sequence
<220> FEATURE:
<223> OTHER INFORMATION: DNA primer

<400> SEQUENCE: 59
```

```
ccaaactggg cgatattgaa tttattaaag tgaacaaag                             39
```

```
<210> SEQ ID NO 60
<211> LENGTH: 47
<212> TYPE: DNA
<213> ORGANISM: Artificial sequence
<220> FEATURE:
<223> OTHER INFORMATION: DNA primer

<400> SEQUENCE: 60
gatcctttgt tcactttaat aaattcaata tcgcccagtt tggagct                   47
```

```
<210> SEQ ID NO 61
<211> LENGTH: 42
<212> TYPE: DNA
<213> ORGANISM: Artificial sequence
<220> FEATURE:
<223> OTHER INFORMATION: DNA primer

<400> SEQUENCE: 61
ccgcccacat cgtgatggtg gacgcctaca agccgacgaa gg                        42
```

```
<210> SEQ ID NO 62
<211> LENGTH: 50
<212> TYPE: DNA
<213> ORGANISM: Artificial sequence
<220> FEATURE:
<223> OTHER INFORMATION: DNA primer

<400> SEQUENCE: 62
gatcccttcg tcggcttgta ggcgtccacc atcacgatgt gggcggagct                50
```

```
<210> SEQ ID NO 63
<211> LENGTH: 72
<212> TYPE: DNA
<213> ORGANISM: Artificial sequence
<220> FEATURE:
<223> OTHER INFORMATION: DNA primer

<400> SEQUENCE: 63
ccggctcggc tagcggtgcc cacatcgtga tggtggacgc ctacaagccg acgaagggtg    60
agggaaccgg cg                                                         72
```

```
<210> SEQ ID NO 64
<211> LENGTH: 80
<212> TYPE: DNA
<213> ORGANISM: Artificial sequence
<220> FEATURE:
<223> OTHER INFORMATION: DNA primer

<400> SEQUENCE: 64
gatccgccgg ttccctcacc cttcgtcggc ttgtaggcgt ccaccatcac gatgtgggca    60
ccgctagccg agccggagct                                                 80
```